(12) United States Patent
Koura et al.

(10) Patent No.: US 8,551,985 B2
(45) Date of Patent: Oct. 8, 2013

(54) CARBINOL DERIVATIVES HAVING HETEROCYCLIC LINKER

(75) Inventors: Minoru Koura, Higashimurayama (JP); Hisashi Sumida, Higashimurayama (JP); Sayaka Kurobuchi, Higashimurayama (JP); Sumiko Kurobuchi, legal representative, Higashimurayama (JP); Takayuki Matsuda, Higashimurayama (JP); Yuichiro Watanabe, Higashimurayama (JP); Takashi Enomoto, Higashimurayama (JP); Kimiyuki Shibuya, Higashimurayama (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 233 days.

(21) Appl. No.: 12/769,104

(22) Filed: Apr. 28, 2010

(65) Prior Publication Data

US 2010/0280013 A1  Nov. 4, 2010

Related U.S. Application Data

(60) Provisional application No. 61/173,690, filed on Apr. 29, 2009.

(51) Int. Cl.
| | | |
|---|---|---|
| A61K 31/496 | (2006.01) |
| A61K 31/551 | (2006.01) |
| C07D 233/72 | (2006.01) |
| C07D 401/04 | (2006.01) |
| C07D 401/14 | (2006.01) |
| C07D 405/04 | (2006.01) |
| C07D 405/14 | (2006.01) |
| C07D 491/048 | (2006.01) |
| C07D 491/056 | (2006.01) |

(52) U.S. Cl.
USPC .............. 514/218; 514/253.04; 514/253.09; 514/254.07; 514/254.05; 540/575; 544/362; 544/364; 544/370

(58) Field of Classification Search
None
See application file for complete search history.

(56) References Cited

U.S. PATENT DOCUMENTS

| 6,316,503 B1 | 11/2001 | Li et al. |
| 2005/0215577 A1 | 9/2005 | Dehmlow et al. |
| 2005/0239769 A1 | 10/2005 | Jones et al. |
| 2006/0074115 A1 | 4/2006 | Dehmlow et al. |
| 2010/0048610 A1 | 2/2010 | Yamaguchi et al. |

FOREIGN PATENT DOCUMENTS

| EP | 2 098 515 A1 | 9/2009 |
| JP | 2002-539155 A | 11/2002 |
| JP | 2004-509161 A | 3/2004 |
| WO | 00/54759 A1 | 9/2000 |
| WO | 02/24632 A2 | 3/2002 |
| WO | 03/082192 A2 | 10/2003 |
| WO | 2004/011448 A1 | 2/2004 |
| WO | 2004//024161 A1 | 3/2004 |
| WO | 2004/058717 A1 | 7/2004 |
| WO | 2004/072046 A2 | 8/2004 |
| WO | 2005/023188 A2 | 3/2005 |
| WO | 2005/058834 A2 | 6/2005 |
| WO | 2005/058834 A3 | 6/2005 |
| WO | 2008/065754 A1 | 6/2008 |
| WO | 2009-144961 A1 | 12/2009 |

OTHER PUBLICATIONS

Vippagunta et al Advanced Drug Delivery Reviews, vol. 48, pp. 3-26 (2001).*
Edwards et al. Current Medicinal Chemistry vol. 15 (2),p. 195-209 (2008) (Abstract provided).*
International Search Report of PCT/JP2010/003039, date of mailing Jun. 1, 2010.
Extended European Search Report dated Oct. 10, 2012, issued in corresponding European Patent Application No. 10769511.6 (7 pages).

(Continued)

Primary Examiner — Emily Bernhardt
(74) Attorney, Agent, or Firm — Westerman, Hattori, Daniels & Adrian, LLP

(57) ABSTRACT

[Object]
It is to provide a novel LXRβ agonist useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.
[Solving Means]
A carbinol compound represented by the following general formula (I) or salt thereof, or their solvate:

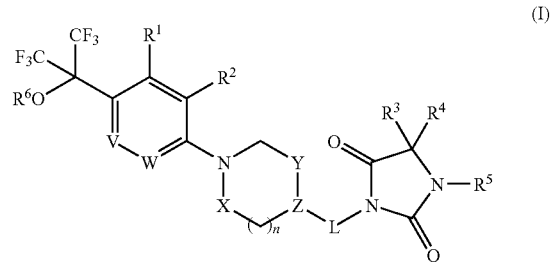

(wherein, each V and W independently show N or C—$R^7$; each X and Y independently show $CH_2$, C=O, $SO_2$, etc; Z shows CH or N; each $R^1$, $R^2$ and $R^7$ independently show a hydrogen atom, $C_{1-8}$ alkyl group, etc.; $R^3$ shows $C_{1-8}$ alkyl group; $R^4$ shows an optionally substituted $C_{6-10}$ aryl group or an optionally substituted 5- to 11-membered heterocyclic group; $R^5$ and $R^6$ show a hydrogen atom, etc.; L shows a $C_{1-8}$ alkyl chain optionally substituted with an oxo group, etc.; and n shows any integer of 0 to 2.)

21 Claims, 7 Drawing Sheets

(56) References Cited

OTHER PUBLICATIONS

Alberti S. et al.; "Hepatic cholesterol metabolism and resistance to dietary cholesterol in LXR Beta-deficient mice"; The Journal of Clinical Investigation; Mar. 2001; vol. 107 pp. 565-573.

Auboeuf, Didier et al; "Tissue Distribution and Quantification of the Expression of mRNAs of Peroxisome Proliferator-Activated Receptors and Liver X Receptor-Alpha in Humans"; Diabetes, vol. 46, Aug. 1997, pp. 1319-1327.

Hu, Baihua et al; "Further modification on phenyl acetic acid based quinolines as liver X receptor modulators"; Bioorganic & Medicinal Chemistry, vol. 15, 2007, pp. 3321-3333.

Hu Baihua et al.; "Carboxylic acid based quinolines as liver X receptor modulators that have LXR beta receptor binding selectivity"; Bioorganic & Medicinal Chemistry Letter, vol. 18, 2008, pp. 54-59.

Bradley, Michelle et al.; LXR: A Nuclear receptor target for cardiovascular disease?; Elsevier Ltd.; pp. 97-103, (2005).

Cao, Guoqing et al.; "Antidiabetic Action of a liver X Receptor Agonist Mediated by Inhibition of Hepatic Gluconeogenesis"; The Journal of Biological Chemistry, vol. 278, No. 2, Jan. 10, 2003, p. 1131-1136.

Fu, Xuan et al.; "27-Hydroxycholesterol Is an Endogenous Ligand for Liver X Receptor in Cholesterol-loaded Cells"; The Journal of Biological Chemistry, vol. 276, No. 42, Oct. 19, 2001, pp. 38378-38387.

Geyeregger R. et al.; "Liver X receptors in cardiovascular and metabolic disease"; Cell. Mol. Life Sci., vol. 63, 2006, pp. 524-539.

Janowski, Bethany A. et al.; "An oxysterol signalling pathway mediated by the nuclear receptor LXR Alpha"; Nature, vol. 383,Oct. 24, 1996, pp. 728-731.

Hu, Baihua et al.; "Discovery of Phenyl Acetic Acid Substituted Quinolines as Novel Liver X Receptor Agonists for the Treatment of Atherosclerosis"; J. Med. Chem. 2006, vol. 49, pp. 6151-6154.

Laffitte, Bryan A. et al.; "Activation of liver X receptor improves glucose tolerance through coordinate regulation of glucose metabolism in liver and adipose tissue; "PNAS; Apr. 29, 2003; vol. 100, No. 9, pp. 5419-5424.

Lala Deepak S; "The liver X receptors"; DBD DNA-binding domain, LBD ligand-binding domain, pp. 934-943, (2005).

Lehmann, Jurgen M. et al.; "Activation of the Nuclear Receptor LXR by Oxysterols Defines a New Hormone Response Pathway"; The Journal of Biological Chemistry, vol. 272, No. 6, Feb. 7, 1997, pp. 3137-3140.

Lu, Timothy T. et al.; "Orphan Nuclear Receptors as eLiXiRs and FiXeRs of Sterol Metabolism"; The Journal of Biological Chemistry, vol. 276, No. 41, Oct. 12, 2001, pp. 37735-37738.

Lund, Erik G. et al.; "Liver X Receptor Agonists as Potential Therapeutic Agents for Dyslipidemia and Atherosclerosis"; Arterioscler Thromb Vasc Biol., p. 1169-1177, (2003).

Joseph, Sean B. et al.; Reciprocal regulation of inflammation and lipid metabolism by liver X receptors; Nature Medicine, vol. 9, No. 2, Feb. 2003 pp. 213-219.

Peet, Daniel J. et al.; "Cholesterol and Bile Acid Metabolism Are Impaired in Mice Lacking the Nuclear Oxysterol Receptor LXR alpha"; Cell, vol. 93,May 29, 1998, pp. 693-704.

Groot, Pieter H. E.; "Synthetic LXR agonists increase LDL in CETP species"; Journal of Lipid Research; vol. 45, 2005 pp. 2182-2191.

Schultz, Joshua R. et al.; "Role of LXRs in control of lipogenesis"; Gene & Development, vol. 14, 2000, pp. 2831-2838.

Tangirala, Rajendra K. et al.; "Identification of macrophage liver X receptors as inhibitors of atherosclerosis"; PNAS, vol. 99, No. 18, Sep. 3, 2002, pp. 11896-11901.

Terasaka, Naoki et al. "T-0901317, a synthetic liver X receptor ligand, inhibits development of atherosclerosis in LDL receptor-deficient mice"; Federation of European Biochemical Societies Letters, vol. 536, 2006, pp. 6-11.

Zelcer, Noam et al.; "Liver X receptors as integrators of metabolic and inflammatory signaling"; The Journal of Clinical Investigation, vol. 116, No. 3, Mar. 2006, pp. 607-614.

\* cited by examiner

Example 6

Example 7

Example 9

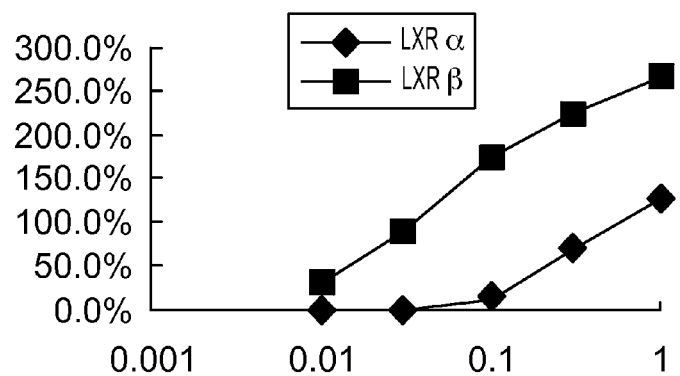
Fig.1d Example 12
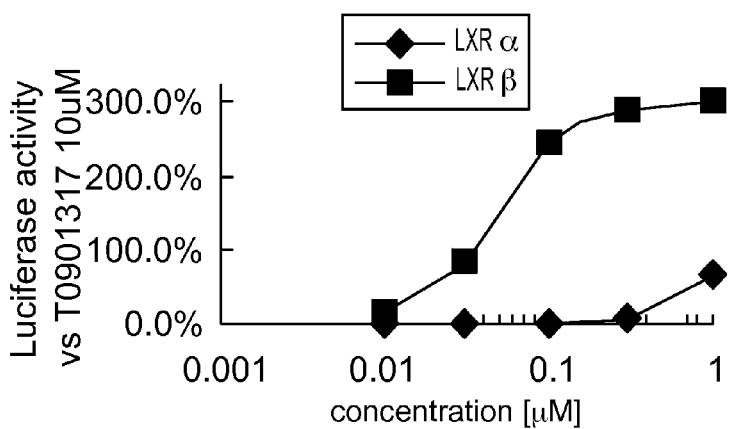
Fig.1e Example 13
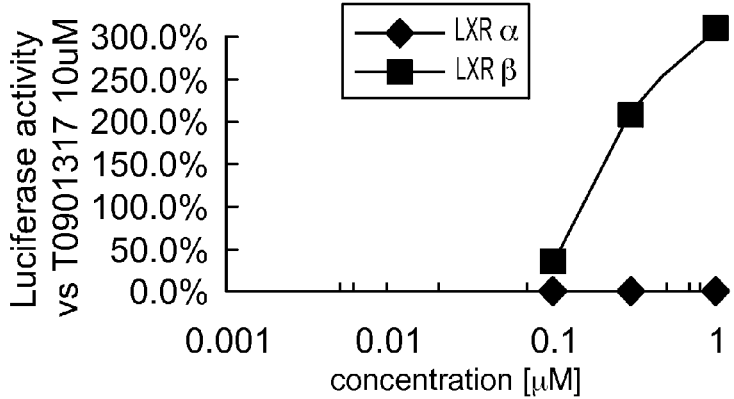
Fig.1f Example 14

Example15

Example18

Example 19

Example 24

Example 25

T0901317

Example 23

Example 28

Example 39

Example 50

Example 57

Example 61

T0901317

CARBINOL DERIVATIVES HAVING HETEROCYCLIC LINKER

TECHNICAL FIELD

The present invention relates to a carbinol compound having a heterocyclic linker, which is a novel LXRβ agonist useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

BACKGROUND ART

Liver X receptor (LXR) is a nuclear receptor that was cloned as an orphan receptor whose ligand and function were both unknown. Subsequent study reported that some oxysterols including 22-R-hydroxycholesterol act as a ligand for LXR (non-patent documents 1 to 3). LXR, together with retinoid X receptor (RXR) which is another nuclear receptor, forms a heterodimer to ligand-dependently control the transcription of a target gene.

As mammal LXR sub-types, two types of LXR genes (α and β) are known to exist. LXRα and LXRβ recognize the same sequence on a DNA and activate the transcription of a neighboring target gene. However, the expression-distributions of the two genes differ greatly. LXRα is specifically expressed on cholesterol metabolism-related tissues such as the liver, small intestines and adipose tissues, whereas LXRβ is expressed ubiquitously on almost all tissues that have been examined (non-patent documents 4 and 5).

Many of the group of genes identified as target genes of LXRs are genes (ApoE, CETP, and LPL) related to a reverse cholesterol transport (RCT), including ABC transporters (ABCA1, ABCG1, ABCG5, and ABCG8). Therefore, it is expected that the activation of LXRs elevates the expression of these genes and activates reverse cholesterol transport pathways, thereby increases cholesterol efflux from the periphery and then increases HDL cholesterols and also lowers cholesterol content at an arteriosclerosis-affected region (non-patent document 6).

Further, LXRs are reported to play an important role via NF-κB suppression, in the expression control of inflammatory mediators such as NO-synthase, cyclooxygenase-2 (COX-2), and interleukin-6 (IL-6) (non-patent document 7). It is well known that the inflammation is very important at an arteriosclerosis-affected region, and it is expected that LXR ligands or LXR agonists will prevent arteriosclerosis exacerbation due to the expression of macrophage-inflammatory mediators at the affected region (non-patent documents 6 and 8).

Further, LXR α- and LXR β-deficient mice fed on high-cholesterol diet have been reported to show symptoms such as fatty liver and elevated LDL-cholesterol level as well as reduced HDL-cholesterol level in the blood as compared to the case of normal mice fed on high-cholesterol diet (non-patent documents 9 and 10). More specifically, it is strongly suggested that LXRs play an important role in cholesterol metabolism. Moreover, by analyzing the symptoms of arteriosclerosis mouse models having normal LXRα and LXRβ functions in the liver, small intestines and the like but lacking LXRα and LXRβ in macrophages, it has been revealed that LXRα and LXRβ activities in macrophages strongly affect the incidence of arteriosclerosis (non-patent document 11). Therefore, the activation of reverse cholesterol transport through the LXR activation especially in macrophages is considered to be important for the treatment of arteriosclerosis.

As for the applications, LXR regulators or LXR agonists disclosed in the prior art documents are reported to have been applied to diseases such as hypercholesterolemia and atherosclerosis (patent documents 1 and 2). Further, LDL-receptor-deficient mice loaded with high-fat food, and administered with LXR ligand, have been reported to show an elevated HDL cholestserol level, lowered VLDL and LDL cholesterol levels, and reduced area of arteriosclerosis-affected region (non-patent document 12).

Further, LXR ligands or LXR agonists are expected to control sugar metabolism in the liver and adipose tissues, and thus to improve diabetes (non-patent documents 6 and 8). Recently, it has been reported that an administration of LXR agonist improved insulin sensitivity and blood glucose level in diabetes animal models (non-patent documents 13 and 14). Moreover, it is indicated as a potential therapeutic drug for Alzheimer's disease, inflammatory diseases, or skin diseases (non-patent document 15).

LXR agonists, however, are reported to increase LDL cholesterol in animal species having cholesteryl ester transfer proteins (CETP) (non-patent document 16). Further, in animal experiments, it has been observed that LXR activation in the liver by the LXR agonist administration enhances fatty-acid and triglyceride syntheses through the transcriptional activation of enzymes that are important for fatty-acid synthesis, for example, fatty-acid synthase (FAS) or stearyl-CoA fatty-acid desaturase (SCD-1) (non-patent document 17). Meanwhile, nothing is disclosed in the prior art documents on LXR α/β selectivity in relation to the disclosed LXR regulators, LXR ligands, LXR agonists and the like.

Therefore, there have been demands for an ideal synthetic LXR-binding compound without a dyslipidemia-exacerbating effect which acts through an elevated fatty-acid and triglyceride syntheses, while maintaining the agonist activity for reverse cholesterol transport activation by ABC transporters and for increased cholesterol-efflux from macrophages. As one approach to solve the problem, a compound that selectively activates LXRβ is considered to have an ideal profile that is expected to suppress the activation of LXRα highly expressed on the liver, as compared to the LXR regulators disclosed in the prior art documents, and to suppress the concerned side-effects of fatty-acid and triglyceride synthesis elevations (non-patent documents 6, 8, 15, 18, and 19). However, because ligand-binding sites of LXRα and LXRβ are highly homologous, it is considered that the creation of a compound that acts differently on LXRα and LXRβ is not easy.

In fact, compounds having an LXR-agonist effect have been reported, such as a benzofuran-5-acetic acid derivative (patent document 3), 2-aminoquinazolin-4-one derivative (patent document 4), tetrahydroquinoline derivative (non-patent document 5), tetrahydrocarbazol derivative (patent document 6), isoquinoline derivative (patent document 7), and naphthalene derivative (patent document 8), GW3965 which is an aromatic aminoalcohol derivative (Example 16 described in patent document 9), and T0901317 which is a benzenesulfonamide derivative (Example 12 described in patent document 10), but no agonist with high LXRβ selectivity has been reported to date and a compound with high LXRβ selectivity has been awaited.

Meanwhile, an LXR agonist having a quinoline skeleton has been reported (patent document 11, non-patent documents 20 to 22). For example, WAY-254011 (compound 4 of non-patent document 22) which is a quinoline derivative has been reported to have LXRβ-selective binding affinity (α/β ratio is 1 to 5). Non-patent document 22 further reports on a compound showing an α/β ratio of up to 1 to 50 in terms of binding-affinity. However, as for an agonist effect which was measured by Gal 4 transactivation activity, the highest selectivity confirmed was an α/β ratio of merely up to about 1 to 2.7. This shows that the effect of the compound on LXR for expressing the target gene is weak despite the selective binding of the compound to LXRβ. Therefore, there are still strong demands for a compound having an effect of expressing a target gene in an LXRβ selective manner.

[Patent Document 1] Published Japanese translation of PCT international publication No. 2002-539155
[Patent Document 2] Published Japanese translation of PCT international publication No. 2004-509161
[Patent Document 3] WO2003/82192
[Patent Document 4] WO2004/24161
[Patent Document 5] WO2004/72046
[Patent Document 6] U.S Patent publication No. 2005/215577
[Patent Document 7] WO2004/58717
[Patent Document 8] WO2005/23188
[Patent Document 9] WO2002/24632
[Patent Document 10] WO2000/54759
[Patent Document 11] WO2005/58834
[Non-patent Document 1] Janowski et al., Nature, 383, pp. 728-731, 1996
[Non-patent Document 2] Lehmann et al., J. Biol. Chem., 272, pp. 3137-3140, 1997
[Non-patent Document 3] Fu et al., J. Biol. Chem., 276, pp. 38378-38387, 2001
[Non-patent Document 4] Auboeuf et al., Diabetes, 46, pp. 1319-1327, 1997
[Non-patent Document 5] Lu et al., J. Biol. Chem., 276, pp. 37735-37738, 2001
[Non-patent Document 6] Zelcer et al., J. Clin. Invest., 116, pp. 607-614, 2006
[Non-patent Document 7] Mangelsdorf et al., Nat. Med., 9, pp. 213-219, 2003
[Non-patent Document 8] Geyeregger et al., Cell. Mol. Life Sci. 63, pp. 524-539, 2006
[Non-patent Document 9] Peet et al., Cell, 93, pp. 693-704, 1998
[Non-patent Document 10] Alberti et al., J. Clin. Invest., 107, pp. 565-573, 2001
[Non-patent Document 11] Tangirala et al., Proc. Natl. Acad. Sci. USA, 99, pp. 11896-11901, 2002
[Non-patent Document 12] Terasaka et al., FEBS Lett., 536, pp. 6-11, 2003
[Non-patent Document 13] Cao et al., J. Biol. Chem., 278, pp. 1131-1136, 2003
[Non-patent Document 14] Laffitte et al., Proc. Natl. Acad. Sci. USA, 100, pp. 5419-5424, 2003
[Non-patent Document 15] Lala et al., Curr. Opin. Investig. Drugs, 6, pp. 934-943, 2005
[Non-patent Document 16] Pieter et al., J. Lipid Res., 46, pp. 2182-2191, 2005
[Non-patent Document 17] Schultz et al., Genes Dev., 14, pp. 2831-2838, 2000
[Non-patent Document 18] Lund et al., Arterioscler. Thromb. Vasc. Biol., 23, pp. 1169-1177, 2003
[Non-patent Document 19] Bradley et al., Drug Discov. Today Ther. Strateg. 2, pp. 97-103, 2005
[Non-patent Document 20] Hu et al., J. Med. Chem., 49, pp. 6151-6154, 2006
[Non-patent Document 21] Hu et al., Bioorg. Med. Chem., 15, pp. 3321-3333, 2007
[Non-patent Document 22] Hu et al., Bioorg. Med. Chem. Lett., 18, pp. 54-59, 2008

DISCLOSURE OF THE INVENTION

Problem to be Solved by the Invention

Therefore, the present invention is to produce a novel compound showing a high selective agonist activity to LXRβ.

Means to Solve the Problem

The present inventors made a keen study to achieve the above object and consequently, found that a compound having a structure wherein a carbinol skeleton and an imidazolidine-2,4-dione skeleton are bound via a heterocyclic linker, that is, a compound represented by general formula (I) described herein below has an agonist activity with high LXRβ selectivity, and thus completed the present invention.

Specifically, the present invention relates to:

[1] a carbinol compound represented by the following general formula (I) or salt thereof, or their solvate:

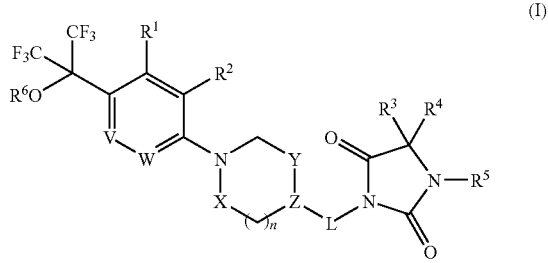

(wherein, each V and W independently show N or C—$R^7$;
each X and Y independently show $CH_2$, $CH(C_{1-8}$ alkyl), $C(C_{1-8}$alkyl)$_2$, C=O or $SO_2$;
Z shows CH or N;
each $R^1$, $R^2$ and $R^7$ independently show a hydrogen atom, halogen atom, or an optionally substituted $C_{1-8}$ alkyl group or $C_{2-8}$ alkenyl group;
$R^3$ shows $C_{1-8}$ alkyl group;
$R^4$ shows an optionally substituted $C_{6-10}$ aryl group or an optionally substituted 5- to 11-membered heterocyclic group;
$R^5$ shows a hydrogen atom or $C_{1-8}$ alkyl group;
$R^6$ shows a hydrogen atom, $C_{1-8}$ alkoxy $C_{1-8}$ alkyl group or an optionally substituted $C_{6-10}$ aryl $C_{1-8}$ alkyl group;
L shows a $C_{1-8}$ alkyl chain optionally substituted with an oxo group or sulfonyl group; and
n shows any integer of 0 to 2.)

[2] a medicine containing the carbinol compound or salt thereof, or their solvate according to [1] as an active ingredient;

[3] the medicine according to [2], which is a preventative and/or therapeutic agent for atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease;

[4] an LXR regulator containing the carbinol compound or salt thereof, or their solvate according to [1] as an active ingredient;

[5] a pharmaceutical composition consisting of the carbinol compound or salt thereof, or their solvate according to [1] and a pharmaceutically acceptable carrier;

[6] a method for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease, which method comprises administering an effective amount of the carbinol compound or salt thereof, or their solvate according to [1] to a patient in need of a treatment; and

[7] use of the carbinol compound or salt thereof, or their solvate according to [1] for a production of a formulation for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease.

Effect of the Invention

The carbinol compound represented by general formula (I) of the present invention has an LXRβ agonist effect and is useful as a preventative and/or therapeutic agent or the like for atherosclerosis, arteriosclerosis such as those resulting from diabetes; dyslipidemia; hypercholesterolemia; lipid-related diseases; inflammatory diseases caused by inflammatory cytokines, such as rheumatoid arthritis, osteoarthritis, allergic diseases, asthma, sepsis, psoriasis, and osteoporosis; autoimmune diseases such as systemic erythematosus, ulcerative colitis, and Crohn's disease; cardiovascular diseases such as ischemic cardiac disease and heart failure; cerebrovascular diseases; kidney diseases; diabetes; diabetes complications such as retinopathy, nephropathy, nerve disease, and coronary arterial disease; skin diseases such as allergic skin disease; obesity; nephritis; hepatitis; cancer; or Alzheimer's disease, and more preferably, as a preventative and/or therapeutic agent or the like for atherosclerosis, arteriosclerosis such as those resulting from diabetes, dyslipidemia, hypercholesterolemia, lipid-related diseases, inflammatory diseases that are caused by inflammatory cytokines, skin diseases such as allergic skin diseases, diabetes, or Alzheimer's disease.

BRIEF DESCRIPTION OF THE DRAWINGS

FIGS. 1a to 1l show the luciferase activity results as activity values (% eff) at the respective concentration of the test compound Examples 6, 7, 9, 12, 13, 14, 15, 18, 19, 24, and 25, relative to the T0901317 luminescence intensity of 100 at 10 μM.

BEST MODE OF CARRYING OUT THE INVENTION

Figure 1A:
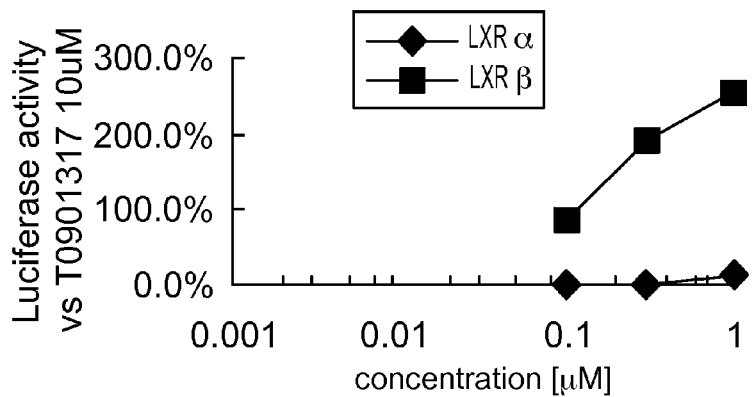

The terms in the present invention are defined as follows.
In the present invention, examples of a "halogen" atom include a fluorine atom, chlorine atom, bromine atom, iodine atom, etc.

In the present invention, a "$C_{1-8}$ alkyl group" means a straight-chained or branched-chained alkyl group with 1 to 8 carbons, and the examples include a methyl group, ethyl group, n-propyl group, isopropyl group, n-butyl group, isobutyl group, tert-butyl group, n-pentyl group, isopentyl group, neopentyl group, 2-methylbutyl group, 2,2-dimethylpropyl group, n-hexyl group, isohexyl group, n-heptyl group, n-octyl group, etc.

In the present invention, a "$C_{2-8}$ alkenyl group" means a straight-chained or branched-chained alkenyl group with 2 to 8 carbons, having a carbon-carbon double bond at any one or more sites on the alkyl chain. The examples include an ethenyl group, prop-1-en-1-yl group, prop-2-en-1-yl group, prop-1-en-2-yl group, but-1-en-1-yl group, but-2-en-1-yl group, but-3-en-1-yl group, but-1-en-2-yl group, but-3-en-2-yl group, pent-1-en-1-yl group, pent-4-en-1-yl group, pent-1-en-2-yl group, pent-4-en-2-yl group, 3-methyl-but-1-en-1-yl group, hex-1-en-1-yl group, hex-5-en-1-yl group, hept-1-en-1-yl group, hept-6-en-1-yl group, oct-1-en-1-yl group, oct-7-en-1-yl group, etc.

Specific examples of a "$C_{1-8}$ alkoxy group" in the present invention include a methoxy group, ethoxy group, n-propoxy group, 1-methylethoxy group, n-butoxy group, isobutoxy group, sec-butoxy group, tert-butoxy group, n-pentoxy group, isopentoxy group, neopentoxy group, 1-methylbutoxy group, 1-ethylpropoxy group, n-hexyloxy group, isohexyloxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group, 2-ethylbutoxy group, etc. Further, a "$C_{1-8}$ alkoxy $C_{1-8}$ alkyl group" refers to a group wherein a "$C_{1-8}$ alkoxy group" is bound to the above $C_{1-8}$ alkyl group, and the examples include a methoxymethyl group, methoxyethyl group, ethoxymethyl group, ethoxyethyl group, etc.

In the present invention, the examples of "$C_{3-8}$ cycloalkoxy group" include a cyclopropoxy group, cyclobutoxy group, cyclopentoxy group, cyclohexyloxy group, cycloheptyloxy group, cyclooctyloxy group, etc.

In the present invention, examples of a "$C_{1-8}$ acyl group" include an alkylcarbonyl group such as a formyl group, acetyl group, propionyl group, butyryl group, isobutyryl group, valeryl group, isovaleryl group, pivaloyl group, etc.; an alkenylcarbonyl group such as an acryloyl group, etc.; and an arylcarbonyl group such as a benzoyl group, etc. Further, examples of a "$C_{1-8}$ acyloxy group" include an alkylcarbonyloxy group such as a formyloxy group, acetyloxy group, propionyloxy group, butyryloxy group, isobutyryloxy group, valeryloxy group, isovaleryloxy group, pivaloyloxy group, etc; an alkenylcarbonyloxy group such as an acryloyloxy group, etc; and an arylcarbonyloxy group such as a benzoyloxy group, etc.

In the present invention, a "$C_{6-10}$ aryl group" means a monocyclic or polycyclic aryl group with 6 to 10 carbons. Here, a polycyclic aryl group encompasses partially saturated groups in addition to fully unsaturated groups. The examples include a phenyl group, naphthyl group, azulenyl group, indenyl group, indanyl group, tetralinyl group, etc.

In the present invention, a "$C_{6-10}$ aryl $C_{1-8}$ alkyl group" means a group wherein the above $C_{6-10}$ aryl group and the above $C_{1-8}$ alkyl group are bound. The examples include a benzyl group, phenethyl group, 3-phenyl-n-propyl group, 4-phenyl-n-butyl group, 5-phenyl-n-pentyl group, 8-phenyl-n-octyl group, naphthylmethyl group, etc.

In the present invention, a "5- to 11-membered heterocyclic group" means a 5- to 7-membered aromatic heterocycle, saturated heterocycle, unsaturated heterocycle or a condensed heterocycle made by a condensation of the above heterocycles and a benzene ring, wherein the above heterocycles contain 1 to 4 heteroatoms selected from a nitrogen atom, oxygen atom and sulfur atom in addition to a carbon atom, as atoms constituting the ring. The examples include a 2-furyl group, 3-furyl group, 2-thienyl group, 3-thienyl group, pyrrol-1-yl group, pyrrol-2-yl group, pyrrol-3-yl group, pyridin-2-yl group, pyridin-3-yl group, pyridin-4-yl group, pyrazin-2-yl group, pyrazin-3-yl group, pyrimidin-2-yl group, pyrimidin-4-yl group, pyrimidin-5-yl group, pyrimidin-6-yl group, pyridazin-3-yl group, pyridazin-4-yl group, 1,3-benzodioxol-4-yl group, 1,3-benzodioxol-5-yl group, 1,4-benzodioxin-5-yl group, 1,4-benzodioxin-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group, benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, quinoxalin-2-yl group, quinoxalin-5-yl group, quinoxalin-6-yl group, indol-1-yl group, indol-2-yl group, indol-3-yl group, indol-4-yl group, indol-5-yl group, indol-6-yl group, indol-7-yl group, isoindol-1-yl group, isoindol-2-yl group, isoindol-4-yl group, isoindol-5-yl group, isoindol-6-yl group, isoindol-7-yl group, isobenzofuran-1-yl group, isobenzofuran-4-yl group, isobenzofuran-5-yl group, isobenzofuran-6-yl group, isobenzofuran-7-yl group, chromen-2-yl group, chromen-3-yl group, chromen-4-yl group, chromen-5-yl group, chromen-6-yl group, chromen-7-yl group, chromen-8-yl group, imidazol-1-yl group, imidazol-2-yl group, imidazol-4-yl group, imidazol-5-yl group, pyrazol-1-yl group, pyrazol-3-yl group, pyrazol-4-yl group, pyrazol-5-yl group, thiazol-2-yl group, thiazol-4-yl group, thiazol-5-yl group, oxazol-2-yl group, oxazol-4-yl group, oxazol-5-yl group, isoxazol-3-yl group, isoxazol-4-yl group, isoxazol-5-yl group, pyrrolidin-2-yl group, pyrrolidin-3-yl group, benzoimidazol-1-yl group, benzoimidazol-2-yl group, benzoimidazol-4-yl group, benzoimidazol-5-yl group, benzothiazol-2-yl group, benzothiazol-4-yl group, benzothiazol-5-yl group, benzoxazol-2-yl group, benzoxazol-4-yl group, benzoxazol-5-yl group, quinolin-2-yl group, quinolin-3-yl group, quinolin-4-yl group, quinolin-5-yl group, quinolin-6-yl group, quinolin-7-yl group, quinolin-8-yl group, isoquinolin-1-yl group, isoquinolin-3-yl group, isoquinolin-4-yl group, isoquinolin-5-yl group, isoquinolin-6-yl group, isoquinolin-7-yl group, isoquinolin-8-yl group, 1,3,4-thiadiazol-2-yl group, morpholino group, 1,2,3-triazol-1-yl group, 1,2,3-triazol-4-yl group, 1,2,3-triazol-5-yl group, 1,2,4-triazol-1-yl group, 1,2,4-triazol-3-yl group, 1,2,4-triazol-5-yl group, tetrazol-1-yl group, tetrazol-2-yl group, indolin-4-yl group, indolin-5-yl group, indolin-6-yl group, indolin-7-yl group, 1,2,3,4-tetrahydroquinolin-5-yl group, 1,2,3,4-tetrahydroquinolin-6-yl group, 1,2,3,4-tetrahydroquinolin-7-yl group, 1,2,3,4-tetrahydroquinolin-8-yl group, 1,2,3,4-tetrahydroisoquinolin-5-yl group, 1,2,3,4-tetrahydroisoquinolin-6-yl group, 1,2,3,4-tetrahydroisoquinolin-7-yl group, 1,2,3,4-tetrahydroisoquinolin-8-yl group, etc.

In the present invention, "$C_{1-8}$ alkyl chain" means a straight-chained or branched-chained divalent hydrocarbon chain with 1 to 8 carbons, and the examples include a methylene chain, ethylene chain, trimethylene chain, methylethylene chain, tetramethylene chain, 1,2-dimethylethylene chain, pentamethylene chain, 1-methyltetramethylene chain, 2-methyltetramethylene chain, hexamethylene chain, heptamethylene chain, octamethylene chain, etc.

In the present invention, examples of "substituents" of an "optionally substituted $C_{1-8}$ alkyl group", "optionally substituted $C_{6-10}$ aryl group", "optionally substituted 5- to 11-membered heterocyclic group", and "optionally substituted $C_{6-10}$ aryl $C_{1-8}$ alkyl group" include the following groups:

halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, cyano group, nitro group, hydroxy group, amino group, mono $C_{1-8}$ alkylamino group, di $C_{1-8}$ alkylamino group, $C_{1-8}$ alkoxy group, halo $C_{1-8}$ alkoxy group, $C_{1-8}$ acyl group, carboxyl group, $C_{1-8}$ acyloxy group, $C_{1-8}$ alkoxycarbonyl group, carbamoyl group, $C_{6-10}$ aryl group, 5- to 11-membered heteroaryl group, $C_{6-10}$ aryl $C_{1-8}$ alkoxy group, $C_{1-8}$ alkylthio group, $C_{1-8}$ alkylsulfinyl group, $C_{1-8}$ alkylsulfonyl group, $C_{6-10}$ arylthio group, $C_{6-10}$ arylsulfinyl group, $C_{6-10}$ arylsulfonyl group, $C_{3-8}$ cycloalkylthio group, $C_{3-8}$ cycloalkoxy group, etc.

Among the above substituents, "halogen atom", "$C_{1-8}$ alkyl group", "$C_{2-8}$ alkenyl group", "$C_{1-8}$ alkoxy group", "$C_{1-8}$ acyl group", and "$C_{6-10}$ aryl group" have the same meaning as in the above.

Among the above substituents, a "halo $C_{1-8}$ alkyl group" means a group wherein preferably, 1 to 9 halogen atoms are bound to the $C_{1-8}$ alkyl group and the examples include trifluoromethyl group, 2-fluoroethyl group, 2-chloroethyl group, 2-bromoethyl group, 3-fluoropropyl group, 3-chloropropyl group, 4-fluorobutyl group, 4-chlorobutyl group, 2,2,2-trifluoroethyl group, 3,3,3-trifluoropropyl group, pentafluoroethyl group, and 2,2,2-trifluoro-1-trifluoromethylethyl group, etc.

Among the above substituents, a "halo $C_{1-8}$ alkoxy group" means a group wherein the above halo $C_{1-8}$ alkyl group is bound to an oxygen atom, and the examples include a trifluoromethoxy group, 2-fluoroethoxy group, 2-chloroethoxy group, 2-bromoethoxy group, 3-fluoropropoxy group, 3-chloropropoxy group, 4-fluorobutoxy group, 4-chlorobutoxy group, 2,2,2-trifluoroethoxy group, 3,3,3-trifluoropropoxy group, pentafluoroethoxy group, 2,2,2-trifluoro-1-(trifluoromethyl)ethoxy group, etc.

Among the above substituents, a "$C_{2-8}$ alkynyl group" means a straight-chained or branched-chained alkynyl group with 2 to 8 carbons, having a carbon-carbon triple bond at any one or more sites on the alkyl chain. The examples include an ethynyl group, prop-1-yn-1-yl group, prop-2-yn-1-yl group, but-1-yn-1-yl group, but-3-yn-1-yl group, 1-methylprop-2-yn-1-yl group, pent-1-yn-1-yl group, pent-4-yn-1-yl group, hex-1-yn-1-yl group, hex-5-yn-1-yl group, etc.

Among the above substituents, examples of "$C_{3-8}$ cycloalkyl group" include a cyclopropyl group, cyclobutyl group, cyclopentyl group, cyclohexyl group, cycloheptyl group, cyclooctyl group, etc.

Among the above substituents, examples of "mono $C_{1-8}$ alkylamino group" include a methylamino group, ethylamino group, n-propylamino group, isopropylamino group, n-butylamino group, sec-butylamino group, tert-butylamino group, n-pentylamino group, isopentylamino group, neopentylamino group, 1-methylbutylamino group, 1-ethylpropylamino group, n-hexylamino group, isohexylamino group, 3-methylpentylamino group, 2-methylpentylamino group, 1-methylpentylamino group, 3,3-dimethylbutylamino group, 2,2-dimethylbutylamino group, 1,1-dimethylbutylamino group, 1,2-dimethylbutylamino group, 1,3-dimethylbutylamino group, 2,3-dimethylbutylamino group, 1-ethylbutylamino group, 2-ethylbutylamino group, etc.

Among the above substituents, examples of "di $C_{1-8}$ alkylamino group" include a dimethylamino group, methylethylamino group, diethylamino group, methyl-n-propylamino group, ethyl-n-propylamino group, di-n-propylamino group, methyl isopropylamino group, ethyl isopropylamino group, diisopropylamino group, methyl-n-butylamino group, ethyl-n-butylamino group, n-propyl-n-butylamino group, di-n-butylamino group, di-sec-butylamino group, di-tert-butylamino group, dipentylamino group, dihexylamino group, etc.

Among the above substituents, examples of "$C_{1-8}$ acyloxy group" include an acetoxy group, propionyloxy group, butyryloxy group, isobutyryloxy group, valeryloxy group, isovaleryloxy group, pivaloyloxy group, etc.

Among the above substituents, examples of "$C_{1-8}$ alkoxycarbonyl group" include a methoxycarbonyl group, ethoxycarbonyl group, n-propoxycarbonyl group, 1-methylethoxycarbonyl group, n-butoxycarbonyl group, isobutoxycarbonyl group, sec-butoxycarbonyl group, tert-butoxycarbonyl group, n-pentoxycarbonyl group, isopentoxycarbonyl group, neopentoxycarbonyl group, 1-methylbutoxycarbonyl group, 1-ethylpropoxycarbonyl group, n-hexyloxycarbonyl group, isohexyloxycarbonyl group, 3-methylpentoxycarbonyl group, 2-methylpentoxycarbonyl group, 1-methylpentoxycarbonyl group, 3,3-dimethylbutoxycarbonyl group, 2,2-dimethylbutoxycarbonyl group, 1,1-dimethylbutoxycarbonyl group, 1,2-dimethylbutoxycarbonyl group, 1,3-dimethylbutoxycarbonyl group, 2,3-dimethylbutoxycarbonyl group, 1-ethylbutoxycarbonyl group, 2-ethylbutoxycarbonyl group, etc.

Among the above substituents, a "5- to 11-membered heteroaryl group" means a 5- to 7-membered aromatic heterocycle, saturated heterocycle, unsaturated heterocycle or a condensed heterocycle made by a condensation of the above heterocycles and a benzene ring, wherein the above heterocycles contain 1 to 4 heteroatoms selected from a nitrogen atom, oxygen atom and sulfur atom in addition to a carbon atom, as atoms constituting the ring. The examples include a 2-furyl group, 3-furyl group, 2-thienyl group, 3-thienyl group, pyrrol-1-yl group, pyrrol-2-yl group, pyrrol-3-yl group, pyridin-2-yl group, pyridin-3-yl group, pyridin-4-yl group, pyrazin-2-yl group, pyrazin-3-yl group, pyrimidin-2-yl group, pyrimidin-4-yl group, pyrimidin-5-yl group, pyrimidin-6-yl group, pyridazin-3-yl group, pyridazin-4-yl group, 1,3-benzodioxol-4-yl group, 1,3-benzodioxol-5-yl group, 1,4-benzodioxan-5-yl group, 1,4-benzodioxan-6-yl group, 3,4-dihydro-2H-1,5-benzodioxepin-6-yl group, 3,4-dihydro-2H-1,5-benzodioxepin-7-yl group, 1,4-dihydrobenzodioxin-5-yl group, 1,4-dihydrobenzodioxin-6-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group, benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, quinoxalin-2-yl group, furopyridin-2-yl group, furopyridin-3-yl group, furopyridin-4-yl group, furopyridin-5-yl group, furopyridin-6-yl group, furopyridin-7-yl group, 2,3-dihydrofuropyridin-2-yl group, 2,3-dihydrofuropyridin-3-yl group, 2,3-dihydrofuropyridin-4-yl group, 2,3-dihydrofuropyridin-5-yl group, 2,3-dihydrofuropyridin-6-yl group, 2,3-dihydrofuropyridin-7-yl group, 2,3-dihydro1,4-dioxinopyridin-5-yl group, 2,3-dihydro1,4-dioxinopyridin-6-yl group, 2,3-dihydro1,4-dioxinopyridin-7-yl group, 2,3-dihydro1,4-dioxinopyridin-8-yl group, etc.

Among the above substituents, "$C_{6-10}$ aryl $C_{1-8}$ alkoxy group" means a group wherein the above "$C_{6-10}$ aryl $C_{1-8}$ alkyl group" is bound to an oxygen atom. The examples include a benzyloxy group, phenethyloxy group, naphthylmethyloxy group, etc.

Among the above substituents, examples of "$C_{1-8}$ alkylthio group" include a methylthio group, ethylthio group, n-propylthio group, isopropylthio group, n-butylthio group, isobutylthio group, sec-butylthio group, tert-butylthio group, n-pentylthio group, isopentylthio group, neopentylthio group, 1-methylbutylthio group, 1-ethylpropylthio group, n-hexylthio group, isohexylthio group, 3-methylpentylthio group, 2-methylpentylthio group, 1-methylpentylthio group, 3,3-dimethylbutylthio group, 2,2-dimethylbutylthio group, 1,1-dimethylbutylthio group, 1,2-dimethylbutylthio group, 1,3-dimethylbutylthio group, 2,3-dimethylbutylthio group, 1-ethylbutylthio group, 2-ethylbutylthio group, etc.

Among the above substituents, examples of "$C_{1-8}$ alkylsulfinyl group" include a methylsulfinyl group, ethylsulfinyl group, n-propylsulfinyl group, isopropylsulfinyl group, n-butylsulfinyl group, isobutylsulfinyl group, sec-butylsulfinyl group, tert-butylsulfinyl group, n-pentylsulfinyl group, isopentylsulfinyl group, neopentylsulfinyl group, 1-methylbutylsulfinyl group, 1-ethylpropylsulfinyl group, n-hexylsulfinyl group, isohexylsulfinyl group, 3-methylpentylsulfinyl group, 2-methylpentylsulfinyl group, 1-methylpentylsulfinyl group, 3,3-dimethylbutylsulfinyl group, 2,2-dimethylbutylsulfinyl group, 1,1-dimethylbutylsulfinyl group, 1,2-dimethylbutylsulfinyl group, 1,3-dimethylbutylsulfinyl group, 2,3-dimethylbutylsulfinyl group, 1-ethylbutylsulfinyl group, 2-ethylbutylsulfinyl group, etc.

Among the above substituents, examples of "$C_{1-8}$ alkylsulfonyl group" include a methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, neopentylsulfonyl group, 1-methylbutylsulfonyl group, 1-ethylpropylsulfonyl group, n-hexylsulfonyl group, isohexylsulfonyl group, 3-methylpentylsulfonyl group, 2-methylpentylsulfonyl group, 1-methylpentylsulfonyl group, 3,3-dimethylbutylsulfonyl group, 2,2-dimethylbutylsulfonyl group, 1,1-dimethylbutylsulfonyl group, 1,2-dimethylbutylsulfonyl group, 1,3-dimethylbutylsulfonyl group, 2,3-dimethylbutylsulfonyl group, 1-ethylbutylsulfonyl group, 2-ethylbutylsulfonyl group, etc.

Among the above substituents, examples of "$C_{6-10}$ arylthio group" include a phenylthio group, naphthylthio group, azulenylthio group, etc.

Among the above substituents, examples of "$C_{6-10}$ arylsulfinyl group" include a benzenesulfinyl group, p-toluenesulfinyl group, p-chlorobenzenesulfinyl group, naphthalen-1-ylsulfinyl group, naphthalen-2-ylsulfinyl group, etc.

Among the above substituents, examples of "$C_{6-10}$ arylsulfonyl group" include a benzenesulfonyl group, p-toluenesulfonyl group, p-chlorobenzenesulfonyl group, naphthalen-1-ylsulfonyl group, naphthalen-2-ylsulfonyl group, etc.

Among the above substituents, examples of "$C_{3-8}$ cycloalkylthio group" include a cyclopropylthio group, cyclobutylthio group, cyclopentylthio group, cyclohexylthio group, cycloheptylthio group, cyclooctylthio group, etc.

Among the above substituents, examples of "$C_{3-8}$ cycloalkoxy group" include a cyclopropoxy group, cyclobutoxy group, cyclopentoxy group, cyclohexyloxy group, cycloheptyloxy group, cyclooctyloxy group, etc.

Other groups that are not defined herein follow common definitions.

Followings are examples of the preferred modes of the present invention.

In general formula (I), optionally substituted $C_{1-8}$ alkyl group of $R^1$, $R^2$ and $R^7$ is preferably $C_{1-4}$ alkyl group, and more preferably n-propyl group.

In general formula (I), $C_{2-8}$ alkenyl group of $R^1$, $R^2$ and $R^7$ is preferably $C_{2-4}$ alkenyl group, and more preferably prop-2-en-1-yl group.

In general formula (I), $C_{1-8}$ alkyl group of $R^3$ is preferably $C_{1-4}$ alkyl group, and more preferably a methyl group.

In general formula (I), $C_{6-10}$ aryl group of $R^4$ is preferably a phenyl group. The phenyl group is preferably one having a substituent, and the substituent is preferably a $C_{1-8}$ alkoxy group such as 1-methylethoxy group, etc., $C_{3-8}$ cycloalkoxy group such as cyclopropoxy group, etc., $C_{3-8}$ cycloalkylthio group such as cyclopropylthio group, etc.

In general formula (I), a 5- to 11-membered heterocyclic group of $R^4$ is preferably a 5- to 7-membered aromatic heterocycle, unsaturated heterocycle or a condensed heterocycle made by a condensation of the above heterocycles and a benzene ring or pyridine ring, wherein the above heterocycles contain 1 or 2 heteroatoms selected from a nitrogen atom and oxygen atom in addition to a carbon atom, as atoms constituting the ring, and a pyridyl group, 1,3-benzodioxonyl group, 1,4-dihydrobenzodioxinyl group, 2,3-dihydrobenzofuranyl group, benzofuranyl group, furopyridinyl group, 2,3-dihydrofuropyridinyl group, and 2,3-dihydro-1,4-dioxinopyridinyl group are more preferred. These 5- to 11-membered heterocyclic groups may have one to the possible maximum number of substituent that may be substituted, and the substituent is preferably a $C_{1-8}$ alkyl group such as methyl group, etc., $C_{1-8}$ alkoxy group such as a methoxy group, 1-methylethoxy group, etc., and $C_{3-8}$ cycloalkoxy group such as cyclopropoxy group, etc.

In general formula (I), $R^5$ is preferably a hydrogen atom.

In general formula (I), a $C_{1-8}$ alkoxy $C_{1-8}$ alkyl group of $R^6$ is preferably a methoxymethyl group, ethoxyethyl group, etc.

In general formula (I), an optionally substituted $C_{6-10}$ aryl $C_{1-8}$ alkyl group of $R^6$ is preferably a benzyl group, p-methoxybenzyl group, etc.

In general formula (I), the "alkyl" moiety of $CH(C_{1-8}$ alkyl), $C(C_{1-8}$ alkyl$)_2$ of X and Y is preferably a methyl or ethyl.

In general formula (I), a $C_{1-8}$ alkyl chain that may be substituted with an oxo group of L is preferably 1,2-ethylene chain, 1-oxo-1,2-ethylene chain or 1,2-propylene chain.

In general formula (I), the "alkyl chain" of $C_{1-8}$ alkyl chain that may be substituted with a sulfonyl group of L is preferably a methylene chain or ethylene chain.

In general formula (I), n is preferably any integer of 0 to 2, and an integer of 1 or 2 is more preferred.

Examples of an addition salt of a carbinol compound represented by general formula (I) include alkaline metal salts such as sodium salt, potassium salt, etc; alkaline earth metal salts such as calcium salt, magnesium salt, etc.; organic base salts such as ammonium salt, trialkylamine salt, etc.; mineral acid salts such as hydrochloride salt, sulfate, etc.; and organic acid salts such as acetate, etc. There is no particular limitation as long as it is a pharmaceutically acceptable salt.

Examples of a solvate of a carbinol compound represented by general formula (I) include a hydrate, etc. When there is a geometric isomer or optical isomer of a compound of the present invention, such isomers are also included in the scope of the present invention.

Compound (I) can be produced by various known methods without particular limitation, and for example, can be produced according to the following reaction process. More specifically, by reacting a derivative shown by general formula (II) with an imidazolidine-2,4-dione compound shown by general formula (III), a compound (I) can be produced. This reaction path shown by a chemical reaction formula is as follows:

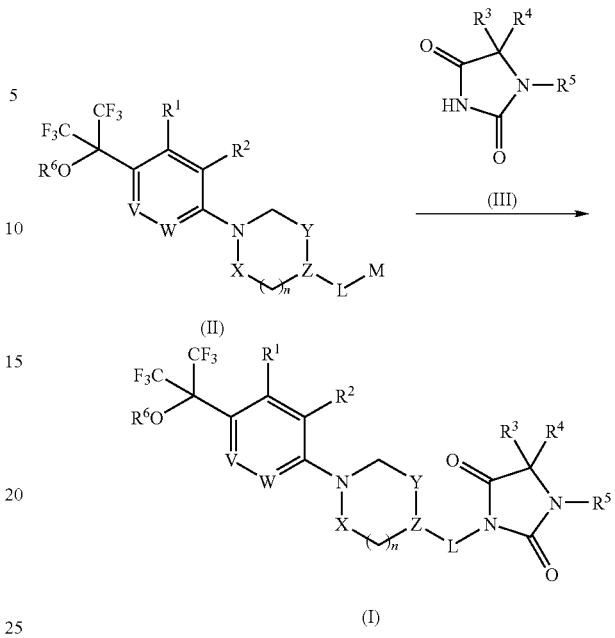

(wherein $R^1$, $R^2$, $R^3$, $R^4$, $R^5$, $R^6$, X, Y, Z, V, W, L and n represent the same thing as in the above, M represents elimination group such as a halogen atom, hydroxyl group, etc.)

When M is a halogen atom, a substance of interest (I) can be produced by reacting a derivative shown by general formula (II) with an imidazolidine-2,4-dione compound (III) in a solvent in the presence or absence of a base. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, water, etc. The base is not particularly limited, and for example, the followings can be used: alkaline metal hydrides such as lithium hydride, sodium hydride, potassium hydride, etc.; alkaline metal hydroxides such as lithium hydroxide, sodium hydroxide, potassium hydroxide, etc.; alkaline metal carbonates such as lithium carbonate, sodium carbonate, potassium carbonate, cesium carbonate, etc.; alcohol metallic salts such as sodium methoxide, potassium methoxide, sodium ethoxide, potassium ethoxide, sodium tert-butoxide, potassium tert-butoxide, etc.; lithium diisopropylamide, sodium diisopropylamide, potassium diisopropylamide, lithium hexamethyldisilazide, sodium hexamethyldisilazide, potassium hexamethyldisilazide, n-butyllithium, sec-butyllithium, or tert-butyllithium, etc. The substance of interest can be obtained by conducting a reaction under the reaction conditions of −80 to 150° C., preferably of 0 to 100° C., for 1 minute to 5 days, preferably for 1 hour to 3 days.

When M is a hydroxyl group, a compound (I) can be produced by dissolving a derivative shown by general formula (II), an imidazolidine-2,4-dione compound shown by general formula (III), and a phosphine reagent in a reaction solvent, then adding thereto an azo reagent or an ethylenedicarboxylic acid reagent, and allowing the Mitsunobu reaction to take place under an argon or nitrogen atmosphere at 0° C. to 100° C., preferably at room temperature to 80° C. for 2 hours to 1 day. The followings can be used as a solvent in this reaction: N,N-dimethylformamide, tetrahydrofuran, dioxane, acetonitrile, nitromethane, acetone, ethyl acetate, benzene, chlorobenzene, toluene, chloroform, methylene chloride, etc. Among these, N,N-dimethylformamide, tetrahydrofuran, dioxane, and acetonitrile are preferred, and N,N-dimethylformamide and tetrahydrofuran are particularly preferred. Examples of a phosphine reagent include trialkylphosphines such as trimethylphosphine, triethylphosphine, tripropylphosphine, triisopropylphosphine, tributylphosphine, triisobutylphosphine, tricyclohexylphosphine, etc.; and triarylphosphines such as triphenylphosphine, diphenylphosphino polystyrene, etc. Among these, trimethylphosphine, tributylphosphine, and triphenylphosphine are preferred. Examples of an azo reagent include diethyl azodicarboxylate (DEAD), diisopropyl azodicarboxylate (DIAD), di-tert-butyl azodicarboxylate (DBAD), diisopropyl azodicarboxylate, 1,1'-azobis(N,N-dimethylformamide) (TMAD), 1,1'-(azodicarbonyl)dipiperidine (ADDP), 1,1'-azobis(N,N-diisopropylformamide) (TIPA), 1,6-dimethyl-1,5,7-hexahydro-1,4,6,7-tetrazocine-2,5-dione (DHTD), etc., and diethyl azodicarboxylate is particularly preferred.

Further, if there are other functional groups that react with an imidazolidine-2,4-dione compound shown by general formula (III), a compound of interest can be obtained by a protection by a commonly used method (Protective Groups in Organic Synthesis Third Edition, John Wiley & Sons, Inc.) followed by a deprotection at an appropriate time.

A derivative shown by general formula (II) can be produced by the following reaction process:

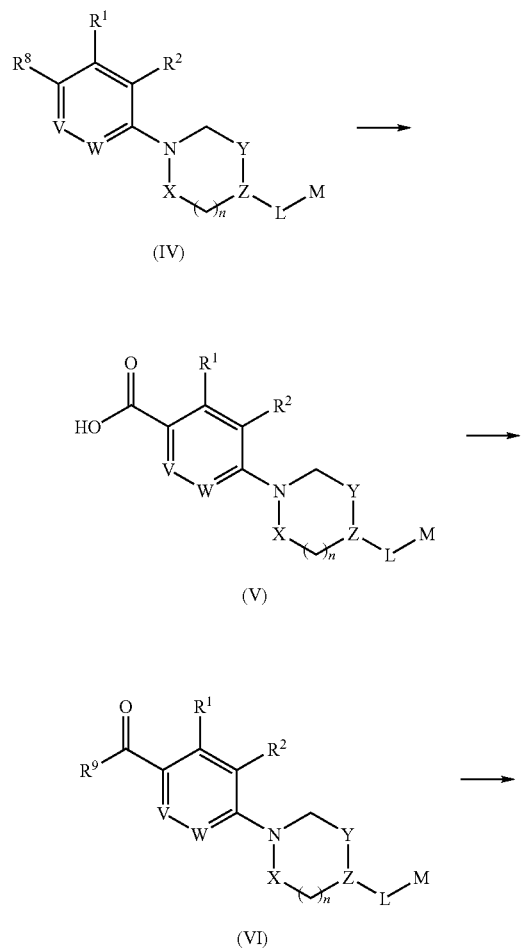

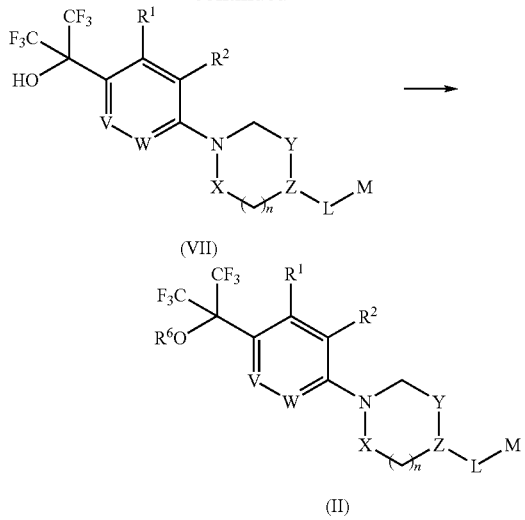

(wherein $R^1$, $R^2$, $R^6$, X, Y, Z, V, W, L, M and n represent the same thing as in the above, $R^8$ represents a group that may be converted to a carboxyl group, and $R^9$ represents a halogen atom or an elimination group).

The reaction of general formula (IV) to general formula (V) is a process of converting a substituent $R^8$ to a carboxyl group, and for example, various known carboxyl group generating reaction such as oxidation of methyl group, hydroxymethyl group or aldehyde, hydrolysis of ester, amide and nitrile, or a method of converting a halogeno group to Grignard reagent and then reacting with carbon dioxide, may be applied.

A hexafluorocarbinol compound (VII) can be produced from the carboxylic acid compound (V) obtained by the above method with reference to a known literature (Tetrahedron 61 (2005) 1813-1819). Specifically, the carboxylic acid compound (V) is converted to an acid halide, acid anhydride or ester (VI) with reference to a commonly used method (Comprehensive Organic Transformations Second Edition, John Wiley & Sons, Inc.), and then a hexafluorocarbinol compound (VII) can be derived using (trifluoromethyl)trimethylsilane and tetramethylammoniumfluoride.

The literature uses (trifluoromethyl)trimethylsilane as a source of trifluoromethyl, but such sources are not limited to the same and the followings can also be used: triethyl(trifluoromethyl)silane, triisopropyl(trifluoromethyl)silane, methyldiphenyl(trifluoromethyl)silane, dimethyl(diphenyl)trifluoromethyl silane, etc. Further, a perfluoroalkylation is also possible when perfluoroalkylsilanes such as (pentafluoroethyl)trimethylsilane, (heptafluoropropyl)trimethylsilane, etc. are used. Further, a tetramethylammonium fluoride can be used as a fluorine compound, but such compounds are not limited to the same and the followings can also be used: tetraalkylammonium salts such as tetraethylammonium fluoride, tetrabutylammonium fluoride, etc.; and metallic salts such as lithium fluoride, sodium fluoride, potassium fluoride, cesium fluoride, etc. In addition to dimethoxyethane, the followings can be used independently or in combination as a solvent: tetrahydrofuran, toluene, dioxane, N,N-dimethylformamide, N-methylpyrrolidone, tetramethylurea, dimethylsulfoxide, acetonitrile, propionitrile, acetone, methylethylketone, etc. Examples of ester include ester with aliphatic alcohol such as methanol, ester with aromatic alcohol such as pentafluorophenol, etc. Examples of acid anhydride include acid anhydride with aliphatic carboxylic acid such as acetic acid, acid anhydride with aromatic carboxylic acid such as benzoic acid, etc.

A substance of interest (II) can be produced by reacting a halide of $R^6$ with the obtained hexafluorocarbinol compound (VII) in a solvent, in the presence or absence of a base. The solvent is not particularly limited, and for example, the followings can be used independently or in combination: tetrahydrofuran, toluene, dioxane, N,N-dimethylformamide, N-methylpyrrolidone, tetramethylurea, dimethylsulfoxide, acetonitrile, propionitrile, acetone, methylethyl ketone, water, etc. The base is not particularly limited, and for example, the followings can be used: alkaline metal hydrides such as lithium hydride, sodium hydride, potassium hydride, etc.; alkaline metal hydroxides such as lithium hydroxide, sodium hydroxide, potassium hydroxide, etc.; alkaline metal carbonates such as lithium carbonate, sodium carbonate, potassium carbonate, cesium carbonate, etc.; alcohol metallic salts such as sodium methoxide, potassium methoxide, sodium ethoxide, potassium ethoxide, sodium tert-butoxide, potassium tert-butoxide, etc.; organic metals such as lithium diisopropylamide, sodium diisopropylamide, potassium diisopropylamide, lithium hexamethyldisilazide, sodium hexamethyldisilazide, potassium hexamethyldisilazide, n-butyllithium, sec-butyllithium, tert-butyllithium, etc.

When M is a hydroxyl group, each reaction may be conducted by protecting the hydroxyl group, in order to avoid side reactions. Protection and deprotection conditions may be performed by referring to a commonly used method (Protective Groups in Organic Synthesis Third Edition, John Wiley & Sons, Inc.).

A derivative shown by general formula (IV) can be produced according to the following reaction process.

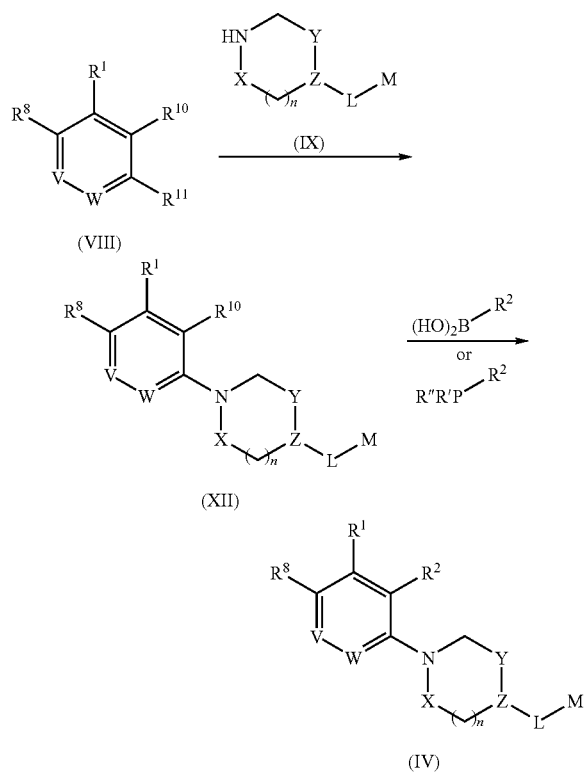

(wherein $R^1$, $R^2$, $R^8$, X, Y, Z, V, W, Z, L, M and n represent the same thing as in the above, $R^{10}$ represents an aldehyde group, a functional group that may be converted to an aldehyde group or a halogen atom, and $R^{11}$ represents a halogen atom or hydroxyl group)

When $R^{11}$ is a halogen atom, the substance of interest (XII) can be produced by reacting a derivative shown by general formula (VIII) with a general formula (IX) in a solvent, in the presence or absence of a base, and in the presence or absence of a metal catalyst. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, water, etc. The base is not particularly limited, and for example, the followings can be used: alkaline metal hydrides such as lithium hydride, sodium hydride, potassium hydride, etc.; alkaline metal hydroxides such as lithium hydroxide, sodium hydroxide, potassium hydroxide, etc.; alkaline metal carbonates such as lithium carbonate, sodium carbonate, potassium carbonate, cesium carbonate, etc.; alcohol metallic salts such as sodium methoxide, potassium methoxide, sodium ethoxide, potassium ethoxide, sodium tert-butoxide, potassium tert-butoxide, etc.; lithium diisopropylamide, sodium diisopropylamide, potassium diisopropylamide, lithium hexamethyldisilazide, sodium hexamethyldisilazide, potassium hexamethyldisilazide, n-butyllithium, sec-butyllithium, tert-butyllithium, etc. The metal catalyst is not particularly limited, and a palladium catalyst, nickel catalyst, cupric oxide, copper salt, etc. can be used. Preferably tetrakis (triphenylphosphine) palladium (O) can be used. The substance of interest can be obtained by conducting a reaction under the reaction conditions of −80 to 150° C., preferably of 0 to 100° C., for 1 minute to 5 days, preferably for 30 minutes to 3 days. The reaction may be conducted under microwave irradiation, according to need.

When $R^{11}$ is a hydroxyl group, a substance of interest (XII) can be produced by leading to an elimination group such as sulfonyl group, etc., and reacting a derivative shown by general formula (VIII) with a general formula (IX) in a solvent, in the presence or absence of a base, in the presence or absence of a metal catalyst. The solvent that conduct the reaction leading to an elimination group including sulfonyl group, etc. is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, water, etc. The base is not particularly limited, and for example, the followings can be used: alkaline metal hydrides such as lithium hydride, sodium hydride, potassium hydride, etc; alkaline metal hydroxides such as lithium hydroxide, sodium hydroxide, potassium hydroxide, etc.; alkaline metal carbonates such as lithium carbonate, sodium carbonate, potassium carbonate, cesium carbonate, etc.; alcohol metallic salts such as sodium methoxide, potassium methoxide, sodium ethoxide, potassium ethoxide, sodium tert-butoxide, potassium tert-butoxide, etc.; lithium diisopropylamide, sodium diisopropylamide, potassium diisopropylamide, lithium hexamethyldisilazide, sodium hexamethyldisilazide, potassium hexamethyldisilazide, n-butyllithium, sec-butyllithium, tert-butyllithium, etc. The metal catalyst is not particularly limited, and a palladium catalyst, nickel catalyst, cupric oxide, copper salt, etc. can be used. Preferably tetrakis(triphenylphosphine) palladium (O) can be used. The substance of interest can be obtained by conducting a reaction under the reaction conditions of −80 to 150° C., preferably of 0 to 100° C., for 1 minute to 5 days, preferably for 30 minutes to 3 days. Further, a substance of interest (XII) can be produced by converting the hydroxyl group of $R^{11}$ to a halogen atom, and via the above reaction.

When $R^{10}$ is a halogen atom, a derivative of general formula (IV) which is the substance of interest can be obtained by reacting the derivative shown by general formula (XII) obtained by the above method, with a boronic acid derivative in a solvent, in the presence of a base and in the presence of a metal catalyst. The solvent is not particularly limited, and for example, the followings can be used independently or in combination: dichloromethane, chloroform, carbon tetrachloride, tetrahydrofuran, toluene, dioxane, N,N-dimethylformamide, N-methylpyrrolidone, dimethylsulfoxide, acetonitrile, propionitrile, etc. The base is not particularly limited, and for example, organic amines such as pyridine, triethylene amine, etc.; alkaline metal carbonates such as lithium carbonate, sodium carbonate, potassium carbonate, cesium carbonate, etc.; cesium fluoride, etc. can be used. The metal catalyst is not particularly limited, and a palladium catalyst, nickel catalyst, cupric oxide, copper salt, etc. can be used. Preferably, tetrakis(triphenylphosphine) palladium (O) can be used. A derivative of general formula (IV) which is the substance of interest can be obtained by conducting a reaction under the reaction conditions of −80 to 150° C., preferably of 0 to 100° C. for 1 minute to 5 days, preferably for 1 hour to 3 days.

When $R^{10}$ is an aldehyde group, or a functional group that can be converted to an aldehyde group, a derivative of general formula (IV) which is a substance of interest can be obtained by reacting a derivative shown by general formula (XII) obtained by the above method in the presence or absence of a base, with a Wittig reagent or Horner-Wadsworth-Emmons reagent in a solvent. The solvent is not particularly limited, and for example, the followings can be used independently or in combination: dichloromethane, chloroform, carbon tetrachloride, tetrahydrofuran, toluene, dioxane, etc. The base is not particularly limited, and for example, organic amines such as pyridine, triethyleneamine, etc.; alkyl lithiums such as butyl lithium; alkaline metal carbonates such as lithium carbonate, sodium carbonate, potassium carbonate, cesium carbonate, etc.; cesium fluoride, etc. can be used. A derivative of general formula (IV) which is the substance of interest can be obtained by conducting a reaction under the reaction conditions of −80 to 150° C., preferably of 0 to 100° C. for 1 minute to 5 days, preferably for 1 hour to 3 days.

Further, among the derivatives shown by general formula (VIII), when one of V or W is N, for example, it can be produced according to the following reaction process.

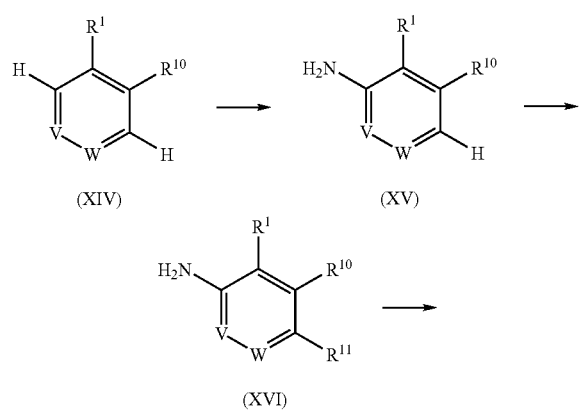

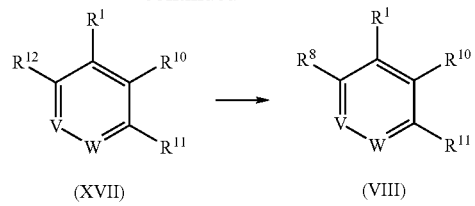

(wherein $R^1$, $R^8$, $R^{10}$, $R^{11}$, V, and W represent the same thing as in the above. $R^{12}$ represents a halogen atom or hydroxyl group)

By using, for example, a substitution reaction to an amino group known as Chichibabin reaction on a derivative shown by general formula (XIV), a derivative shown by general formula (XV) can be obtained. The process is a reaction for reacting in the presence of an alkaline metal amide in a solvent. The solvent is not particularly limited, and for example, the followings can be used independently or in combination: dichloromethane, chloroform, carbon tetrachloride, tetrahydrofuran, toluene, dioxane, N,N-dimethylformamide, N-methylpyrrolidone, dimethylsulfoxide, acetonitrile, propionitrile, etc. The alkali metal amide is not particularly limited, and lithium amide, sodium amide, potassium amide, etc. can be used. A derivative of general formula (XV) which is the substance of interest can be obtained by conducting a reaction under the reaction conditions of −80 to 150° C., preferably of 0 to 120° C. for 1 minute to 5 days, preferably for 1 hour to 3 days.

A derivative of general formula (XVI) can be obtained by reacting the general formula (XV) obtained by the above method with a halogenating agent in a solvent. The halogenating agent used herein is not particularly limited, and for example, chlorine, bromine, iodine, tetrabutylammonium chloride, tetrabutylammonium bromide, tetrabutylammonium iodide, N-chlorosuccinimide, N-bromosuccinimide, N-iodo succinimide, carbon tetrabromide, etc. can be used. Further, a halide salt such as potassium bromide, potassium iodide, sodium bromide, sodium iodide, etc. can be oxidized with an oxidant such as a hydrogen peroxide solution, an aqueous solution of sodium hypochlorite, etc. to produce a halogenating agent in the system, which is to be used in the reaction. The solvent is not particularly limited, and for example, the followings can be used independently or in combination: diochloromethane, chlolroform, carbon tetrachloride, tetrahydrofuran, toluene, dioxane, N,N-dimethylformamide, N-methylpyrrolidone, dimethylsulfoxide, acetonitrile, propionitrile, etc. A derivative of general formula (XVI) which is the substance of interest can be obtained by conducting a reaction under the reaction conditions of −80 to 150° C., preferably of 0 to 120° C. for 1 minute to 5 days, preferably for 1 minute to 1 day.

By thermally decomposing diazonium salt obtained by diazotizing a compound (XVI) in an acid aqueous solution, a halogenated aromatic ring compound (XVII) can be derived. The acid used herein is not particularly limited, and for example, p-toluene sulfonic acid, benzene sulfonic acid, methane sulfonic acid, trifluoromethane sulfonic acid, acetic acid, formic acid, hydrochloric acid, sulfuric acid, phosphoric acid, trifluoroacetic acid, etc. can be used. The solvent is not particularly limited, and for example, the followings can be used independently or in combination: tetrahydrofuran, toluene, dioxane, N,N-dimethylformamide, N-methylpyrrolidone, tetramethylurea, dimethylsulfoxide, acetonitrile, propionitrile, acetone, methylethylketone, water, etc.

A method for converting the halogen atom or hydroxyl group of the general formula (XVII) obtained by the above method to a group that can be converted to a carboxyl group can be performed by referring to a commonly used method (Comprehensive Organic Transformations Second Edition, John Wiley & Sons, Inc). Specifically, the general formula (VIII) can be derived by the reaction with the general formula (XVII) in a solvent under basic conditions and carbon monoxide or N,N-dimethylformamide, etc. Further, the general formula (VIII) can be derived by the reaction with the general formula (XVII) in a solvent, in the presence or absence of a metal reagent, and a nitrilating agent.

Further the derivative shown by the general formula (II) can be produced by the following reaction process:

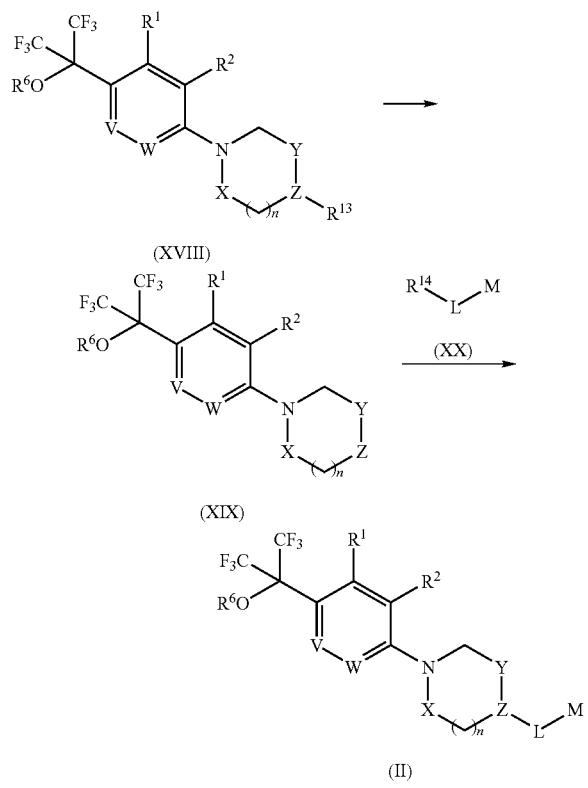

(wherein $R^1$, $R^2$, $R^6$, X, Y, Z, V, W, L, M and n represent the same thing as in the above, $R^{13}$ represents a protecting group, and $R^{14}$ represents a halogen atom or hydroxyl group.)

The protecting group shown by $R^{13}$ may be a commonly used one, and as for the deprotecting conditions from the general formula (XVIII) to general formula (XIX), it can be performed with reference to, for example, a literature (Protective Groups in Organic Synthesis Third Edition, John Wiley & Sons, Inc.).

When $R^{14}$ is a halogen atom, a substance of interest (II) can be produced by reacting a derivative shown by the general formula (XIX) with the general formula (XX) in a solvent, in the presence or absence of a base. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, water, etc. The base is not particularly limited, and for example, the followings can be used: alkaline metal hydrides such as lithium hydride, sodium hydride, potassium hydride, etc.; alkaline metal hydroxides such as lithium hydroxide, sodium hydroxide, potassium hydroxide, etc.; alkaline metal carbonates such as lithium carbonate, sodium carbonate, potassium carbonate, cesium carbonate, etc.; alcohol metallic salts such as sodium methoxide, potassium methoxide, sodium ethoxide, potassium ethoxide, sodium tert-butoxide, potassium tert-butoxide, etc.; lithium diisopropylamide, sodium diisopropylamide, potassium diisopropylamide, lithium hexamethyldisilazide, sodium hexamethyldisilazide, potassium hexamethyldisilazide, n-butyllithium, sec-butyllithium, or tert-butyllithium, etc. The substance of interest can be obtained by conducting a reaction under the reaction conditions of −80 to 150° C., preferably of 0 to 100° C., for 1 minute to 5 days, preferably for 1 hour to 3 days.

When $R^{14}$ is a hydroxyl group, a compound (I) can be produced by dissolving a derivative shown by general formula (XIX) and a derivative shown by general formula (XX) in a reaction solvent, then adding thereto an azo reagent or an ethylenedicarboxylic acid reagent, and allowing the Mitsunobu reaction to take place under an argon or nitrogen atmosphere at 0° C. to 100° C., preferably at room temperature to 80° C. for 2 hours to 1 day. The followings can be used as a solvent in this reaction: N,N-dimethylformamide, tetrahydrofuran, dioxane, acetonitrile, nitromethane, acetone, ethyl acetate, benzene, chlorobenzene, toluene, chloroform, methylene chloride, etc. Among these, N,N-dimethylformamide, tetrahydrofuran, dioxane, and acetonitrile are preferred, and N,N-dimethylformamide and tetrahydrofuran are particularly preferred. Examples of a phosphine reagent include trialkylphosphines such as trimethylphosphine, triethylphosphine, tripropylphosphine, triisopropylphosphine, tributylphosphine, triisobutylphosphine, tricyclohexylphosphine, etc.; and triarylphosphines such as triphenylphosphine, diphenylphosphino polystyrene, etc. Among these, trimethylphosphine, tributylphosphine, and triphenylphosphine are preferred. Examples of an azo reagent include diethyl azodicarboxylate (DEAD), diisopropyl azodicarboxylate (DIAD), 1,1'-azobis(N,N-dimethylformamide) (TMAD), 1,1'-(azodicarbonyl)dipiperidine (ADDP), 1,1'-azobis(N,N-diisopropylformamide) (TIPA), 1,6-dimethyl-1,5,7-hexahydro-1,4,6,7-tetrazocine-2,5-dione (DHTD), etc., and diethyl azodicarboxylate is particularly preferred.

When L-$R^{14}$ is a carboxylic acid, a compound (II) can be produced by dissolving a derivative shown by general formula (XIX) and a derivative shown by general formula (XX) in a reaction solvent, then adding thereto a commonly used condensing agent and allowing a reaction to take place under an argon or nitrogen atmosphere, at 0° C. to 100° C., preferably at room temperature to 80° C. for 2 hours to 1 day. The followings can be used as a solvent in this reaction: N,N-dimethylformamide, tetrahydrofuran, dioxane, acetonitrile, nitromethane, acetone, ethyl acetate, benzene, chlorobenzene, toluene, chloroform, methylene chloride, etc. Among these, ethyl acetate, toluene, chloroform, methylene chloride, etc. are preferred, and chloroform and methylene chloride are particularly preferred. Examples of a condensing agent include carbodiimide reagents such as dicyclohexylcarbodiimide (DCC), 1-ethyl-3-(3-dimethylaminopropyl)carbodiimide (EDC), diisopropylcarbodiimide (DIPCDI), etc.; phosphonium salt-type or guanidium salt type reagent such as (1H-benzotriazol-1-yloxy)tris(dimethylamino)phosphonium hexafluorophosphate (BOP), 1-[bis(dimethylamino) methylene]-1H-benzotriazolium-3-oxide hexafluorophophate (HBTU), 1-[bis(dimethylamino)methylene]-1H-benzotriazolium-3-oxide tetrafluoroborate (TBTU), 1-[bis (dimethylamino)methylene]-5-chloro-1H-benzotriazolium-3-oxide hexafluorophosphate (HCTU), 1-[bis(dimethylamino)methylene]-5-chloro-1H-benzotriazolium-3-oxide tetrafluoroborate (TCTU), etc. Among these, dicyclohexylcarbodiimide (DCC) and 1-ethyl-3-(3-dimethylaminopropyl)carbodiimide (EDC) are preferred. Additives include, for example, 1-hydroxybenzotriazole (HOBt), 6-chloro-1-hydroxybenzotriazole (6-Cl—HOBt), 3,4-dihydro-3-hydroxy-4-oxo-1,2,3-benzotriazine (HOOBt), 1-hydroxy-7-azabenzotriazole (HOAt), etc.

Further, a derivative shown by general formula (XVIII) can be produced by the following reaction process by reacting a derivative shown by general formula (XXI) obtained in the above method according to the production process of the above-mentioned general formula (XII) to (IV).

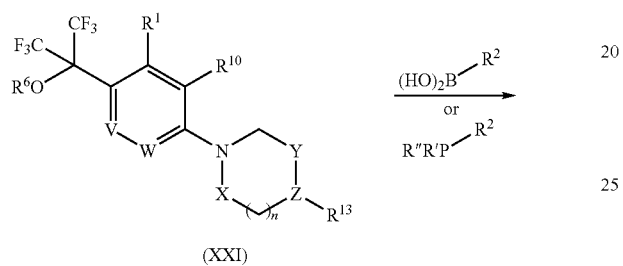

(XXI)

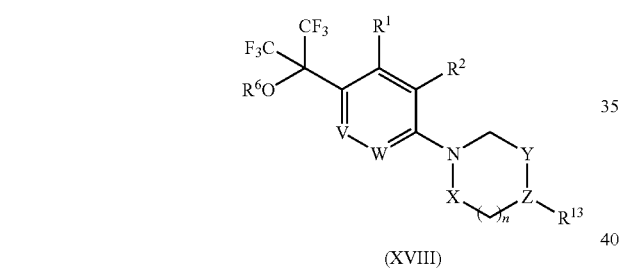

(XVIII)

(wherein $R^1$, $R^2$, $R^6$, $R^{10}$, $R^{13}$, X, Y, Z, V, W, Z and n represent the same thing as in the above).

Further, a derivative shown by general formula (XXI) can be produced by the following reaction process.

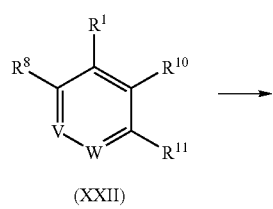

(XXII)

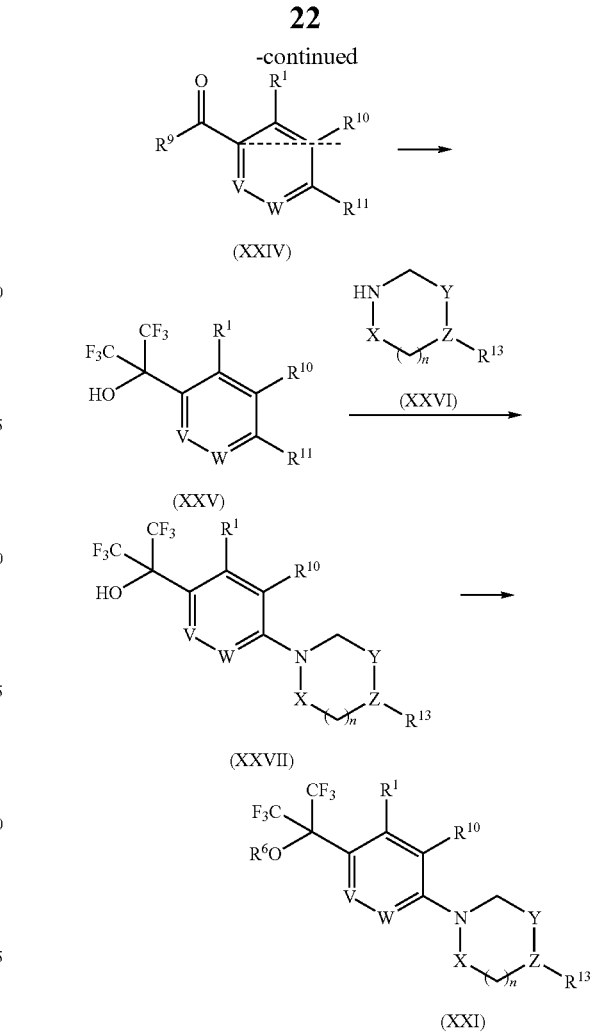

(wherein $R^1$, $R^6$, $R^8$, $R^9$, $R^{10}$, $R^{11}$, $R^{13}$, X, Y, Z, V, W, and n represent the same thing as in the above).

The reaction of obtaining general formula (XXV) from general formula (XXII) via (XXIII) and (XXIV) can be conducted according to the step of generating general formula (VII) from general formula (IV) via (V) and (VI) mentioned in the above.

The reaction of obtaining general formula (XXVII) from general formula (XXV) can be conducted according to the step of generating general formula (XII) from general formula (VIII) mentioned in the above.

The reaction of obtaining general formula (XXI) from general formula (XXVII) can be conducted according to the step of generating general formula (II) from general formula (VII) mentioned in the above.

A method for producing imidazolidine-2,4-dione derivative (III) is described in German Patent No. 335993, and various imidazolidine-2,4-dione derivatives can be produced with reference to this patent.

A carbinol compound represented by general formula (I) of the present invention can be obtained by the above-mentioned methods, and further and optionally, can be purified using an ordinary purifying method such as recrystallization method, a column chromatography, etc. Moreover, the above compound can optionally be processed into an above-mentioned desired salt or solvate by a usual method.

So obtained carbinol compound represented by general formula (I) or salt thereof, or their solvate (hereinafter, sometimes collectively described as "compounds represented by general formula (I)") shows a superior LXRβ agonist effect as shown in test examples described hereinbelow, and is useful as an active ingredient of a preventative and/or therapeutic agent for diseases of animal including humans, resulting from abnormal cholesterol metabolism, for example, atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

The pharmaceutical composition of the present invention contains a carbinol compound represented by general formula (I) or salt thereof, or their solvate. The pharmaceutical composition may be used independently, but generally, is used by formulating with a pharmaceutically acceptable carrier, additive, etc. The administration form of the pharmaceutical composition is not particularly limited, and can be selected as desired according to the therapeutic purpose. For example, the administration form can be any of oral preparation, injection, suppository, ointment, inhalation, eye-drops, nasal preparation, adhesive patch, etc. The pharmaceutical composition suitable for these administration forms can be produced according to a known method of drug formulation.

When prepared into a solid oral formulation, a carbinol compound represented by general formula (I) can be added with an excipient and optionally, further with a binder, disintegrant, lubricant, coloring agent, flavoring agent, odor improving agent, etc., and then processed into a tablet, coated tablet, granules, powder, capsule, etc. by a usual method. The additive may be those commonly used in this field. Examples of the excipient include lactose, sucrose, sodium chloride, glucose, starch, calcium carbonate, Kaolin, microcrystalline cellulose, silicate, etc. Examples of the binder include water, ethanol, propanol, simple syrup, dextrose solution, starch solution, gelatin solution, carboxymethylcellulose, hydroxypropylcellulose, hydroxypropyl starch, methylcellulose, ethylcellulose, shellack, calcium phosphate, polyvinylpyrrolidone, etc. Examples of the disintegrant include dry starch, sodium alginate, powdered agar, sodium hydrogen carbonate, calcium carbonate, sodium lauryl sulfate, monoglyceride stearate, lactose, etc. Examples of the lubricant include purified talc, stearate, borax, polyethyleneglycol, etc. Examples of the flavoring agent include sucrose, orange peel, citric acid, tartaric acid, etc.

When prepared into a liquid oral formulation, a carbinol compound represented by general formula (I) can be added with a flavoring agent, buffer, stabilizer, odor improving agent, etc., and then processed into an internal liquid formulation, syrup, elixir or the like by a usual method. The flavoring agent may be those mentioned above, and examples of the buffer include sodium citrate, etc., and examples of the stabilizer include tragacanth, gum Arabic, gelatin, etc.

When prepared into an injection, a carbinol compound represented by general formula (I) can be added with a pH adjuster, buffer, stabilizer, isotonic agent, local anesthetic, etc., and then processed into a subcutaneous, intramuscular, and intravenous injection by a usual method. Examples of the pH adjuster and buffer include sodium citrate, sodium acetate, sodium phosphate, etc. Examples of the stabilizer include sodium pyrosulfite, EDTA, thioglycolic acid, thiolactic acid, etc. Examples of the local anesthetic include procaine hydrochloride, lidocaine hydrochloride, etc. Examples of the isotonic agent include sodium chloride, glucose, etc.

When prepared into a suppository, a carbinol compound represented by general formula (I) can be added with a known carrier for suppository, for example, with polyethyleneglycol, lanolin, cacao butter, fatty acid triglyceride, etc. and optionally, further with a surfactant such as Tween®, etc. and then processed into a suppository by a usual method.

When prepared into an ointment, a carbinol compound represented by general formula (I) can be optionally formulated with a commonly used base, stabilizer, moisturizer, preservative, etc., and then mixed and formulated by a usual method. Examples of the base include liquid paraffin, white petrolatum, white beeswax, octyldodecyl alcohol, paraffin, etc. Examples of the preservative include methyl p-hydroxybenzoate, ethyl p-hydroxybenzoate, propyl p-hydroxybenzoate, etc.

In addition to the above, a carbinol compound represented by general formula (I) can be processed into an inhalation, eye-drops, or nasal preparation by a usual method.

The dose of a carbinol compound represented by general formula (I) varies depending on the age, weight, symptom, administration form, the number of doses, etc., but generally, it is preferable to administer a carbinol compound represented by general formula (I) to an adult in an amount of 1 to 1000 mg per day as a single or several separate doses either orally or parenterally.

EXAMPLES

The present invention will be described further with reference to the following examples, while the scope of the present invention will not be limited to these examples.

Example 1

Preparation of 3-(2-{4-[5-(1,1,1,3,3,3-hexafluoro-2-hydroxypropan-2-yl)-4-propylpyridin-2-yl]piperazin-1-yl}ethyl)-5-[4-(1-methylethoxy)phenyl]-5-methylimidazolidine-2,4-dione

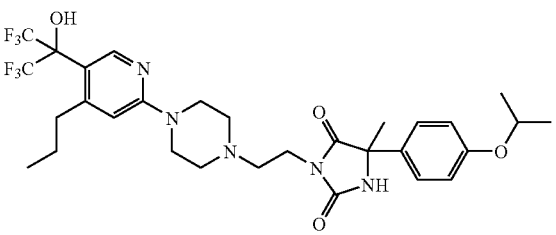 [SMILES: CCCc1cc(N2CCN(CCN3C(=O)NC(C)(c4ccc(OC(C)C)cc4)C3=O)CC2)ncc1C(O)(C(F)(F)F)C(F)(F)F]

a) Preparation of 6-chloro-N-methylnicotinamide

2-Chloronicotinoyl chloride (5.65 g, 32.1 mol) was dissolved in tetrahydrofuran (64 mL), added triethylamine (5.59 mL, 40.1 mol), and a solution of methylamine in tetrahydrofuran (20.1 mL, 40.1 mol) sequentially under ice-cold conditions, and stirred at room temperature for 3.5 hours. The reaction solution was concentrated in vacuo, recrystallized (ethyl acetate/hexane). The title compound (5.06 g (yield 92%)) was obtained as a light brown crystal.

$^1$H-NMR (CDCl$_3$) δ: 3.05 (3H, d, J=4.6 Hz), 6.14 (1H, brs), 7.42 (1H, d, J=8.3 Hz), 8.09 (1H, dd, J=2.4, 8.3 Hz), 8.72 (1H, d, J=2.4 Hz).

b) Preparation of 6-chloro-N-methyl-4-propylnicotinamide

6-Chloro-N-methylnicotinamide (2.00 g, 11.7 mol) was dissolved in tetrahydrofuran (59 mL), added propylmagnesium bromide (46.9 mL, 46.9 mol) under ice-cold conditions, and stirred at room temperature for 4.5 hours. Then, propylmagnesium bromide (46.9 mL, 46.9 mol) was added under ice-cold conditions and the mixture was further stirred at room temperature for 9 hours. The reaction solution was added methanol (140 mL) and ammonium chloride (7.5 g) under ice-cold conditions, and stirred at room temperature for 0.5 hours. The reaction solution was added DDQ (3.19 g, 14.1 mmol) under ice-cold conditions, and stirred at room temperature for 2 hours. The reaction solution was added tert-butyl methylether, and filtered through a pad of celite, concentrated in vacuo, and extracted with ethyl acetate. The organic layer was washed with brine, dried over anhydrous sodium sulfate, and concentrated in vacuo. The obtained residue was purified by silica-gel column chromatography (chloroform/methanol). The title compound (1.88 g (yield 75%)) was obtained as a light brown crystal.

$^1$H-NMR (CDCl$_3$) δ: 0.96 (3H, t, J=7.3 Hz), 1.64 (2H, qt, J=7.3, 7.8 Hz), 2.76 (2H, t, J=7.8 Hz), 3.01 (3H, d, J=4.9 Hz), 6.14 (1H, brs), 7.21 (1H, s), 8.30 (1H, s).

c) Preparation of 6-[4-(2-hydroxyethyl)piperazin-1-yl]-N-methyl-4-propylnicotinamide 6-Chloro-N-methyl-4-propylnicotinamide (123 mg, 0.578 mol) was dissolved in tetrahydrofuran (2 mL), added 1-piperazineethanol (355 μL, 2.89 mol) at room temperature, and stirred at 100° C. for 18 hours. The reaction solution was purified by silica-gel column chromatography (chloroform/methanol). The title compound (177 mg (yield >99%)) was obtained as a yellow crystal.

$^1$H-NMR (CD$_3$OD) δ: 0.93 (3H, t, J=7.3 Hz), 1.59 (2H, qt, J=7.3, 7.6 Hz), 2.58 (2H, t, J=5.8 Hz), 2.63 (4H, t, J=4.9 Hz), 2.74 (2H, t, J=7.6 Hz), 2.86 (3H, s), 3.60 (4H, t, J=4.9 Hz), 3.72 (2H, t, J=5.8 Hz), 6.65 (1H, s), 8.09 (1H, s).

d) Preparation of 6-[4-(2-acetoxyethyl)piperazin-1-yl]-N-methyl-4-propylnicotinamide 6-[4-(2-Hydroxyethyl)piperazin-1-yl]-N-methyl-4-propylnicotinamide (477 mg, 1.56 mol) was dissolved in acetic anhydride (1.5 mL), added sulfuric acid (50 μL) under ice-cold conditions, and stirred at room temperature for 10 minutes. The reaction solution was concentrated in vacuo, and extracted with ethyl acetate. The organic layer was washed with brine, dried over anhydrous sodium sulfate, and concentrated in vacuo. The title compound (496 mg (yield 91%)) was obtained as a yellow oil.

$^1$H-NMR (CDCl$_3$) δ: 0.95 (3H, t, J=7.3 Hz), 1.61 (2H, qt, J=7.3, 7.6 Hz), 2.08 (3H, s), 2.60 (4H, t, J=4.9 Hz), 2.68 (2H, t, J=5.7 Hz), 2.76 (2H, t, J=7.6 Hz), 2.97 (3H, d, J=4.9 Hz), 3.60 (4H, t, J=4.9 Hz), 4.24 (2H, t, J=5.7 Hz), 5.73 (1H, brs), 6.44 (1H, s), 8.18 (1H, s).

e) Preparation of tert-butyl 6-[4-(2-acetoxyethyl)piperazin-1-yl]-4-propylnicotinoyl(methyl)carbamate 6-[4-(2-Acetoxyethyl)piperazin-1-yl]-N-methyl-4-propylnicotinamide (496 mg, 1.42 mol) was dissolved in acetonitrile (7.0 mL), added N,N'-dimethylaminopyridine (35 mg, 0.284 mmol) and di-tert-butyldicarbonate (Boc$_2$O) under ice-cold conditions, and stirred at room temperature overnight. The reaction solution was extracted with ethyl acetate, and the organic layer was washed with brine, dried over anhydrous sodium sulfate, and concentrated in vacuo. The title compound (754 mg) was obtained as a crude product.

$^1$H-NMR (CDCl$_3$) δ: 0.97 (3H, t, J=7.3 Hz), 1.23 (9H, s), 1.48 (2H, qt, J=7.3, 7.6 Hz), 2.09 (3H, s), 2.60 (4H, t, J=4.9 Hz), 2.66-2.71 (4H, m), 3.29 (3H, s), 3.61 (4H, t, J=4.9 Hz), 4.24 (2H, t, J=5.7 Hz), 6.45 (1H, s), 8.03 (1H, s).

f) Preparation of methyl 6-[4-(2-hydroxyethyl)piperazin-1-yl]-4-propyl nicotinate Methanol (7.5 mL) was added sodium hydride (341 mg, 7.10 mmol) under ice-cold conditions, added tert-butyl 6-[4-(2-acetoxyethyl)piperazin-1-yl]-4-propylnicotinoyl (methyl) carbamate (754 mg) in methanol (1.5 mL) at room temperature, and the mixture was stirred at room temperature for 1.5 hours. The reaction solution was extracted with ethyl acetate, and the organic layer was washed with brine, dried over anhydrous sodium sulfate, and concentrated in vacuo. The obtained residue was purified by silica-gel column chromatography (chloroform/methanol). The title compound (441 mg (yield >99%)) was obtained as a yellow oil.

$^1$H-NMR (CDCl$_3$) δ: 0.98 (3H, t, J=7.3 Hz), 1.59 (2H, qt, J=7.3, 7.6 Hz), 2.59-2.63 (6H, m), 2.89 (2H, t, J=7.6 Hz), 3.65-3.69 (7H, m), 3.84 (3H, s), 6.39 (1H, s), 8.74 (1H, s).

g) Preparation of 1,1,1,3,3,3-hexafluoro-2-{6-[4-(2-hydroxyethyl)piperazin-1-yl]-4-propylpyridin-3-yl}propane-2-ol Methyl 6-[4-(2-hydroxyethyl)piperazin-1-yl]-4-propyl nicotinate (441 mg, 1.43 mmol) was dried with a vacuum pump, and dissolved in ethylene glycol dimethylether (7.2 mL). Under −78° C., trifluoromethyltrimethylsilane (2.11 mL, 14.3 mmol) and tetramethyl ammonium fluoride (1.20 g, 12.9 mmol) were added sequentially, heated gradually to room temperature, and stirred overnight. The reaction solution was added 5% aqueous solution of hydrochloric acid under ice-cold conditions, extracted with chloroform. The organic layer was washed with brine, dried over anhydrous sodium sulfate, and concentrated in vacuo. The obtained residue was purified by silica-gel column chromatography (chloroform/methanol). The title compound (296 mg (yield 50%)) was obtained as a brown crystal.

$^1$H-NMR (CDCl$_3$) δ: 0.98 (3H, t, J=7.3 Hz), 1.64 (2H, qt, J=7.3, 7.8 Hz), 2.59-2.65 (6H, m), 2.67 (1H, s), 2.84 (2H, t, J=7.8 Hz), 3.60 (4H, t, J=5.1 Hz), 3.64 (1H, s), 3.67 (2H, t, J=5.4 Hz), 6.48 (1H, s), 8.30 (1H, s).

h) Preparation of 2-{4-[5-(1,1,1,3,3,3-hexafluoro-2-hydroxypropan-2-yl)-4-propylpyridin-2-yl]piperazin-1-yl}ethyl acetate 1,1,1,3,3,3-Hexafluoro-2-{6-[4-(2-hydroxyethyl)piperazin-1-yl]-4-propylpyridin-3-yl}propan-2-ol (208 mg, 0.501 mol) was dissolved in dichloromethane (2.5 mL), added pyridine (121 μL, 1.50 mmol) and anhydrous acetic acid (142 μL, 1.50 mmol) under ice-cold conditions, and the mixture was stirred at room temperature for 3 hours. The reaction solution was added methanol, stirred at room temperature for 0.5 hours. The reaction solution was concentrated in vacuo, extracted with chloroform. The organic layer was washed with brine, dried over anhydrous sodium sulfate, and concentrated in vacuo. The title compound (247 mg) was obtained as a red-brown oil.

$^1$H-NMR (CDCl$_3$) δ: 0.97 (3H, t, J=7.3 Hz), 1.64 (2H, qt, J=7.3, 7.8 Hz), 2.08 (3H, s), 2.64 (4H, t, J=4.6 Hz), 2.71 (2H, t, J=5.7 Hz), 2.84 (2H, t, J=7.8 Hz), 3.61 (4H, t, J=4.6 Hz), 3.62 (1H, s), 4.25 (2H, t, J=5.7 Hz), 6.47 (1H, s), 8.30 (1H, s).

i) Preparation of 2-(4-{5-[1,1,1,3,3,3-hexafluoro-2-(4-methoxybenzyloxy)propan-2-yl]-4-propylpyridin-2-yl}piperazin-1-yl)ethyl acetate 2-{4-[5-(1,1,1,3,3,3-Hexafluoro-2-hydroxypropan-2-yl)-4-propylpyridin-2-yl]piperazin-1-yl}ethyl acetate (211 mg, 0.461 mol) was dissolved in N,N'-dimethylformamide (2.3 mL), and added potassium carbonate (191 mg, 1.38 mmol) at room temperature. Under ice-cold conditions, methoxybenzyl chloride (125 μL, 0.923 mmol) was added, and the mixture was stirred at room temperature overnight. Subsequently, potassium carbonate (96 mg, 0.690 mmol) was further added at room temperature, methoxybenzyl chloride (63 μL, 0.462 mmol) was added under ice-cold conditions, and the mixture was stirred at room temperature for 8 hours. The reaction solution was added water, extracted with chloroform. The organic layer was washed with brine, dried over anhydrous sodium sulfate, and concentrated in vacuo. The title compound (479 mg) was obtained as a red-brown oil.

$^1$H-NMR (CDCl$_3$) δ: 0.79 (3H, t, J=7.3 Hz), 1.54 (2H, qt, J=7.3, 8.3 Hz), 2.08 (3H, s), 2.62 (4H, t, J=4.9 Hz), 2.69 (2H, t, J=5.8 Hz), 2.77 (2H, t, J=8.3 Hz), 3.62 (4H, t, J=4.9 Hz), 3.81 (3H, s), 4.24 (2H, t, J=5.8 Hz), 4.53 (2H, s), 6.57 (1H, s), 6.90 (2H, d, J=8.6 Hz), 7.27 (2H, d, J=8.6 Hz), 8.30 (1H, s).

j) Preparation of 2-(4-{5-[1,1,1,3,3,3-hexafluoro-2-(4-methoxybenzyloxy)propan-2-yl]-4-propylpyridin-2-yl}piperazin-1-yl)ethanol 2-(4-{5-[1,1,1,3,3,3-Hexafluoro-2-(4-methoxybenzyloxy)propan-2-yl]-4-propylpyridin-2-yl}piperazin-1-yl)ethyl acetate (479 mg) was dissolved in methanol (2.3 mL), added potassium carbonate (127 mg, 0.722 mmol), and the mixture was stirred at room temperature for 0.5 hours. The reaction solution was concentrated in vacuo. The obtained residue was purified by silica-gel column chromatography (chloroform/methanol). The title compound (117 mg (yield 47%)) was obtained as a yellow oil.

$^1$H-NMR (CDCl$_3$) δ: 0.79 (3H, t, J=7.3 Hz), 1.54 (2H, qt, J=7.3, 8.3 Hz), 2.62 (2H, t, J=5.2 Hz), 2.66 (4H, t, J=5.1 Hz), 2.77 (2H, t, J=8.3 Hz), 3.11 (1H, s), 3.65 (4H, t, J=5.1 Hz), 3.70 (2H, t, J=5.2 Hz), 3.82 (3H, s), 4.53 (2H, s), 6.58 (1H, s), 6.90 (2H, d, J=8.8 Hz), 7.27 (2H, d, J=8.8 Hz), 8.31 (1H, s).

k) Preparation of 1-[4-(1-methylethoxy)phenyl]ethanone 1-(4-Hydroxyphenyl)ethanone (15.0 g, 110 mmol) was dissolved in acetone (125 mL), added sequentially with potassium carbonate (30.4 g, 220 mmol) and 1-methylethyl iodide (16.5 mL, 165 mmol), and the mixture was stirred at 70° C. for 8 hours. The reaction solution was filtered, washed with acetone and concentrated in vacuo. The obtained residue was added water and ethyl acetate, extracted with ethyl acetate. The organic layer was washed with 1N aqueous solution of sodium hydroxide and brine, dried over anhydrous sodium sulfate, and concentrated in vacuo. 1-[4-(1-methylethoxy)phenyl]ethanone (18.2 g (yield 93%)) was obtained as a white crystal.

$^1$H-NMR (CDCl$_3$) δ: 1.37 (6H, d, J=5.9 Hz), 2.56 (3H, s), 4.65 (1H, quint, J=5.9 Hz), 6.90 (2H, d, J=8.9 Hz). 7.92 (2H, d, J=8.9 Hz).

l) Preparation of 5-methyl-5-(4-(1-methylethoxy)phenyl)imidazolidine-2,4-dione

1-[4-(1-Methylethoxy)phenyl]ethanone (35.2 g, 196 mmol) was dissolved in ethanol (200 mL) and water (200 mL), added sodium cyanide (14.4 g, 294 mmol) and ammonium carbonate (226 g, 9.41 mol), and the mixture was stirred at 70° C. for 13 hours. The reaction solution was filtered, washed with water and hexane/ethyl acetate, and dried. The title compound (35.1 g (yield 72%)) was obtained as a white crystal.

$^1$H-NMR (CDCl$_3$) δ: 1.28 (6H, d, J=5.9 Hz), 1.72 (3H, s), 4.59 (1H, quint, J=5.9 Hz), 6.89 (2H, d, J=8.6 Hz), 7.38 (2H, d, J=8.6 Hz).

m) Preparation of 3-[2-(4-{5-[1,1,1,3,3,3-hexafluoro-2-(4-methoxybenzyloxy)propan-2-yl]-4-propylpyridin-2-yl}piperazin-1-yl)ethyl]-5-[4-(1-methylethoxy)phenyl]-5-methylimidazolidine-2,4-dione 2-(4-{5-[1,1,1,3,3,3-Hexafluoro-2-(4-methoxybenzyloxy)propan-2-yl]-4-propylpyridin-2-yl}piperazin-1-yl)ethanol (20 mg, 0.0373 mmol), 5-methyl-5-(4-(1-methylethoxy)phenyl)imidazolidine-2,4-dione (34.3 mg, 0.138 mmol) and triphenylphosphine (34.5 mg, 0.132 mmol) were dried with a vacuum pump, dissolved in N,N-dimethylformamide (3 mL), added DEAD (51 μL, 0.111 mmol) under ice-cold conditions, and the mixture was stirred at room temperature for 1 hour. Under ice-cold conditions, the reaction solution was added water (1.0 mL) and 2N aqueous solution of hydrochloric acid (1.0 mL), extracted with ethyl acetate. The organic layer was washed with brine, dried over anhydrous sodium sulfate, and concentrated in vacuo. The obtained residue was purified by silica-gel column chromatography (hexane/acetone). The title compound (30 mg (yield 99%)) was obtained as a yellow oil.

$^1$H-NMR (CDCl$_3$) δ: 0.79 (3H, t, J=7.3 Hz), 1.26 (6H, d, J=6.1 Hz), 1.53 (2H, qt, J=7.3, 8.3 Hz), 1.81 (3H, s), 2.55-2.60 (4H, m), 2.64 (2H, t, J=6.1 Hz), 2.76 (2H, t, J=8.3 Hz), 3.45-3.49 (4H, m), 3.69 (2H, t, J=6.1 Hz), 3.81 (3H, s), 4.49 (1H, q, J=6.1 Hz), 4.52 (2H, s), 6.02 (1H, brs), 6.53 (1H, s), 6.85 (2H, d, J=8.8 Hz), 6.90 (2H, d, J=8.6 Hz), 7.27 (2H, d, J=8.6 Hz), 7.40 (2H, d, J=8.8 Hz), 8.29 (1H, s).

n) Preparation of 3-(2-{4-[5-(1,1,1,3,3,3-hexafluoro-2-hydroxypropan-2-yl)-4-propylpyridin-2-yl]piperazin-1-yl}ethyl)-5-[4-(1-methylethoxy)phenyl]-5-methylimidazolidine-2,4-dione 3-[2-(4-{5-[1,1,1,3,3,3-Hexafluoro-2-(4-methoxybenzyloxy)propan-2-yl]-4-propylpyridin-2-yl}piperazin-1-yl)ethyl]-5-[4-(1-methylethoxy)phenyl]-5-methylimidazolidine-2,4-dione (10 mg, 0.0131 mmol) was dissolved in ethyl acetate (2 mL), added palladium carbon (1.0 mg), and the mixture was stirred at room temperature for 6 hours under a hydrogen atmosphere. The reaction solution was filtered through a pad of celite, and concentrated in vacuo. The title compound (7.3 mg (yield 86%)) was obtained as a yellow oil.

$^1$H-NMR (CDCl$_3$) δ: 0.97 (3H, t, J=7.3 Hz), 1.27 (6H, d, J=6.1 Hz), 1.62 (2H, qt, J=7.3, 7.8 Hz), 1.81 (3H, s), 2.52-2.59 (4H, m), 2.64 (2H, t, J=6.1 Hz), 2.80 (2H, t, J=7.8 Hz), 3.42-3.46 (5H, m), 3.68 (2H, t, J=6.1 Hz), 4.48 (1H, q, J=6.1 Hz), 5.82 (1H, brs), 6.42 (1H, s), 6.85 (2H, d, J=8.8 Hz), 7.39 (2H, d, J=8.8 Hz), 8.28 (1H, s).

Example 2

Preparation of 3-(2-{4-[5-(1,1,1,3,3,3-hexafluoro-2-hydroxypropan-2-yl)-4-propylpyridin-2-yl]piperazin-1-yl}ethyl)-5-(6-methoxypyridin-3-yl)-5-methylimidazolidine-2,4-dione

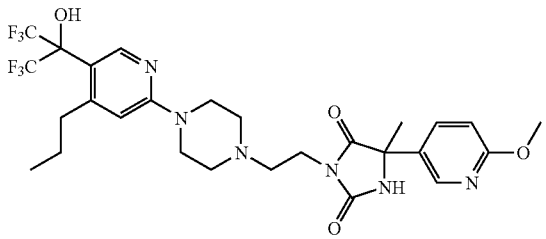 [SMILES: CCCc1cc(N2CCN(CCN3C(=O)NC(C)(c4ccc(OC)nc4)C3=O)CC2)ncc1C(O)(C(F)(F)F)C(F)(F)F]

a) Preparation of 5-(6-methoxypyridin-3-yl)-5-methylimidazolidine-2,4-dione 1-(6-Methoxypyridin-3-yl)ethanone was used for a similar reaction and treatment as Example 1-l). The title compound was obtained as a white crystal.

$^1$H-NMR (CDCl$_3$) δ: 1.74 (3H, s), 3.90 (3H, s), 6.81 (1H, d, J=8.6 Hz), 7.81 (1H, dd, J=2.7, 8.6 Hz), 8.23 (1H, d, J=2.7 Hz).

b) Preparation of 3-(2-{4-[5-(1,1,1,3,3,3-hexafluoro-2-hydroxypropan-2-yl)-4-propylpyridin-2-yl]piperazin-1-yl}ethyl)-5-(6-methoxypyridin-3-yl)-5-methylimidazolidine-2,4-dione 5-(6-Methoxypyridin-3-yl)-5-methylimidazolidine-2,4-dione was used for a similar reaction and treatment as Example 1. The title compound was obtained as a yellow oil.

$^1$H-NMR (CDCl$_3$) δ: 0.91 (3H, t, J=7.3 Hz), 1.55 (2H, qt, J=7.3, 7.6 Hz), 1.76 (3H, s), 2.50-2.58 (6H, m), 2.74 (2H, t, J=7.6 Hz), 3.31-3.42 (5H, m), 3.61-3.65 (2H, m), 3.77 (3H, s), 5.89 (1H, brs), 6.36 (1H, s), 6.65 (1H, d, J=8.8 Hz), 7.66 (1H, dd, J=2.2, 8.8 Hz), 8.21 (1H, s), 8.24 (1H, d, J=2.2 Hz).

Example 3

Preparation of 5-(2,3-dihydrobenzofuran-5-yl)-3-(2-{4-[5-(1,1,1,3,3,3-hexafluoro-2-hydroxypropan-2-yl-4-propylpyridin-2-yl]piperazin-1-yl}ethyl)-5-methylimidazolidine-2,4-dione

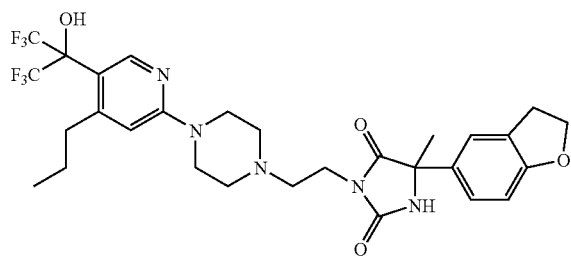 [SMILES: CCCc1cc(N2CCN(CCN3C(=O)NC(C)(c4ccc5c(c4)CCO5)C3=O)CC2)ncc1C(O)(C(F)(F)F)C(F)(F)F]

a) Preparation of 5-(2,3-dihydrobenzofuran-5-yl)-5-methylimidazolidine-2,4-dione 2,3-Dihydrobenzofuran (10 g, 83.2 mmol) was dissolved in dichloromethane (400 mL), added sequentially with acetyl chloride (11.8 mL, 167 mmol) and alminium chloride (33.3 g, 250 mmol) at −10° C., and the mixture was stirred at −10° C. for 0.5 hours. The reaction solution was added 5% aqueous solution of hydrochloric acid, extracted with ethyl acetate. The organic layer was washed with a saturated aqueous solution of sodium hydrogen carbonate and brine, dried over anhydrous sodium sulfate, and concentrated in vacuo. 1-(2,3-Dihydrobenzofuran-5-yl)ethanone (13.4 g (yield 99%)) was obtained as a colorless oil.

$^1$H-NMR (CDCl$_3$) δ: 2.55 (3H, s), 3.25 (2H, t, J=8.6 Hz), 4.67 (2H, t, J=8.6 Hz), 6.80 (1H, d, J=8.1 Hz), 7.80 (1H, dd, j=1.9, 8.1 Hz), 7.85 (1H, d, J=1.9 Hz).

1-(2,3-Dihydrobenzofuran-5-yl)ethanone was used for a similar reaction and treatment as Example 1-l). The title compound was obtained as a white crystal.

$^1$H-NMR (CDCl$_3$) δ: 2.62 (3H, s), 3.32 (2H, t, J=8.6 Hz), 4.74 (2H, t, J=8.6 Hz), 6.87 (1H, d, J=8.8 Hz), 7.22 (1H, dd, J=2.2, 8.8 Hz), 7.34 (1H, d, J=2.2 Hz).

b) Preparation of 5-(2,3-dihydrobenzofuran-5-yl)-3-(2-{4-[5-(1,1,1,3,3,3-hexafluoro-2-hydroxypropan-2-yl)-4-propylpyridin-2-yl]piperazin-1-yl}ethyl)-5-methylimidazolidine-2,4-dione 5-(2,3-Dihydrobenzofuran-5-yl)-5-methylimidazolidine-2,4-dione was used for a similar reaction and treatment as Example 1. The title compound was obtained as a yellow oil.

$^1$H-NMR (CDCl$_3$) δ: 0.98 (3H, t, J=7.3 Hz), 1.63 (2H, qt, J=7.3, 8.0 Hz), 1.81 (3H, s), 2.53-2.59 (4H, m), 2.64 (2H, t, J=6.1 Hz), 2.81 (2H, t, J=8.0 Hz), 3.14 (2H, t, J=8.8 Hz), 3.41-3.44 (4H, m), 3.46 (1H, s), 3.69 (2H, t, J=6.1 Hz), 4.49 (2H, t, J=8.8 Hz), 5.57 (1H, s), 6.42 (1H, s), 6.74 (1H, d, J=8.6 Hz), 7.22 (1H, dd, J=2.0, 8.6 Hz), 7.33 (1H, d, J=2.0 Hz), 8.28 (1H, s).

Example 4

Preparation of 3-(2-{4-[4-(1,1,1,3,3,3-hexafluoro-2-hydroxypropan-2-yl)-2-propylphenyl]piperazin-1-yl}ethyl)-5-[4-(1-methylethoxy)phenyl]-5-methylimidazolidine-2,4-dione

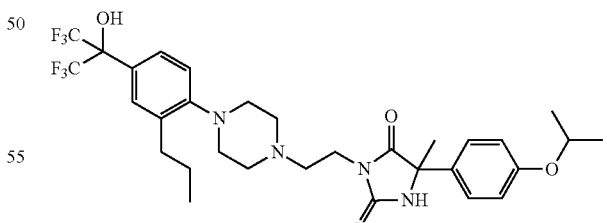

a) Preparation of 3-bromo-4-fluoromethyl benzoate

3-Bromo-4-fluorobenzoic acid (3.33 g, 15.2 mmol) was dissolved in methanol (30 mL), added acetyl chloride (4.3 mL, 60.8 mmol) under ice-cold conditions, and the mixture was stirred at room temperature for 20 hours. The reaction solution was concentrated in vacuo. The obtained residue was purified by silica-gel column chromatography (hexane/ethyl acetate). The title compound (3.2 g (yield 90%)) was obtained as a colorless oil.

¹H-NMR (CDCl₃) δ: 3.92 (3H, s), 7.18 (1H, dd, J=8.0, 8.2 Hz), 7.99 (1H, ddd, J=1.9, 4.9, 8.0 Hz), 8.27 (1H, dd, J=1.9, 6.5 Hz).

b) Preparation of methyl 3-bromo-4-[4-(2-hydroxyethyl)piperazin-1-yl]benzoate

Methyl 3-bromo-4-fluoro benzoate (1.39 g, 5.96 mmol) was dissolved in N,N-dimethylformamide (12 mL), added 1-piperazineethanol (3.88 g, 29.8 mmol) and potassium carbonate (2.47 g, 17.9 mmol), and the mixture was stirred under microwave irradiation at 100° C. for 0.5 hours. The reaction solution was added water at room temperature, extracted with ethyl acetate. The organic layer was washed with brine, dried over anhydrous sodium sulfate, and concentrated in vacuo. The obtained residue was purified by silica-gel column chromatography (hexane/acetone). The title compound (730 mg (yield 36%)) was obtained as a yellow oil.

¹H-NMR (CDCl₃) δ: 2.64 (2H, t, J=5.1 Hz), 2.71-2.75 (5H, m), 3.15-3.19 (4H, m), 3.67 (2H, t, J=5.1 Hz), 3.89 (3H, s), 7.03 (1H, d, J=8.6 Hz), 7.94 (1H, dd, J=1.6, 8.6 Hz), 8.22 (1H, d, J=1.6 Hz).

c) Preparation of methyl 4-{4-[2-(benzyloxy)ethyl]piperazin-1-yl}-3-bromobenzoate Methyl 3-bromo-4-[4-(2-hydroxyethyl)piperazin-1-yl]benzoate (100 mg, 0.291 mmol) was dried with a vacuum pump, and dissolved in N,N-dimethylformamide (2.9 mL). Under ice-cold conditions, sodium hydride (15.2 mg, 0.350 mmol) and benzyl bromide (38 µL, 0.320 mmol) were added sequentially, and the mixture was stirred at room temperature for 15 hours. The reaction solution was added water under ice-cold conditions, extracted with ethyl acetate. The organic layer was washed with brine, dried over anhydrous sodium sulfate, and concentrated in vacuo. The obtained residue was purified by silica-gel column chromatography (hexane/acetone). The title compound (43 mg (yield 34.3%)) was obtained as a yellow oil.

¹H-NMR (CDCl₃) δ: 2.70-2.73 (6H, m), 3.11-3.65 (4H, m), 3.63 (2H, t, J=5.6 Hz), 3.86 (3H, s), 4.56 (2H, s), 7.03 (1H, d, J=8.6 Hz), 7.28-7.42 (5H, m), 7.93 (1H, dd, J=1.9, 8.6 Hz), 8.22 (1H, d, J=1.9 Hz).

d) Preparation of methyl(Z)-4-{4-[2-(benzyloxy)ethyl]piperazin-1-yl}-3-(prop-1-en-1-yl)benzoate Methyl 4-{4-[2-(benzyloxy)ethyl]piperazin-1-yl}-3-bromobenzoate (78 mg, 0.180 mmol) was dissolved in N,N-dimethylformamide: water=3:1 (1.8 mL). At room temperature, (Z)-propenylboronic acid (containing about 10% E-isomer; Hereinafter the same is used for all) (37 mg, 0.433 mmol), tetrakistriphenylphosphine palladium (10 mg, 0.00902 mmol) and sodium carbonate (76 mg, 0.722 mmol) were added sequentially, and the mixture was stirred at 80° C. for 1 hour under microwave irradiation. The reaction solution was extracted with ethyl acetate. The organic layer was washed with brine, dried over anhydrous sodium sulfate, and concentrated in vacuo. The obtained residue was purified by silica-gel column chromatography (hexane/acetone). The title compound (61 mg (yield 86%)) was obtained as a yellow oil.

¹H-NMR (CDCl₃) δ: 1.89 (3H, dd, J=1.7, 7.1 Hz), 2.63-2.65 (4H, m), 2.69 (2H, t, J=5.6 Hz), 3.09-3.11 (4H, m), 3.62 (2H, t, J=5.6 Hz), 3.88 (3H, s), 4.56 (2H, s), 5.80 (1H, qd, J=7.1, 11.4 Hz), 6.41 (1H, dd, J=1.7, 11.4 Hz), 6.95 (1H, d, J=8.5 Hz), 7.27-7.44 (5H, m), 7.87 (1H, dd, J=1.9, 8.5 Hz), 7.92 (1H, d, J=1.9 Hz).

e) Preparation of (Z)-4-{4-[2-(benzyloxy)ethyl]piperazin-1-yl}-3-(prop-1-en-1-yl)benzoic acid Methyl (Z)-4-{4-[2-(benzyloxy)ethyl]piperazin-1-yl}-3-(prop-1-en-1-yl)benzoate (20 mg, 0.0507 mmol) was dissolved in methanol (1.0 mL). Under ice-cold conditions, 4N aqueous solution of sodium hydroxide (50 µL) was added and stirred at 50° C. overnight. The reaction solution was added 4N aqueous solution of hydrochloric acid under ice-cold conditions, and extracted with chloroform. The organic layer was washed with brine, dried over anhydrous sodium sulfate, and concentrated in vacuo. The obtained residue was purified by silica-gel column chromatography (hexane/acetone). The title compound (13 mg (yield 65%)) was obtained as a yellow oil.

¹H-NMR (CDCl₃) δ: 1.89 (3H, dd, J=1.4, 7.1 Hz), 2.75-2.83 (6H, m), 3.14-3.17 (4H, m), 3.71 (2H, t, J=5.4 Hz), 4.54 (2H, s), 4.71 (1H, s), 5.81 (1H, qd, J=7.1, 11.4 Hz), 6.41 (1H, dd, J=1.4, 11.4 Hz), 6.96 (1H, d, J=8.5 Hz), 7.27-7.38 (5H, m), 7.91 (1H, dd, J=2.0, 8.5 Hz), 7.96 (1H, d, J=2.0 Hz).

f) Preparation of perfluorophenyl (Z)-4-{4-[2-(benzyloxy)ethyl]piperazin-1-yl}-3-(prop-1-en-1-yl)benzoate (Z)-4-{4-[2-(benzyloxy)ethyl]piperazin-1-yl}-3-(prop-1-en-1-yl)benzoic acid (13 mg, 0.0331 mmol) was dissolved in ethyl acetate (3.3 mL). At room temperature, pentafluorophenol (7.3 mg, 0.0397 mmol) and N,N'-dicyclohexylcarbodiimide (8.2 mg, 0.0397 mmol) were added sequentially, and the mixture was stirred at room temperature for 14 hours. The reaction solution was added water, extracted with ethyl acetate. The organic layer was washed with brine, dried over anhydrous sodium sulfate, and concentrated in vacuo. The obtained residue was purified by silica-gel column chromatography (hexane/acetone). The title compound (16 mg (yield 86%)) was obtained as a pale yellow crystal.

¹H-NMR (CDCl₃) δ: 1.91 (3H, dd, J=1.7, 7.1 Hz), 2.66-2.68 (4H, m), 2.71 (2H, t, J=5.6 Hz), 3.17-3.19 (4H, m), 3.63 (2H, t, J=5.6 Hz), 4.56 (2H, s), 5.86 (1H, qd, J=7.1, 11.4 Hz), 6.40 (1H, dd, J=1.7, 11.4 Hz), 7.02 (1H, d, J=9.3 Hz), 7.27-7.38 (5H, m), 8.01-8.04 (2H, m).

g) Preparation of (Z)-2-(4-{4-[2-(benzyloxy)ethyl]piperazin-1-yl}-3-(prop-1-en-1-yl)phenyl)-1,1,1,3,3,3-hexafluoropropan-2-ol Perfluorophenyl (Z)-4-{4-[2-(benzyloxy)ethyl]piperazin-1-yl}-3-(prop-1-en-1-yl)benzoate (60 mg, 0.110 mmol) was dried with a vacuum pump, and dissolved in ethylene glycol dimethylether (2.2 mL). Under −78° C., trifluoromethyl trimethylsilane (162 µL, 1.10 mmol) and tetramethyl ammonium fluoride (102 mg, 1.10 mmol) were added sequentially, heated gradually to room temperature, and the mixture was stirred for 12 hours. The reaction solution was added water under ice-cold conditions, extracted with ethyl acetate. The organic layer was washed with brine, dried over anhydrous sodium sulfate, and concentrated in vacuo. The obtained residue was purified by silica-gel column chromatography (hexane/acetone), and the title compound (40 mg (yield 73%)) was obtained as an orange oil.

¹H-NMR (CDCl₃) δ: 1.83 (3H, dd, J=1.7, 7.1 Hz), 2.68-2.71 (4H, m), 2.74 (2H, t, J=5.6 Hz), 3.02-3.05 (4H, m), 3.65 (2H, t, J=5.6 Hz), 4.07 (1H, brs), 4.54 (2H, s), 5.80 (1H, qd, J=7.1, 11.4 Hz), 6.44 (1H, dd, J=1.7, 11.4 Hz), 6.99 (1H, d, J=9.3 Hz), 7.27-7.37 (5H, m), 7.54-7.56 (2H, m).

h) Preparation of (Z)-1-[2-(benzyloxy)ethyl]-4-{4-[1,1,1,3,3,3-hexafluoro-2-(methoxymethoxy)propan-2-yl]-2-(prop-1-en-1-yl)phenyl}piperazine (Z)-2-(4-{4-[2-(benzyloxy)ethyl]piperazin-1-yl}-3-(prop-1-en-1-yl)phenyl)-1,1,1,3,3,3-hexafluoropropan-2-ol (40 mg, 0.0796 mmol) was dried with a vacuum pump, and dissolved in dichloromethane (796 μL). Under ice-cold conditions, diisopropylethylamine (42 μL, 0.239 mmol) and chloromethylmethylether (6.6 μL, 0.0876 mmol) were added sequentially, and the mixture was stirred at room temperature for 20 hours. Further, under ice-cold conditions, diisopropylethylamine (84 μL, 0.478 mmol) and chloromethylmethylether (26 μL, 0.350 mmol) were added sequentially, and the mixture was stirred at room temperature overnight. The reaction solution was added water under ice-cold conditions, and extracted with ethyl acetate. The organic layer was washed with brine, dried over anhydrous sodium sulfate, and concentrated in vacuo. The obtained residue was purified by silica-gel column chromatography (hexane/acetone). The title compound (32 mg (yield 73%)) was obtained as a pale yellow oil.

¹H-NMR (CDCl₃) δ: 1.84 (3H, dd, J=1.7, 7.1 Hz), 2.67-2.69 (4H, m), 2.72 (2H, t, J=5.6 Hz), 3.07-3.09 (4H, m), 3.54 (3H, s), 3.64 (2H, t, J=5.6 Hz), 4.54 (2H, s), 4.85 (2H, s), 5.81 (1H, qd, J=7.1, 11.4 Hz), 6.45 (1H, dd, J=1.7, 11.4 Hz), 6.99 (1H, d, J=8.5 Hz), 7.27-7.37 (5H, m), 7.43 (1H, dd, J=2.0, 8.5 Hz), 7.47 (1H, d, J=2.0 Hz).

i) Preparation of 2-(4-{4-[1,1,1,3,3,3-hexafluoro-2-(methoxymethoxy)propan-2-yl]-2-propylphenyl}piperazin-1-yl)ethanol (Z)-1-[2-(benzyloxy)ethyl]-4-{4-[1,1,1,3,3,3-hexafluoro-2-(methoxymethoxy)propan-2-yl]-2-(prop-1-en-1-yl)phenyl}piperazine (33 mg, 0.0604 mmol) was dissolved in methanol (4 mL), added palladium carbon (3.3 mg), and the mixture was stirred at room temperature for 12 hours under a hydrogen atmosphere. The reaction solution was filtered through a pad of celite, and concentrated in vacuo. The obtained residue was purified by silica-gel column chromatography (hexane/acetone). The title compound (7.8 mg (yield 24%)) was obtained as a yellow oil.

¹H-NMR (CDCl₃) δ: 0.96 (3H, t, J=7.3 Hz), 1.65 (2H, qt, J=7.3, 7.6 Hz), 2.62-2.71 (9H, m), 2.96 (4H, t, J=4.6 Hz), 3.55 (3H, s), 3.67 (2H, t, J=5.4 Hz), 4.83 (2H, s), 7.09 (1H, d, J=8.3 Hz), 7.37-7.41 (2H, m).

j) Preparation of 3-[(2-(4-{4-[1,1,1,3,3,3-hexafluoro-2-(methoxymethoxy)propan-2-yl]-2-propylphenyl}piperazin-1-yl)ethyl]-5-[4-(1-methylethoxy)phenyl]-5-methylimidazolidine-2,4-dione 2-(4-{4-[1,1,1,3,3,3-Hexafluoro-2-(methoxymethoxy)propan-2-yl]-2-propylphenyl}piperazin-1-yl)ethanol (7.8 mg, 0.0170 mmol), 5-methyl-5-(4-(1-methylethoxy)phenyl)imidazolidine-2,4-dione (A11)(15.6 mg, 0.0631 mmol) and triphenylphosphine (15.8 mg, 0.0601 mmol) were dried with a vacuum pump, dissolved in N,N-dimethylformamide (284 μL), added DEAD (23 μL, 0.0167 mmol) under ice-cold conditions, and the mixture was stirred at room temperature for 1 hour. Under ice-cold conditions, the reaction solution was added water (1.0 mL) and 2N aqueous solution of hydrochloric acid (1.0 mL), and extracted with ethyl acetate. The organic layer was washed with brine, dried over anhydrous sodium sulfate, and concentrated in vacuo. The obtained residue was purified by silica-gel column chromatography (hexane/acetone). The title compound (3.1 mg (yield 26%)) was obtained as a yellow oil.

¹H-NMR (CDCl₃) δ: 0.94 (3H, t, J=7.3 Hz), 1.30 (6H, d, J=6.1 Hz), 1.62 (2H, qt, J=7.3, 7.6 Hz), 1.83 (3H, s), 2.58-2.71 (8H, m), 2.78-2.80 (4H, m), 3.55 (3H, s), 3.65-3.73 (2H, m), 4.51 (1H, q, J=6.1 Hz), 4.82 (2H, s), 4.57 (1H, s), 6.87 (2H, d, J=8.8 Hz), 7.00 (1H, dd, J=8.3 Hz), 7.35 (1H, dd, J=2.2, 8.3 Hz), 7.38 (1H, d, J=2.2 Hz), 7.42 (2H, d, J=8.8 Hz).

k) Preparation of 3-(2-{4-[4-(1,1,1,3,3,3-hexafluoro-2-hydroxypropan-2-yl)-2-propylphenyl]piperazin-1-yl}ethyl)-5-[4-(1-methylethoxyphenyl)]-5-methylimidazolidine-2,4-dione 3-[2-(4-{4-[1,1,1,3,3,3-Hexafluoro-2-(methoxymethoxy)propan-2-yl]-2-propylphenyl}piperazin-1-yl)ethyl]-5-[4-(1-methylethoxy)phenyl]-5-methylimidazolidine-2,4-dione (3.1 mg, 0.00450 mmol) was dissolved in methanol (1 mL), added 4N aqueous solution of hydrochloric acid (50 μL), and the mixture was stirred at 50° C. for 1.5 hours. The reaction solution was concentrated in vacuo. The obtained residue was added ethyl acetate, and added a saturated aqueous solution of sodium hydrogen carbonate under ice-cold conditions, and extracted with ethyl acetate. The organic layer was washed with brine, dried over anhydrous sodium sulfate, and concentrated in vacuo. The obtained residue was purified by silica-gel column chromatography (hexane/acetone). The title compound (3.0 mg (yield 99%)) was obtained as a yellow oil.

¹H-NMR (CDCl₃) δ: 0.95 (3H, t, J=7.3 Hz), 1.29 (6H, d, J=6.1 Hz), 1.64 (2H, qt, J=7.3, 7.6 Hz), 1.83 (3H, s), 2.59-2.72 (8H, m), 2.76-2.82 (4H, m), 3.39 (1H, s), 3.64-3.71 (2H, m), 4.51 (1H, q, J=6.1 Hz), 5.56 (1H, s), 6.87 (2H, d, J=8.8 Hz), 7.00 (1H, dd, J=8.6 Hz), 7.42 (2H, d, J=8.3 Hz), 7.44 (1H, dd, J=2.2, 8.6 Hz), 7.48 (1H, d, J=2.2 Hz).

Example 5

Preparation of 5-(benzo[d][1,3]dioxol-5-yl)-3-(2-{4-[4-(1,1,1,3,3,3-hexafluoro-2-hydroxypropan-2-yl)-2-propylphenyl]piperazin-1-yl}ethyl)-5-methylimidazolidine-2,4-dione

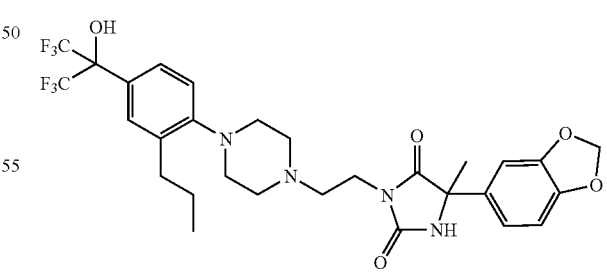

a) Preparation of 5-(benzo[d][1,3]dioxol-5-yl)-5-methylimidazolidine-2,4-dione 5-(Benzo[d][1,3]dioxol-5-yl)ethanone was used for a similar reaction and treatment as Example 1-l). The title compound was obtained as a white crystal.

¹H-NMR (CDCl₃) δ: 1.83 (3H, s), 5.99 (2H, s), 6.81 (1H, d, J=8.3 Hz), 6.95 (1H, dd, J=2.2, 8.3 Hz), 6.99 (1H, d, J=2.2 Hz).

b) Preparation of 5-(benzo[d][1,3]dioxol-5-yl)-3-(2-{4-[4-(1,1,1,3,3,3-hexafluoro-2-hydroxypropan-2-yl)-2-propylphenyl]piperazin-1-yl}ethyl)-5-methylimidazolidine-2,4-dione 5-(Benzo[d][1,3]dioxol-5-yl)-5-methylimidazolidine-2,4-dione was used for a similar reaction and treatment as Example 4. The title compound was obtained as a yellow oil.

¹H-NMR (CDCl₃) δ: 0.94 (3H, t, J=7.3 Hz), 1.64 (2H, qt, J=7.3, 7.6 Hz), 1.81 (3H, s), 2.59-2.73 (8H, m), 2.77-2.79 (4H, m), 3.62-3.76 (3H, m), 5.66 (1H, s), 5.89 (2H, s), 6.80 (1H, d, J=8.0 Hz), 6.98 (1H, dd, J=1.9, 8.0 Hz), 7.01 (1H, d, J=8.3 Hz), 7.05 (1H, d, J=1.9 Hz), 7.44 (1H, dd, J=2.0, 8.3 Hz), 7.48 (1H, d, J=2.0 Hz).

Example 6

Preparation of 3-(2-{4-[4-(1,1,1,3,3,3-hexafluoro-2-hydroxypropan-2-yl)-2-propylphenyl]piperazin-1-yl}-2-oxoethyl)-5-[5-(1-methylethoxy)pyridin-2-yl]-5-methylimidazolidine-2,4-dione

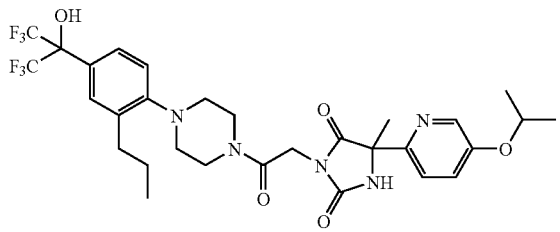 [SMILES: CCCc1cc(C(O)(C(F)(F)F)C(F)(F)F)ccc1N1CCN(C(=O)CN2C(=O)NC(C)(c3ccc(OC(C)C)cn3)C2=O)CC1]

a) Preparation of methyl 4-fluoro-3-nitrobenzoate

3-Nitro-4-fluorobenzoic acid (25.6 g, 138 mmol) was dissolved in methanol (300 mL), added thionyl chloride (18.4 mL, 258 mmol) under −78° C. The mixture was stirred at −78° C. for 10 minutes, and then stirred at room temperature overnight. The reaction solution was concentrated in vacuo. The obtained residue was purified by silica-gel column chromatography (hexane/ethyl acetate). The title compound (29.6 g (yield >99%)) was obtained as a white crystal.

¹H-NMR (CDCl₃) δ: 3.98 (3H, s), 7.39 (1H, dd, J=8.8, 10.3 Hz), 8.32 (1H, ddd, J=2.4, 4.3, 8.8 Hz), 8.75 (1H, dd, J=2.4, 7.2 Hz).

b) Preparation of tert-butyl 4-[4-(methoxycarbonyl)-2-nitrophenyl]piperazine-1-carboxylate To a solution of methyl 4-fluoro-3-nitrobenzoate (2.50 g, 12.6 mmol) in tetrahydrofuran (75 mL), tert-butyl piperazine-1-carboxylate (4.67 g, 25.2 mmol) and potassium carbonate (4.34 g, 25.2 mmol) were added sequentially under ice-cold conditions, and the mixture was stirred at room temperature for 1 hour. The reaction solution was added water under ice-cold conditions, and extracted with ethyl acetate. The organic layer was washed with brine, dried over anhydrous sodium sulfate, and concentrated in vacuo. The obtained residue was purified by silica-gel column chromatography (ethyl acetate). The title compound (4.83 g (yield 100%)) was obtained as a yellow crystal.

¹H-NMR (CDCl₃) δ: 1.48 (9H, s), 3.15 (4H, t, J=4.3 Hz), 3.61 (4H, t, J=4.3 Hz), 3.92 3H, s), 7.08 (1H, d, J=8.6 Hz), 8.09 (1H, dd, J=2.2, 8.6 Hz), 8.47 (1H, d, J=2.2 Hz).

c) Preparation of tert-butyl 4-[2-amino-4-(methoxycarbonyl)phenyl]piperazine-1-carboxylate To a solution of tert-butyl 4-[4-(methoxycarbonyl)-2-nitrophenyl]piperazine-1-carboxylate (200 mg, 0.547 mmol) in 1,4-dioxane-water (2:1) (6.0 mL), iron powder (76 mg, 1.37 mmol) and acetic acid (1 mL) were added under ice-cold conditions, and the mixture was stirred at room temperature overnight. The reaction solution was added water and a saturated aqueous solution of sodium hydrogen carbonate under ice-cold conditions, filtered through a pad of celite, and extracted with ethyl acetate. Then, the organic layer was washed with brine, dried over anhydrous sodium sulfate, and concentrated in vacuo. The obtained residue was purified by silica-gel column chromatography (hexane/acetone). The title compound (83 mg (yield 45%)) was obtained as a yellow oil.

¹H-NMR (CDCl₃) δ: 1.49 (9H, s), 2.91 (4H, t, J=4.6 Hz), 3.58 (4H, t, J=4.6 Hz), 3.87 (3H, s), 4.42 (2H, brs), 6.95 (1H, d, J=7.8 Hz), 7.41 (1H, d, J=7.9 Hz), 7.45 (1H, dd, J=1.9, 7.8 Hz).

d) Preparation of tert-butyl 4-[2-iodo-4-(methoxycarbonyl)phenyl]piperazine-1-carboxylate To a solution of tert-butyl 4-[2-amino-4-(methoxycarbonyl)phenyl]piperazine-1-carboxylate (231 mg, 0.657 mmol) in acetonitrile (6.6 mL), para-toluenesulfonic acid monohydrate (375 mg, 1.97 mmol) was added under ice-cold conditions, and then added a mixed solution of sodium nitrite (91 mg, 1.31 mmol) and potassium iodide (273 mg, 1.64 mmol) under ice-cold conditions, and the mixture was stirred at room temperature overnight. The reaction solution was added water and an aqueous solution of sodium thiosulfate under ice-cold conditions, and extracted with ethyl acetate. Then, the organic layer was washed with brine, dried over anhydrous sodium sulfate, and concentrated in vacuo. The obtained residue was purified by silica-gel column chromatography (hexane/acetone). The title compound (127 mg (yield 43%)) was obtained as a white crystal.

¹H-NMR (CDCl₃) δ: 1.49 (9H, s), 3.01 (4H, t, J=4.9 Hz), 3.64 (4H, t, J=4.9 Hz), 3.89 (3H, s), 6.98 (1H, d, J=8.4 Hz), 7.79 (1H, dd, J=2.0, 8.4 Hz), 8.51 (1H, d, J=2.0 Hz).

e) Preparation of tert-butyl (Z)-4-[4-(methoxycarbonyl)-2-(prop-1-en-1-yl)phenyl]piperazine-1-carboxylate tert-Butyl 4-(2-iodo-4-(methoxycarbonyl)phenyl)piperazine-1-carboxylate (127 mg, 0.285 mmol) was dissolved in N,N-dimethylformamide:water=3:1 (2.8 mL). At room temperature, (Z)-propenylboronic acid (59 mg, 0.684 mmol), tetrakistriphenylphosphine palladium (16 mg, 0.0143 mmol) and sodium carbonate (121 mg, 1.14 mmol) were added sequentially, and the mixture was stirred at 80° C. for 1 hour, under microwave irradiation. The reaction solution was extracted with ethyl acetate. The organic layer was washed with brine, dried over anhydrous sodium sulfate, and concentrated in vacuo. The obtained residue was purified by silicagel column chromatography (hexane/acetone). The title compound (96 mg (yield 94%)) was obtained as a yellow crystal.

$^1$H-NMR (CDCl$_3$) δ: 1.48 (9H, s), 1.89 (3H, dd, J=1.9, 7.2 Hz), 2.99 (4H, t, J=4.9 Hz), 3.54 (4H, t, J=4.9 Hz), 3.89 (3H, s), 5.84 (1H, qd, J=7.2, 11.6 Hz), 6.43 (1H, dd, J=1.9, 11.6 Hz), 6.94 (1H, d, J=8.4 Hz), 7.88 (1H, dd, J=2.2, 8.4 Hz), 7.93 (1H, d, J=2.2 Hz).

f) Preparation of (Z)-4-[4-(tert-butoxycarbonyl)piperazin-1-yl]-3-(prop-1-en-1-yl)benzoic acid tert-Butyl (Z)-4-[4-(methoxycarbonyl)-2-(prop-1-en-1-yl)phenyl]piperazine-1-carboxylate (96 mg, 0.267 mmol) was dissolved in methanol (3.0 mL). Under ice-cold conditions, 4N aqueous solution of sodium hydroxide (334 μL) was added, and the mixture was stirred at 50° C. overnight. Subsequently, 4N aqueous solution of sodium hydroxide (668 μL) was further added under ice-cold conditions, and stirred at 50° C. overnight. The reaction solution was added 4N aqueous solution of hydrochloric acid under ice-cold conditions, and extracted with chloroform. The organic layer was washed with brine, dried over anhydrous sodium sulfate, and concentrated in vacuo. The obtained residue was purified by silica-gel column chromatography (hexane/acetone). The title compound (108 mg (yield >99%)) was obtained as a white crystal.

$^1$H-NMR (CD$_3$OD) δ: 1.47 (9H, s), 1.87 (3H, dd, J=2.0, 7.1 Hz), 2.98 (4H, t, J=4.6 Hz), 3.55 (4H, t, J=4.6 Hz), 5.85 (1H, qd, J=7.1, 11.6 Hz), 6.50 (1H, dd, J=2.0, 11.6 Hz), 7.03 (1H, d, J=8.4 Hz), 7.86 (1H, dd, J=2.2, 8.4 Hz), 7.90 (1H, d, J=2.2 Hz).

g) Preparation of tert-butyl (Z)-4-{4-[(perfluorophenoxy)carbonyl]-2-(prop-1-en-1-yl)phenyl}piperazine-1-carboxylate (Z)-4-[4-(tert-butoxycarbonyl)piperazin-1-yl]-3-(prop-1-en-1-yl)benzoic acid (108 mg, 0.267 mmol) was dissolved in ethyl acetate:acetone=4:1 (5.7 mL). At room temperature, pentafluorophenol (59 mg, 0.320 mmol) and N,N'-dicyclohexylcarbodiimide (66 mg, 0.320 mmol) were added sequentially, and the mixture was stirred at room temperature for 10 hours. The reaction solution was added water, extracted with ethyl acetate. The organic layer was washed with brine, dried over anhydrous sodium sulfate, and concentrated in vacuo. The obtained residue was purified by silica-gel column chromatography (hexane/acetone). The title compound (129 mg (yield 95%)) was obtained as a white crystal.

$^1$H-NMR (CDCl$_3$) δ: 1.49 (9H, s), 1.91 (3H, dd, J=2.0, 7.1 Hz), 3.07 (4H, t, J=4.6 Hz), 3.57 (4H, t, J=4.6 Hz), 5.89 (1H, qd, J=7.1, 11.6 Hz), 6.43 (1H, dd, J=2.0, 11.6 Hz), 7.01 (1H, d, J=8.8 Hz), 8.03-8.06 (2H, m).

h) Preparation of tert-butyl (Z)-4-[4-(1,1,1,3,3,3-hexafluoro-2-hydroxypropan-2-yl)-2-(prop-1-en-1-yl)phenyl]piperazine-1-carboxylate tert-Butyl (Z)-4-{4-[(perfluorophenoxy)carbonyl]-2-(prop-1-en-1-yl)phenyl}piperazine-1-carboxylate (129 mg, 0.252 mmol) was dried with a vacuum pump, and dissolved in ethylene glycol dimethyl ether (5.0 mL). Under −78° C., trifluoromethyltrimethylsilane (186 μL, 1.26 mmol) and tetramethyl ammonium fluoride (118 mg, 1.26 mmol) were added sequentially, heated gradually to room temperature; and stirred for 14 hours. The reaction solution was added water under ice-cold conditions, extracted with ethyl acetate. The organic layer was washed with brine, dried over anhydrous sodium sulfate, and concentrated in vacuo. The obtained residue was purified by silica-gel column chromatography (hexane/acetone). The title compound (85 mg (yield 72%)) was obtained as a yellow crystal.

$^1$H-NMR (CDCl$_3$) δ: 1.48 (9H, s), 1.86 (3H, dd, J=1.7, 7.1 Hz), 2.95 (4H, t, J=4.9 Hz), 3.54 (4H, t, J=4.9 Hz), 3.55 (1H, s), 5.84 (1H, qd, J=7.11, 11.3 Hz), 6.49 (1H, dd, J=1.7, 11.3 Hz), 6.99 (1H, d, J=8.4 Hz), 7.54 (1H, dd, J=1.7, 8.4 Hz), 7.58 (1H, d, J=1.7 Hz).

i) Preparation of tert-butyl (Z)-4-{4-[2-(benzyloxy)-1,1,1,3,3,3-hexafluoropropan-2-yl]-2-(prop-1-en-1-yl)phenyl}piperazine-1-carboxylate tert-Butyl (Z)-4-[4-(1,1,1,3,3,3-hexafluoro-2-hydroxypropan-2-yl)-2-(prop-1-en-1-yl)phenyl]piperazine-1-carboxylate (85 mg, 0.181 mmol) was dissolved in N,N'-dimethylformamide (1.8 mL), added sodium hydride (9.5 mg, 217 mmol) and benzyl bromide (23 μL, 0.190 mmol) under ice-cold conditions, and the mixture was stirred at room temperature overnight. The reaction solution was added water, and extracted with ethyl acetate. The organic layer was washed with brine, dried over anhydrous sodium sulfate, and concentrated in vacuo. The obtained residue was purified by silica-gel column chromatography (hexane/acetone). The title compound (67 mg) was obtained as a yellow oil.

$^1$H-NMR (CDCl$_3$) δ: 1.48 (9H, s), 1.73 (3H, dd, J=1.7, 7.1 Hz), 2.96 (4H, t, J=4.9 Hz), 3.54 (4H, t, J=4.9 Hz), 4.67 (2H, s), 5.80 (1H, qd, J=7.1, 11.6 Hz), 6.47 (1H, dd, J=1.7, 11.6 Hz), 6.89 (1H, d, J=8.6 Hz), 7.31-7.39 (5H, m), 7.44 (1H, dd, J=1.7, 8.6 Hz), 7.50 (1H, d, J=1.7 Hz).

j) Preparation of (Z)-1-{4-[2-(benzyloxy)-1,1,1,3,3,3-hexafluoropropan-2-yl]-2-(prop-1-en-1-yl)phenyl}piperazine tert-Butyl (Z)-4-{4-[2-(benzyloxy)-1,1,1,3,3,3-hexafluoropropan-2-yl]-2-(prop-1-en-1-yl)phenyl}piperazine-1-carboxylate (67 mg, 0.119 mmol) was dissolved in dichloromethane (2.0 mL). Under ice-cold conditions, trifluoroacetic acid (200 μL) was added and stirred at room temperature for 0.5 hours. The reaction solution was added a saturated aqueous solution of sodium hydrogen carbonate under ice-cold conditions, and extracted with chloroform. The organic layer was washed with brine, dried over anhydrous sodium sulfate, and concentrated in vacuo. The obtained residue was purified by silica-gel column chromatography (chloroform). The title compound (77 mg (yield >99%)) was obtained as a white pink oil.

$^1$H-NMR (CDCl$_3$) δ: 1.70 (3H, dd, J=2.0, 7.1 Hz), 3.30 (4H, t, J=4.9 Hz), 3.78 (4H, t, J=4.9 Hz), 4.67 (2H, s), 5.88 (1H, qd, J=7.1, 11.1 Hz), 6.43 (1H, dd, J=2.0, 11.1 Hz), 7.05 (1H, d, J=8.3 Hz), 7.34-7.40 (5H, m), 7.49 (1H, dd, J=1.7, 8.3 Hz), 7.53 (1H, d, J=1.7 Hz).

k) Preparation of (Z)-1-(4-{4-[2-(benzyloxy)-1,1,1,3,3,3-hexafluoropropan-2-yl]-2-(prop-1-en-1-yl)phenyl}piperazin-1-yl)-2-bromoethanone (Z)-1-{4-[2-(benzyloxy)-1,1,1,3,3,3-hexafluoropropan-2-yl]-2-(prop-1-en-1-yl)phenyl}piperazine (38 mg, 0.0595 mmol) was dissolved in dichloromethane (1.0 mL). Under ice-cold conditions, N,N'-dimethylaniline (9.0 μL, 0.0714 mmol) and bromoacetylbromide (5.5 μL, 0.0625 mmol) were added, and the mixture was stirred under ice-cold conditions for 0.5 hours. Then, under ice-cold conditions, N,N'-dimethylaniline (9.0 μL, 0.0714 mmol) and bromoacetylbromide (5.5

µL, 0.0625 mmol) were added, and the mixture was stirred under ice-cold conditions for 0.5 hours. The reaction solution was concentrated in vacuo, and the obtained residue was purified by silica-gel column chromatography (hexane/acetone). The title compound (16 mg (yield 47%)) was obtained as a yellow oil.

$^1$H-NMR (CDCl$_3$) δ: 1.74 (3H, dd, J=1.7, 7.1 Hz), 3.02 (2H, t, J=4.6 Hz), 3.09 (2H, t, J=4.6 Hz), 3.64 (2H, t, J=4.6 Hz), 3.76 (2H, t, J=4.6 Hz), 5.84 (1H, qd, J=7.1, 11.13 Hz), 6.84 (1H, dd, J=1.7, 11.7 Hz), 7.00 (1H, d, J=8.8 Hz), 7.49 (1H, dd, J=2.0, 8.8 Hz), 7.52 (1H, d, J=2.0 Hz).

l) Preparation of 5-[5-(1-methylethoxy)pyridin-2-yl]-5-methylimidazolidine-2,4-dione 5-hydroxy-2-methylpyridine (11.0 g, 100 mmol) was dissolved in N,N'-dimethylformamide (100 mL), added sodium hydride (7.2 g, 150 mmol) and 1-methylethane iodide (12 mL, 121 mmol) under ice-cold conditions, and the mixture was stirred at room temperature overnight. Then, 1-methylethane iodide (4 mL) was added, and the mixture was stirred at 60° C. for 4 hours. The reaction solution was added water, and extracted with diethylether. The organic layer was washed with brine, dried over sodium sulfate, and concentrated in vacuo. The obtained residue was purified by silica-gel column chromatography (hexane/ethyl acetate), and 5-(1-methylethoxy)-2-methylpyridine (12.7 g (yield 84%)) was obtained as a yellow oil.

$^1$H-NMR (CDCl$_3$) δ: 1.34 (6H, d, J=6.0 Hz), 2.48 (3H, s), 4.52 (1H, quint, J=6.0 Hz), 7.03-7.10 (2H, m), 8.17 (1H, d, J=2.4 Hz).

5-(1-methylethoxy)-2-methylpyridine (227 mg, 0.661 mmol) was dissolved in dichloromethane (7.5 mL), added 3-chloroperoxybenzoic acid (408 mg, 0.733 mmol) under ice-cold conditions, and the mixture was stirred at 0° C. for 45 minutes. The reaction solution was added ethyl acetate, saturated aqueous solution of sodium metabisulfite, and an aqueous solution of sodium hydrogen carbonate, and extracted with ethyl acetate. The organic layer was washed with brine, dried over sodium sulfate, and concentrated in vacuo. The obtained residue was purified by silica-gel column chromatography (ethyl acetate), and 5-(1-methylethoxy)-2-methylpyridine 1-oxide (240 mg (yield 6%)) was obtained as a colorless oil.

$^1$H-NMR (CDCl$_3$) δ: 1.35 (6H, d, J=6.2 Hz), 2.46 (3H, s), 4.47 (1H, quint, J=6.2 Hz), 6.82 (1H, dd, J=2.2, 8.9 Hz), 7.11 (1H, d, J=8.9 Hz), 8.05 (1H, d, J=2.2 Hz).

5-(1-methylethoxy)-2-methylpyridine 1-oxide (234 mg, 1.40 mmol) was dissolved in acetic anhydride (3.0 mL), and the mixture was stirred at 140° C. for 1 hour. At room temperature, the reaction solution was added methanol, stirred, concentrated in vacuo, and extracted with ethyl acetate. The organic layer was washed with an aqueous solution of sodium hydrogen carbonate and brine, dried over sodium sulfate, and concentrated in vacuo. The obtained residue was purified by silica-gel column chromatography (hexane/ethyl acetate) and [5-(1-methylethoxy)pyridin-2-yl]methyl acetate (209 mg (yield 71%)) was obtained as a yellow oil.

$^1$H-NMR (CDCl$_3$) δ: 1.36 (6H, d, J=6.2 Hz), 2.13 (3H, s), 4.58 (1H, quint, J=6.2 Hz), 5.13 (2H, s), 7.17 (1H, dd, J=2.4, 8.1 Hz), 7.26-7.30 (1H, m), 8.27 (1H, d, J=2.4 Hz).

[5-(1-Methylethoxy)pyridin-2-yl]methyl acetate (209 mg) was dissolved in methanol (2.0 mL), added potassium carbonate (276 mg, 2.0 mmol), and the mixture was stirred at room temperature for 1 hour. The reaction solution was concentrated in vacuo, added water and extracted with ethyl acetate. The organic layer was washed with brine, dried over sodium sulfate, and concentrated in vacuo. The obtained residue was purified by silica-gel column chromatography (hexane/ethyl acetate), and [5-(1-methylethoxy)pyridin-2-yl]methanol (137 mg (yield 83%)) was obtained as a yellow oil.

$^1$H-NMR (CDCl$_3$) δ: 1.36 (6H, d, J=6.0 Hz), 4.57 (1H, quint, J=6.0 Hz), 4.69 (2H, s), 7.15-7.22 (2H, m), 8.23 (1H, s).

[5-(1-Methylethoxy)pyridin-2-yl]methanol (30 mg, 0.198 mmol) was dissolved in acetone (2.0 mL), added 2,2,6,6-tetramethylpiperidine 1-oxyl (3.1 mg, 0.020 mmol) and trichloroisocyanuric acid (50 mg, 0.218 mmol) under ice-cold conditions, and the mixture was stirred at 0° C. for 5 minutes. The reaction solution was concentrated in vacuo, and the reaction solution was added an aqueous solution of sodium hydrogen carbonate, and extracted with ethyl acetate. The organic layer was washed with brine, dried over sodium sulfate, and concentrated in vacuo. The obtained residue was purified by silica-gel column chromatography (hexane/ethyl acetate), and 5-(1-methylethoxy)-picolinaldehyde (25 mg (yield 85%)) was obtained as a yellow oil.

$^1$H-NMR (CDCl$_3$) δ: 1.41 (6H, d, J=6.4 Hz), 4.71 (1H, quint, J=6.4 Hz), 7.25-7.27 (1H, m), 7.95 (1H, d, J=8.4 Hz), 8.39 (1H, d, J=2.8 Hz), 9.98 (1H, s).

5-(1-Methylethoxy)picolinaldehyde (24 mg, 0.145 mmol) was dissolved in tetrahydrofuran (1.5 mL), added methylmagnesium bromide (230 µL, 0.218 mmol) under ice-cold conditions, and the mixture was stirred at 0° C. for 0.5 hours. The mixture was further stirred at room temperature for 0.5 hours. The reaction solution was added 1N aqueous solution of hydrochloric acid and an aqueous solution of sodium hydrogen carbonate, and extracted with ethyl acetate. The organic layer was washed with brine, dried over sodium sulfate, and concentrated in vacuo. The obtained residue was purified by silica-gel column chromatography (hexane/ethyl acetate), and 1-[5-(1-methylethoxy)pyridin-2-yl]ethanol (27 mg (yield 98%)) was obtained as a brown oil.

$^1$H-NMR (CDCl$_3$) δ: 1.36 (6H, d, J=6.0 Hz), 1.48 (3H, d, J=6.4 Hz), 4.57 (1H, quint, J=6.0 Hz), 4.85 (1H, q, 6.4 Hz), 7.17-7.21 (2H, m), 8.19-8.20 (1H, m).

1-[5-(1-Methylethoxy)pyridin-2-yl]ethanol (22 mg, 0.119 mmol) was dissolved in acetone (1.2 mL), added 2,2,6,6-tetramethylpiperidine 1-oxyl (2.0 mg, 0.012 mmol) and trichloroisocyanuric acid (30 mg, 0.131 mmol) under ice-cold conditions, and the mixture was stirred at 0° C. for 10 minutes. The reaction solution was concentrated in vacuo, added an aqueous solution of sodium hydrogen carbonate, and extracted with ethyl acetate. The organic layer was washed with brine, dried over sodium sulfate, and concentrated in vacuo. The obtained residue was purified by silica-gel column chromatography (hexane/ethyl acetate), and 1-[5-(1-methylethoxy)pyridin-2-yl]ethanone (20 mg (yield 94%)) was obtained as a yellow oil.

$^1$H-NMR (CDCl$_3$) δ: 1.40 (6H, d, J=6.2 Hz), 2.68 (3H, s), 4.68 (1H, quint, J=6.2 Hz), 7.22 (1H, dd, J=2.7, 8.6 Hz), 8.03 (1H, d, J=8.6 Hz), 8.28 (1H, d, J=2.7 Hz).

1-[5-(1-Methylethoxy)pyridin-2-yl]ethanone was used for a similar reaction and treatment as Example 1-l), and the title compound was obtained as a white crystal.

$^1$H-NMR (CDCl$_3$) δ: 1.33 (6H, d, J=6.2 Hz), 1.79 (3H, s), 4.67 (1H, quint, J=6.2 Hz), 7.36 (1H, dd, J=2.7, 8.9 Hz), 7.46 (1H, d, J=8.9 Hz), 8.18 (1H, d, J=2.7 Hz).

m) Preparation of (Z)-3-[2-(4-{4-[2-(benzyloxy)-1,1,1,3,3,3-hexafluoropropan-2-yl]-2-(prop-1-en-1-yl)phenyl}piperazin-1-yl)-2-oxoethyl]-5-[5-(1-methylethoxy)pyridin-2-yl]-5-methylimidazolidine-2,4-dione 5-Methyl-5-[5-(1-methylethoxy)pyridin-2-yl]imidazolidine-2,4-dione (7.7 mg, 0.0309 mmol) was dissolved in N,N-dimethylformamide (2.8 mL), added potassium carbonate (9.3 mg, 0.0674 mmol) under ice-cold conditions, and the mixture was stirred at room temperature for 5 minutes. Then, under ice-cold conditions, 1-(4-{4-[2-(benzyloxy)-1,1,1,3,3,3-hexafluoropropan-2-yl]-2-(prop-1-en-1-yl)phenyl}piperazin-1-yl)-2-bromoethanone (16 mg, 0.0281 mmol) was added, and stirred at room temperature overnight. Then, the mixture was stirred at 60° C. for 10 hours. Under ice-cold conditions, the reaction solution was added water, and extracted with ethyl acetate. The organic layer was washed with brine, dried over anhydrous sodium sulfate, and concentrated in vacuo. The obtained residue was purified by silica-gel column chromatography (hexane/acetone), and the title compound (17 mg (yield 80%)) was obtained as a yellow oil.

$^1$H-NMR (CDCl$_3$) δ: 1.35 (6H, d, J=6.1 Hz), 1.73 (3H, dd, J=1.7, 7.1 Hz), 1.86 (3H, s), 3.00 (2H, t, J=4.6 Hz), 3.07 (2H, t, J=4.6 Hz), 3.59 (2H, t, J=4.6 Hz), 3.73 (2H, t, J=4.6 Hz), 4.36 (2H, s), 4.56 (1H, q, J=6.1 Hz), 4.67 (2H, s), 5.84 (1H, qd, J=7.1, 11.13 Hz), 4.33 (1H, s), 6.47 (1H, dd, J=1.7, 7.1 Hz), 6.99 (1H, dd, J=2.4, 8.8 Hz), 7.18 (1H, dd, J=2.4, 8.8 Hz), 7.31-7.39 (5H, m), 7.46 (1H, dd, J=2.0, 8.6 Hz), 7.52 (1H, d, J=2.0 Hz), 7.62 (1H, d, J=8.8 Hz), 8.20 (1H, d, J=2.4 Hz).

n) Preparation of 3-(2-{4-[4-(1,1,1,3,3,3-hexafluoro-2-hydroxpropan-2-yl)-2-propylphenyl]piperazin-1-yl}-2-oxoethyl)-5-[5-(1-methylethoxy)pyridin-2-yl]-5-methylimidazolidine-2,4-dione (Z)-3-[2-(4-{4-[2-(benzyloxy)-1,1,1,3,3,3-hexafluoropropan-2-yl]-2-(prop-1-en-1-yl)phenyl}piperazin-1-yl)-2-oxoethyl]-5-[5-(1-methylethoxy)pyridin-2-yl]-5-methylimidazolidine-2,4-dione (17 mg, 0.0225 mmol) was dissolved in methanol (2.0 mL), added palladium hydroxide (6.0 mg), and the mixture was stirred at room temperature for 12 hours under a hydrogen atmosphere. The reaction solution was filtered through a pad of celite, and concentrated in vacuo. The obtained residue was purified by silica-gel column chromatography (chloroform), and the title compound (10 mg (yield 67%)) was obtained as a pale yellow oil.

$^1$H-NMR (CDCl$_3$) δ: 0.96 (3H, t, J=7.3 Hz), 1.35 (6H, d, J=5.6 Hz), 1.67 (2H, qt, J=7.3, 7.8 Hz), 1.87 (3H, s), 2.66 (2H, t, J=7.8 Hz), 2.89 (2H, t, J=4.6 Hz), 2.96 (2H, t, J=4.6 Hz), 3.58 (1H, s), 3.62 (2H, t, J=4.6 Hz), 3.75 (2H, t, J=4.6 Hz), 4.38 (2H, s), 4.56 (1H, q, J=5.6 Hz), 6.41 (1H, brs), 7.07 (1H, d, J=8.3 Hz), 7.18 (1H, dd, J=2.4, 8.8 Hz), 7.50 (1H, dd, J=2.0, 8.3 Hz), 7.54 (1H, d, J=2.0 Hz), 87.63 (1H, d, J=8.8 Hz), 8.20 (1H, d, J=2.4 Hz).

Example 7

Preparation of 3-(2-{4-[4-(1,1,1,3,3,3-hexafluoro-2-hydroxypropan-2-yl)-2-propylphenyl]piperazin-1-yl}-2-oxoethyl)-5-[4-(1-methylethoxy)phenyl]-5-methylimidazolidine-2,4-dione

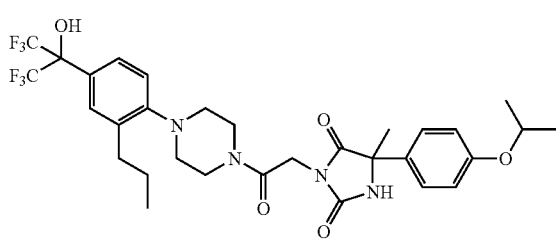 [SMILES: CCCc1cc(C(O)(C(F)(F)F)C(F)(F)F)ccc1N1CCN(C(=O)CN2C(=O)NC(C)(c3ccc(OC(C)C)cc3)C2=O)CC1]

5-[4-(1-Methylethoxy)phenyl]-5-methylimidazolidine-2,4-dione was used for a similar reaction and treatment as Example 6, and the title compound was obtained as a yellow oil.

$^1$H-NMR (CDCl$_3$) δ: 0.96 (3H, t, J=7.3 Hz), 1.32 (6H, d, J=6.1 Hz), 1.66 (2H, qt, J=7.3, 8.0 Hz), 1.90 (3H, s), 2.66 (2H, t, J=8.0 Hz), 2.88 (2H, t, J=4.6 Hz), 2.96 (2H, t, J=4.6 Hz), 3.60 (2H, t, J=4.6 Hz), 3.74 (2H, t, J=4.6 Hz), 3.75 (1H, s), 4.31-4.40 (2H, m), 4.54 (1H, q, J=6.1 Hz), 5.84 (1H, brs), 6.90 (2H, d, J=8.8 Hz), 7.06 (1H, d, J=8.6 Hz), 7.45 (2H, d, J=8.8 Hz), 7.50 (1H, dd, J=2.0, 8.8 Hz), 7.53 (1H, d, J=2.0 Hz).

Example 8

Preparation of 5-(2,3-dihydrobenzofuran-5-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione

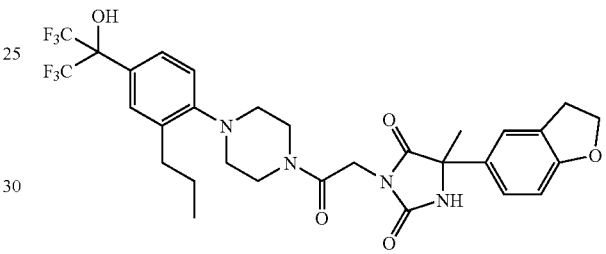

5-(2,3-Dihydrobenzofuran-5-yl)-5-methylimidazolidine-2,4-dione was used for a similar reaction and treatment as Example 6, and the title compound was obtained as a yellow oil.

$^1$H-NMR (CDCl$_3$) δ: 0.96 (3H, t, J=7.3 Hz), 1.66 (2H, qt, J=7.3, 8.0 Hz), 1.89 (3H, s), 2.65 (2H, t, J=8.0 Hz), 2.87 (2H, t, J=4.6 Hz), 2.96 (2H, t, J=4.6 Hz), 3.21 (2H, t, J=8.6 Hz), 3.48 (1H, s), 3.60 (2H, t, J=4.6 Hz), 3.74 (2H, t, J=4.6 Hz), 4.35 (2H, dd, J=4.4, 20.5 Hz), 4.57 (2H, t, J=8.6 Hz), 5.99 (1H, brs), 6.78 (1H, d, J=8.5 Hz), 7.05 (1H, J=8.5 Hz), 7.29 (1H, dd, J=4.9, 8.5 Hz), 7.41 (1H, d, J=4.9 Hz), 7.50 (1H, dd, J=2.0, 8.5 Hz), 7.99 (1H, d, J=2.0 Hz).

Example 9

Preparation of 5-(benzo[d][1,3]dioxol-5-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione

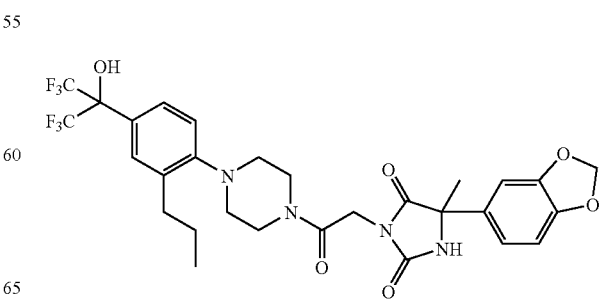

5-(Benzo[d][1,3]dioxol-5-yl)-5-methylimidazolidine-2,4-dione was used for a similar reaction and treatment as Example 6, and the title compound was obtained as a yellow oil.

$^1$H-NMR (CDCl$_3$) δ: 0.97 (3H, t, J=7.3 Hz), 1.67 (2H, qt, J=7.3, 7.8 Hz), 1.89 (3H, s), 2.66 (2H, t, J=7.8 Hz), 2.89 (2H, t, J=4.6 Hz), 2.96 (2H, t, J=4.6 Hz), 3.61 (2H, t, J=4.6 Hz), 3.65 (1H, s), 3.76 (2H, t, J=4.6 Hz), 4.31-4.40 (2H, m), 5.73 (1H, s), 5.97 (2H, s), 6.82 (1H, d, J=8.3 Hz), 7.03 (1H, dd, J=2.0, 8.3 Hz), 7.06-7.09 (2H, m), 7.49-7.53 (2H, m).

Example 10

Preparation of 5-(2,3-dihydrobenzofuran-5-yl)-3-(2-{4-[6-(1,1,1,3,3,3-hexafluoro-2-hydroxypropan-2-yl)-4-propylpyridin-3-yl]piperazin-1-yl}-2-oxoethyl)-5-methylimidazolidine-2,4-dione

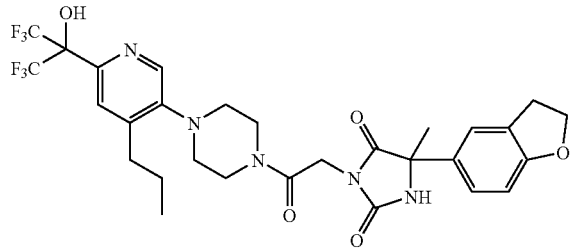 [SMILES: CCCc1cc(C(O)(C(F)(F)F)C(F)(F)F)ncc1N1CCN(C(=O)CN2C(=O)NC(C)(c3ccc4c(c3)CCO4)C2=O)CC1]

a) Preparation of 4-propylpyridine-2-amine

To a solution of 4-propylpyridine (10.0 g, 82.5 mmol) in toluene (170 mL), sodium amide (6.4 g, 165 mmol) was added at room temperature, and the mixture was stirred at 140° C. for 2 days. Under ice-cold conditions, the reaction solution was added 6N aqueous solution of hydrochloric acid (30 mL), and extracted with ethyl acetate. The organic layer was washed with brine, dried over anhydrous sodium sulfate, and concentrated in vacuo. The obtained residue was purified by silica-gel column chromatography (hexane/ethyl acetate/1% triethylamine), and the title compound (5.70 g (yield 51%)) was obtained as a red-brown solid.

$^1$H-NMR (CDCl$_3$) δ: 0.94 (3H, t, J=7.3 Hz), 1.57-1.66 (2H, m), 2.46 (2H, J=7.8 Hz), 4.32 (2H, br), 6.32 (1H, s), 6.49 (1H, d, J=4.2 Hz), 7.95 (1H, d, J=, 4.2 Hz).

b) Preparation of 5-bromo-4-propylpyridin-2-amine

To a solution of 4-propylpyridin-2-amine (5.70 g, 41.8 mmol) in ethanol (210 mL), a solution of bromine in ethanol (bromine 2.38 mL/ethanol 50 mL) was added under ice-cold conditions, and the mixture was stirred under ice-cold conditions for 0.5 hours. Under ice-cold conditions, the reaction solution was added an aqueous solution of sodium hydrogen carbonate, concentrated in vacuo, and extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (4.34 g (yield 48%)) was obtained as a brown oil.

$^1$H-NMR (CDCl$_3$) δ: 0.99 (3H, t, J=7.6 Hz), 1.58-1.70 (2H, m), 2.54-2.60 (2H, m), 4.36 (2H, br), 6.38 (1H, s), 8.08 (1H, s).

c) Preparation of 2,5-dibromo-4-propylpyridine

5-Bromo-4-propylpyridine-2-amine (5.67 g, 26.3 mmol) was added 48% hydrogen bromide (21 mL) at 10° C. The mixture was added bromine (4.0 mL) under ice-cold conditions, and added dropwise with an aqueous solution (4.5 mL) of sodium nitrite (4.54 g) at −10° C. The mixture was stirred at −10° C. for 0.5 hours, then added 1N aqueous solution of sodium hydroxide (10 mL), and stirred at room temperature for 2 hours. The reaction solution was added water, extracted with diethylether. The organic layer was washed with brine, dried over anhydrous sodium sulfate, and concentrated in vacuo. The obtained residue was purified by silica-gel column chromatography (diethylether), and the title compound (6.96 g (yield 95%)) was obtained as a brown oil.

$^1$H-NMR (CDCl$_3$) δ: 1.01 (3H, t, J=7.3 Hz), 1.62-1.69 (2H, m), 2.66 (2H, t, J=7.8 Hz), 7.33 (1H, s), 8.40 (1H, s).

d) Preparation of 5-bromo-4-propylpicolinonitrile

To a solution of 2,5-dibromo-4-propylpyridine (100 mg, 0.444 mmol) in N,N-dimethylformamide (0.9 mL), dinitrile zinc (57 mg, 0.449 mmol) and tetrakistriphenylphosphine palladium (25 mg, 0.0222 mmol) were added at room temperature, and the mixture was stirred under microwave irradiation at 100° C. for 20 minutes. The reaction solution was added a saturated aqueous solution of sodium hydrogen carbonate, and extracted with hexane/ethyl acetate (4/1). The organic layer was washed with brine, dried over anhydrous sodium sulfate, and concentrated in vacuo. The obtained residue was purified by silica-gel column chromatography (hexane/ethyl acetate), and the title compound (60 mg (yield 60%)) was obtained as a colorless crystal.

$^1$H-NMR (CDCl$_3$) δ: 1.02 (3H, t, J=7.6 Hz), 1.66-1.72 (2H, m), 2.75 (2H, t, J=7.6 Hz), 7.53 (1H, s), 8.74 (1H, s).

e) Preparation of methyl 5-bromo-4-propyl picolinate

To a solution of 5-bromo-4-propylpicolinonitrile (15 mg, 0.0670 mmol) in methanol (1.3 mL), sulfuric acid (180 μL, 0.0670 mmol) was added under ice-cold conditions, and the mixture was stirred at 80° C. overnight. The reaction solution was added 1N-aqueous solution of sodium hydroxide and a saturated aqueous solution of sodium hydrogen carbonate under ice-cold conditions, methanol was concentrated in vacuo, and extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (11 mg (yield 62%)) was obtained as a brown crystal.

$^1$H-NMR (CDCl$_3$) δ: 1.02 (3H, t, J=7.3 Hz), 1.66-1.75 (2H, m), 2.74-2.80 (2H, m), 4.01 (3H, s), 8.00 (1H, s), 8.75 (1H, s).

f) Preparation of tert-butyl 4-[6-(methoxycarbonyl)-4-propylpyridin-3-yl]piperazine-1-carboxylate To a solution of methyl 5-bromo-4-propyl picolinate I(100 mg, 0.387 mmol) in toluene (1.94 mL), 1-tert-butoxycarbonylpiperazine (84 mg, 0.453 mmol), tris(dibenzylidene acetone)dipalladium (8.3 mg, 0.00902 mmol), BINAP (11.2 mg, 0.0180 mmol) and cesium carbonate (295 mg, 0.906 mmol) were added, and the mixture was stirred at 110° C. for 14 hours. The reaction solution was added water, and extracted with chloroform. The organic layer was washed with brine, dried over anhydrous sodium sulfate, and concentrated in vacuo. The obtained residue was purified by silica-gel column chromatography (ethyl acetate), and the title compound (70 mg (yield 49%)) was obtained as a pale yellow crystal.

$^1$H-NMR (CDCl$_3$) δ: 0.99 (3H, t, J=7.0 Hz), 1.49 (9H, s), 1.73 (2H, qt, J=7.0, 7.6 Hz), 2.66 (2H, t, J=7.6 Hz), 2.99 (4H, t, J=5.1 Hz), 3.60 (4H, t, J=5.1 Hz), 3.98 (3H, s), 7.99 (1H, s), 8.33 (1H, s).

g) Preparation of 5-[4-(tert-butoxycarbonyl)piperazin-1-yl]-4-propyl picolinic acid To a solution of tert-butyl 4-[6-(methoxycarbonyl)-4-propylpyridin-3-yl]piperazine-1-carboxylate (111 mg, 0.307 mmol) in methanol (3.0 mL), 4N aqueous solution of sodium hydroxide (383 μL, 1.53 mmol) was added under ice-cold conditions, and the mixture was stirred at room temperature overnight. The reaction solution was added 4N aqueous solution of hydrochloric acid under ice-cold conditions, and extracted with chloroform. The organic layer was washed with brine, dried over anhydrous sodium sulfate, and concentrated in vacuo. The obtained residue was purified by silica-gel column chromatography (chloroform), and the title compound (134 mg (yield >99%)) was obtained as a yellow crystal.

$^1$H-NMR (CDCl$_3$) δ: 1.01 (3H, t, J=7.3 Hz), 1.49 (9H, s), 1.77 (2H, qt, J=7.3, 7.6 Hz), 2.79 (2H, t, J=7.6 Hz), 3.03 (4H, t, J=5.1 Hz), 3.61 (4H, t, J=5.1 Hz), 4.90 (1H, brs), 8.06 (1H, s), 8.28 (1H, s).

h) Preparation of tert-butyl 4-{6-[(perfluorophenoxy)carbonyl]-4-propylpyridin-3-yl}piperazine-1-carboxylate 5-[4-(tert-Butoxycarbonyl)piperazin-1-yl]-4-propyl picolinic acid (134 mg, 0.307 mmol) was dissolved in ethyl acetate (6.2 mL). At room temperature, pentafluorophenol (68 mg, 0.368 mmol) and N,N'-dicyclohexylcarbodiimide (76 mg, 0.368 mmol) were added sequentially, and the mixture was stirred at room temperature overnight. The reaction solution was added water under ice-cold conditions, and extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (189 mg (yield >99%)) was obtained as a yellow brown crystal.

$^1$H-NMR (CDCl$_3$) δ: 1.03 (3H, t, J=7.2 Hz), 1.50 (9H, s), 1.78 (2H, qt, J=7.2, 8.0 Hz), 2.71 (2H, t, J=8.0 Hz), 3.06 (4H, t, J=5.2 Hz), 3.63 (4H, t, J=5.2 Hz), 8.13 (1H, s), 8.42 (1H, s).

i) Preparation of tert-butyl 4-[6-(1,1,1,3,3,3-hexafluoro-2-hydroxypropan-2-yl)-4-propylpyridin-3-yl]piperazine-1-carboxylate tert-Butyl 4-{6-[(perfluorophenoxy)carbonyl]-4-propylpyridin-3-yl}piperazine-1-carboxylate (189 mg, 0.307 mmol) was dried with a vacuum pump, and dissolved in ethylene glycol dimethyl ether (6.2 mL). Under −78° C., trifluoromethyltrimethylsilane (227 μL, 1.53 mmol) and tetramethyl ammonium fluoride (143 mg, 1.53 mmol) were added sequentially, heated gradually to room temperature, and the mixture was stirred overnight. The reaction solution was added water under ice-cold conditions, and extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (60 mg (yield 41%)) was obtained as a yellow oil.

$^1$H-NMR (CDCl$_3$) δ: 1.00 (3H, t, J=7.3 Hz), 1.50 (9H, s), 1.71 (2H, qt, J=7.3, 7.6 Hz), 2.70 (2H, t, J=7.6 Hz), 2.97 (4H, t, J=4.9 Hz), 3.60 (4H, t, J=4.9 Hz), 3.90 (1H, brs), 7.53 (1H, s), 8.25 (1H, s).

j) Preparation of tert-butyl 4-{6-[2-(benzyloxy)-1,1,1,3,3,3-hexafluoropropan-2-yl]-4-propylpyridin-3-yl}piperazine-1-carboxylate tert-Butyl 4-[6-(1,1,1,3,3,3-hexafluoro-2-hydroxypropan-2-yl)-4-propylpyridin-3-yl]piperazine-1-carboxylate (60 mg, 0.126 mmol) was dried with a vacuum pump, and dissolved in N,N-dimethylformamide (2.5 mL). Sodium hydride (7.3 mg, 0.152 mmol) and benzyl bromide (17 μL, 0.139 mmol) were added sequentially under ice-cold conditions, and the mixture was stirred at room temperature overnight. The reaction solution was added water under ice-cold conditions, and extracted with ethyl acetate. The organic layer was washed with brine, dried over anhydrous sodium sulfate, and concentrated in vacuo. The obtained residue was purified by silica-gel column chromatography (hexane/acetone), and the title compound (54 mg (yield 76%)) was obtained as a yellow oil.

$^1$H-NMR (CDCl$_3$) δ: 0.91 (3H, t, J=7.2 Hz), 1.49 (9H, s), 1.56 (2H, qt, J=7.2, 7.6 Hz), 2.61 (2H, t, J=7.6 Hz), 2.96 (4H, t, J=4.8 Hz), 3.58 (4H, t, J=4.8 Hz), 4.68 (2H, s), 7.32-7.41 (5H, m), 7.46 (1H, s), 8.39 (1H, s).

k) Preparation of 1-{6-[2-(benzyloxy)-1,1,1,3,3,3-hexafluoropropan-2-yl]-4-propylpyridin-3-yl}piperazine tert-Butyl 4-{6-[2-(benzyloxy)-1,1,1,3,3,3-hexafluoropropan-2-yl]-4-propylpyridin-3-yl}piperazine-1-carboxylate (32 mg, 0.0563 mmol) was dissolved in dichloromethane (10 mL). Under ice-cold conditions, trifluoro acetic acid (43 μL, 0.563 mmol) was added and the mixture was stirred at room temperature for 0.5 hours. The reaction solution was added a saturated aqueous solution of sodium hydrogen carbonate under ice-cold conditions, and extracted with chloroform. The organic layer was washed with brine, dried over anhydrous sodium sulfate, and concentrated in vacuo. The obtained residue was purified by silica-gel column chromatography (chloroform), and the title compound (27 mg (yield >99%)) was obtained as a yellow oil.

$^1$H-NMR (CDCl$_3$) δ: 0.91 (3H, t, J=7.2 Hz), 1.56 (2H, qt, J=7.3, 7.6 Hz), 2.61 (2H, t, J=7.6 Hz), 2.99-3.05 (8H, m), 3.58 (1H, s), 4.68 (2H, s), 7.32-7.41 (5H, m), 7.46 (1H, s), 8.41 (1H, s).

l) Preparation of 1-(4-{6-[2-(benzyloxy)-1,1,1,3,3,3-hexafluoropropan-2-yl]-4-propylpyridin-3-yl}piperazin-1-yl)-2-bromoethanone 1-{6-[2-(Benzyloxy)-1,1,1,3,3,3-hexafluoropropan-2-yl]-4-propylpyridin-3-yl}piperazine (27 mg, 0.0563 mmol) was dissolved in dichloromethane (1.0 mL). Under ice-cold conditions, N,N'-dimethylaniline (15 μL, 0.118 mmol) and bromoacetylbromide (5.1 μL, 0.0591 mmol) were added, and the mixture was stirred under ice-cold conditions for 20 minutes. The reaction solution was concentrated in vacuo. The obtained residue was purified by silica-gel column chromatography (hexane/acetone), and the title compound (25 mg (yield 78%)) was obtained as a yellow oil.

$^1$H-NMR (CDCl$_3$) δ: 0.92 (3H, t, J=7.2 Hz), 1.57 (2H, qt, J=7.2, 7.6 Hz), 2.63 (2H, t, J=7.6 Hz), 3.02 (2H, t, J=4.8 Hz), 3.10 (2H, t, J=4.8 Hz), 3.69 (2H, t, J=4.8 Hz), 3.80 (2H, t, J=4.8 Hz), 3.92 (2H, s), 4.69 (2H, s), 7.33-7.41 (5H, m), 7.48 (1H, s), 8.41 (1H, s).

m) Preparation of 3-[2-(4-{6-[2-(benzyloxy)-1,1,1,3,3,3-hexafluoropropan-2-yl]-4-propylpyridin-3-yl}piperazin-1-yl)-2-oxoethyl]-5-(2,3-dihydrobenzofuran-5-yl)-5-methylimidazolidine-2,4-dione 5-(2,3-Dihydrobenzofuran-5-yl)-5-methylimidazolidine-2,4-dione (5.6 mg, 0.0240 mmol) was dissolved in N,N-dimethylformamide (500 μL), and potassium carbonate (7.5 mg, 0.0545 mmol) was added under ice-cold conditions. The mixture was stirred at room temperature for 5 minutes. Then, under ice-cold conditions, 1-(4-{6-[2-(benzyloxy)-1,1,1,3,3,3-hexafluoropropan-2-yl]-4-propylpyridin-3-yl}piperazin-1-yl)-2-bromoethanone (13 mg, 0.0218 mmol) was added and stirred at room temperature for 18 hours. Under ice-cold conditions, the reaction solution was added water, and extracted with ethyl acetate. The organic layer was washed with brine, dried over anhydrous sodium sulfate, and concentrated in vacuo. The obtained residue was purified by silica-gel column chromatography (hexane/acetone), and the title compound (13 mg (yield 78%)) was obtained as a yellow oil.

$^1$H-NMR (CDCl$_3$) δ: 0.91 (3H, t, J=7.3 Hz), 1.56 (2H, qt, J=7.3, 8.0 Hz), 1.90 (3H, s), 2.62 (2H, t, J=8.0 Hz), 3.00 (2H, t, J=4.8 Hz), 3.08 (2H, t, J=4.8 Hz), 3.22 (2H, t, J=8.8 Hz), 3.63 (2H, t, J=4.8 Hz), 3.77 (2H, t, J=4.8 Hz), 4.31-4.41 (2H, m), 4.58 (2H, t, J=8.8 Hz), 4.68 (2H, s), 5.75 (1H, s), 6.78 (1H, d, J=8.3 Hz), 7.29 (1H, dd, J=2.0, 8.3 Hz), 7.33-7.41 (6H, m), 7.48 (1H, s), 8.40 (1H, s).

n) Preparation of 5-(2,3-dihydrobenzofuran-5-yl)-3-(2-{4-[6-(1,1,1,3,3,3-hexafluoro-2-hydroxypropan-2-yl)-4-propylpyridin-3-yl]piperazin-1-yl}-2-oxoethyl)-5-methylimidazolidine-2,4-dione 3-[2-(4-{6-[2-(Benzyloxy)-1,1,1,3,3,3-hexafluoropropan-2-yl]-4-propylpyridin-3-yl}piperazin-1-yl)-2-oxoethyl]-5-(2,3-dihydrobenzofuran-5-yl)-5-methylimidazolidine-2,4-dione (13 mg, 0.0170 mmol) was dissolved in methanol (1.5 mL), added palladium carbon (2.0 mg), and the mixture was stirred at room temperature for 2 hours under a hydrogen atomosphere. The reaction solution was filtered through a pad of celite, and concentrated in vacuo. The obtained residue was purified by silica-gel column chromatography (hexane/acetone), and the title compound (7.3 mg (yield 80%)) was obtained as a yellow oil.

$^1$H-NMR (CDCl$_3$) δ: 1.00 (3H, t, J=7.3 Hz), 1.72 (2H, qt, J=7.3, 7.6 Hz), 1.90 (3H, s), 2.71 (2H, t, J=7.6 Hz), 3.01 (2H, t, J=4.6 Hz), 3.09 (2H, t, J=4.6 Hz), 3.22 (2H, t, J=8.8 Hz), 3.65 (2H, t, J=4.6 Hz), 3.76 (1H, s), 3.80 (2H, t, J=4.6 Hz), 4.32-4.41 (2H, m), 4.58 (2H, t, J=8.8 Hz), 5.59 (1H, s), 6.79 (1H, d, J=8.3 Hz), 7.30 (1H, dd, J=2.0, 8.3 Hz), 7.40 (1H, d, J=2.0 Hz), 7.55 (1H, s), 8.27 (1H, s).

Example 11

Preparation of 3-(2-{4-[6-(1,1,1,3,3,3-hexafluoro-2-hydroxypropan-2-yl)-4-propylpyridin-3-yl]piperazin-1-yl}-2-oxoethyl)-5-[4-(1-methylethoxy)phenyl]-5-methylimidazolidine-2,4-dione

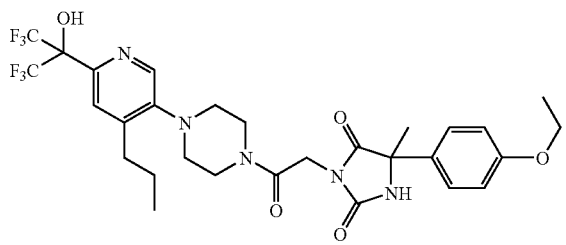 [SMILES: CCCc1cc(C(O)(C(F)(F)F)C(F)(F)F)ncc1N1CCN(C(=O)CN2C(=O)NC(C)(c3ccc(OCC)cc3)C2=O)CC1]

5-[4-(1-Methylethoxy)phenyl]-5-methylimidazolidine-2,4-dione was used for a similar reaction and treatment as Example 10, and the title compound was obtained as a yellow oil.

$^1$H-NMR (CDCl$_3$) δ: 1.00 (3H, t, J=7.3 Hz), 1.33 (6H, d, J=6.1 Hz), 1.72 (2H, qt, J=7.3, 7.6 Hz), 1.91 (3H, s), 2.71 (2H, t, J=7.6 Hz), 3.01 (2H, t, J=4.9 Hz), 3.09 (2H, t, J=4.9 Hz), 3.65 (2H, t, J=4.9 Hz), 3.75 (1H, s), 3.79 (2H, t, J=4.9 Hz), 4.32-4.41 (2H, m), 4.54 (1H, t, J=6.1 Hz), 5.70 (1H, s), 6.90 (2H, d, J=8.8 Hz), 7.45 (2H, d, J=8.8 Hz), 7.54 (1H, s), 8.27 (1H, s).

Example 12

Preparation of (R)-3-(2-{4-[4-(1,1,1,3,3,3-hexafluoro-2-hydroxypropan-2-yl)-2-propylphenyl]-3-methylpiperazin-1-yl}-2-oxoethyl)-5-[4-(1-methylethoxy)phenyl]-5-methylimidazolidine-2,4-dione

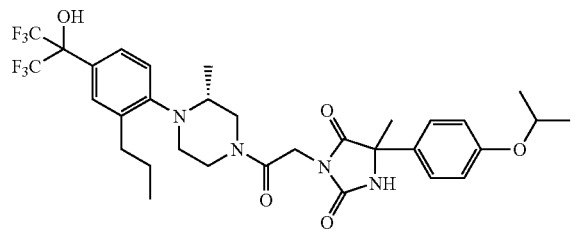 [SMILES: CCCc1cc(C(O)(C(F)(F)F)C(F)(F)F)ccc1N1CCN(C(=O)CN2C(=O)NC(C)(c3ccc(OC(C)C)cc3)C2=O)C[C@H]1C]

a) Preparation of tert-butyl (R)-4-[4-(methoxycarbonyl)-2-nitrophenyl]-3-methylpiperazine-1-carboxylate (R)-3-methyl-1-tert-butoxycarbonylpiperazine was used in place of 1-tert-butoxycarbonylpiperazine for a similar reaction and treatment as Example 6-b), and the title compound was obtained as a yellow oil.

$^1$H-NMR (CDCl$_3$) δ: 1.04 (3H, d, J=6.8 Hz), 1.48 (9H, s), 2.83-2.92 (1H, m), 3.34-3.51 (6H, m), 3.92 (3H, s), 7.14 (1H, d, J=8.6 Hz), 8.10 (1H, dd, J=1.9, 8.6 Hz), 8.39 (1H, d, J=1.9 Hz).

b) Preparation of tert-butyl (R)-4-[2-amino-4-(methoxycarbonyl)phenyl]-3-methylpiperazine-1-carboxylate By conducting a similar reaction and treatment as Example 6-c), the title compound (7.3 mg (yield 80%)) was obtained as a yellow oil.

$^1$H-NMR (CDCl$_3$) δ: 0.86 (3H, d, J=5.9 Hz), 1.49 (9H, s), 2.56-2.66 (1H, m), 2.82-3.2 (6H, m), 3.87 (3H, s), 4.18 (2H, brs), 7.02 (1H, d, J=8.6 Hz), 7.39-7.42 (2H, m).

c) Preparation of tert-butyl (R)-4-[2-iodo-4-(methoxycarbonyl)phenyl]-3-methylpiperazine-1-carboxylate By conducting a similar reaction and treatment as Example 6-d), the title compound (7.3 mg (yield 80%)) was obtained as a yellow oil.

$^1$H-NMR (CDCl$_3$) δ: 1.00 (3H, t, J=7.3 Hz), 1.33 (6H, d, J=6.1 Hz), 1.72 (2H, qt, J=7.3, 7.6 Hz), 1.91 (3H, s), 2.71 (2H, t, J=7.6 Hz), 3.01 (2H, t, J=4.9 Hz), 3.09 (2H, t, J=4.9 Hz), 3.65 (2H, t, J=4.9 Hz).

d) Preparation of tert-butyl (R,Z)-4-[4-(methoxycarbonyl)-2-(prop-1-en-1-yl)phenyl]-3-methylpiperazine-1-carboxylate By conducting a similar reaction and treatment as Example 6-e), the title compound was obtained as a yellow oil.

$^1$H-NMR (CDCl$_3$) δ: 0.91 (3H, d, J=6.2 Hz), 1.48 (9H, s), 1.88 (3H, d, J=6.8 Hz), 2.70-2.78 (1H, m), 3.10-3.55 (6H, m), 3.89 (3H, s), 5.76-5.88 (1H, m), 6.49 (1H, d, J=11.6 Hz), 6.96 (1H, d, J=8.6 Hz), 7.87 (1H, dd, J=1.9, 8.6 Hz), 7.94 (1H, d, J=1.9 Hz).

e) Preparation of (R,Z)-4-[4-(tert-butoxycarbonyl)-2-methylpiperazin-1-yl]-3-(prop-1-en-1-yl)benzoic acid By conducting a similar reaction and treatment as Example 6-f), the title compound was obtained as a yellow oil.

$^1$H-NMR (CDCl$_3$) δ: 0.93 (3H, d, J=6.2 Hz), 1.48 (9H, s), 1.89 (3H, d, J=6.2 Hz), 2.72-2.80 (1H, m), 3.19-3.57 (6H, m), 5.75-5.90 (1H, m), 6.47 (1H, d, J=10.8 Hz), 6.97 (1H, d, J=8.4 Hz), 7.93 (1H, d, J=8.4 Hz), 8.00 (1H, s).

f) Preparation of tert-butyl (R,Z)-3-methyl-4-{4-[(perfluorophenoxy)carbonyl]-2-(prop-1-en-1-yl)phenyl}piperazine-1-carboxylate By conducting a similar reaction and treatment as Example 6-g), the title compound was obtained as a yellow oil.

$^1$H-NMR (CDCl$_3$) δ: 0.97 (3H, d, J=6.5 Hz), 1.49 (9H, s), 1.90 (3H, d, J=7.0 Hz), 2.80-2.90 (1H, m), 3.20-3.70 (6H, m), 5.81-5.93 (1H, m), 6.46 (1H, d, J=11.0 Hz), 7.02 (1H, d, J=8.1 Hz), 8.04 (1H, d, J=8.1 Hz), 8.06 (1H, s).

g) Preparation of tert-butyl (R,Z)-4-[4-(1,1,1,3,3,3-hexafluoro-2-hydroxypropan-2-yl)-2-(prop-1-en-1-yl)phenyl]-3-methylpiperazine-1-carboxylate By conducting a similar reaction and treatment as Example 6-h), the title compound was obtained as a yellow oil.

$^1$H-NMR (CDCl$_3$) δ: 0.90 (3H, d, J=6.2 Hz), 1.48 (9H, s), 1.83 (3H, d, J=6.8 Hz), 2.65-2.73 (1H, m), 3.08-3.18 (1H, m), 3.25-3.68 (5H, m), 5.76-5.88 (1H, m), 6.56 (1H, d, J=13.2 Hz), 7.02 (1H, d, J=8.4 Hz), 7.53 (1H, d, J=8.4 Hz), 7.59 (1H, s).

h) Preparation of (R,Z)-1,1,1,3,3,3-hexafluoro-2-[4-(2-methylpiperazin-1-yl)-3-(prop-1-en-1-yl)phenyl]propan-2-ol By conducting a similar reaction and treatment as Example 6-j), the title compound was obtained as a yellow oil.

$^1$H-NMR (CDCl$_3$) δ: 0.96 (3H, d, J=6.2 Hz), 1.81 (3H, d, J=6.8 Hz), 2.76-2.85 (2H, m), 3.08-3.29 (4H, m), 3.45-3.55 (1H, m), 5.78-5.90 (1H, m), 6.59 (1H, d, J=13.2 Hz), 7.14 (1H, d, J=8.9 Hz), 7.61 (1H, d, J=8.9 Hz), 7.62 (1H, s).

i) Preparation of (R,Z)-1-{4-[1,1,1,3,3,3-hexafluoro-2-(methoxymethoxy)propan-2-yl]-2-(prop-1-en-1-yl)phenyl}-2-methylpiperazine A similar reaction and treatment as Example 6-i) was conducted except that methoxymethyl ether chloride was used in place of benzyl bromide, and the title compound (7.3 mg (yield 90%)) was obtained as a yellow oil.

$^1$H-NMR (CDCl$_3$) δ: 0.94 (3H, d, J=5.9 Hz), 1.82 (3H, d, J=6.5 Hz), 2.70-2.76 (3H, m), 2.95-3.18 (3H, m), 3.35-3.49 (1H, m), 3.55 (3H, s), 4.87 (2H, s), 5.76-5.89 (1H, m), 6.58 (1H, d, J=11.3 Hz), 7.08 (1H, d, J=8.4 Hz), 7.44 (1H, d, J=8.4 Hz), 7.51 (1H, s).

j) Preparation of (R,Z)-2-bromo-1-(4-{4-[1,1,1,3,3,3-hexafluoro-2-(methoxymethoxy)propan-2-yl]-2-(prop-1-en-1-yl)phenyl}-3-methylpiperazin-1-yl)ethanone By conducting a similar reaction and treatment as Example 6-k), the title compound was obtained as a yellow oil.

$^1$H-NMR (CDCl$_3$) δ: 0.94 (3H, d, J=5.9 Hz), 1.82 (3H, d, J=7.0 Hz), 2.75-2.87 (2H, m), 3.11-3.39 (2H, m), 3.49-3.81 (3H, m), 3.55 (3H, s), 3.89 (1H, d, J=10.0 Hz), 3.92 (1H, d, J=10.0 Hz), 4.87 (2H, s), 5.79-5.82 (1H, m), 6.56 (1H, d, J=11.9 Hz), 7.03 (1H, d, J=7.3 Hz), 7.45 (1H, d, J=7.3 Hz), 7.52 (1H, s).

k) Preparation of (R)-3-(2-{4-[4-(1,1,1,3,3,3-hexafluoro-2-hydroxypropan-2-yl)-2-propylphenyl]-3-methylpiperazin-1-yl}-2-oxoethyl)-5-[4-(1-methylethoxy)phenyl]-5-methylimidazolidine-2,4-dione 5-[4-(1-Methylethoxy)phenyl]-5-methylimidazolidine-2,4-dione (7.7 mg, 0.0311 mmol) was dissolved in N,N-dimethylformamide (500 μL), added potassium carbonate (8.6 mg, 0.0622 mmol) under ice-cold conditions, and the mixture was stirred at room temperature for 5 minutes. Then, under ice-cold conditions, (R,Z)-2-bromo-1-(4-{4-[1,1,1,3,3,3-hexafluoro-2-(methoxymethoxy)propan-2-yl]-2-(prop-1-en-1-yl)phenyl}-3-methylpiperazin-1-yl)ethanone (17 mg, 0.0311 mmol) was added, and stirred at room temperature for 18 hours. Under ice-cold conditions, the reaction solution was added water, and extracted with ethyl acetate. The organic layer was washed with brine, dried over anhydrous sodium sulfate, and concentrated in vacuo. The obtained crude product was dissolved in ethyl acetate (1.0 mL), added a solution of 4N-hydrochloric acid-ethyl acetate (1.0 mg), and stirred at room temperature for 1 hour. Under ice-cold conditions, the reaction solution was added water and a saturated aqueous solution of sodium hydrogen carbonate, and extracted with ethyl acetate. The organic layer was washed with brine, dried over anhydrous sodium sulfate, and concentrated in vacuo. The obtained residue was purified by silica-gel column chromatography (hexane/ethyl acetate), and (R,Z)-3-(2-{4-[4-(1,1,1,3,3,3-hexafluoro-2-hydroxypropan-2-yl)-2-(prop-1-en-1-yl)phenyl]-3-methylpiperazin-1-yl}-2-oxoethyl)-5-[4-(1-methylethoxy)phenyl]-5-methylimidazolidine-2,4-dione (17.4 mg (yield 83%)) was obtained as a yellow oil.

$^1$H-NMR (CDCl$_3$) δ: 0.87-0.96 (3H, m), 1.32 (6H, d, J=5.9 Hz), 1.83 (3H, dd, J=6.5, 7.3 Hz), 1.90 (3H, s). 2.67-2.80 (1H, m), 3.08-4.05 (7H, m), 4.25-4.42 (2H, m), 4.53 (1H, q, J=5.9 Hz), 5.84 (1H, qd, J=7.3, 11.5 Hz), 5.96 (1H, brs), 6.67 (1H, dd, J=6.5, 11.5 Hz), 6.89 (2H, d, J=8.6 Hz), 7.02 (1H, d, J=8.1 Hz), 7.45 (2H, d, J=8.6 Hz), 7.56 (1H, dd, J=2.0, 8.1 Hz), 7.61 (1H, d, J=2.0 Hz).

(R,Z)-3-(2-{4-[4-(1,1,1,3,3,3-hexafluoro-2-hydroxypropan-2-yl)-2-(prop-1-en-1-yl)phenyl]-3-methylpiperazin-1-yl}-2-oxoethyl)-5-[4-(1-methylethoxy)phenyl]-5-methylimidazolidine-2,4-dione was used for a similar reaction and treatment as Example 6-m) and n), and the title compound was obtained as a yellow oil.

$^1$H-NMR (CDCl$_3$) δ: 0.79-0.86 (3H, m), 0.95 (3H, t, J=7.3 Hz), 1.32 (6H, d, J=5.9 Hz), 1.62 (2H, qt, J=7.3, 7.6 Hz), 1.90 (3H, s), 2.70-2.80 (2H, m), 2.89-3.46 (3H, m), 3.63-3.70 (2H, m), 3.95-4.05 (2H, m), 4.26-4.43 (2H, m), 4.54 (1H, q, J=5.9

Hz), 5.94 (1H, s), 6.89 (2H, d, J=8.6 Hz), 7.10-7.15 (1H, m), 7.46 (2H, d, J=8.6 Hz), 7.49-7.53 (1H, m), 7.53 (1H, d, J=2.0 Hz).

Example 13

Preparation of (S)-3-(2-{4-[4-(1,1,1,3,3,3-hexafluoro-2-hydroxypropan-2-yl)-2-propylphenyl]-3-methylpiperazin-1-yl}-2-oxoethyl)-5-[4-(1-methylethoxy)phenyl]-5-methylimidazolidine-2,4-dione

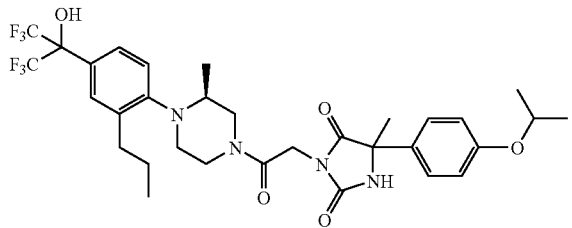

A similar reaction and treatment as Example 12 was conducted except that (S)-3-methyl-1-tert-butoxycarbonylpiperazine was used in place of (R)-3-methyl-1-tert-butoxycarbonylpiperazine, and the title compound was obtained as a yellow oil.

$^1$H-NMR (CDCl$_3$) δ: 0.79-0.86 (3H, m), 0.95 (3H, t, J=7.3 Hz), 1.32 (6H, d, J=6.2 Hz), 1.62 (2H, qt, J=7.3, 7.6 Hz), 1.91 (3H, s), 2.60-2.80 (2H, m), 2.90-3.49 (3H, m), 3.63-3.70 (2H, m), 4.20-4.25 (2H, m), 4.25-4.43 (2H, m), 4.54 (1H, q, J=6.2 Hz), 5.86 (1H, s), 6.99 (2H, d, J=8.6 Hz), 7.10-7.14 (1H, m), 7.46 (2H, d, J=8.6 Hz), 7.49-7.53 (1H, m), 7.53 (1H, d, J 2.0 Hz).

Example 14-1

Preparation of (2R,5S,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[4-(1-methylethoxy)phenyl]-5-methylimidazolidine-2,4-dione

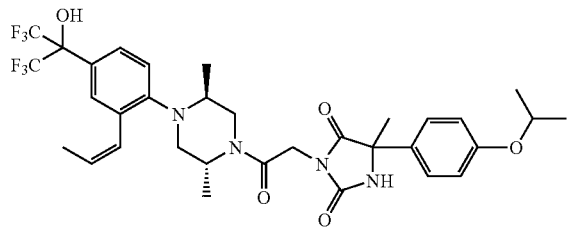 [SMILES: C/C=C\c1cc(C(O)(C(F)(F)F)C(F)(F)F)ccc1N1C[C@@H](C)N(C(=O)CN2C(=O)NC(C)(c3ccc(OC(C)C)cc3)C2=O)C[C@@H]1C]

a-1) Preparation of tert-butyl trans-2,5-dimethylpiperazine-1-carboxylate

To a solution of trans-2,5-dimethylpiperazine (100 mg, 0.876 mmol) in dichloromethane (3 mL), triethylamine (245 μL, 1.75 mmol) and di-tert-butyl dicarbonate (201 μL, 0.876 mmol) were added sequentially under ice-cold conditions, and the mixture was stirred at room temperature overnight. The reaction solution was added water under ice-cold conditions, and extracted with chloroform. The organic layer was washed with brine, dried over anhydrous sodium sulfate, and concentrated in vacuo. The obtained residue was purified by silica-gel column chromatography (chloroform/methanol), and the title compound (111 mg (yield 59%)) was obtained as a colorless oil.

$^1$H-NMR (CDCl$_3$) δ: 1.16 (3H, d, J=6.6 Hz), 1.21 (3H, d, J=6.6 Hz), 1.46 (9H, s), 2.48 (1H, d, J=12.8 Hz), 3.09-3.16 (1H, m), 3.18-3.24 (2H, m), 3.54 (1H, d, J=13.4 Hz), 4.15-4.30 (1H, m), 5.68 (1H, brs).

a-2-1) Preparation of (2R,5S)-tert-butyl 2,5-dimethylpiperazine-1-carboxylate a-2-1-1) Preparation of (S)-methyl 2-(benzylamino)propanoate

L-alanine methyl ester hydrochloride (15.0 g, 107 mmol) was dissolved in N,N'-dimethylformamide (150 mL), added potassium carbonate (32.5 g, 235 mmol) and benzyl bromide (18.4 g, 107 mmol) and the mixture was stirred at 80° C. overnight. Then, the mixture was reverted to room temperature, the reaction solution was filtered through a pad of celite, extracted with ethyl acetate, washed with water and brine, dried over sodium sulfate, and concentrated in vacuo. The obtained residue was purified by silica-gel column chromatography (hexane/ethyl acetate), and the title compound (12.7 g, 61%) was obtained as a colorless oil.

$^1$H-NMR (CDCl$_3$) δ: 1.32 (3H, d, J=7.1 Hz), 3.40 (1H, q, J=7.1 Hz), 3.69 (1H, d, J=12.7 Hz), 3.73 (3H, s), 3.80 (1H, d, J=12.7 Hz), 7.25-7.36 (5H, m).

a-2-1-2) Preparation of (S)-methyl 2-{(R)—N-benzyl-2-[(tert-butoxycarbonyl)amino]propane amide}propanoate To a solution of (S)-methyl. 2-(benzylamino)propanoate (9.28 g, 48.1 mmol) in dichloromethane (100 mL), added Boc-D-alanine (10 g, 52.9 mmol), and then 4-dimethylaminopyridine (587 mg, 4.81 mmol) and EDCl (11 g, 57.7 mmol) under ice-cold conditions, and the mixture was stirred at room temperature overnight. The reaction solution was extracted with chloroform, washed with 5% aqueous solution of citric acid, water and a saturated aqueous solution of sodium hydrogen carbonate, dried over sodium sulfate, and concentrated in vacuo. The obtained residue was purified by silica-gel column chromatography (hexane/ethyl acetate), and the title compound (9.34 g, 53%) was obtained as a colorless oil.

$^1$H-NMR (CDCl$_3$) δ: 1.24 (3H, d, J=6.8 Hz), 1.38 (3H, d, J=7.1 Hz), 1.43 (9H, s), 3.67 (3H, s), 4.20 (1H, q, J=7.1 Hz), 4.59 (1H, d, J=16.8 Hz), 4.61-4.73 (1H, m), 4.77 (1H, d, J=16.8 Hz), 5.31 (1H, d, J=7.8 Hz), 7.22-7.39 (5H, m).

a-2-1-3) Preparation of (3R,6S)-1-benzyl-3,6-dimethylpiperazine-2,5-dione

To a solution of (S)-methyl 2-{(R)—N-benzyl-2-[(tert-butoxycarbonyl)amino]propaneamide}propanoate (9.34 g, 25.6 mmol) in dichlromethane (100 mL), trifluoroacetic acid (14.6 g, 128 mmol) was added under ice-cold conditions, and the mixture was stirred at room temperature overnight. The reaction solution was concentrated in vacuo, then added methanol (40 mL), added a saturated aqueous solution of sodium hydrogen carbonate (until it becomes pH=8) under ice-cold conditions, and the mixture was stirred at 80° C. overnight. The reaction solution was concentrated in vacuo, extracted with ethyl acetate, washed with brine, dried over sodium sulfate, and concentrated in vacuo. The obtained residue was purified by silica-gel column chromatography (ethyl acetate), and the title compound (4.05 g (yield 68%)) was obtained as a colorless oil.

$^1$H-NMR (CDCl$_3$) δ: 1.42 (3H, d, J=7.1 Hz), 1.54 (3H, d, J=6.8 Hz), 3.87 (1H, q, J=7.1 Hz), 4.09 (1H, d, J=14.9 Hz), 4.16 (1H, q, J=6.8 Hz), 5.17 (1H, d, J=14.9 Hz), 6.51 (1H, s), 7.23-7.36 (5H, m).

a-2-1-4) Preparation of (2R,5S)-1-benzyl-2,5-dimethylpiperazine

To a solution of (3R,6S)-1-benzyl-3,6-dimethylpiperazine-2,5-dione (4.05 g, 17.4 mmol) in tetrahydrofuran (70 mL), added lithium aluminum hydride (993 mg, 26.2 mmol) under ice-cold conditions, under an argon atmosphere. The mixture was stirred at room temperature for 10 minutes, and then stirred at 80° C. for 4 hours. Then, the reaction solution was added lithium aluminum hydride (331 mg, 8.72 mmol) under ice-cold conditions and stirred at 80° C. for 1.5 hours. Then, the reaction solution was added tetrahydrofuran and water under ice-cold conditions, and stirred at room temperature overnight.

The reaction solution was filtered through a pad of celite, washed with ethyl acetate and water, dried over sodium sulfate, then concentrated in vacuo, and the title compound (3.52 g (yield 99%)) was obtained as a yellow oil.

$^1$H-NMR (CDCl$_3$) δ: 0.93 (3H, d, J=6.3 Hz), 1.14 (3H, d, J=6.1 Hz), 1.63 (1H, dd, J=10.2, 11.2 Hz), 2.18-2.26 (1H, m), 2.63 (1H, dd, J=10.5, 12.2 Hz), 2.68 (1H, dd, J=2.7, 11.2 Hz), 2.75-2.83 (1H, m), 2.91 (1H, dd, J=2.9, 12.2 Hz), 3.09 (1H, d, J=13.4 Hz), 4.10 (1H, d, J=13.4 Hz), 7.22-7.32 (5H, m).

a-2-1-5) Preparation of (2R,5S)-tert-butyl 4-benzyl-2,5-dimethylpiperazine-1-carboxylate To a solution of (2R,5S)-1-benzyl-2,5-dimethylpiperazine (3.52 g, 17.2 mmol) in tetrahydrofuran (50 mL), trimethylamine (2.12 g, 20.9 mmol) and di-tert-butylcarbonate (4.56 g, 20.9 mmol) were added under ice-cold conditions, and the mixture was stirred for 15 minutes. Then, the mixture was stirred at room temperature for 5.5 hours. The reaction solution was added water, extracted with ethyl acetate, washed with brine, dried over sodium sulfate, and concentrated in vacuo. The obtained residue was purified by silica-gel column chromatography (hexane/ethyl acetate), and the title compound (3.16 g, 60%) was obtained as a pale yellow oil.

$^1$H-NMR (CDCl$_3$) δ: 0.98 (3H, d, J=6.6 Hz), 1.23 (3H, d, J=6.6 Hz), 1.46 (9H, s), 2.19 (1H, d, J=12.2 Hz), 2.70 (1H, dd, J=4.4, 12.2 Hz), 2.91-2.98 (1H, m), 3.31 (1H, dd, J=3.6, 12.9 Hz), 3.46 (1H, d, J=13.5 Hz), 3.62 (1H, d, J=13.5 Hz), 3.65 (1H, d, J=12.9 Hz), 4.17-4.25 (1H, m), 7.22-7.37 (5H, m).

a-2-1-6) Preparation of (2R,5S)-tert-butyl 2,5-dimethylpiperazine-1-carboxylate

Under an argon atmosphere, (2R,5S)-tert-butyl 4-benzyl-2,5-dimethylpiperazine-1-carboxylate (2.0 g, 6.57 mmol) was dissolved in methanol (60 mL), and added 10% palladium carbon (670 mg) and formic acid (1.5 g, 32.9 mmol). The mixture was stirred at room temperature for 2 hours. Then, the reaction solution was filtered through a pad of celite, and concentrated in vacuo. The obtained residue was added chloroform and a saturated aqueous solution of sodium hydrogen carbonate, extracted with chloroform, dried over sodium sulfate, concentrated in vacuo, and the title compound (1.56 g, >100%) was obtained as a yellow oil.

$^1$H-NMR (CDCl$_3$) δ: 1.17 (3H, d, J=6.6 Hz), 1.21 (3H, d, J=6.8 Hz), 1.46 (9H, s), 2.48 (1H, dd, J=2.9, 13.0 Hz), 3.03-3.15 (1H, m), 3.18-3.23 (2H, m), 3.54 (1H, dd, J=2.0, 13.4 Hz), 4.08-4.14 (1H, m).

a-2-2) Preparation of (2S,5R)-tert-butyl 2,5-dimethylpiperazine-1-carboxylate

D-alanine methyl ester hydrochloride was used in place of L-alanine methyl ester hydrochloride for a similar reaction and treatment as Example 14-1 a-2-1-1) to a-2-1-6), and the title compound was obtained as a colorless oil.

a-3-1) Preparation of (2S,5R)-tert-butyl 2,5-dimethylpiperazine-1-carboxylate a-3-1-1) Preparation of racemic trans-1-benzyl-2,5-dimethylpiperazine trans-2,5-Dimethylpiperazine (25 g, 219 mmol) was dissolved in cyclohexane (250 mL)-water (35 mL), and added tetra-butyl ammonium chloride (2.2 g, 15.5 mmol), aqueous solution of sodium hydrate (23 mL), benzyl chloride (26.5 g, 208 mmol) at room temperature. The mixture was stirred at 40° C. for 18 hours. Then, the mixture was reverted to room temperature, and the reaction solution was extracted with cyclohexane. The organic layer was added 37% aqueous solution of hydrochloric acid, and stirred. To the aqueous layer obtained from the extracting operation, 2-methyltetrahydrofuran and 50% aqueous solution of sodium hydroxide were added, and extracted with 2-methyltetrahydrofuran. The obtained organic layer was dried with anhydrous sodium sulfate, concentrated in vacuo and the title compound (34 g (yield 76%) was obtained as a colorless oil.

$^1$H-NMR (CDCl$_3$) δ: 0.93 (3H, d, J=6.3 Hz), 1.14 (3H, d, J=6.1 Hz), 1.63 (1H, dd, J=10.2, 11.2 Hz), 2.18-2.26 (1H, m), 2.63 (1H, dd, J=10.5, 12.2 Hz), 2.68 (1H, dd, J=2.7, 11.2 Hz), 2.75-2.83 (1H, m), 2.91 (1H, dd, J=2.9, 12.2 Hz), 3.09 (1H, d, J=13.4 Hz), 4.10 (1H, d, J=13.4 Hz), 7.22-7.32 (5H, m).

a-3-1-2) Preparation of (2S,5R)-1-benzyl-2,5-dimethylpiperazine-2-tartrate

Racemic trans-1-benzyl-2,5-dimethylpiperazine (2.35 g, 11.5 mmol) was dissolved in methanol (14 mL), added D-(–)-tartaric acid (3.45 g, 23.0 mmol), and allowed to leave at 5° C. for 20 hours. The resultant was filtered with methanol, concentrated in vacuo, and the title compound (2.66 g (yield 44%)) was obtained as a white crystal. Further, the obtained white crystal was dissolved in methanol (27 mL), recrystallized, and the title compound (1.7 g, (yield 28%, 99.9% ee)) was obtained as a white crystal.

$^1$H-NMR (D$_2$O) δ: 1.18 (3H, d, J=6.5 Hz), 1.51 (3H, d, J=6.3 Hz), 1.92 (1H, bs), 2.89 (1H, t, J=12.9 Hz), 3.18 (1H, t, J=13.8 Hz), 3.29 (1H, dd. J=3.0, 13.8 Hz), 3.47 (1H, m), 3.53 (1H, m), 3.62 (1H, dd, J=3.0, 12.9 Hz), 3.98 (1H, d, J=13.1 Hz), 4.41 (4H, s), 4.71 (1H, d, J=13.1 Hz), 7.39-7.48 (5H, m).

a-3-1-3) Preparation of (2S,5R)-tert-butyl 4-benzyl-2,5-dimethylpiperazine-1-carboxylate (2S,5R)-1-benzyl-2,5-dimethylpiperazine-2-tartrate (5.0 g, 9.91 mmol) was dissolved in 2-methyltetrahydrofuran (30 mL), added an aqueous solution of sodium hydroxide (sodium hydroxide: 2.62 g, 65.4 mmol, water: 18 mL), and a solution of di-tert-butyl dicarbonate (2.2 g, 9.91 mmol) in 2-methyltetrahydrofuran under ice-cold conditions, and the mixture was stirred at room temperature overnight. Then, the reaction solution was extracted with 2-methyltetrahydrofuran, washed with brine, dried over anhydrous sodium sulfate, concentrated in vacuo, and the title compound (3.11 g (yield >100%)) was obtained as a white crystal.

$^1$H-NMR (CDCl$_3$) δ: 0.98 (3H, d, J=6.2 Hz), 1.23 (3H, d, J=6.5 Hz), 1.46 (9H, s), 2.19 (1H, dd, J=1.6, 11.9 Hz), 2.69 (1H, dd, J=4.3, 11.9 Hz), 2.92-3.00 (1H, m), 3.31 (1H, dd, J=3.5, 12.4 Hz), 3.46 (1H, d, J=13.5 Hz), 3.62 (1H, d, J=13.5 Hz), 3.66 (1H, dd, J=2.4, 12.4 Hz), 4.15-4.23 (1H, m), 7.20-7.37 (5H, m).

a-3-1-4) Preparation of (2S,5R)-tert-butyl 2,5-dimethylpiperazine-1-carboxylate (2S,5R)-tert-butyl 4-benzyl-2,5-dimethylpiperazine-1-carboxylate (3.11 g, 10.2 mmol) was dissolved in methanol (19 mL), added palladium carbon (156 mg) under an argon atmosphere, and added formic acid (2.4 g, 51.1 mmol) under ice-cold conditions. The solution was reverted to room temperature, and stirred overnight. Then, the reaction solution was filtered through a pad of celite, and the filtrate was concentrated in vacuo. The obtained residue was added water and hexane, and extracted. An aqueous solution of sodium hydroxide was added to the aqueous layer, extracted with 2-methyltetrahydrofuran, dried over anhydrous sodium sulfate, concentrated in vacuo, and the title compound (2.21 g (yield >100%)) was obtained as a colorless oil.

$^1$H-NMR (CDCl$_3$) δ: 1.16 (3H, d, J=6.6 Hz), 1.21 (3H, d, J=6.6 Hz), 1.46 (9H, s), 2.48 (1H, d, J=12.8 Hz), 3.09-3.16 (1H, m), 3.18-3.24 (2H, m), 3.54 (1H, d, J=13.4 Hz), 4.15-4.30 (1H, m), 5.68 (1H, brs).

a-3-2) Preparation of (2R,5S)-tert-butyl 2,5-dimethylpiperazine-1-carboxylate L-(+)-tartaric acid was used in place of D-(−)-tartaric acid for a similar reaction and treatment as Example 14-1-a-3-1-2) and after, and the title compound was obtained as a colorless oil.

b) Preparation of tert-butyl (2R,5S)-4-[4-(methoxycarbonyl)-2-nitrophenyl]-2,5-dimethylpiperazine-1-carboxylate By conducting a similar reaction and treatment as Example 6-b) using (2R,5S)-tert-butyl 2,5-dimethylpiperazine-1-carboxylate in place of tert-butyl piperazine-1-carboxylate, the title compound was obtained as a yellow oil.

$^1$H-NMR (CDCl$_3$) δ: 1.09 (3H, d, J=6.3 Hz), 1.26 (3H, d, J=6.3 Hz), 1.48 (9H, s), 2.75 (1H, d, J=11.7 Hz), 3.54-3.68 (4H, m), 3.91 (3H, s), 4.35-4.42 (1H, m), 7.03 (1H, d, J=8.6 Hz), 8.06 (1H, dd, J=1.9, 8.6 Hz), 8.45 (1H, d, J=1.9 Hz).

c) Preparation of tert-butyl (2R,5S)-4-[2-amino-4-(methoxycarbonyl)phenyl]-2,5-dimethylpiperazine-1-carboxylate By conducting a similar reaction and treatment as Example 6-c) using tert-butyl (2R,5S)-4-[4-(methoxycarbonyl)-2-nitrophenyl]-2,5-dimethylpiperazine-1-carboxylate, the title compound was obtained as a yellow oil.

$^1$H-NMR (CDCl$_3$) δ: 0.92 (3H, d, J=6.6 Hz), 1.30 (3H, d, J=6.8 Hz), 1.49 (9H, s), 2.55 (1H, d, J=11.9 Hz), 3.41-3.45 (1H, m), 3.59-3.63 (2H, m), 3.78 (1H, d, J=13.4 Hz), 3.87 (3H, s), 3.93 (1H, brs), 4.40-4.47 (1H, m), 6.84 (1H, d, J=8.3 Hz), 7.40 (1H, dd, J=1.9, 8.3 Hz), 7.43 (1H, d, J=1.9 Hz).

d) Preparation of tert-butyl (2R,5S)-4-[2-iodo-4-(methoxycarbonyl)phenyl]-2,5-dimethylpiperazine-1-carboxylate By conducting a similar reaction and treatment as Example 6-d) using tert-butyl (2R,5S)-4-[2-amino-4-(methoxycarbonyl)phenyl]-2,5-dimethylpiperazine-1-carboxylate, the title compound was obtained as a yellow oil.

$^1$H-NMR (CDCl$_3$) δ: 0.93 (3H, d, J=6.6 Hz), 1.35 (3H, d, J=6.8 Hz), 1.49 (9H, s), 2.56 (1H, d, J=11.2 Hz), 3.61-3.65 (2H, m), 3.77-3.80 (2H, m), 3.89 (3H, s), 4.41-4.46 (1H, m), 6.86 (1H, d, J=8.3 Hz), 7.96 (1H, dd, J=2.0, 8.3 Hz), 8.50 (1H, d, J=2.0 Hz).

e) Preparation of tert-butyl (2R,5S,Z)-4-[4-(methoxycarbonyl)-2-(prop-1-en-1-yl)phenyl]-2,5-dimethylpiperazine-1-carboxylate By conducting a similar reaction and treatment as Example 6-e) using tert-butyl (2R,5S)-4-[2-iodo-4-(methoxycarbonyl)phenyl]-2,5-dimethylpiperazine-1-carboxylate, the title compound was obtained as a yellow oil.

$^1$H-NMR (CDCl$_3$) δ: 0.90 (3H, d, J=6.3 Hz), 1.28 (3H, d, J=6.6 Hz), 1.48 (9H, s), 1.90-1.92 (3H, m), 2.73 (1H, d, J=11.7 Hz), 3.41-3.44 (1H, m), 3.53-3.58 (1H, m), 3.69-3.72 (2H, m), 3.89 (3H, s), 4.41-4.46 (1H, m), 5.79-5.88 (1H, m), 6.45 (1H, d, J=11.5 Hz), 6.84 (1H, d, J=8.6 Hz), 7.86 (1H, dd, J=2.0, 8.6 Hz), 7.93 (1H, d, J=2.0 Hz).

f) Preparation of (2S,5R,Z)-4-[4-(tert-butoxycarbonyl)-2,5-dimethylpiperazin-1-yl]-3-(prop-1-en-1-yl)benzoic acid By conducting a similar reaction and treatment as Example 6-f) using tert-butyl (2R,5S,Z)-4-[(4-(methoxycarbonyl)-2-(prop-1-en-1-yl)phenyl]-2,5-dimethylpiperazine-1-carboxylate, the title compound was obtained as a yellow oil.

$^1$H-NMR (CDCl$_3$) δ: 0.92 (3H, d, J=5.9 Hz), 1.27 (3H, d, J=6.6 Hz), 1.48 (9H, s), 1.91-1.93 (3H, m), 2.77 (1H, d, J=11.7 Hz), 3.43-3.76 (4H, m), 4.12-4.21 (1H, m), 4.42-4.49 (1H, m), 5.81-5.89 (1H, m), 6.44 (1H, d, J=10.5 Hz), 6.87 (1H, d, J=8.5 Hz), 7.93 (1H, dd, J=2.0, 8.5 Hz), 7.99 (1H, d, J=2.0 Hz).

g) Preparation of tert-butyl (2R,5S,Z)-2,5-dimethyl-4-{4-[(perfluorophenoxy)carbonyl]-2-(prop-1-en-1-yl)phenyl}piperazine-1-carboxylate By conducting a similar reaction and treatment as Example 6-g) using (2R,5S,Z)-4-[4-(tert-butoxycarbonyl)-2,5-dimethylpiperazin-1-yl]-3-(prop-1-en-1-yl)benzoic acid, the title compound (7.3 mg (yield 80%)) was obtained as a yellow oil.

$^1$H-NMR (CDCl$_3$) δ: 0.96 (3H, d, J=6.6 Hz), 1.29 (3H, d, J=6.8 Hz), 1.49 (9H, s), 1.92-1.94 (3H, m), 2.82 (1H, d, J=11.0 Hz), 3.43-3.87 (4H, m), 4.42-4.49 (1H, m), 5.85-5.93 (1H, m), 6.44 (1H, d, J=11.7 Hz), 6.92 (1H, d, J=8.5 Hz), 8.03 (1H, dd, J=2.0, 8.5 Hz), 8.05 (1H, d, J=2.0 Hz).

h) Preparation of (2R,5S)-tert-butyl 4-(4-(1,1,1,3,3,3-hexafluoro-2-hydroxypropan-2-yl)-2-((Z)-prop-1-en-1-yl)phenyl)-2,5-dimethylpiperazine-1-carboxylate By conducting a similar reaction and treatment as Example 6-h) using tert-butyl (2R,5S,Z)-2,5-dimethyl-4-{4-[(perfluorophenoxy)carbonyl]-2-(prop-1-en-1-yl)phenyl}piperazine-1-carboxylate, the title compound was obtained as a yellow oil.

¹H-NMR (CDCl₃) δ: 0.89 (3H, d, J=6.5 Hz), 1.29 (3H, d, J=6.5 Hz), 1.48 (9H, s), 1.87 (3H, dd, J=1.6, 7.0 Hz), 2.67 (1H, d, J=11.6 Hz), 3.38-3.74 (4H, m), 4.37-4.46 (1H, m), 5.77-5.90 (1H, m), 6.51 (1H, dd, J=1.6, 11.7 Hz), 6.88 (1H, d, J=8.6 Hz), 7.37 (1H, dd, J=2.0, 8.6 Hz), 7.57 (1H, d, J=2.0 Hz).

i) Preparation of (2R,5S,Z)-2-[4-(2,5-dimethylpiperazin-1-yl)-3-(prop-1-en-1-yl)phenyl]-1,1,1,3,3,3-hexafluoropropan-2-ol By conducting a similar reaction and treatment as Example 6-j) using (2R,5S)-tert-butyl 4-[4-(1,1,1,3,3,3-hexafluoro-2-hydroxypropan-2-yl)-2-((z)-prop-1-en-1-yl)phenyl]-2,5-dimethylpiperazine-1-carboxylate, the title compound was obtained as a yellow oil.

¹H-NMR (CDCl₃) δ: 0.85 (3H, d, J=6.2 Hz), 1.07 (3H, d, J=6.2 Hz), 1.82 (3H, dd, J=1.6, 7.3 Hz), 2.26-3.20 (8H, m), 5.82 (1H, qd, J=7.3, 11.6 Hz), 6.69 (1H, dd, J=1.6, 11.6 Hz), 7.19 (1H, d, J=8.1 Hz), 7.61-7.66 (2H, m).

j) Preparation of (2R,5S,Z)-1-{4-[1,1,1,3,3,3-hexafluoro-2-(methoxymethoxy)propan-2-yl]-2-(prop-1-en-1-yl) phenyl}-2,5-dimethylpiperazine By conducting a similar reaction and treatment as Example 12-i) using (2R,5S,Z)-2-[4-(2,5-dimethylpiperazin-1-yl)-3-(prop-1-en-1-yl)phenyl]-1,1,1,3,3,3-hexafluoropropan-2-ol, the title compound was obtained as a yellow oil.

¹H-NMR (CDCl₃) δ: 0.88 (3H, d, J=5.9 Hz), 1.14 (3H, d, J=6.2 Hz), 1.81 (3H, dd, J=1.6, 7.2 Hz), 2.32-2.45 (1H, m), 2.67-2.96 (2H, m), 3.05-3.29 (4H, m), 3.55 (3H, s), 4.87 (2H, s), 5.77-5.90 (1H, m), 6.66 (1H, dd, J=1.6, 11.9 Hz), 7.18 (1H, d, J=8.4 Hz), 7.46 (1H, dd, J=2.0, 8.4 Hz), 7.55 (1H, d, J=2.0 Hz).

k) Preparation of (2R,5S,Z)-2-bromo-1-(4-{4-[1,1,1,3,3,3-hexafluoro-2-(methoxymethoxy)propan-2-yl]-2-(prop-1-en-1-yl)phenyl}-2,5-dimethylpiperazin-1-yl)ethanone By conducting a similar reaction and treatment as Example 6-k) using (2R,5S,Z)-1-{4-[1,1,1,3,3,3-hexafluoro-2-(methoxymethoxy)propan-2-yl]-2-(prop-1-en-1-yl)phenyl}-2,5-dimethylpiperazine, the title compound was obtained as a yellow oil.

¹H-NMR (CDCl₃) δ: 0.89-0.99 (3H, m), 1.31-1.50 (3H, m), 1.87 (3H, dd, 1.6, 7.2 Hz), 2.74-2.81 (1H, m), 3.28-3.46 (2H, m), 3.55 (3H, s), 3.67-3.98 (4H, m), 4.16-4.28 (1H, m), 4.86 (2H, s), 5.86 (1H, qd, J=7.2, 11.3 Hz), 6.50 (1H, dd, J=1.6, 11.3 Hz), 6.89 (1H, d, J=8.6 Hz), 7.43 (1H, dd, J=2.0, 8.6 Hz), 7.49 (1H, d, J=2.0 Hz).

l) Preparation of (2R,5S,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-(4-isopropoxyphenyl)-5-methylimidazolidine-2,4-dione 5-[4-(1-Methylethoxy)phenyl]-5-methylimidazolidine-2,4-dione (7.7 mg, 0.0311 mmol) was dissolved in N,N-dimethylformamide (500 μL), added potassium carbonate (8.6 mg, 0.0622 mmol) under ice-cold conditions, and the mixture was stirred at room temperature for 5 minutes. Then, under ice-cold conditions, (2R,5S,Z)-2-bromo-1-(4-{4-[1,1,1,3,3,3-hexafluoro-2-(methoxymethoxy)propan-2-yl]-2-(prop-1-en-1-yl)phenyl}-2,5-dimethylpiperazin-1-yl)ethanone (17 mg, 0.0311 mmol) was added and stirred at room temperature for 18 hours. Under ice-cold conditions, the reaction solution was added water, and extracted with ethyl acetate. The organic layer was washed with brine, dried over anhydrous sodium sulfate, and concentrated in vacuo. The obtained residue was dissolved in ethyl acetate (1.0 mL), added a solution of 4N-hydrochloric acid-ethyl acetate (1.0 mg), and the mixture was stirred at room temperature for 1 hour. Under ice-cold conditions, the reaction solution was added water and a saturated aqueous solution of sodium hydrogen carbonate, and extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (17.4 mg (yield 83%)) was obtained as a yellow oil.

¹H-NMR (CDCl₃) δ: 0.88-1.05 (3H, m), 1.26-1.34 (9H, m), 1.83-1.90 (6H, m), 2.68-2.80 (1H, m), 3.30-3.85 (4H, m), 4.05-4.34 (3H, m), 4.54 (1H, q, J=6.1 Hz), 4.87 (1H, s), 5.83-5.96 (2H, m), 6.53-6.58 (1H, m), 6.86-6.91 (3H, m), 7.36-7.59 (4H, m).

Example 14-2

Preparation of (2S,5R,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[4-(1-methylethoxy)phenyl]-5-methylimidazolidine-2,4-dione (2S,5R)-tert-butyl 2,5-dimethylpiperazine-1-carboxylate was used in place of (2R,5S)-tert-butyl 2,5-dimethylpiperazine-1-carboxylate for a similar reaction and treatment as the preparation (2R,5S,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[4-(1-methylethoxy)phenyl]-5-methylimidazolidine-2,4-dione of Example 14-1, and the title compound was obtained as a yellow oil.

Example 15-1

Preparation of (2R,5S)-3-(2-{4-[4-(1,1,1,3,3,3-hexafluoro-2-hydroxypropan-2-yl-2-propylphenyl]-2,5-dimethylpiperazin-1-yl}-2-oxoethyl)-5-[4-(1-methylethoxy)phenyl]-5-methylimidazolidine-2,4-dione

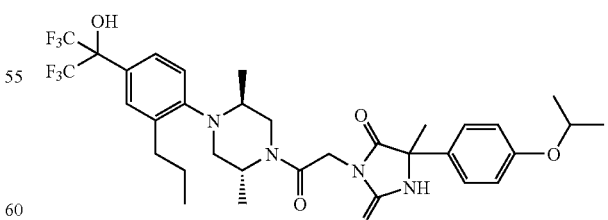

(2R,5S,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[4-(1-methylethoxy)phenyl]-5-methylimidazolidine-2,4-dione (Example 14-1) (6.0 mg, 0.0088 mmol) was dissolved in methanol (1.0 mL), added palladium carbon (5.0 mg), and the mixture was stirred at room temperature for 1 hour under a hydrogen atomosphere. The reaction solution was filtered through a pad of celite, and concentrated in vacuo. The obtained residue was purified by silica-gel column chromatography (hexane/ethyl acetate), and the title compound (4.7 mg (yield 78%)) was obtained as a yellow oil.

$^1$H-NMR (CDCl$_3$) δ: 0.95-1.00 (6H, m), 1.26-1.33 (9H, m), 1.68 (2H, qt, J=7.0, 7.6 Hz), 1.90 (3H, s), 2.46-2.64 (2H, m), 2.77-2.89 (1H, m), 3.39-3.90 (5H, m), 4.20-4.30 (2H, m), 4.54 (1H, q, J=5.9 Hz), 4.84 (1H, s), 5.99 (1H, s), 6.88-6.94 (3H, m), 7.36-7.52 (4H, m).

Example 15-2

Preparation of (2S,5R)-3-(2-{4-[4-(1,1,1,3,3,3-hexafluoro-2-hydroxypropan-2-yl-2-propylphenyl]-2,5-dimethylpiperazin-1-yl}-2-oxoethyl)-5-[4-(1-methylethoxy)phenyl]-5-methylimidazolidine-2,4-dione (2S,5R,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[4-(1-methylethoxy)phenyl]-5-methylimidazolidine-2,4-dione (Example 14-2) was used in place of (2R,5S,Z)-3-(2-{4-[4-(1,1,1,3,3,3-hexafluoro-2-hydroxypropan-2-yl)-2-(prop-1-en-1-yl)phen yl]-2,5-dimethylpiperazin-1-yl}-2-oxoethyl)-5-[4-(1-methylethoxy)phenyl]-5-methylimidazolidine-2,4-dione (Example 14-1) for a similar treatment and reaction as the preparation of Example 15-1, and the title compound was obtained as a yellow oil.

Example 16

Preparation of (R)-5-(2,3-dihydrobenzofuran-5-yl)-3-(2-{4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

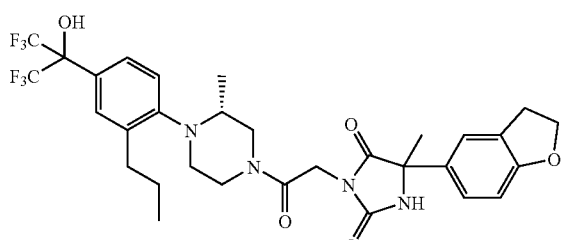

5-(2,3-Dihydrobenzofuran-5-yl)-5-methylimidazolidine-2,4-dione was used for a similar reaction and treatment as Example 12, and the title compound was obtained as a yellow oil.

$^1$H-NMR (CDCl$_3$) δ: 0.79-0.86 (3H, m), 0.95 (3H, t, J=7.3 Hz), 1.62 (2H, qt, J=7.3, 7.6 Hz), 1.96 (3H, s), 2.60-2.80 (2H, m), 2.94-3.49 (3H, m), 3.22 (2H, t, J=8.4 Hz), 3.63-3.70 (2H, m), 3.91-3.95 (2H, m), 4.27-4.46 (2H, m), 4.58 (2H, t, J=8.4 Hz), 5.90 (1H, s), 6.78 (1H, d, J=8.4 Hz), 7.10-7.15 (1H, m), 7.26-7.31 (1H, m), 7.41 (1H, s), 7.49-7.54 (1H, m), 7.54 (1H, s).

Example 17

Preparation of (S)-5-(2,3-dihydrobenzofuran-5-yl)-3-(2-{4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

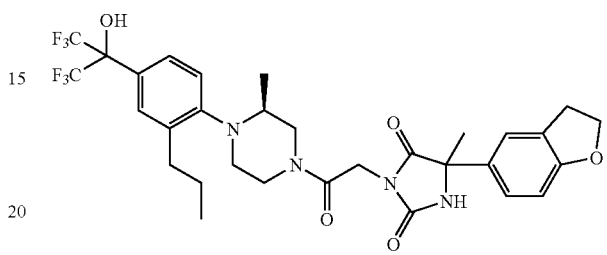

A similar reaction and treatment as Example 12 was conducted except that (S)-2-methyl-1-tert-butoxycarbonylpiperazine was used in place of (R)-2-methyl-1-tert-butoxycarbonylpiperazine, and 5-(2,3-dihydrobenzofuran-5-yl)-5-methylimidazolidine-2,4-dione was used. The title compound was obtained as a yellow oil.

$^1$H-NMR (CDCl$_3$) δ: 0.79-0.86 (3H, m), 0.95 (3H, t, J=7.3 Hz), 1.62 (2H, qt, J=7.3, 7.6 Hz), 1.90 (3H, s), 2.60-2.80 (2H, m), 2.90-3.48 (3H, m), 3.22 (2H, t, J=8.6 Hz), 3.64-3.74 (2H, m), 3.97-4.00 (2H, m), 4.27-4.44 (2H, m), 4.58 (2H, t, J=8.6 Hz), 5.90 (1H, s), 6.79 (1H, d, J=8.6 Hz), 7.10-7.15 (1H, m), 7.26-7.30 (1H, m), 7.41 (1H, s), 7.49-7.54 (1H, m), 7.54 (1H, s).

Example 18-1

Preparation of (2R,5S,Z)-5-(2,3-dihydrobenzofuran-5-yl)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-methylimidazolidine-2,4-dione

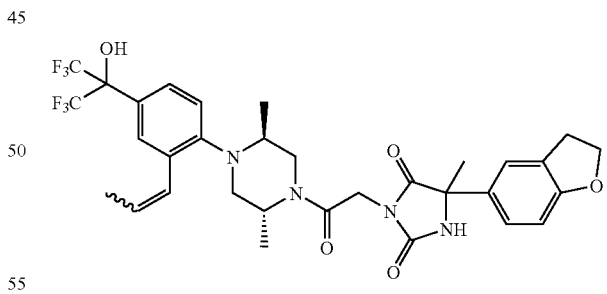

5-(2,3-Dihydrobenzofuran-5-yl)-5-methylimidazolidine-2,4-dione was used for a similar reaction and treatment as Example 14-1, and the title compound was obtained as a yellow oil.

$^1$H-NMR (CDCl$_3$) δ: 0.88-1.01 (3H, m), 1.49-1.71 (3H, m), 1.86-1.95 (6H, m), 3.22 (2H, t, J=8.6 Hz), 3.28-3.84 (6H, m), 4.08-4.24 (2H, m), 4.58 (2H, t, J=8.6 Hz), 4.88 (1H, s), 5.75-5.90 (2H, m), 6.49-6.53 (1H, m), 6.78 (1H, dd, J=4.9, 8.2 Hz), 6.88 (1H, d, J=8.6 Hz), 7.29 (1H, d, J=8.2 Hz), 7.41 (1H, d, J=4.9 Hz), 7.53 (1H, dd, J=2.0, 8.6 Hz), 7.58 (1H, d, J=2.0 Hz).

Example 18-2

Preparation of (2S,5R,Z)-5-(2,3-dihydrobenzofuran-5-yl)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-methylimidazolidine-2,4-dione By conducting a similar reaction and treatment as Example 18-1, the title compound was obtained as a yellow oil.

Example 19-1

Preparation of (2R,5S)-5-(2,3-dihydrobenzofuran-5-yl)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-methylimidazolidine-2,4-dione

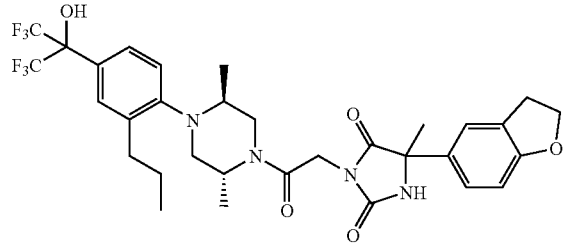 [SMILES: CCCc1cc(C(O)(C(F)(F)F)C(F)(F)F)ccc1N1C[C@@H](C)N(C(=O)CN2C(=O)NC(C)(c3ccc4c(c3)CCO4)C2=O)C[C@@H]1C]

5-(2,3-Dihydrobenzofuran-5-yl)-5-methylimidazolidine-2,4-dione was used for a similar reaction and treatment as Examples 14-1 and 15-1, and the title compound was obtained as a yellow oil.
$^1$H-NMR (CDCl$_3$) δ: 0.95-1.00 (6H, m), 1.35-1.50 (3H, m), 1.64-1.75 (2H, m), 1.90 (3H, s), 2.46-2.63 (2H, m), 2.74-2.89 (1H, m), 3.22 (2H, t, J=8.6 Hz), 3.38-3.95 (5H, m), 4.20-4.34 (2H, m), 4.58 (2H, t, J=8.6 Hz), 4.86 (1H, s), 5.81 (1H, s), 6.78 (1H, dd, J=2.2, 8.6 Hz), 6.92 (1H, d, J=8.1 Hz), 7.28-7.31 (1H, m), 7.40-7.48 (2H, m), 7.52 (1H, d, J=2.0 Hz).

Example 19-2

Preparation of (2S,5R)-5-(2,3-dihydrobenzofuran-5-yl)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-methylimidazolidine-2,4-dione By conducting a similar reaction and treatment as Example 19-1, the title compound was obtained as a yellow oil.

Example 20

Preparation of (R)-5-(2,3-dihydrobenzo[b][1,4]dioxin-6-yl)-3-(2-{4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

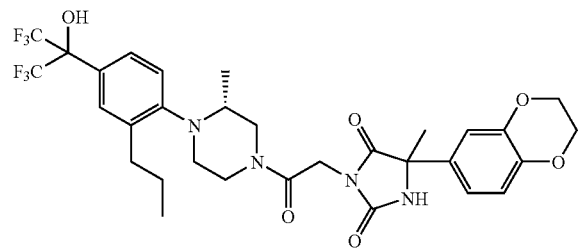 [SMILES: CCCc1cc(C(O)(C(F)(F)F)C(F)(F)F)ccc1N1CCN(C(=O)CN2C(=O)NC(C)(c3ccc4c(c3)OCCO4)C2=O)C[C@H]1C]

a) Preparation of 5-(2,3-dihydrobenzo[b][1,4]dioxin-6-yl)-5-methylimidazolidine-2,4-dione 1-(2,3-Dihydrobenzo[b][1,4]dioxin-6-yl)ethanone was used for a similar reaction and treatment as Example 1-l), and the title compound was obtained as a white crystal.
$^1$H-NMR (CDCl$_3$) δ: 1.69 (3H, s), 4.21 (4H, s), 6.8.1 (1H, d, J=8.1 Hz), 6.93 (1H, dd, J=2.2, 8.1 Hz), 6.95 (1H, d, J=2.2 Hz).

b) 5-(2,3-Dihydrobenzo[b][1,4]dioxin-6-yl)-5-methylimidazolidine-2,4-dione was used for a similar reaction and treatment as Example 12, and the title compound was obtained as a yellow oil.
$^1$H-NMR (CDCl$_3$) δ: 0.79-0.85 (3H, m), 0.95 (3H, t, J=7.3 Hz), 1.62 (2H, qt, J=7.3, 7.6 Hz), 1.88 (3H, s), 2.60-2.80 (2H, m), 2.89-3.50 (3H, m), 3.63-3.70 (2H, m), 4.00-4.02 (2H, m), 4.24 (4H, s), 4.30-4.45 (2H, m), 5.96 (1H, s), 6.88 (1H, d, J=8.6 Hz), 7.03 (1H, dd, J=2.2, 8.6 Hz), 7.08 (1H, d, J=2.2 Hz), 7.10-7.15 (1H, m), 7.49-7.53 (1H, m), 7.53 (1H, s).

Example 21

Preparation of (S)-5-(2,3-dihydrobenzo[b][1,4]dioxin-6-yl)-3-(2-{4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

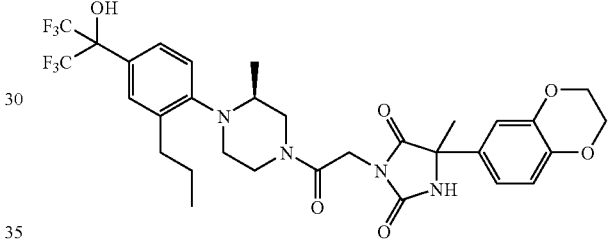

A similar reaction and treatment as Example 12 was conducted except that (S)-2-methyl-1-tert-butoxycarbonylpiperazine was used in place of (R)-2-methyl-1-tert-butoxycarbonylpiperazine, and that 5-(2,3-dihydrobenzo[b][1,4]dioxin-6-yl)-5-methylimidazolidine-2,4-dione was used, and the title compound was obtained as a yellow oil.
$^1$H-NMR (CDCl$_3$) δ: 0.79-0.86 (3H, m), 0.95 (3H, t, J=7.3 Hz), 1.62 (2H, qt, J=7.3, 7.6 Hz), 1.88 (3H, s), 2.60-2.80 (2H, m), 2.89-3.47 (3H, m), 3.63-3.70 (2H, m), 3.90-3.95 (2H, m), 4.24 (4H, s), 4.24-4.40 (2H, m), 5.86 (1H, s), 6.88 (1H, d, J=8.6 Hz), 7.03 (1H, dd, J=2.4, 8.6 Hz), 7.08 (1H, d, J=2.4 Hz), 7.10-7.14 (1H, m), 7.49-7.54 (1H, m), 7.54 (1H, s).

Example 22

Preparation of (R)-5-(2,2-dimethyl-2,3-dihydrobenzofuran-5-yl)-3-(2-{4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

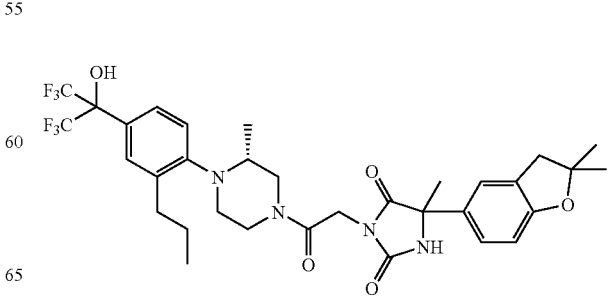

a) Preparation of 5-(2,2-dimethyl-2,3-dihydrobenzofuran-5-yl)-5-methylimidazolidine-2,4-dione 1-(4-Hydroxyphenyl)ethanone (1.36 g, 10 mmol) was dissolved in acetone (50 mL), tetrabutyl ammonium iodide (370 mg, 1.0 mmol), potassium carbonate (2.76 g, 20 mmol) and 3-chloro-2-methyl-1-propene (1.5 mL, 15 mmol) were added sequentially, and the mixture was stirred at 70° C. overnight. The reaction solution was filtered, washed with acetone and concentrated in vacuo. The obtained residue was added water and ethyl acetate, and extracted with ethyl acetate. The organic layer was washed with 1N-aqueous solution of sodium hydroxide and brine, dried over anhydrous sodium sulfate, and concentrated in vacuo. 1-(4-(2-Methylallyloxy)phenyl)ethanone (1.71 g (yield 90%)) was obtained as a colorless oil.

$^1$H-NMR (CDCl$_3$) δ: 1.84 (3H, s), 2.56 (3H, s), 4.50 (2H, s), 5.06 (2H, d, J=20.8 Hz), 6.95 (2H, d, J=8.9 Hz), 7.93 (2H, d, J=8.9 Hz).

1-(4-(2-Methylallyloxy)phenyl)ethanone (85 mg, 0.450 mmol) was dissolved in PEG400 (0.3 mL), and stirred under microwave irradiation at 250° C. for 2 hours. The reaction solution was added water, extracted with ethyl acetate, washed with brine, dried over sodium sulfate, and concentrated in vacuo. The obtained residue was purified by silicagel column chromatography (hexane/ethyl acetate), and 1-(2,2-dimethyl-2,3-dihydrobenzofuran-5-yl)ethanone (42 mg (yield 50%)) was obtained as a yellow oil.

$^1$H-NMR (CDCl$_3$) δ: 1.50 (6H, s), 2.54 (3H, s), 3.04 (2H, s), 6.74 (1H, d, J=9.2 Hz), 7.78-7.81 (2H, m).

1-(2,2-Dimethyl-2,3-dihydrobenzofuran-5-yl)ethanone was used for a similar reaction and treatment as Example 1-l), and the title compound was obtained as a white crystal.

$^1$H-NMR (CDCl$_3$) δ: 1.43 (6H, s), 1.72 (3H, s), 3.02 (2H, s), 6.64 (1H, d, J=8.4 Hz), 7.21 (1H, d, J=8.4 Hz), 7.28 (1H, s).

b) 5-(2,2-Dimethyl-2,3-dihydrobenzofuran-5-yl)-5-methylimidazolidine-2,4-dione was used for a similar reaction and treatment as Example 12, and the title compound was obtained as a yellow oil.

$^1$H-NMR (CDCl$_3$) δ: 0.80-0.87 (3H, m), 0.95 (3H, t, J=7.3 Hz), 1.46 (6H, s), 1.62 (2H, qt, J=7.3, 7.6 Hz), 1.90 (3H, s), 2.60-2.80 (2H, m), 2.90-3.48 (3H, m), 3.02 (2H, s), 3.64-3.70 (2H, m), 3.90-3.94 (2H, m), 4.27-4.44 (2H; m), 5.86 (1H, s), 6.72 (1H, d, J=8.4 Hz), 7.10-7.15 (1H, m), 7.26-7.30 (1H, m), 7.34 (1H, s), 7.49-7.54 (1H, m), 7.54 (1H, s).

Example 23

Preparation of (S)-5-(2,2-dimethyl-2,3-dihydrobenzofuran-5-yl)-3-(2-{4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

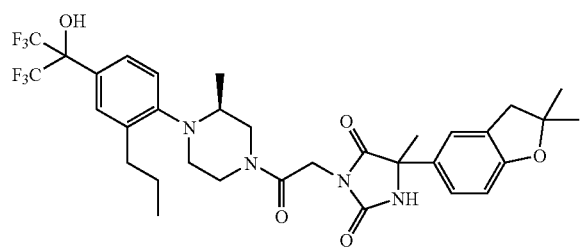 [SMILES: CCCc1cc(C(O)(C(F)(F)F)C(F)(F)F)ccc1N1CCN(C(=O)CN2C(=O)NC(C)(c3ccc4c(c3)CC(C)(C)O4)C2=O)C[C@@H]1C]

A similar reaction and treatment as Example 12 was conducted except that (S)-2-methyl-1-tert-butoxycarbonylpiperazine was used in place of (R)-2-methyl-1-tert-butoxycarbonylpiperazine, and that 5-(2,2-dimethyl-2,3-dihydrobenzofuran-5-yl)-5-methylimidazolidine-2,4-dione was used, and the title compound was obtained as a yellow oil.

$^1$H-NMR (CDCl$_3$) δ: 0.80-0.87 (3H, m), 0.95 (3H, t, J=7.3 Hz), 1.46 (6H, s), 1.62 (2H, qt, J=7.3, 7.6 Hz), 1.96 (3H, s), 2.68-2.76 (2H, m), 2.95-3.48 (3H, m), 3.02 (2H, s), 3.64-3.70 (2H, m), 3.90-4.00 (2H, m), 4.27-4.40 (2H, m), 5.85 (1H, s), 6.72 (1H, d, J=8.4 Hz), 7.10-7.15 m), 7.29-7.32 (1H, m), 7.34 (1H, s), 7.49-7.54 (1H, m), 7.54 (1H, s).

Example 24-1

Preparation of (2R,5S,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[5-(1-methylethoxy)pyridin-2-yl]-5-methylimidazolidine-2,4-dione

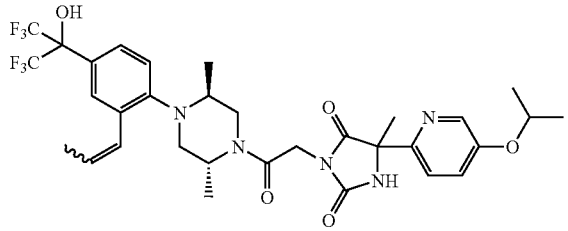

5-(5-(1-Methylethoxy)pyridin-2-yl)-5-methylimidazolidine-2,4-dione was used for a similar reaction and treatment as Example 14-1, and the title compound was obtained as a yellow oil.

$^1$H-NMR (CDCl$_3$) δ: 0.89-1.00 (3H, m), 1.34-1.36 (9H, m), 1.82-1.93 (6H, m), 2.68-2.80 (1H, m), 3.28-3.85 (5H, m), 4.08-4.33 (2H, m), 4.57 (1H, q, J=5.9 Hz), 4.86 (1H, s), 5.83-5.90 (1H, m), 6.33 (1H, s), 6.49-6.65 (1H, m), 6.88 (1H, d, J=8.6 Hz), 7.19 (1H, dd, J=3.0, 8.6 Hz), 7.52-7.70 (3H, m), 8.19 (1H, d, J=3.0 Hz).

Example 24-2

Preparation of (2S,5R,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[5-(1-methylethoxy)pyridin-2-yl]-5-methylimidazolidine-2,4-dione By conducting a similar reaction and treatment as Example 24-1, the title compound was obtained as a yellow oil.

Example 25-1

Preparation of (2R,5S)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-[5-(1-methylethoxy)pyridin-2-yl]-5-methylimidazolidine-2,4-dione

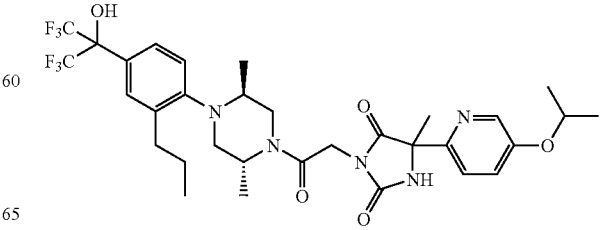

5-[5-(1-Methylethoxy)pyridin-2-yl]-5-methylimidazolidine-2,4-dione was used for a similar reaction and treatment as Examples 14-1 and 15-1, and the title compound was obtained as a yellow oil.

$^1$H-NMR (CDCl$_3$) δ: 0.95-1.00 (6H, m), 1.34-1.50 (9H, m), 1.68 (2H, qt, J=7.0, 7.3 Hz), 1.93 (3H, s), 2.47-2.60 (2H, m), 2.77-2.89 (1H, m), 3.29-3.95 (5H, m), 4.27-4.33 (2H, m), 4.57 (1H, q, J=5.9 Hz), 5.86 (1H, s), 6.43 (1H, s), 6.93 (1H, d, J=8.6 Hz), 7.20 (1H, dt, J=2.7, 6.2 Hz), 7.47 (1H, dd, J=2.0, 8.6 Hz), 7.53 (1H, d, J=2.0 Hz), 7.64 (1H, dd, J=5.9, 8.8 Hz), 8.19 (1H, d, J=2.7 Hz).

Example 25-2

Preparation of (2S,5R)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-[5-(1-methylethoxy)pyridin-2-yl]-5-methylimidazolidine-2,4-dione By conducting a similar reaction and treatment as Example 25-1, the title compound was obtained as a yellow oil.

Example 26-1

Preparation of (2R,5S,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[3-(1-methylethoxy)phenyl]-5-methylimidazolidine-2,4-dione

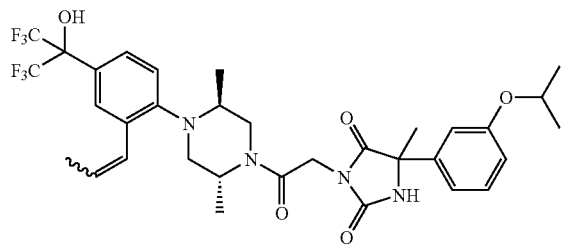

a) Preparation of 5-[3-(1-methylethoxy)phenyl]-5-methylimidazolidine-2,4-dione 1-(3-Hydroxyphenyl)ethanone (1.36 g, 10 mmol) was dissolved in acetone (50 mL) and potassium carbonate (2.76 g, 20 mmol) and 1-methylethyl iodide (1.5 mL, 15 mmol) were added sequentially, and the mixture was stirred at 70° C. overnight. The reaction solution was filtered, washed with acetone and concentrated in vacuo. The obtained residue was added water and ethyl acetate, and extracted with ethyl acetate. The organic layer was washed with 1N aqueous solution of sodium hydroxide and brine, dried over anhydrous sodium sulfate, and concentrated in vacuo. 1-(3-(1-methylethoxy)-phenyl)ethanone (1.67 g (yield 94%)) was obtained as a yellow oil.

$^1$H-NMR (CDCl$_3$) δ: 1.35 (6H, d, J=6.0 Hz), 2.55 (3H, s), 4.63 (1H, quint, J=6.0 Hz), 7.09 (1H, dd, J=2.4, 8.3 Hz). 7.35 (1H, t, J=8.0 Hz), 7.48-7.52 (2H, m).

1-[3-(1-Methylethoxy)phenyl]ethanone was used for a similar reaction and treatment as Example 1-1), and the title compound was obtained as a white crystal.

$^1$H-NMR (CDCl$_3$) δ: 1.30 (6H, d, J=6.0 Hz), 1.73 (3H, s), 4.60 (1H, quint, J=6.0 Hz), 6.85 (1H, dd, J=1.6, 8.3 Hz), 7.03-7.10 (2H, m), 7.27 (1H, t, J=8.3 Hz).

b) 5-(3-(1-Methylethoxy)phenyl)-5-methylimidazolidine-2,4-dione was used for a similar reaction and treatment as Example 14-1, and the title compound was obtained as a yellow oil.

$^1$H-NMR (CDCl$_3$) δ: 0.85-0.99 (3H, m), 1.31-1.34 (9H, m), 1.86-1.95 (6H, m), 2.68-2.82 (1H, m), 3.28-3.85 (5H, m), 4.16-4.31 (2H, m), 4.59 (1H, q, J=5.9 Hz), 4.85 (1H, s), 5.79-5.90 (2H, m), 6.48-6.66 (1H, m), 6.84-6.89 (2H, m), 7.08-7.12 (2H, m), 7.26-7.33 (1H, m), 7.52-7.58 (2H, m).

Example 26-2

Preparation of (2S,5R,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[3-(1-methylethoxy)phenyl]-5-methylimidazolidine-2,4-dione By conducting a similar reaction and treatment as Example 26-1, the title compound was obtained as a yellow oil.

Example 27-1

Preparation of (2R,5S)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-[3-(1-methylethoxy)phenyl]-5-methylimidazolidine-2,4-dione

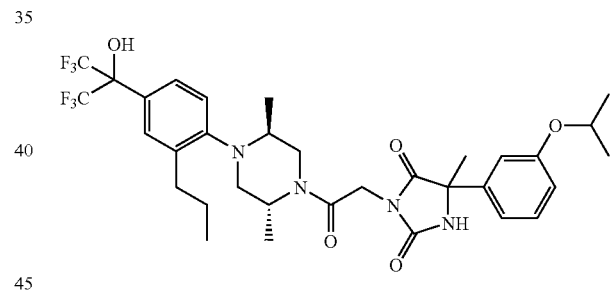

5-(3-(1-Methylethoxy)phenyl)-5-methylimidazolidine-2,4-dione was used for a similar reaction and treatment as Examples 14-1 and 15-1, and the title compound was obtained as a yellow oil.

$^1$H-NMR (CDCl$_3$) δ: 0.95-1.00 (6H, m), 1.31-1.45 (9H, m), 1.68 (2H, qt, J=7.3, 7.6 Hz), 1.91 (3H, s), 2.46-2.61 (3H, m), 2.77-2.88 (1H, m), 3.36-3.43 (2H, m), 3.58-3.62 (2H, m), 4.24-4.32 (2H, m), 4.59 (1H, q, J=6.5 Hz), 5.83 (1H, s), 5.79 (1H, s), 6.85 (1H, d, J=7.0 Hz), 6.92 (1H, d, J=8.6 Hz), 7.10 (2H, dd, J=5.0, 5.4 Hz), 7.27-7.33 (1H, m), 7.45 (1H, dd, J=2.0, 7.8 Hz), 7.52 (1H, d, J=2.0 Hz).

Example 27-2

Preparation of (2S,5R)-3-(2-{4-[4-(1,1,1,3,3,3-hexafluoro-2-hydroxpropan-2-yl)-2-propylphenyl]-2,5-dimethylpiperazin-1-yl}-2-oxoethyl)-5-[3-(1-methylethoxy)phenyl]-5-methylimidazolidine-2,4-dione By conducting a similar reaction and treatment as Example 27-1, the title compound was obtained as a yellow oil.

Example 28-1

Preparation of (2R,5S,Z)-5-[4-(cyclopropylthio)phenyl]-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-methylimidazolidine-2,4-dione

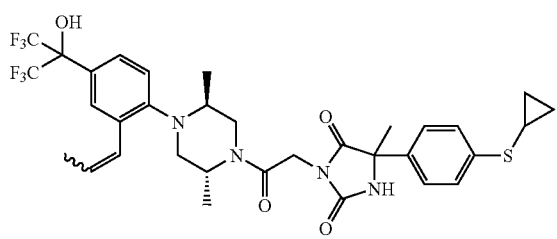

a) Preparation of 5-(4-(cyclopropylthio)phenyl)-5-methylimidazolidine-2,4-dione To dichloromethane (6.7 mL), acetyl chloride (189 μL, 2.66 mmol) and alminium chloride (267 mg, 2.0 mmol) were added sequentially at 0° C., and the mixture was stirred at 0° C. for 10 minutes. Then, a solution of cyclopropyl(phenyl)sulfane (200 mg, 1.33 mmol) in dichloromethane (890 μL) was added, and stirred at 0° C. for 0.5 hours. The reaction solution was added 5% aqueous solution of hydrochloric acid, and extracted with ethyl acetate. The organic layer was washed with a saturated aqueous solution of sodium hydrogen carbonate and brine, dried over anhydrous sodium sulfate, and concentrated in vacuo. The obtained residue was purified by silica-gel column chromatography (hexane/ethyl acetate), and 1-(4-(cyclopropylthio)phenyl)ethanone (181 mg (yield 71%)) was obtained as a colorless oil.

$^1$H-NMR (CDCl$_3$) δ: 0.69-0.75 (2H, m), 1.12-1.19 (2H, m), 2.16-2.25 (1H, m), 2.58 (3H, s), 7.41 (2H, d, J=8.9 Hz), 7.87 (2H, d, J=8.9 Hz).

1-(4-(Cyclopropylthio)phenyl)ethanone was used for a similar reaction and treatment as Example 1-l), and the title compound was obtained as a white crystal.

$^1$H-NMR (CDCl$_3$) δ: 0.56-0.62 (2H, m), 1.05-1.12 (2H, m), 1.74 (1H, m), 2.18-2.26 (1H, m), 7.34-7.44 (4H, m).

b) 5-(4-(Cyclopropylthio)phenyl)-5-methylimidazolidine-2,4-dione was used for a similar reaction and treatment as Example 14-1, and the title compound was obtained as a yellow oil.

$^1$H-NMR (CDCl$_3$) δ: 0.65-0.70 (3H, m), 0.88-1.45 (7H, m), 1.86-1.95 (6H, m), 2.14-2.21 (1H, m), 2.67-2.82 (1H, m), 3.28-3.86 (5H, m), 4.23-4.29 (2H, m), 4.86 (1H, s), 5.84-5.96 (2H, m), 6.49-6.65 (1H, m), 6.88 (1H, d, J=8.6 Hz), 7.36-7.58 (6H, m).

Example 28-2

Preparation of (2S,5R,Z)-5-[4-(cyclopropylthio)phenyl]-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-methylimidazolidine-2,4-dione By conducting a similar reaction and treatment as Example 28-1, the title compound was obtained as a yellow oil.

Example 29

Preparation of 3-(2-{(R)-4-[4-(1,1,1,3,3,3-hexafluoro-2-hydroxypropan-2-yl)-2-propylphenyl]-2-methylpiperazin-1-yl}-2-oxoethyl)-5-[4-(1-methylethoxy)phenyl]-5-methylimidazolidine-2,4-dione

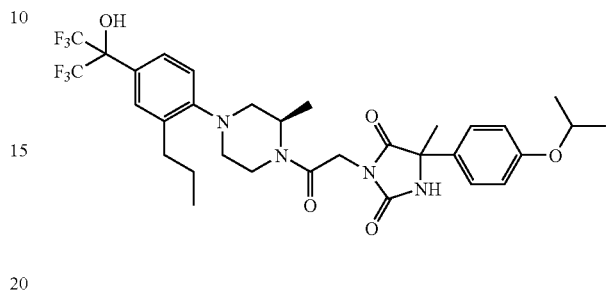

a) Preparation of (R)-4-(4-benzyl-3-methylpiperazin-1-yl)-3-nitrobenzoic acid methyl ester A similar reaction and treatment as Example 6-b) was conducted except that (R)-2-methyl-1-benzylpiperazine was used in place of tert-butyl piperazine-1-carboxylate, and the title compound was obtained as a yellow oil.

$^1$H-NMR (CDCl$_3$) δ: 1.20 (3H, d, J=5.9 Hz), 2.28-2.37 (1H, m), 2.67-2.80 (2H, m), 2.89-2.97 (1H, m), 3.03-3.25 (3H, m), 3.23 (1H, d, J=13.2 Hz), 3.90 (3H, s), 4.07 (1H, d, J=13.2 Hz), 7.04 (1H, d, J=8.9 Hz), 7.26-7.34 (5H, m), 8.04 (1H, dd, J=2.2, 8.9 Hz), 8.42 (1H, d, J=2.2 Hz).

b) Preparation of (R)-3-amino-4-(4-benzyl-3-methylpiperazin-1-yl)benzoic acid methyl ester By conducting a similar reaction and treatment as Example 6-c), the title compound was obtained as a yellow oil.

$^1$H-NMR (CDCl$_3$) δ: 1.23 (3H, d, J=5.7 Hz), 2.28-2.38 (1H, m), 2.59-2.71 (2H, m), 2.77-2.86 (2H, m), 2.99-3.11 (2H, m), 3.26 (1H, d, J=13.2 Hz), 3.86 (3H, s), 3.94 (2H, s), 4.19 (1H, d, J=13.2 Hz), 6.95 (1H, d, J=8.1 Hz), 7.26-7.35 (5H, m), 7.38 (1H, d, J=1.9 Hz), 7.43 (1H, dd, J=1.9, 8.1 Hz).

c) Preparation of (R)-4-(4-benzyl-3-methylpiperazin-1-yl)-3-iodobenzoic acid methyl ester By conducting a similar reaction and treatment as Example 6-d), the title compound was obtained as a yellow oil.

$^1$H-NMR (CDCl$_3$) δ: 1.23 (3H, d, J=6.1 Hz), 2.39-2.45 (1H, m), 2.66-2.92 (4H, m), 3.13-3.16 (1H, m), 3.22-3.29 (2H, m), 3.88 (3H, s), 4.11 (1H, d, J=13.7 Hz), 6.98 (1H, d, J=8.3 Hz), 7.24-7.37 (5H, m), 7.96 (1H, dd, J=2.0, 8.3 Hz), 8.49 (1H, d, J=2.0 Hz).

d) Preparation of (R)-4-(4-benzyl-3-methylpiperazin-1-yl)-3-(prop-1-en-1-yl)benzoic acid methyl ester By conducting a similar reaction and treatment as Example 6-e), the title compound was obtained as a yellow oil.

$^1$H-NMR (CDCl$_3$) δ: 1.21 (3H, d, J=5.9 Hz), 1.88 (3H, d, J=7.0. Hz), 2.27-2.34 (1H, m), 2.63-2.88 (4H, m), 3.15-3.25 (2H, m), 3.23 (1H, d, J=12.4 Hz), 3.88 (3H, s), 4.09 (1H, d, J=12.4 Hz), 5.79 (1H, qd, J=7.0, 9.7 Hz), 6.41 (1H, d, J=9.7 Hz), 6.92 (1H, d, J=8.1 Hz), 7.29-7.35 (5H, m), 7.86 (1H, dd, J=2.4, 8.1 Hz), 7.90 (1H, d, J=2.4 Hz).

e) Preparation of (R)-4-(4-benzyl-3-methylpiperazin-1-yl)-3-(prop-1-en-1-yl)benzoic acid By conducting a similar reaction and treatment as Example 6-f), the title compound was obtained as a yellow oil.

¹H-NMR (CDCl₃) δ: 1.22 (3H, d, J=6.2 Hz), 1.89 (3H, d, J=7.0 Hz), 2.25-2.40 (1H, m), 2.60-2.90 (4H, m), 3.17-3.27 (2H, m), 3.25 (1H, d, J=13.0 Hz), 4.10 (1H, d, J=13.0 Hz), 5.80 (1H, qd, J=7.0, 12.2 Hz), 6.40 (1H, d, J=12.2 Hz), 6.94 (1H, d, J=8.1 Hz), 7.29-7.35 (5H, m), 7.91 (1H, d, J=8.1 Hz), 7.94 (1H, s).

f) Preparation of (R)-4-(4-benzyl-3-methylpiperazin-1-yl)-3-(prop-1-en-1-yl)benzoic acid pentafluorophenyl ester By conducting a similar reaction and treatment as Example 6-g), the title compound was obtained as a yellow oil.

¹H-NMR (CDCl₃) δ: 1.23 (3H, d, J=5.9 Hz), 1.89 (3H, dd, J=1.9, 7.3 Hz), 2.26-2.39 (1H, m), 2.61-2.96 (4H, m), 3.23-3.33 (3H, m), 3.25 (1H, d, J=13.2 Hz), 5.80-5.91 (1H, m), 6.37-6.44 (1H, m), 6.98 (1H, d, J=9.2 Hz), 7.32-7.36 (5H, m), 8.00-8.03 (2H, m).

g) Preparation of (R)-2-[4-(4-benzyl-3-methylpiperazin-1-yl)-3-(prop-1-en-1-yl)phenyl]-1,1,1,3,3,3-hexafluoro propan-2-ol By conducting a similar reaction and treatment as Example 6-h), the title compound was obtained as a yellow oil.

¹H-NMR (CDCl₃) δ: 1.22 (3H, d, J=6.2 Hz), 1.84 (3H, d, J=6.8 Hz), 2.25-2.36 (1H, m), 2.61-2.87 (4H, m), 3.07-3.28 (3H, m), 4.09 (1H, d, J=11.6 Hz), 5.75-5.85 (1H, m), 6.43-6.48 (1H, m), 6.98 (1H, d, J=8.4 Hz), 7.27-7.35 (5H, m), 7.51 (1H, d, J=8.4 Hz), 7.54 (1H, s).

h) Preparation of (R)-1-benzyl-4-{4-[1,1,1,3,3,3-hexafluoro-2-(methoxymethoxy)propan-2-yl]-2-(prop-1-en-1-yl)phenyl}-2-methylpiperazine A similar reaction and treatment as Example 6-i) was conducted except that methoxymethyl ether chloride was used in place of benzyl bromide, and the title compound was obtained as a yellow oil.

¹H-NMR (CDCl₃) δ: 1.21 (3H, d, J=5.7 Hz), 1.83 (3H, d, J=7.0 Hz), 2.26-2.35 (1H, m), 2.62-2.88 (4H, m), 3.08-3.21 (2H, m), 3.23 (1H, d, J=13.2 Hz), 3.54 (3H, s), 4.08 (1H, d, J=13.2 Hz), 4.85 (2H, s), 5.80 (1H, qd, J=7.0, 11.3 Hz), 6.46 (1H, d, J=11.3 Hz), 6.96 (1H, d, J=8.6 Hz), 7.26-7.34 (5H, m), 7.41 (1H, d, J=8.6 Hz), 7.45 (1H, s).

i) Preparation of (R)-1-{4-[1,1,1,3,3,3-hexafluoro-2-(methoxymethoxy)propan-2-yl]-2-propylphenyl}-3-methyl piperazine By conducting a similar reaction and treatment as Example 6-j), the title compound was obtained as a yellow oil.

¹H-NMR (CDCl₃) δ: 0.96 (3H, t, J=7.6 Hz), 1.10 (3H, d, J=6.2 Hz), 1.65 (2H, qt, J=7.6, 7.8 Hz), 2.36-2.44 (1H, m), 2.64 (2H, t, J=7.8 Hz), 2.71-2.78 (1H, m), 2.96-3.09 (5H, m), 3.55 (3H, s), 4.83 (2H, s), 7.07 (1H, d, J=8.1 Hz), 7.37 (1H, d, J=8.1 Hz), 7.39 (1H, s).

j) Preparation of (R)-2-bromo-1-(4-{4-[1,1,1,3,3,3-hexafluoro-2-(methoxymethoxy)propan-2-yl]-2-propylphenyl)-yl}-2-methylpiperazin-1-yl)ethanone By conducting a similar reaction and treatment as Example 6-k), the title compound was obtained as a yellow oil.

¹H-NMR (CDCl₃) δ: 0.98 (3H, t, J=7.3 Hz), 1.42 (3H, d, J=6.5 Hz), 1.59-1.73 (2H, m), 2.70 (2H, t, J=7.3 Hz), 2.86-3.10 (4H, m), 3.55 (3H, s), 3.65-3.75 (1H, m), 3.89 (2H, s), 4.10-4.20 (1H, m), 4.45-4.55 (1H, m), 4.83 (2H, s), 7.08 (1H, d, J=8.4 Hz), 7.41 (1H, d, J=8.4 Hz), 7.43 (1H, s).

In step a) of the present Example, by using (S)-2-methyl-1-benzylpiperazine in place of (R)-2-methyl-1-benzylpiperazine, (S)-2-bromo-1-(4-{4-[1,1,1,3,3,3-hexafluoro-2-(methoxymethoxy)propan-2-yl]-2-propylphenyl}-2-methylpiperazin-1-yl)ethanone was obtained as a yellow oil.

k) (R)-2-bromo-1-(4-{4-[1,1,1,3,3,3-hexafluoro-2-(methoxymethoxy)propan-2-yl]-2-propylphenyl}-2-methyl piperazin-1-yl)ethanone and 5-(3-(1-methylethoxy)phenyl)-5-methylimidazolidine-2,4-dione were used for a similar reaction and treatment as Examples 14-1 and 15-1, and the title compound was obtained as a yellow oil.

¹H-NMR (CDCl₃) δ: 0.98 (3H, t, J=7.6 Hz), 1.32 (6H, d, J=6.2 Hz), 1.59-1.73 (5H, m), 1.91 (3H, s), 2.70 (2H, t, J=7.6 Hz), 2.80-3.05 (4H, m), 3.55-3.65 (1H, m), 4.00-4.80 (4H, m), 4.47-4.60 (1H, m), 5.68 (1H, s), 6.90 (2H, d, J=8.9 Hz), 7.07 (1H, d, J=8.4 Hz), 7.44-7.48 (2H, m), 7.50 (1H, d, J=8.4 Hz), 7.52 (1H, s).

Example 30

Preparation of 5-(2,3-dihydrobenzo[b][1,4]dioxin-6-yl)-3-(2-{(R)-4-[4-(1,1,1,3,3,3-hexafluoro-2-hydroxypropan-2-yl)-2-propylphenyl]-2-methylpiperazin-1-yl}-2-oxoethyl)-5-methylimidazolidine-2,4-dione

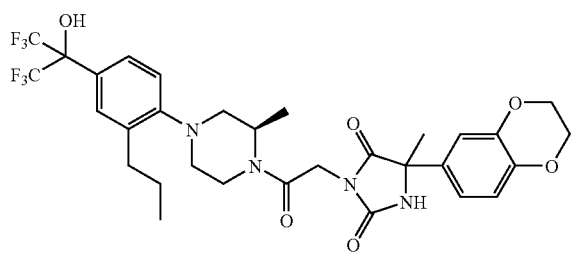 [SMILES: CCCc1cc(C(O)(C(F)(F)F)C(F)(F)F)ccc1N1CCN(C(=O)CN2C(=O)NC(C)(c3ccc4c(c3)OCCO4)C2=O)[C@H](C)C1]

(R)-2-bromo-1-(4-{4-[1,1,1,3,3,3-hexafluoro-2-(methoxymethoxy)propan-2-yl]-2-propylphenyl}-2-methylpiperazin-1-yl)ethanone and 5-(2,3-dihydrobenzo[b][1,4]dioxin-6-yl)-5-methylimidazolidine-2,4-dione were used for a similar reaction and treatment as Examples 14-1 and 15-1, and the title compound was obtained as a yellow oil.

¹H-NMR (CDCl₃) δ: 0.97 (3H, t, J=7.3 Hz), 1.60-1.73 (5H, m), 1.88 (3H, s), 2.69 (2H, t, J=7.6 Hz), 2.89-3.05 (4H, m), 3.53-3.70 (1H, m), 4.00-4.80 (4H, m), 4.25 (4H, s), 5.73 (1H, s), 6.88 (1H, d, J=8.6 Hz), 7.00-7.09 (3H, m), 7.50 (1H, d, J=8.6 Hz), 7.52 (1H, s).

Example 31

Preparation of 5-(2,3-dihydrobenzofuran-5-yl)-3-(2-[(R)-4-{4-(1,1,1,3,3,3-hexafluoro-2-hydroxypropan-2-yl)-2-propylphenyl}-2-methylpiperazin-1-yl]-2-oxoethyl)-5-methylimidazolidine-2,4-dione

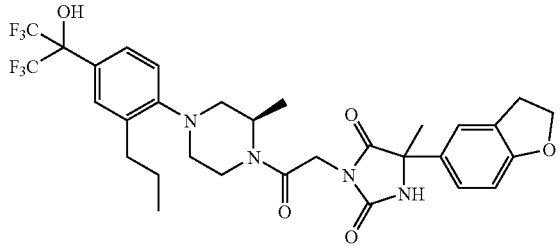 [SMILES: CCCc1cc(C(O)(C(F)(F)F)C(F)(F)F)ccc1N1CCN(C(=O)CN2C(=O)NC(C)(c3ccc4c(c3)CCO4)C2=O)[C@H](C)C1]

(R)-2-bromo-1-(4-{4-[1,1,1,3,3,3-hexafluoro-2-(methoxymethoxy)propan-2-yl]-2-propylphenyl}-2-methylpiperazin-1-yl)ethanone and 5-(2,3-dihydrobenzofuran-5-yl)-5-methylimidazolidine-2,4-dione were used for a similar reaction and treatment as Examples 14-1 and 15-1, and the title compound was obtained as a yellow oil.

$^1$H-NMR (CDCl$_3$) δ: 0.97 (3H, t, J=7.3 Hz), 1.58-1.71 (5H, m), 1.90 (3H, s), 2.69 (2H, t, J=7.3 Hz), 2.89-3.05 (4H, m), 3.22 (2H, t, J=8.6 Hz), 3.55-3.65 (1H, m), 4.05-4.77 (4H, m), 4.58 (2H, t, J=8.6 Hz), 5.79 (1H, s), 6.78 (1H, d, J=8.6 Hz), 7.07 (1H, d, J=8.4 Hz), 7.25-7.32 (1H, m), 7.41 (1H, s), 7.50 (1H, d, J=8.4 Hz), 7.52 (1H, s).

Example 32

Preparation of 3-(2-[(R)-4-{4-(1,1,1,3,3,3-hexafluoro-2-hydroxypropan-2-yl)-2-propylphenyl}-2-methylpiperazin-1-yl]-2-oxoethyl)-5-[5-(1-methylethoxy)pyridin-2-yl]-5-methylimidazolidine-2,4-dione

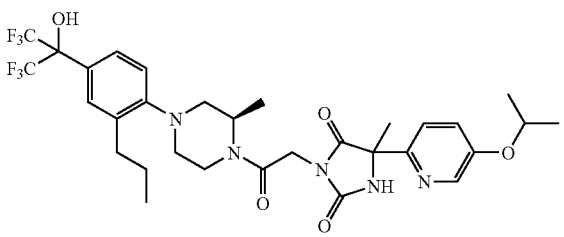 [SMILES: CCCc1cc(C(O)(C(F)(F)F)C(F)(F)F)ccc1N1CCN(C(=O)CN2C(=O)NC(C)(c3ccc(OC(C)C)cn3)C2=O)[C@H](C)C1]

(R)-2-bromo-1-(4-{4-[1,1,1,3,3,3-hexafluoro-2-(methoxymethoxy)propan-2-yl]-2-propylphenyl}-2-methylpiperazin-1-yl)ethanone and 5-[5-(1-methylethoxy)pyridin-2-yl]-5-methylimidazolidine-2,4-dione were used for a similar reaction and treatment as Examples 14-1 and 15-1, and the title compound was obtained as a yellow oil.

$^1$H-NMR (CDCl$_3$) δ: 0.98 (3H, t, J=7.3 Hz), 1.35 (6H, d, J=5.9 Hz), 1.60-1.71 (5H, m), 1.87 (3H, s), 2.70 (2H, t, J=7.6 Hz), 2.89-3.05 (4H, m), 3.62-3.69 (1H, m), 4.05-4.75 (4H, m), 4.52-4.61 (1H, m), 6.33 (1H, s), 7.07 (1H, d, J=8.4 Hz), 7.19 (1H, dd, J=2.7, 8.6 Hz), 7.50 (1H, d, J=8.4 Hz), 7.52 (1H, s), 7.61-7.65 (1H, m), 8.19 (1H, d, J=2.7 Hz).

Example 33

Preparation of 3-(2-{(S)-4-[4-(1,1,1,3,3,3-hexafluoro-2-hydroxypropan-2-yl)-2-propylphenyl]-2-methylpiperazin-1-yl}-2-oxoethyl)-5-[4-(1-methylethoxy)phenyl]-5-methylimidazolidine-2,4-dione

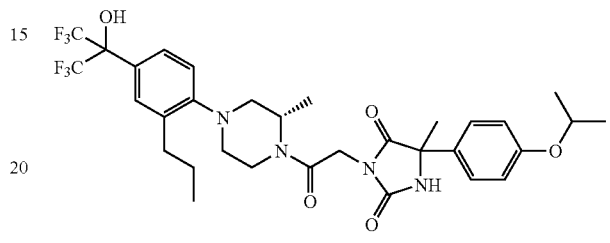

(S)-2-bromo-1-(4-{4-[1,1,1,3,3,3-hexafluoro-2-(methoxymethoxy)propan-2-yl]-2-propylphenyl}-2-methylpiperazin-1-yl)ethanone and 5-(3-(1-methylethoxy)phenyl)-5-methylimidazolidine-2,4-dione were used for a similar reaction and treatment as Examples 14-1 and 15-1, and the title compound was obtained as a yellow oil.

$^1$H-NMR (CDCl$_3$) δ: 0.98 (3H, t, J=7.3 Hz), 1.32 (6H, d, J=6.2 Hz), 1.59-1.73 (5H, m), 1.91 (3H, s), 2.70 (2H, t, J=7.3 Hz), 2.80-3.05 (4H, m), 3.55-3.65 (1H, m), 4.00-4.80 (4H, m), 4.47-4.60 (1H, m), 5.69 (1H, s), 6.90 (2H, d, J=8.9 Hz), 7.07 (1H, d, J=8.1 Hz), 7.44-7.48 (2H, m), 7.50 (1H, d, J=8.1 Hz), 7.52 (1H, s).

Example 34

Preparation of 5-(2,3-dihydrobenzo[b][1,4]dioxin-6-yl)-3-(2-{(S)-4-[4-(1,1,1,3,3,3-hexafluoro-2-hydroxypropan-2-yl)-2-propylphenyl]-2-methylpiperazin-1-yl}-2-oxoethyl)-5-methylimidazolidine-2,4-dione

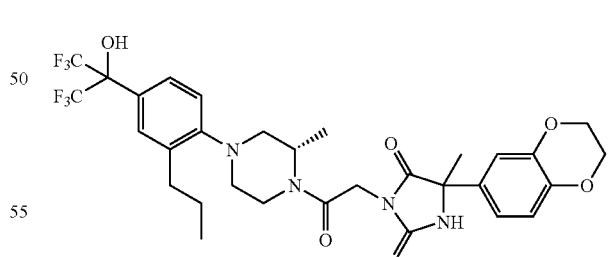

(S)-2-bromo-1-(4-{4-[1,1,1,3,3,3-hexafluoro-2-(methoxymethoxy)propan-2-yl]-2-propylphenyl}-2-methylpiperazin-1-yl)ethanone and 5-(2,3-dihydrobenzo[b][1,4]dioxin-6-yl)-5-methylimidazolidine-2,4-dione were used for a similar reaction and treatment as Examples 14-1 and 15-1, and the title compound was obtained as a yellow oil.

$^1$H-NMR (CDCl$_3$) δ: 0.97 (3H, t, J=7.3 Hz), 1.60-1.73 (5H, m), 1.88 (3H, s), 2.69 (2H, t, J=7.6 Hz), 2.89-3.05 (4H, m), 3.53-3.70 (1H, m), 4.00-4.80 (4H, m), 4.25 (4H, s), 5.71 (1H, s), 6.88 (1H, d, J=8.6 Hz), 7.00-7.09 (3H, m), 7.50 (1H, d, J=8.6 Hz), 7.52 (1H, s).

Example 35

Preparation of 5-(2,3-dihydrobenzofuran-5-yl)-3-(2-{(S)-4-[4-(1,1,1,3,3,3-hexafluoro-2-hydroxypropan-2-yl)-2-propylphenyl]-2-methylpiperazin-1-yl}-2-oxoethyl)-5-methylimidazolidine-2,4-dione

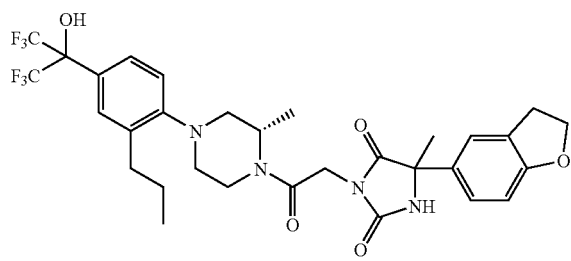 [SMILES: CCCc1cc(C(O)(C(F)(F)F)C(F)(F)F)ccc1N1CCN(C(=O)CN2C(=O)NC(C)(c3ccc4c(c3)CCO4)C2=O)[C@@H](C)C1]

(S)-2-bromo-1-(4-{4-[1,1,1,3,3,3-hexafluoro-2-(methoxymethoxy)propan-2-yl]-2-propylphenyl}-2-methylpiperazin-1-yl)ethanone and 5-(2,3-dihydrobenzofuran-5-yl)-5-methylimidazolidine-2,4-dione were used for a similar reaction and treatment as Examples 14-1 and 15-1, and the title compound was obtained as a yellow oil.

$^1$H-NMR (CDCl$_3$) δ: 0.98 (3H, t, J=7.3 Hz), 1.58-1.71 (5H, m), 1.91 (3H, s), 2.69 (2H, t, J=7.6 Hz), 2.89-3.05 (4H, m), 3.22 (2H, t, J=8.9 Hz), 3.55-3.65 (1H, m), 4.05-4.77 (4H, m), 4.58 (2H, t, J=8.9 Hz), 5.73 (1H, s), 6.78 (1H, d, J=8.1 Hz), 7.07 (1H, d, J=8.6 Hz), 7.25-7.32 (1H, m), 7.41 (1H, s), 7.50 (1H, d, J=8.6 Hz), 7.52 (1H, s).

Example 36

Preparation of 3-(2-{(S)-4-[4-(1,1,1,3,3,3-hexafluoro-2-hydroxypropan-2-yl)-2-propylphenyl]-2-methylpiperazin-1-yl}-2-oxoethyl)-5-[5-(1-methylethoxy)pyridin-2-yl]-5-methylimidazolidine-2,4-dione

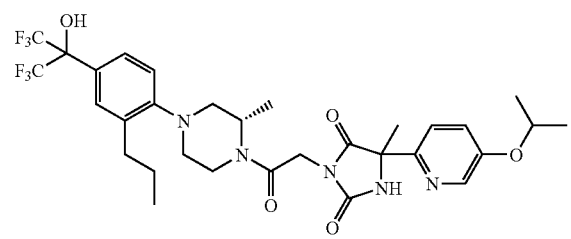 [SMILES: CCCc1cc(C(O)(C(F)(F)F)C(F)(F)F)ccc1N1CCN(C(=O)CN2C(=O)NC(C)(c3ccc(OC(C)C)cn3)C2=O)[C@@H](C)C1]

(S)-2-bromo-1-(4-{4-[1,1,1,3,3,3-hexafluoro-2-(methoxymethoxy)propan-2-yl]-2-propyl phenyl}-2-methylpiperazin-1-yl)ethanone and 5-[5-(1-methylethoxy)pyridin-2-yl]-5-methylimidazolidine-2,4-dione were used for a similar reaction and treatment as Examples 14-1 and 15-1, and the title compound was obtained as a yellow oil.

$^1$H-NMR (CDCl$_3$) δ: 0.98 (3H, t, J=7.3 Hz), 1.35 (6H, d, J=5.9 Hz), 1.60-1.71 (5H, m), 1.87 (3H, s), 2.70 (2H, t, J=7.8 Hz), 2.89-3.05 (4H, m), 3.62-3.69 (1H, m), 4.05-4.75 (4H, m), 4.52-4.61 (1H, m), 6.31 (1H, s), 7.08 (1H, d, J=8.1 Hz), 7.19 (1H, dd, J=2.7, 8.6 Hz), 7.50 (1H, d, J=8.1 Hz), 7.52 (1H, s), 7.61-7.65 (1H, m), 8.19 (1H, d, J=2.7 Hz).

Example 37

Preparation of 3-(2-{4-[4-(1,1,1,3,3,3-hexafluoro-2-hydroxypropan-2-yl)-2-propylphenyl]-1,4-diazepan-1-yl}-2-oxoethyl)-5-[4-(1-methylethoxy)phenyl]-5-methylimidazolidine-2,4-dione

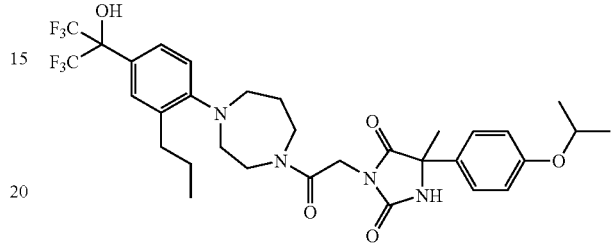

a) Preparation of 4-[4-(methoxycarbonyl)-2-nitrophenyl]-1,4-diazepan-1-carboxylic acid tert-butyl ester 1-tert-Butyl-1,4-diazepan-1-carboxylate was used in place of tert-butyl piperazine-1-carboxylate for a similar reaction and treatment as Example 6-b), and the title compound was obtained as a yellow oil.

$^1$H-NMR (CDCl$_3$) δ: 1.30 (9H, s), 1.95-2.01 (2H, m), 3.24-3.28 (1H, m), 3.41-3.65 (7H, m), 3.90 (3H, s), 7.06 (1H, d, J=8.3 Hz), 7.99 (1H, d, J=8.3 Hz), 8.36 (1H, s).

b) Preparation of 4-[2-amino-4-(methoxycarbonyl)phenyl]-1,4-diazepan-1-carboxylic acid tert-butyl ester By conducting a similar reaction and treatment as Example 6-c), the title compound was obtained as a yellow oil.

$^1$H-NMR (CDCl$_3$) δ: 1.48 (9H, s), 1.87-2.01 (2H, m), 3.04-3.14 (4H, m), 3.52-3.64 (4H, m), 3.86 (3H, s), 4.00 (2H, s), 6.99 (1H, d, J=7.8 Hz), 7.38-7.42 (2H, m).

c) Preparation of 4-[2-iodo-4-(methoxycarbonyl)phenyl]-1,4-diazepan-1-carboxylic acid tert-butyl ester By conducting a similar reaction and treatment as Example 6-d), the title compound was obtained as a yellow oil.

$^1$H-NMR (CDCl$_3$) δ: 1.49 (9H, s), 2.04-2.13 (2H, m), 3.12-3.20 (4H, m), 3.57-3.71 (4H, m), 3.89 (3H, s), 7.06 (1H, d, J=8.6 Hz), 7.94 (1H, dd, J=1.9, 8.6 Hz), 8.50 (1H, d, J=1.9 Hz).

d) Preparation of 4-[4-(methoxycarbonyl)-2-(prop-1-en-1-yl)phenyl]-1,4-diazepan-1-carboxylic acid tert-butyl ester By conducting a similar reaction and treatment as Example 6-e), the title compound was obtained as a yellow oil.

$^1$H-NMR (CDCl$_3$) δ: 1.47 (9H, s), 1.85 (3H, d, J=7.0 Hz), 1.90-2.00 (2H, m), 3.21-3.35 (4H, m), 3.47-3.61 (4H, m), 3.88 (3H, s), 5.81 (1H, qd, J=7.0, 10.5 Hz), 6.40 (1H, d, J=10.5 Hz), 6.97 (1H, d, J=8.4 Hz), 7.83 (1H, d, J=8.4 Hz), 7.85 (1H, s).

e) Preparation of 4-[4-carboxy-2-(prop-1-en-1-yl)phenyl]-1,4-diazepan-1-carboxylic acid tert-butyl ester By conducting a similar reaction and treatment as Example 6-f), the title compound was obtained as a yellow oil.

$^1$H-NMR (CDCl$_3$) δ: 1.22 (3H, d, J=6.2 Hz), 1.89 (3H, d, J=7.0 Hz), 2.25-2.40 (1H, m), 2.60-2.90 (4H, m), 3.17-3.27 (2H, m), 3.25 (1H, d, J=13.0 Hz), 4.10 (1H, d, J=13.0 Hz), 5.80 (1H, dq, J=7.0, 12.2 Hz), 6.40 (1H, d, J=12.2 Hz), 6.94 (1H, d, J=8.1 Hz), 7.29-7.35 (5H, m), 7.91 (1H, d, J=8.1 Hz), 7.94 (1H, s).

f) Preparation of 4-{4-[(perfluorophenoxy)carbonyl]-2-(prop-1-en-1-yl)phenyl}-1,4-diazepan-1-carboxylic acid tert-butyl ester By conducting a similar reaction and treatment as Example 6-g), the title compound was obtained as a yellow oil.

$^1$H-NMR (CDCl$_3$) δ: 1.47 (9H, s), 1.86 (3H, d, J=7.0 Hz), 1.90-2.05 (2H, m), 3.38-3.62 (8H, m), 5.85 (1H, qd, J=7.0, 10.5 Hz), 6.39 (1H, d, J=10.5 Hz), 7.01 (1H, d, J=8.9 Hz), 7.95 (1H, s), 7.97 (1H, d, J=8.9 Hz).

g) Preparation of 4-[4-(1,1,1,3,3,3-hexafluoro-2-hydroxypropan-2-yl)-2-(prop-1-en-1-yl)phenyl]-1,4-diazepan-1-carboxylic acid tert-butyl ester By conducting a similar reaction and treatment as Example 6-h), the title compound was obtained as a yellow oil.

$^1$H-NMR (CDCl$_3$) δ: 1.47 (9H, s), 1.82 (3H, d, J=7.0 Hz), 1.88-1.98 (2H, m), 3.14-3.25 (4H, m), 3.50-3.61 (4H, m), 5.82 (1H, qd, J=7.0, 11.1 Hz), 6.46 (1H, d, J=11.1 Hz), 7.03 (1H, d, J=8.6 Hz), 7.48 (1H, d, J=8.6 Hz), 7.51 (1H, s).

h) Preparation of 2-[4-(1,4-diazepan-1-yl)-3-(prop-1-en-1-yl)phenyl]-1,1,1,3,3,3-hexafluoropropan-2-ol By conducting a similar reaction and treatment as Example 12-h), the title compound was obtained as a yellow oil.

$^1$H-NMR (CDCl$_3$) δ: 1.79 (3H, d, J=7.0 Hz), 2.12-2.22 (2H, m), 3.28-3.40 (8H, m), 5.86 (1H, qd, J=7.0, 11.4 Hz), 6.47 (1H, d, J=11.4 Hz), 7.06 (1H, d, J=8.9 Hz), 7.53 (1H, d, J=8.9 Hz), 7.55 (1H, s).

i) Preparation of 1-{4-[1,1,1,3,3,3-hexafluoro-2-(methoxymethoxy)propan-2-yl]-2-(prop-1-en-1-yl)phenyl}-1,4-diazepane By conducting a similar reaction and treatment as Example 12-i), the title compound was obtained as a yellow oil.

$^1$H-NMR (CDCl$_3$) δ: 1.79 (3H, d, J=7.3 Hz), 2.19-2.29 (2H, m), 3.29-3.48 (8H, m), 3.55 (3H, s), 4.85 (2H, s), 5.87 (1H, qd, J=7.3, 11.1 Hz), 6.48 (1H, d, J=11.1 Hz), 7.07 (1H, d, J=8.9 Hz), 7.43 (1H, d, J=8.9 Hz), 7.45 (1H, s).

j) Preparation of 1-{4-[1,1,1,3,3,3-hexafluoro-2-(methoxymethoxy)propan-2-yl]-2-propylphenyl}-1,4-diazepane By conducting a similar reaction and treatment as Example 6-j), the title compound was obtained as a yellow oil.

$^1$H-NMR (CDCl$_3$) δ: 0.98 (3H, d, J=7.3 Hz), 1.61 (2H, qt, J=7.3, 7.6 Hz), 2.13-2.33 (2H, m), 2.66 (2H, t, J=7.6 Hz), 3.17-3.21 (2H, m), 3.37-3.52 (6H, m), 3.55 (3H, s), 4.83 (2H, s), 7.16 (1H, d, J=8.4 Hz), 7.41 (1H, d, J=8.4 Hz), 7.42 (1H, s).

k) Preparation of 2-bromo-1-(4-{4-[1,1,1,3,3,3-hexafluoro-2-(methoxymethoxy)propan-2-yl]-2-propylphenyl}-1,4-diazepan-1-yl)ethanone By conducting a similar reaction and treatment as Example 6-k), the title compound was obtained as a yellow oil.

$^1$H-NMR (CDCl$_3$) δ: 0.97 (3H, d, J=7.6 Hz), 1.64 (2H, qt, J=7.6, 7.6 Hz), 2.05-2.15 (2H, m), 2.65 (2H, t, J=7.6 Hz), 3.06-3.28 (4H, m), 3.55 (3H, s), 3.69-3.85 (4H, m), 3.93 (2H, s), 4.83 (2H, s), 7.10 (1H, d, J=8.4 Hz), 7.37 (1H, d, J=8.4 Hz), 7.39 (1H, s).

l) 2-Bromo-1-(4-{4-[1,1,1,3,3,3-hexafluoro-2-(methoxymethoxy)propan-2-yl]-2-propylphenyl}-1,4-diazepan-1-yl)ethanone and 5-(3-(1-methylethoxy)phenyl)-5-methylimidazolidine-2,4-dione were used for a similar reaction and treatment as Examples 14-1 and 15-1, and the title compound was obtained as a yellow oil.

$^1$H-NMR (CDCl$_3$) δ: 0.96 (3H, t, J=7.3 Hz), 1.32 (6H, d, J=6.2 Hz), 1.60-1.70 (2H, m), 1.90 (3H, s), 2.01-2.10 (2H, m), 2.65 (2H, t, J=7.6 Hz), 3.08-3.15 (2H, m), 3.29-3.37 (1H, m), 3.53-3.78 (5H, m), 4.30-4.40 (2H, m), 4.49-4.58 (1H, m), 5.75 (1H, s), 6.89 (2H, d, J=8.6 Hz), 7.08 (1H, d, J=8.4 Hz), 7.40-7.47 (4H, m).

Example 38

Preparation of 5-(2,3-dihydrobenzo[b][1,4]dioxin-6-yl)-3-(2-{4-[4-(1,1,1,3,3,3-hexafluoro-2-hydroxypropan-2-yl)-2-propylphenyl]-1,4-diazepan-1-yl}-2-oxoethyl)-5-methylimidazolidine-2,4-dione

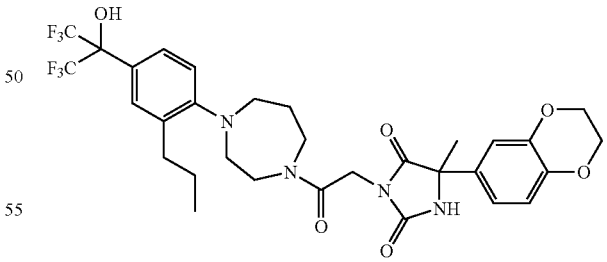

2-Bromo-1-(4-{4-[1,1,1,3,3,3-hexafluoro-2-(methoxymethoxy)propan-2-yl]-2-propylphenyl}-1,4-diazepan-1-yl)ethanone and 5-(2,3-dihydrobenzo[b][1,4]dioxin-6-yl)-5-methylimidazolidine-2,4-dione were used for a similar reaction and treatment as Examples 14-1 and 15-1, and the title compound was obtained as a yellow oil.

$^1$H-NMR (CDCl$_3$) δ: 0.96 (3H, t, J=7.3 Hz), 1.60-1.70 (2H, m), 1.88 (3H, s), 2.00-2.15 (2H, m), 2.65 (2H, t, J=7.6 Hz), 3.10-3.15 (2H, m), 3.28-3.35 (1H, m), 3.53-3.78 (5H, m), 4.24 (4H, s), 4.25-4.40 (2H, m), 5.70 (1H, s), 6.88 (1H, d, J=8.6 Hz), 6.99-7.13 (3H, m), 7.45 (1H, d, J=8.4 Hz), 7.48 (1H, s).

Example 39

Preparation of 5-(2,3-dihydrobenzofuran-5-yl)-3-(2-{4-[4-(1,1,1,3,3,3-hexafluoro-2-hydroxypropan-2-yl)-2-propylphenyl]-1,4-diazepan-1-yl}-2-oxoethyl)-5-methylimidazolidine-2,4-dione

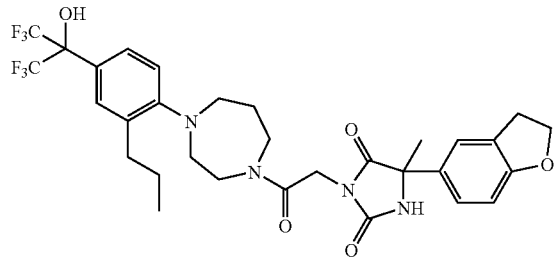 [SMILES: CCCc1cc(C(O)(C(F)(F)F)C(F)(F)F)ccc1N1CCCN(C(=O)CN2C(=O)NC(C)(c3ccc4c(c3)CCO4)C2=O)CC1]

2-Bromo-1-(4-{4-[1,1,1,3,3,3-hexafluoro-2-(methoxymethoxy)propan-2-yl]-2-propylphenyl}-1,4-diazepan-1-yl)ethanone and 5-(2,3-dihydrobenzofuran-5-yl)-5-methylimidazolidine-2,4-dione were used for a similar reaction and treatment as Examples 14-1 and 15-1, and the title compound was obtained as a yellow oil.
$^1$H-NMR (CDCl$_3$) δ: 0.96 (3H, t, J=7.6 Hz), 1.57-1.70 (2H, m), 1.90 (3H, s), 2.05-2.15 (2H, m), 2.65 (2H, t, J=7.8 Hz), 3.08-3.14 (2H, m), 3.21 (2H, t, J=8.4 Hz), 3.28-3.35 (1H, m), 3.55-3.80 (5H, m), 4.25-4.42 (2H, m), 4.57 (2H, t, J=8.4 Hz), 5.75 (1H, s), 6.78 (1H, d, J=8.4 Hz), 7.08 (1H, d, J=8.4 Hz), 7.40-7.48 (3H, m), 7.48 (1H, s).

Example 40

Preparation of 3-(2-{4-[4-(1,1,1,3,3,3-hexafluoro-2-hydroxypropan-2-yl)-2-propylphenyl]-1,4-diazepan-1-yl}-2-oxoethyl)-5-[5-(1-methylethoxy)pyridin-2-yl]-5-methylimidazolidine-2,4-dione

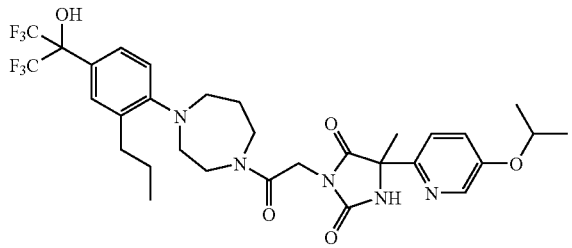 [SMILES: CCCc1cc(C(O)(C(F)(F)F)C(F)(F)F)ccc1N1CCCN(C(=O)CN2C(=O)NC(C)(c3ccc(OC(C)C)cn3)C2=O)CC1]

2-Bromo-1-(4-{4-[1,1,1,3,3,3-hexafluoro-2-(methoxymethoxy)propan-2-yl]-2-propylphenyl}-1,4-diazepan-1-yl)ethanone and 5-[5-(1-methylethoxy)pyridin-2-yl]-5-methylimidazolidine-2,4-dione were used for a similar reaction and treatment as Examples 14-1 and 15-1, and the title compound was obtained as a yellow oil.
$^1$H-NMR (CDCl$_3$) δ: 0.96 (3H, t, J=7.3 Hz), 1.35 (6H, d, J=6.5 Hz), 1.60-1.71 (2H, m), 1.87 (3H, s), 2.02-2.15 (2H, m), 2.65 (2H, t, J=7.6 Hz), 3.08-3.18 (2H, m), 3.30-3.40 (1H, m), 3.53-3.78 (5H, m), 4.35-4.45 (2H, m), 4.52-4.60 (1H, m), 6.30 (1H, s), 7.09 (1H, d, J=8.6 Hz), 7.16 (1H, dd, J=2.4, 8.9 Hz), 7.45 (1H, d, J=8.6 Hz), 7.48 (1H, s), 7.63 (1H, d, J=8.9 Hz), 8.19 (1H, d, J=2.4 Hz).

Example 41

Preparation of 5-(5-cyclopropoxypyridin-2-yl)-3-(2-{4-[4-(1,1,1,3,3,3-hexafluoro-2-hydroxypropan-2-yl)-2-propylphenyl]-1,4-diazepan-1-yl}-2-oxoethyl)-5-methylimidazolidine-2,4-dione

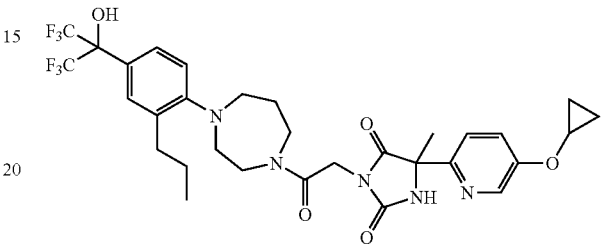

a) Preparation of 2-methyl-5-[1-(phenylthio)cyclopropoxy]pyridine

Cyclopropylphenylthioether (5.0 g, 33.3 mmol) was dissolved in tetrahydrofuran (50 mL), and n-butyllithium (25.1 mL, 39.9 mmol) was dropped for 5 minutes under an argon atmosphere at 0° C. Then, at −78° C., a solution of N-iodosuccinimide (8.99 g, 39.9 mmol) in tetrahydrofuran (100 mL) was dropped. The mixture was stirred overnight and allowed to warm gradually to room temperature. The reaction solution was added a saturated aqueous solution of sodium hydrogen carbonate, and extracted with hexane. The organic layer was washed with brine, dried over anhydrous sodium sulfate, concentrated in vacuo, and purified by silica-gel column chromatography (hexane). A crude product (5.64 g) ((1-iodocyclopropyl)(phenyl)sulfane:cyclopropylphenylthioether=2.4:1) was obtained. Then, 5-hydroxy-2-methylpyridine (1.82 g, 16.7 mmol) was dissolved in toluene (150 mL), added silver carbonate (9.19 g, 33.3 mmol), and a mixture of (1-iodocyclopropyl)(phenyl)sulfane:cyclopropylphenylthioether (=2.4:1) (5.64 g, 16.7 mmol (*converted in terms of the amount of (1-iodocyclopropyl)(phenyl) sulfane), and the mixture was stirred at room temperature overnight. Then, acetic acid (200 mL) was added and stirred for 10 minutes. The reaction solution was filtered through a pad of celite, and concentrated in vacuo. The obtained residue was purified by silica-gel column chromatography (hexane/ethyl acetate), and the title compound (1.88 g (yield 44%)) was obtained as a yellow oil.
$^1$H-NMR (400 MHz, CDCl$_3$) δ: 1.34-1.37 (2H, m), 1.44-1.50 (2H, m), 2.51 (3H, s), 7.09 (1H, d, J=8.6 Hz), 7.22-7.35 (4H, m), 7.46-7.52 (2H, m), 8.31 (1H, d, J=2.9 Hz).

c) Preparation of 2-methyl-5-[1-(phenylsulfonyl)cyclopropoxy]pyridine

2-Methyl-5-[1-(phenylthio)cyclopropoxy]pyridine (2.04 g, 7.93 mmol) was dissolved in chloroform (15 mL), added alumina (5.0 g) and oxon (3.79 g, 6.18 mmol), and the mixture was stirred at 80° C. for 1 hour. Then, oxon (1.36 g, 2.22 mmol) was further added, and stirred for 1 hour. The reaction solution was filtered through a pad of celite, and concentrated in vacuo. The obtained residue was purified by silica-gel column chromatography (hexane/ethyl acetate), and the title compound (542 mg (yield 24%)) was obtained as a yellow oil.

$^1$H-NMR (400 MHz, CD$_3$OD) δ: 1.42-1.46 (2H, m), 1.91-1.94 (2H, m), 2.47 (3H, s), 7.22 (1H, d, J=8.6 Hz), 7.55 (1H, dd, J=2.8, 8.6 Hz), 7.64 (2H, tt, J=1.7, 7.0 Hz), 7/6 (1H, tt, J=1.7, 7.0 Hz), 7.88 (2H, td, J=1.7, 7.0 Hz), 8.16 (1H, d, J=2.8 Hz).

d) Preparation of 5-cyclopropoxy-2-methylpyridine

2-Methyl-5-[1-(phenylsulfonyl)cyclopropoxy]pyridine (540 mg, 1.87 mmol) was dissolved in methanol (5.5 mL), added sodium phosphite (671 mg, 5.598 mmol), and sodium amalgam (3.58 g, 7.47 mmol) under ice-cold conditions, stirred at the same temperature for 30 minutes, and then stirred at room temperature for 3 hours. The reaction solution was added a saturated aqueous solution of sodium hydrogen carbonate, and extracted with diethylether. The organic layer was washed with brine, dried over anhydrous sodium sulfate, and concentrated in vacuo. The obtained residue was purified by distillation, and the title compound (240 mg (yield 86%)) was obtained as a yellow oil.

$^1$H-NMR (400 MHz, CDCl$_3$) δ: 0.77-0.83 (4H, m), 2.49 (3H, s), 3.76 (1H, tt, J=3.0, 5.7 Hz), 7.06 (1H, d, J=8.3 Hz), 7.25 (1H, dd, J=2.9, 8.6 Hz), 8.31 (1H, d, J=2.9 Hz).

e) Preparation of 5-cyclopropoxy-2-methylpyridine 1-oxide

5-Cyclopropoxy-2-methylpyridine was used for a similar reaction and treatment as Example 6-l), and the title compound was obtained as a white crystal.

$^1$H-NMR (400 MHz, CDCl$_3$) δ: 0.77-0.86 (4H, m), 2.47 (3H, s), 3.74 (1H, tt, J=3.0, 5.7 Hz), 6.91 (1H, dd, J=2.2, 8.8 Hz), 7.12 (1H, d, J=8.8 Hz), 8.27 (1H, d, J=2.2 Hz).

f) Preparation of (5-cyclopropoxypyridin-2-yl)methanol

5-Cyclopropoxy-2-methylpyridine 1-oxide was used for a similar reaction and treatment as Example 6-l), and the title compound was obtained as a white crystal.

$^1$H-NMR (400 MHz, CDCl$_3$) δ: 0.80-0.83 (4H, m), 3.39 (1H, br s), 3.80 (1H, tt, J=3.0, 5.9 Hz), 4.71 (2H, s), 7.18 (1H, d, J=8.5 Hz), 7.36 (1H, dd, J=2.7, 8.5 Hz), 8.37 (1H, d, J=2.7 Hz).

g) Preparation of 5-cyclopropoxypicolinaldehyde (5-Cyclopropoxypyridin-2-yl)methanol was used for a similar reaction and treatment as Example 6-l), and the title compound was obtained as a white crystal.

$^1$H-NMR (270 MHz, CDCl$_3$) δ: 0.82-0.92 (4H, m), 3.89 (1H, tt, J=3.0, 5.8 Hz), 7.50 (1H, dd, J=2.8, 8.8 Hz), 7.98 (1H, d, J=8.8 Hz), 8.53 (1H, d, J=2.8 Hz), 10.00 (1H, s).

h) Preparation of 1-(5-cyclopropoxypyridin-2-yl)ethanol

5-Cyclopropoxypicolinaldehyde was used for a similar reaction and treatment as Example 6-l), and the title compound was obtained as a white crystal.

$^1$H-NMR (400 MHz, CDCl$_3$) δ: 0.79-0.83 (4H, m), 1.49 (3H, d, J=6.6 Hz), 3.79 (1H, tt, J=3.0, 5.6 Hz), 3.94 (1H, d, J=4.4 Hz), 4.85 (1H, dq, J=4.4, 6.6 Hz), 7.20 (1H, d, J=8.6 Hz), 7.36 (1H, dd, J=2.8, 8.6 Hz), 8.34 (1H, d, J=2.8 Hz).

i) Preparation of 1-(5-cyclopropoxypyridin-2-yl)ethanone 1-(5-Cyclopropoxypyridin-2-yl)ethanol was used for a similar reaction and treatment as Example 6-l), and the title compound was obtained as a white crystal.

$^1$H-NMR (400 MHz, CDCl$_3$) δ: 0.81-0.91 (4H, m), 2.68 (3H, s), 3.86 (1H, tt, J=3.0, 6.0 Hz), 7.44 (1H, dd, J=2.7, 8.8 Hz), 8.05 (1H, d, J=8.8 Hz), 8.42 (1H, d, J=2.7 Hz).

j) Preparation of 5-(5-cyclopropoxypyridin-2-yl)-5-methylimidazolidine-2,4-dione 1-(5-Cyclopropoxypyridin-2-yl)ethanone was used for a similar reaction and treatment as Example 1-l), and the title compound was obtained as a white crystal.

$^1$H-NMR (400 MHz, CDCl$_3$) δ: 0.79-0.84 (4H, m), 1.80 (3H, s), 3.80 (1H, tt, J=3.0, 5.9 Hz), 6.27 (1H, br s), 7.38 (1H, dd, J=2.9, 8.8 Hz), 7.51 (1H, br s), 7.58 (1H, d, J=8.8 Hz), 8.35 (1H, d, J=2.9 Hz).

2-Bromo-1-(4-{4-[1,1,1,3,3,3-hexafluoro-2-(methoxymethoxy)propan-2-yl]-2-propylphenyl}-1,4-diazepan-1-yl)ethanone and 5-(5-cyclopropoxypyridin-2-yl)-5-methylimidazolidine-2,4-dione were used for a similar reaction and treatment as Examples 14-1 and 15-1, and the title compound was obtained as a yellow oil.

$^1$H-NMR (CDCl$_3$) δ: 0.78-1.00 (7H, m), 1.60-1.70 (2H, m), 1.87 (3H, s), 2.00-2.11 (2H, m), 2.65 (2H, t, J=7.8 Hz), 3.07-3.16 (2H, m), 3.28-3.40 (1H, m), 3.54-3.81 (6H, m), 4.35-4.42 (2H, m), 6.34 (1H, s), 7.08 (1H, d, J=8.4 Hz), 7.38 (1H, dd, J=2.4, 8.9 Hz), 7.46 (1H, d, J=8.4 Hz), 7.48 (1H, s), 7.66 (1H, d, J=8.9 Hz), 8.33 (1H, d, J=2.4 Hz).

Example 42

Preparation of 5-(2,3-dihydrobenzofuran-6-yl)-3-(2-{4-[4-(1,1,1,3,3,3-hexafluoro-2-hydroxypropan-2-yl)-2-propylphenyl]-1,4-diazepan-1-yl}-2-oxoethyl)-5-methylimidazolidine-2,4-dione

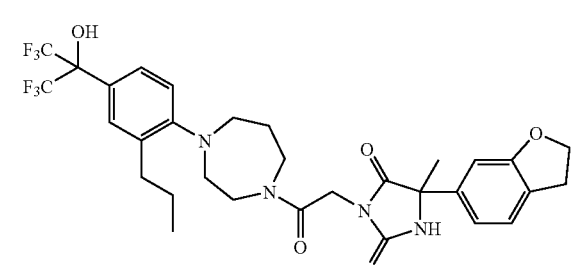

a) Preparation of 1-bromo-3-(2,2-diethoxyethoxy)benzene

To a solution of 3-bromophenol (1.68 g, 9.77 mmol) in N,N'-dimethylformamide (32 mL), sodium hydride (purity 50%) (516 mg, 10.7 mmol) was added under ice-cold conditions, bromoacetaldehyde diethyl acetal (1.76 mL, 11.7 mmol) was added at 0° C., and the mixture was stirred at 120° C. overnight. The reaction solution was added water at room temperature, and extracted with diethylether. The organic layer was washed with brine, dried over anhydrous sodium sulfate, concentrated in vacuo, and purified by silica-gel column chromatography (hexane). The title compound (2.69 g (yield >100%)) was obtained as a yellow oil.

¹H-NMR (CDCl₃) δ: 1.25 (6H, t, J=7.2 Hz), 3.57-3.70 (2H, m), 3.72-3.80 (2H, m), 3.98 (2H, d, J=5.2 Hz), 4.82 (1H, t, J=5.2 Hz), 6.84-6.87 (1H, m), 7.07-7.15 (3H, m).

b) Preparation of 6-bromobenzofuran

To a solution of 1-bromo-3-(2,2-diethoxyethoxy)benzene (2.3 g, 8.35 mmol) in toluene (28 mL), was added PPA (5.0 mL) and refluxed for overnight. The reaction solution was added water at room temperature, and extracted with ethyl acetate. The organic layer was washed with brine, dried over anhydrous sodium sulfate, concentrated in vacuo, and purified by silica-gel column chromatography (hexane). The title compound (1.2 g (yield 68%, mixture with 7-bromobenzofuran)) was obtained as a yellow oil.

¹H-NMR (CDCl₃) δ: 6.75 (1H, d, J=2.4 Hz), 7.36 (1H, d, J=8.1 Hz), 7.46 (1H, d, J=8.1 Hz), 7.60 (1H, d, J=2.4 Hz), 7.68 (1H, s).

c) Preparation of 1-(benzofuran-6-yl)ethanone

To a solution of a mixture of 6-bromobenzofuran and 7-bromobenzofuran (1.12 g, 5.68 mmol) in toluene (19 mL), tetrakistriphenyl phosphine palladium (650 mg, 0.57 mmol) and tributyl(1-ethoxyvinyl)tin (2.11 mL, 6.25 mmol) were added, and the mixture was stirred at 100° C. overnight. The reaction solution was added water at room temperature, and extracted with ethyl acetate. The organic layer was washed with brine, dried over anhydrous sodium sulfate, concentrated in vacuo, and purified by silica-gel column chromatography (hexane). The title compound (280 mg) was obtained as a yellow crystal.

¹H-NMR (CDCl₃) δ: 2.67 (3H, s), 6.83 (1H, d, J=1.9 Hz), 7.65 (1H, d, J=8.4 Hz), 7.78 (1H, d, J=1.9 Hz), 7.89 (1H, d, J=8.4 Hz), 8.12 (1H, s).

d) Preparation of 5-(benzofuran-6-yl)-5-methylimidazolidine-2,4-dione 1-(Benzofuran-6-yl)ethanone was used for a similar reaction and treatment as Example 1-l), and the title compound was obtained as a white crystal.

¹H-NMR (CDCl₃) δ: 1.82 (3H, s), 6.83 (1H, d, J=2.2 Hz), 7.32 (1H, d, J=8.4 Hz), 7.63 (1H, d, J=8.4 Hz), 7.67 (1H, s), 7.78 (1H, d, J=2.2 Hz).

e) Preparation of 5-(2,3-dihydrobenzofuran-6-yl)-5-methylimidazolidine-2,4-dione 5-(Benzofuran-6-yl)-5-methylimidazolidine-2,4-dione was used for a similar reaction and treatment as Example 1-l), and the title compound was obtained as a white crystal.

¹H-NMR (CD₃OD) δ: 1.75 (3H, s), 3.18 (2H, t, J=8.6 Hz), 4.57 (2H, t, J=8.6 Hz), 7.00 (1H, s), 7.04 (1H, d, J=7.8 Hz), 7.20 (1H, d, J=7.8 Hz).

2-Bromo-1-(4-{4-[1,1,1,3,3,3-hexafluoro-2-(methoxymethoxy)propan-2-yl]-2-propylphenyl}-1,4-diazepan-1-yl)ethanone and 5-(2,3-dihydrobenzofuran-6-yl)-5-methylimidazolidine-2,4-dione were used for a similar reaction and treatment as Examples 14-1 and 15-1, and the title compound was obtained as a yellow oil.

¹H-NMR (CDCl₃) δ: 0.96 (3H, t, J=7.3 Hz), 1.58-1.70 (2H, m), 1.90 (3H, s), 2.00-2.11 (2H, m), 2.65 (2H, t, J=7.3 Hz), 3.07-3.15 (2H, m), 3.18 (2H, t, J=8.6 Hz), 3.28-3.38 (1H, m), 3.53-3.80 (5H, m), 4.28-4.40 (2H, m), 4.57 (2H, t, J=8.6 Hz), 5.74 (1H, s), 6.96-7.05 (2H, m), 7.08 (1H, d, J=8.1 Hz); 7.20 (1H, d, J=7.3 Hz), 7.45 (1H, d, J=8.1 Hz), 7.48 (1H, s).

Example 43

Preparation of 3-[2-(4-{4-[2-(benzyloxy)-1,1,1,3,3,3-hexafluoropropan-2-yl]-2-(prop-1-en-1-yl)phenyl}piperazin-1-yl)-2-oxoethyl]-5-(2,3-dihydrobenzofuran-6-yl)-5-methylimidazolidine-2,4-dione

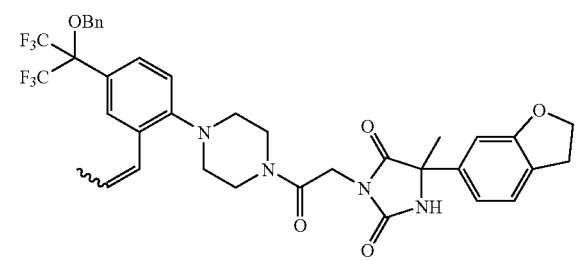

a) Preparation of 1,1,1,3,3,3-hexafluoro-2-(4-fluoro-3-nitrophenyl)propan-2-ol

4-Fluoro-3-nitrobenzoic acid (1.5 g, 8.10 mmol) was dissolved in N,N-dimethylformamide (1.0 mL), added thionyl chloride (16.6 mL), and heated to reflux for 2 hours. Then, the reaction solution was concentrated in vacuo, to obtain a crude product (3.57 g). Then, under an argon atmosphere, to a solution of crude product (3.57 g) in ethylene glycol dimethyl ether (81 mL), trimethylsilyl trifluoromethane (3.0 mL. 20.26 mmol), tetramethylammonium fluoride (1.89 g. 20.26 mmol)) were added under ice-cold conditions, and the mixture was stirred at the same temperature for 20 minutes. Then, the mixture was further stirred at room temperature for 12 hours. Under ice-cold conditions, the reaction solution was added water, and extracted with ethyl acetate. The organic layer was washed with brine, dried over anhydrous sodium sulfate, concentrated in vacuo, and purified by silica-gel column chromatography (hexane). The title compound (2.99 g (yield >100%)) was obtained as a yellow oil.

¹H-NMR (CDCl₃) δ: 7.42 (1H, dd, J=8.6, 10.3 Hz), 8.37 (1H, ddd, J=2.4, 4.3, 8.6 Hz), 8.81 (1H, dd, J=2.4, 7.3 Hz).

b) Preparation of 4-[4-(1,1,1,3,3,3-hexafluoro-2-hydroxypropan-2-yl)-2-nitrophenyl]piperazine-1-carboxylic acid tert-butyl ester 1,1,1,3,3,3-Hexafluoro-2-(4-fluoro-3-nitrophenyl)propan-2-ol and tert-butyl piperazine-1-carboxylate were used for a similar reaction and treatment as Example 6-b), and the title compound was obtained as a yellow oil.

¹H-NMR (CDCl₃) δ: 1.48 (9H, s), 3.07-3.12 (4H, m), 3.58-3.61 (4H, m), 3.87 (1H, brs), 7.15 (1H, d, J=8.9 Hz), 7.77 (1H, dd, J=2.4, 8.9 Hz), 8.18 (1H, d, J=2.4 Hz).

c) Preparation of 4-{4-[2-(benzyloxy)-1,1,1,3,3,3-hexafluoropropan-2-yl]-2-nitrophenyl}piperazine-1-carboxylic acid tert-butyl ester 4-[4-(1,1,1,3,3,3-Hexafluoro-2-hydroxypropan-2-yl)-2-nitrophenyl]piperazine-1-carb oxylic acid tert-butyl ester was used for a similar reaction and treatment as Example 6-i), and the title compound was obtained as a yellow oil.

¹H-NMR (CDCl₃) δ: 1.48 (9H, s), 3.10-3.13 (4H, m), 3.59-3.62 (4H, m), 4.64 (2H, s), 7.16 (1H, d, J=8.9 Hz), 7.36-7.43 (5H, m), 7.69 (1H, dd, J=2.4, 8.9 Hz), 8.07 (1H, d, J=2.4 Hz).

d) Preparation of 4-{2-amino-4-[2-(benzyloxy)-1,1,1,3,3,3-hexafluoropropan-2-yl]phenyl}piperazine-1-carboxylic acid tert-butyl ester 4-{4-[2-(Benzyloxy)-1,1,1,3,3,3-hexafluoropropan-2-yl]-2-nitrophenyl}piperazine-1-carboxylic acid tert-butyl ester was used for a similar reaction and treatment as Example 6-c), and the title compound was obtained as a yellow oil.

¹H-NMR (CDCl₃) δ: 1.49 (9H, s), 2.88-2.90 (4H, m), 3.54-3.60 (4H, m), 4.65 (2H, s), 6.94-7.00 (3H, m), 7.33-7.41 (5H, m).

e) Preparation of 4-{4-[2-(benzyloxy)-1,1,1,3,3,3-hexafluoropropan-2-yl]-2-iodophenyl}piperazine-1-carboxylic acid tert-butyl ester 4-{2-Amino-4-[2-(benzyloxy)-1,1,1,3,3,3-hexafluoropropan-2-yl]phenyl}piperazine-1-carboxylic acid tert-butyl ester was used for a similar reaction and treatment as Example 6-d), and the title compound was obtained as a yellow oil.

¹H-NMR (CDCl₃) δ: 1.49 (9H, s), 2.98-3.02 (4H, m), 3.62-3.66 (4H, m), 4.62 (2H, s), 7.03 (1H, d, J=8.4 Hz), 7.34-7.45 (5H, m), 7.56 (1H, dd, J=1.6, 8.4 Hz), 8.07 (1H, d, J=1.6 Hz).

f) Preparation of 4-{4-[2-(benzyloxy)-1,1,1,3,3,3-hexafluoropropan-2-yl]-2-(prop-1-en-1-yl)phenyl}piperazine-1-carboxylic acid tert-butyl ester 4-{4-[2-(Benzyloxy)-1,1,1,3,3,3-hexafluoropropan-2-yl]-2-iodophenyl}piperazine-1-carboxylic acid tert-butyl ester was used for a similar reaction and treatment as Example 6-e), and the title compound was obtained as a yellow oil.

¹H-NMR (CDCl₃) δ: 1.48 (9H, s), 1.73 (3H, dd, J=1.6, 6.8 Hz), 2.94-2.98 (4H, m), 3.52-3.56 (4H, m), 4.67 (2H, s), 5.80 (1H, qd, J=6.8, 11.1 Hz), 6.46 (1H, qd, J=1.6, 11.1 Hz), 6.98 (1H, d, J=8.6 Hz), 7.32-7.46 (6H, m), 7.50 (1H, s).

g) Preparation of (Z)-1-{4-[2-(benzyloxy)-1,1,1,3,3,3-hexafluoropropan-2-yl]-2-(prop-1-en-1-yl)phenyl}piperazine 4-{4-[2-(Benzyloxy)-1,1,1,3,3,3-hexafluoropropan-2-yl]-2-(prop-1-en-1-yl)phenyl}piperazine-1-carboxylic acid tert-butyl ester was used for a similar reaction and treatment as Example 6-j), and the title compound was obtained as a yellow oil.

¹H-NMR (CDCl₃) δ: 1.70 (3H, dd, J=2.0, 7.1 Hz), 3.30 (4H, t, J=4.9 Hz), 3.78 (4H, t, J=4.9 Hz), 4.67 (2H, s), 5.88 (1H, qd, J=7.1, 11.1 Hz), 6.43 (1H, dd, J=2.0, 11.1 Hz), 7.05 (1H, d, J=8.3 Hz), 7.34-7.40 (5H, m), 7.49 (1H, dd, J=1.7, 8.3 Hz), 7.53 (1H, d, J=1.7 Hz).

h) Preparation of (Z)-1-(4-{4-[2-(benzyloxy)-1,1,1,3,3,3-hexafluoropropan-2-yl]-2-(prop-1-en-1-yl)phenyl}piperazin-1-yl)-2-bromoethanone (Z)-1-{4-[2-(benzyloxy)-1,1,1,3,3,3-hexafluoropropan-2-yl]-2-(prop-1-en-1-yl)phenyl}piperazine was used for a similar reaction and treatment as Example 6-k), and the title compound was obtained as a yellow oil.

¹H-NMR (CDCl₃) δ: 1.74 (3H, dd, J=1.6, 7.0 Hz), 3.00-3.11 (4H, m), 3.63-3.78 (4H, m), 3.90 (2H, s), 4.67 (2H, s), 5.84 (1H, qd, J=2.0, 11.6 Hz), 6.48 (1H, qd, J=1.6, 11.6 Hz), 7.00 (1H, d, J=8.4 Hz), 7.31-7.39 (5H, m), 7.46 (1H, d, J=8.4 Hz), 7.52 (1H, s).

i) Preparation of 3-[2-(4-{4-[2-(benzyloxy)-1,1,1,3,3,3-hexafluoropropan-2-yl]-2-(prop-1-en-1-yl)phenyl}piperazin-1-yl)-2-oxoethyl]-5-(2,3-dihydrobenzofuran-6-yl)-5-methylimidazolidine-2,4-dione (Z)-1-(4-{4-[2-(benzyloxy)-1,1,1,3,3,3-hexafluoropropan-2-yl]-2-(prop-1-en-1-yl)phenyl}piperazin-1-yl)-2-bromoethanone and 5-(2,3-dihydrobenzofuran-6-yl)-5-methylimidazolidine-2,4-dione were used for a similar reaction and treatment as Example 14-1, and the title compound was obtained as a yellow oil.

¹H-NMR (CDCl₃) δ: 1.73 (3H, dd, J=1.7, 7.1 Hz), 1.90 (3H, s), 2.98-3.07 (4H, m), 3.18 (2H, t, J=8.6 Hz), 3.57-3.74 (4H, m), 4.32 (1H, d, J=16.1 Hz), 4.34 (1H, d, J=16.1 Hz), 4.57 (2H, t, J=8.6 Hz), 4.67 (2H, s), 5.81 (1H, s), 5.83 (1H, qd, J=7.1, 11.7 Hz), 6.47 (1H, qd, J=1.7, 11.7 Hz), 6.99 (1H, d, J=8.3 Hz), 7.00 (1H, d, J=1.7 Hz), 7.04 (1H, dd, J=1.7, 7.8 Hz), 7.20 (1H, d, J=7.8 Hz), 7.32-7.42 (5H, m), 7.46 (1H, d, J=8.3 Hz), 7.51 (1H, s).

Example 44

Preparation of 5-(2,3-dihydrobenzofuran-6-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione

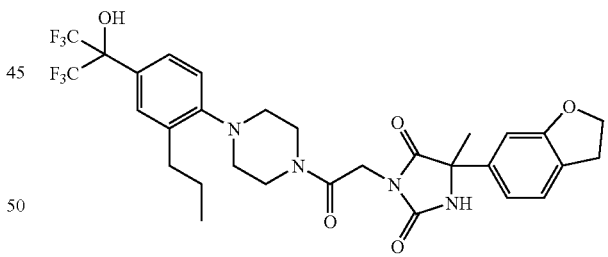

3-[2-(4-{4-[2-(Benzyloxy)-1,1,1,3,3,3-hexafluoropropan-2-yl]-2-(prop-1-en-1-yl)phenyl}piperazin-1-yl)-2-oxoethyl]-5-(2,3-dihydrobenzofuran-6-yl)-5-methylimidazolidine-2,4-dione was used for a similar reaction and treatment as Example 15-1, and the title compound was obtained as a yellow oil.

¹H-NMR (CDCl₃) δ: 0.96 (3H, t, J=7.3 Hz), 1.65 (2H, qt, J=7.3, 7.6 Hz), 1.90 (3H, s), 2.66 (2H, t, J=7.6 Hz), 2.87-2.97 (4H, m), 3.17 (2H, t, J=8.8 Hz), 3.59-3.76 (4H, m), 4.34 (1H, d, J=15.9 Hz), 4.36 (1H, d, J=15.9 Hz), 4.58 (2H, t, J=8.8 Hz), 5.81 (1H, brs), 6.99 (1H, s), 7.04 (1H, d, J=8.8 Hz), 7.07 (1H, d, J=7.8 Hz), 7.20 (1H, d, J=7.8 Hz), 7.50 (1H, d, J=8.8 Hz), 7.53 (1H, s).

Example 45

Preparation of 3-[(2-(4-{4-[2-(benzyloxy)-1,1,1,3,3,3-hexafluoropropan-2-yl]-2-(prop-1-en-1-yl)phenyl}piperazin-1-yl)-2-oxoethyl]-5-(2,3-dihydro-[1,4]dioxino[2,3-b]pyridin-7-yl)-5-methylimidazolidine-2,4-dione

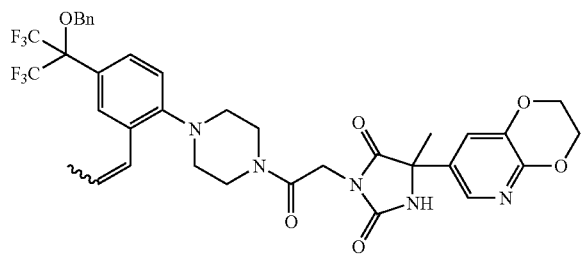

a) Preparation of 7-bromo-2,3-dihydro-[1,4]dioxino[2,3-b]pyridine 2,3-Hydroxy-5-bromopyridine (100 mg, 0.53 mmol) was dissolved in N,N'-dimethylformamide (5 mL), and added sodium hydride (30 mg, 0.63 mmol) under an argon atmosphere and under ice-cold conditions. 5 minutes after, a solution of 1,2-dibromoethane (50 μL, 0.58 mmol) in N,N'-dimethylformamide (5 mL) was added at the same temperature, and the mixture was stirred at 110° C. for 14 hours. The reaction solution was reverted to room temperature, added water, and then extracted with ethyl acetate. The organic layer was washed with brine, dried over anhydrous sodium sulfate, concentrated in vacuo, and purified by preparative thin-layer chromatography (n-hexane/ethyl acetate=2/1). The title compound (20 mg (yield 17%)) was obtained as a white solid.

$^1$H-NMR (CDCl$_3$) δ: 4.25-4.27 (2H, m), 4.42-4.44 (2H, m), 7.33 (1H, d J=2.4 Hz), 7.87 (1H, d, J=2.4 Hz).

b) Preparation of 1-(2,3-dihydro-[1,4]dioxino[2,3-b]pyridin-7-yl)ethanone

Under an argon atmosphere, 7-bromo-2,3-dihydro-[1,4]dioxino[2,3-b]pyridine (65 mg, 0.30 mmol) was dissolved in toluene (1.5 mL), added tetrakis(triphenylphosphine)palladium (35 mg, 0.03 mmol) and 1-ethoxyethenyl tri n-butyl tin (112 ΞL, 0.33 mmol), and the mixture was stirred at 100° C. overnight. The reaction solution was reverted to room temperature, and added 1N hydrochloric acid. The reaction solution was filtered through a pad of celite. The reaction solution was added ethyl acetate for extraction. The organic layer was washed with brine, dried over anhydrous sodium sulfate, concentrated in vacuo, and purified by preparative thin-layer chromatography (n-hexane/ethyl acetate=1/1). The title compound (37 mg (yield 69%)) was obtained as a white solid.

$^1$H-NMR (CDCl$_3$) δ: 2.57 (3H, s), 4.27-4.31 (2H, m), 4.50-4.52 (2H, m), 7.44 (1H, d, J=2.4 Hz), 8.44 (1H, d, J=2.4 Hz).

c) Preparation of 5-(2,3-dihydro-[1,4]dioxino[2,3-b]pyridin-7-yl)-5-methylimidazolidine-2,4-dione 1-(2,3-Dihydro-[1,4]dioxino[2,3-b]pyridin-7-yl)ethanone was used for a similar reaction and treatment as Example 1-l), and the title compound was obtained as a white crystal.

$^1$H-NMR (CDCl$_3$) δ: 1.73 (3H, s), 4.26-4.29 (2H, m), 4.43-4.46 (2H, m), 7.43 (1H, d, J=2.4 Hz), 7.83 (1H, d, J=2.4 Hz).

d) Preparation of 3-[2-(4-{4-[2-(benzyloxy)-1,1,1,3,3,3-hexafluoropropan-2-yl]-2-(prop-1-en-1-yl)phenyl}piperazin-1-yl)-2-oxoethyl]-5-(2,3-dihydro-[1,4]dioxino[2,3-b]pyridin-7-yl)-5-methylimidazolidine-2,4-dione (Z)-1-(4-{4-[2-(benzyloxy)-1,1,1,3,3,3-hexafluoropropan-2-yl]-2-(prop-1-en-1-yl)phenyl}piperazin-1-yl)-2-bromoethanone and 5-(2,3-dihydro-[1,4]dioxino[2,3-b]pyridin-7-yl)-5-methylimidazolidine-2,4-dione were used for a similar reaction and treatment as Example 14-1, and the title compound was obtained as a yellow oil.

$^1$H-NMR (CDCl$_3$) δ: 1.73 (3H, dd, J=2.2, 7.1 Hz), 1.90 (3H, s), 2.99-3.08 (4H, m), 3.57-3.74 (4H, m), 4.24-4.26 (2H, m), 4.34 (1H, d, J=15.8 Hz), 4.35 (1H, d, J=15.8 Hz), 4.42-4.43 (2H, m), 4.67 (2H, s), 5.84 (1H, qd, J=7.1, 12.0 Hz), 6.23 (1H, s), 6.47 (1H, qd, J=2.2, 12.0 Hz), 6.99 (1H, d, J=8.8 Hz), 7.31-7.43 (5H, m), 7.46 (1H, d, J=8.8 Hz), 7.47 (1H, d, J=2.2 Hz), 7.51 (1H, s), 7.98 (1H, d, J=2.2 Hz).

Example 46

Preparation of 5-(2,3-dihydro-[1,4]dioxino[2,3-b]pyridin-7-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione

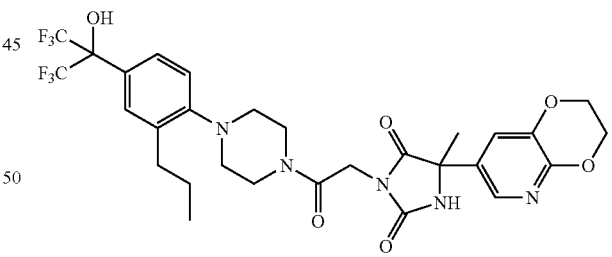

3-[2-(4-{4-[2-(Benzyloxy)-1,1,1,3,3,3-hexafluoropropan-2-yl]-2-(prop-1-en-1-yl)phenyl}piperazin-1-yl)-2-oxoethyl]-5-(2,3-dihydro-[1,4]dioxino[2,3-b]pyridin-7-yl)-5-methylimidazolidine-2,4-dione was used for a similar reaction and treatment as Example 15-1, and the title compound was obtained as a yellow oil.

$^1$H-NMR (CDCl$_3$) δ: 0.96 (3H, t, J=7.3 Hz), 1.66 (2H, qt, J=7.3, 7.6 Hz), 1.90 (3H, s), 2.66 (2H, t, J=7.6 Hz), 2.87-2.97 (4H, m), 3.61-3.75 (4H, m), 4.23-4.25 (2H, m), 4.35 (1H, d, J=16.4 Hz), 4.37 (1H, d, J=16.4 Hz), 4.41-4.43 (2H, m), 6.30

(1H, brs), 7.07 (1H, d, J=8.5 Hz), 7.47 (1H, d, J=2.2 Hz), 7.51 (1H, d, J=8.5 Hz), 7.54 (1H, s), 7.96 (1H, d, J=2.2 Hz).

Example 47

Preparation of 3-[2-((S)-4-{4-[2-(benzyloxy)-1,1,1,3,3,3-hexafluoropropan-2-yl]-2-(prop-1-en-1-yl)phenyl}-3-methylpiperazin-1-yl)-2-oxoethyl]-5-(2,3-dihydrobenzofuran-6-yl)-5-methylimidazolidine-2,4-dione

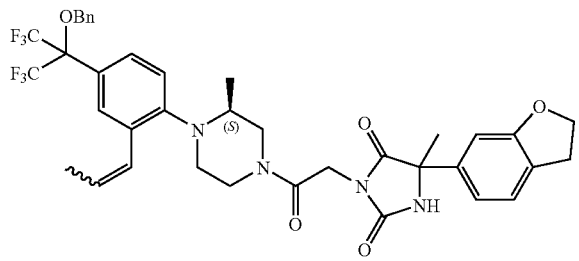

a) Preparation of (S)-4-[4-(1,1,1,3,3,3-hexafluoro-2-hydroxypropan-2-yl)-2-(prop-1-en-1-yl)phenyl]-3-methylpiperazine-1-carboxylic acid tert-butyl ester By conducting a similar reaction and treatment as Example 6-b) except that (S)-3-methyl-1-tert-butoxycarbonylpiperazine was used in place of 1-tert-butoxycarbonylpiperazine, and then by conducting a similar reaction and treatment as Examples 12-b) to g), the title compound was obtained as a yellow oil.

$^1$H-NMR (CDCl$_3$) δ: 0.90 (3H, d, J=6.2 Hz), 1.48 (9H, s), 1.83 (3H, d, J=6.8 Hz), 2.65-2.73 (1H, m), 3.08-3.18 (1H, m), 3.25-3.68 (5H, m), 5.76-5.88 (1H, m), 6.56 (1H, d, J=13.2 Hz), 7.02 (1H, d, J=8.4 Hz), 7.53 (1H, d, J=8.4 Hz), 7.59 (1H, s).

b) Preparation of (S)-4-{4-[2-(benzyloxy)-1,1,1,3,3,3-hexafluoropropan-2-yl]-2-(prop-1-en-1-yl)phenyl}-3-methylpiperazine-1-carboxylic acid tert-butyl ester (S)-4-[4-(1,1,1,3,3,3-hexafluoro-2-hydroxypropan-2-yl)-2-(prop-1-en-1-yl)phenyl]-3-methylpiperazine-1-carboxylic acid tert-butyl ester was used for a similar reaction and treatment as Example 6-i), and the title compound was obtained as a yellow oil.

$^1$H-NMR (CDCl$_3$) δ: 0.91 (3H, d, J=6.2 Hz), 1.48 (9H, s), 1.71 (3H, dd, J=1.6, 7.0 Hz), 2.64-2.73 (1H, m), 3.09-3.78 (6H, m), 4.67 (2H, s), 5.72-5.86 (1H, m), 6.47-6.52 (1H, m), 7.02 (1H, d, J=8.6 Hz), 7.31-7.44 (6H, m), 7.52 (1H, s).

c) Preparation of (S)-1-{4-[2-(benzyloxy)-1,1,1,3,3,3-hexafluoropropan-2-yl]-2-(prop-1-en-1-yl)phenyl}-2-methylpiperazine (S)-4-{4-[2-(benzyloxy)-1,1,1,3,3,3-hexafluoropropan-2-yl]-2-(prop-1-en-1-yl)phenyl}-3-methylpiperazine-1-carboxylic acid tert-butyl ester was used for a similar reaction and treatment as Example 6-j), and the title compound was obtained as a yellow oil.

$^1$H-NMR (CDCl$_3$) δ: 0.96 (3H, d, J=5.9 Hz), 1.71 (3H, d, J=7.0 Hz), 2.78-2.87 (1H, m), 3.19-3.29 (1H, m), 3.48-3.99 (5H, m), 4.68 (2H, s), 5.77-5.89 (1H, m), 6.51-6.57 (1H, m), 7.03 (1H, d, J=8.4 Hz), 7.33-7.39 (5H, m), 7.46 (1H, d, J=8.4 Hz), 7.54 (1H, s).

d) Preparation of (S)-1-(4-{4-[2-(benzyloxy)-1,1,1,3,3,3-hexafluoropropan-2-yl]-2-(prop-1-en-1-yl)phenyl}-3-methylpiperazin-1-yl)-2-bromoethanone (S)-1-{4-[2-(benzyloxy)-1,1,1,3,3,3-hexafluoropropan-2-yl]-2-(prop-1-en-1-yl)phenyl}-2-methylpiperazine was used for a similar reaction and treatment as Example 6-k), and the title compound was obtained as a yellow oil.

$^1$H-NMR (CDCl$_3$) δ: 0.99 (3H, d, J=6.5 Hz), 1.72 (3H, dd, J=1.6, 7.0 Hz), 2.75-2.84 (1H, m), 3.11-3.79 (6H, m), 3.92 (2H, s), 4.67 (2H, s), 5.76-5.88 (1H, m), 6.53-6.57 (1H, m), 7.03 (1H, d, J=8.6 Hz), 7.32-7.43 (6H, m), 7.54 (1H, s).

e) Preparation of 3-[2-((S)-4-{4-[2-(benzyloxy)-1,1,1,3,3,3-hexafluoropropan-2-yl]-2-(prop-1-en-1-yl)phenyl}-3-methylpiperazin-1-yl)-2-oxoethyl]-5-(2,3-dihydrobenzofuran-6-yl)-5-methylimidazolidine-2,4-dione (S)-1-(4-{4-[2-(benzyloxy)-1,1,1,3,3,3-hexafluoropropan-2-yl]-2-(prop-1-en-1-yl)phenyl}-3-methylpiperazin-1-yl)-2-bromoethanone and 5-(2,3-dihydrobenzofuran-6-yl)-5-methylimidazolidine-2,4-dione were used for a similar reaction and treatment as Example 14-1, and the title compound was obtained as a yellow oil.

$^1$H-NMR (CDCl$_3$) δ: 0.98 (3H, d, J=6.1 Hz), 1.71 (3H, d, J=7.1 Hz), 1.90 (3H, s), 2.71-2.82 (1H, m), 3.19 (2H, t, J=8.8 Hz), 3.28-3.90 (6H, m), 4.29-4.34 (2H, m), 4.58 (2H, t, J=8.8 Hz), 4.68 (2H, s), 5.67 (1H, s), 5.77-5.87 (1H, m), 6.53-6.58 (1H, m), 6.99 (1H, s), 7.03-7.05 (2H, m), 7.21 (1H, d, J=7.1 Hz), 7.33-7.40 (5H, m), 7.45 (1H, d, J=8.3 Hz), 7.54 (1H, s).

Example 48

Preparation of 5-(2,3-dihydrobenzofuran-6-yl)-3-(2-((S)-4-(4-(1,1,1,3,3,3-hexafluoro-2-hydroxypropan-2-yl)-2-propylphenyl)-3-methylpiperazin-1-yl)-2-oxoethyl)-5-methylimidazolidine-2,4-dione

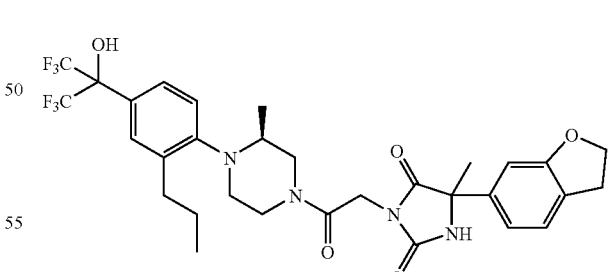

3-[2-((S)-4-{4-[2-(benzyloxy)-1,1,1,3,3,3-hexafluoropropan-2-yl]-2-(prop-1-en-1-yl)phenyl}-3-methylpiperazin-1-yl)-2-oxoethyl]-5-(2,3-dihydrobenzofuran-6-yl)-5-methylimidazolidine-2,4-dione was used for a similar reaction and treatment as Example 15-1, and the title compound was obtained as a yellow oil.

$^1$H-NMR (CDCl$_3$) δ: 0.84-0.96 (6H, m), 1.56-1.59 (2H, m), 1.91 (3H, s), 2.61-3.41 (8H, m), 3.19 (2H, t, J=5.1 Hz), 3.62-3.73 (1H, m), 4.30-4.40 (2H, m), 4.58 (2H, t, J=5.1 Hz), 5.84 (1H, s), 7.00-7.05 (2H, m), 7.15-7.21 (2H, m), 7.37-7.45 (2H, m).

Example 49

Preparation of 3-[2-((S)-4-{4-[2-(benzyloxy)-1,1,1,3,3,3-hexafluoropropan-2-yl]-2-(prop-1-en-1-yl)phenyl}-3-methylpiperazin-1-yl)-2-oxoethyl]-5-(2,3-dihydro-[1,4]dioxino[2,3-b]pyridin-7-yl)-5-methylimidazolidine-2,4-dione

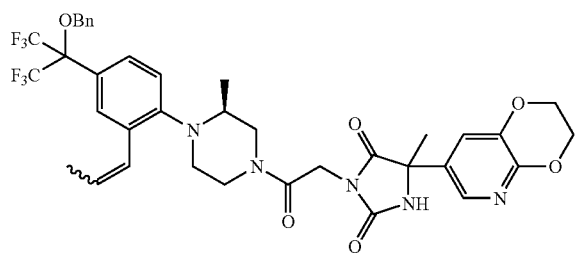

(S)-1-(4-{4-[2-(benzyloxy)-1,1,1,3,3,3-hexafluoropropan-2-yl]-2-(prop-1-en-1-yl)phenyl}-3-methylpiperazin-1-yl)-2-bromoethanone, 5-(2,3-dihydrobenzofuran-6-yl)-5-methylimidazolidine-2,4-dione and 5-(2,3-dihydro-[1,4]dioxino[2,3-b]pyridin-7-yl)-5-methylimidazolidine-2,4-dione were used for a similar reaction and treatment as Example 14-1, and the title compound was obtained as a yellow oil.

$^1$H-NMR (CDCl$_3$) δ: 0.99 (3H, d, J=6.0 Hz), 1.71 (3H, d, J=7.1 Hz), 1.91 (3H, s), 2.73-2.82 (1H, m), 3.17-3.89 (6H, m), 4.24-4.26 (2H, m), 4.31-4.37 (2H, m), 4.42-4.44 (2H, m), 4.67 (1H, d, J=11.0 Hz), 4.69 (1H, d, J=11.0 Hz), 5.78-5.86 (1H, m), 6.07 (1H, s), 6.52-6.58 (1H, m), 7.00-7.05 (1H, m), 7.30-7.47 (7H, m), 7.54 (1H, s), 7.98 (1H, s).

Example 50

Preparation of 5-(2,3-dihydro-[1,4]dioxino[2,3-b]pyridin-7-yl)-3-(2-{(S)-4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

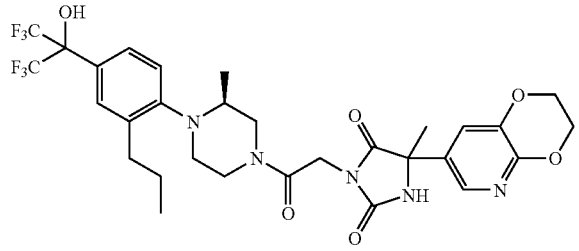 [SMILES: CCCc1cc(C(O)(C(F)(F)F)C(F)(F)F)ccc1N1CCN(C(=O)CN2C(=O)NC(C)(c3cnc4c(c3)OCCO4)C2=O)C[C@@H]1C]

3-[2-((S)-4-{4-[2-(benzyloxy)-1,1,1,3,3,3-hexafluoropropan-2-yl]-2-(prop-1-en-1-yl)phenyl}-3-methylpiperazin-1-yl)-2-oxoethyl]-5-(2,3-dihydro-[1,4]dioxino[2,3-b]pyridin-7-yl)-5-methylimidazolidine-2,4-dione was used for a similar reaction and treatment as Example 15-1, and the title compound was obtained as a yellow oil.

$^1$H-NMR (CDCl$_3$) δ: 0.87 (3H, d, J=6.1 Hz), 0.95 (3H, t, J=7.3 Hz), 1.62 (2H, qt, J=7.3, 7.3 Hz), 1.90 (3H, s), 2.63-3.21 (8H, m), 3.64-3.71 (1H, m), 4.23-4.26 (2H, m), 4.32-4.39 (2H, m), 4.41-4.45 (2H, m), 6.36 (1H, brs), 7.11-7.16 (1H, m), 7.48 (1H, d, J=2.0 Hz), 7.52 (1H, d, J=9.0 Hz), 7.55 (1H, s), 7.97 (1H, d, J=2.0 Hz).

Example 51

Preparation of 3-[2-((S)-4-{4-[2-(benzyloxy)-1,1,1,3,3,3-hexafluoropropan-2-yl]-2-(prop-1-en-1-yl)phenyl}-3-methylpiperazin-1-yl)-2-oxoethyl]-5-[5-(1-methylethoxy)pyridin-2-yl]-5-methylimidazolidine-2,4-dione

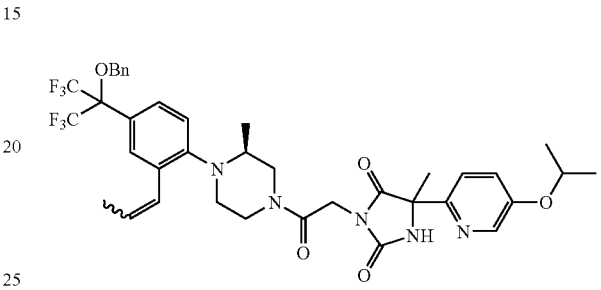

(S)-1-(4-{4-[2-(benzyloxy)-1,1,1,3,3,3-hexafluoropropan-2-yl]-2-(prop-1-en-1-yl)phenyl}-3-methylpiperazin-1-yl)-2-bromoethanone, 5-(2,3-dihydrobenzofuran-6-yl)-5-methylimidazolidine-2,4-dione and 5-[5-(1-methylethoxy)pyridin-2-yl]-5-methylimidazolidine-2,4-dione were used for a similar reaction and treatment as Example 14-1, and the title compound was obtained as a yellow oil.

$^1$H-NMR (CDCl$_3$) δ: 0.99 (3H, d, J=6.5 Hz), 1.35 (6H, d, J=5.9 Hz), 1.71 (3H, d, J=7.0 Hz), 1.86 (3H, s), 2.72-2.85 (1H, m), 3.13-3.91 (6H, m), 4.37 (2H, s), 4.50-4.63 (1H, m), 4.68 (2H, s), 5.76-5.87 (1H, m), 6.28 (1H, s), 6.52-6.60 (1H, m), 7.01 (1H, d, J=8.1 Hz), 7.19 (1H, d, J=8.9 Hz), 7.31-7.39 (5H, m), 7.45 (1H, d, J=8.1 Hz), 7.53 (1H, s), 7.62 (1H, dd, J=2.4, 8.9 Hz), 8.19 (1H, d, J=2.4 Hz).

Example 52

Preparation of 3-(2-{(S)-4-[4-(1,1,1,3,3,3-hexafluoro-2-hydroxypropan-2-yl)-2-propylphenyl]-3-methylpiperazin-1-yl}-2-oxoethyl)-5-[5-(1-methylethoxy)pyridin-2-yl]-5-methylimidazolidine-2,4-dione

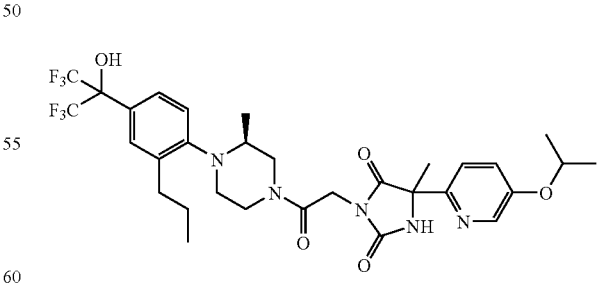

3-(2-((S)-4-(4-(2-(benzyloxy)-1,1,1,3,3,3-hexafluoropropan-2-yl)-2-(prop-1-en-1-yl)phenyl)-3-methylpiperazin-1-yl)-2-oxoethyl)-5-[5-(1-methylethoxy)pyridin-2-yl]-5-methylimidazolidine-2,4-dione was used for a similar reaction and treatment as Example 15-1, and the title compound was obtained as a yellow oil.

$^1$H-NMR (CDCl$_3$) δ: 0.95 (3H, t, J=7.3 Hz), 1.35 (6H, d, J=5.9 Hz), 1.63 (2H, qt, J=7.3, 7.3 Hz), 1.87 (3H, s), 2.64-3.20 (7H, m), 3.45-3.72 (2H, m), 4.36-4.42 (2H, m), 4.52-4.61 (1H, m), 6.30 (1H, s), 7.15 (1H, d, J=8.9 Hz), 7.19 (1H, dd, J=2.2, 8.9 Hz), 7.52 (1H, d, J=8.9 Hz), 7.54 (1H, s), 7.63 (1H, d, J=8.9 Hz), 8.19 (1H, d, J=2.2 Hz).

Example 53

Preparation of 3-[2-(4-{4-[2-(benzyloxy)-1,1,1,3,3,3-hexafluoropropan-2-yl]-2-(prop-1-en-1-yl) phenyl}piperazin-1-yl)-2-oxoethyl]-5-(2,3-dihydro-[1,4]dioxino[2,3-c]pyridin-7-yl)-5-methylimidazolidine-2,4-dione

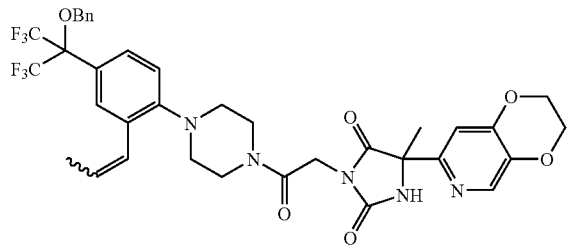

a) Preparation of 5-(methoxymethoxy)-2-methylpyridine

2-Methyl-5-hydroxypyridine was used for a similar reaction and treatment as Example 4-h), and the title compound was obtained as a colorless oil.
$^1$H-NMR (CDCl$_3$) δ: 2.50 (3H, s), 3.48 (3H, s), 5.17 (2H, s), 7.07 (1H, d, J=8.4 Hz), 7.27 (1H, dd, J=3.0, 8.4 Hz), 8.29 (1H, d, J=3.0 Hz).

b) Preparation of 5-(methoxymethoxy)-2-methylpyridine-4-ylboronic acid

To a solution of 5-methoxymethoxy-2-methylpyridine (3.0 g, 19.6 mmol) in tetrahydrofuran (100 mL), n-butyllithium (18.4 mL, 29.4 mmol) was added at −78° C., and the mixture was stirred at −78° C. for 40 minutes. Then, isopropoxy boranic acid ester (6.8 mL, 29.4 mmol) was added and the mixture was stirred at −78° C. for 45 minutes. The reaction solution was added 1N aqueous solution of hydrochloric acid, and then allowed to warm the temperature. The reaction solution was extracted with ethyl acetate. The organic layer was dried over anhydrous sodium sulfate, and concentrated in vacuo. The obtained residue was washed and filtered with diethyl ether, and the title compound (2.08 g (yield 54%)) was obtained as a white crystal.
$^1$H-NMR (CDCl$_3$) δ: 2.53 (3H, s), 3.52 (3H, s), 5.31 (2H, s), 5.80 (2H, s); 7.54 (1H, s), 8.41 (1H, s).

c) Preparation of 5-(methoxymethoxy)-2-methylpyridin-4(1H)-on

To a solution of 5-(methoxymethoxy)-2-methylpyridin-4-ylboronic acid (500 mg, 2.54 mmol) in tetrahydrofuran (12.7 mL), an aqueous solution of hydrogen peroxide (purity 30%) (2.9 mL, 25.4 mmol) was added at room temperature, and the mixture was stirred at room temperature for 4 hours. The reaction solution was added a saturated aqueous solution of sodium persulfate, and concentrated in vacuo. The obtained residue was washed and filtered with chloroform/methanol, and the title compound (440 mg (yield >100%)) was obtained as a yellow amorphous.
$^1$H-NMR (CDCl$_3$) δ: 2.37 (3H, s), 3.44 (3H, s), 5.11 (2H, s), 6.40 (1H, s), 7.66 (1H, s).

d) Preparation of 2-(5-(methoxymethoxy)-2-methylpyridin-4-yloxy)ethanol

To a solution of 5-(methoxymethoxy)-2-methylpyridin-4(1H)-on (1.28 g, 7.56 mmol) in N,N'-dimethylformamide (19 mL), potassium carbonate (2.10 g, 15.1 mmol) and 2-bromoethanol (804 µL, 11.3 mmol) were added sequentially, and the mixture was stirred at 90° C. overnight. After the reaction has terminated, the reaction solution was concentrated in vacuo. The obtained residue was dissolved in chloroform/methanol, the solids were filtered, and the filtrate was concentrated in vacuo. The obtained residue was purified by column chromatography (hexane/acetone) and 2-(5-(methoxymethoxy)-2-methylpyridin-4-yloxy)ethanol (900 mg, yield 56%) was obtained as an orange oil.
$^1$H-NMR (CDCl$_3$) δ: 2.48 (3H, s), 3.54 (3H, s), 3.99 (2H, t, J=4.4 Hz), 4.16 (2H, t, J=4.4 Hz), 5.16 (2H, s), 6.70 (1H, s), 8.21 (1H, s).

e) Preparation of 4-(2-hydroxyethoxy)-6-methylpyridin-3-ol 2-(5-(Methoxymethoxy)-2-methylpyridin-4-yloxy)ethanol (900 mg, 4.22 mmol) was dissolved in ethyl acetate (10 mL), added 4N hydrochloric acid-ethyl acetate solution (10 mL), and the mixture was stirred at room temperature for 5 hours. After the reaction has terminated, under ice-cold conditions, a 4N aqueous solution of sodium hydroxide was used to adjust the reaction solution to pH=8. The reaction solution was concentrated in vacuo. The obtained residue was washed with chloroform/methanol, dried, and as a crude product, 4-(2-hydroxyethoxy)-6-methylpyridin-3-ol (1.2 g) was obtained as a white solid.
$^1$H-NMR (CDCl$_3$) δ: 1.96 (1H, s), 2.44 (3H, s), 3.93 (2H, t, J=4.4 Hz), 4.18 (2H, s), 6.95 (1H, s), 7.76 (1H, s).

f) Preparation of 7-methyl-2,3-dihydro-[1,4]dioxino[2,3-c]pyridine

After drying 4-(2-hydroxyethoxy)-6-methylpyridin-3-ol (714 mg, 4.22 mmol) and triphenylphosphine (1.66 g, 6.33 mmol) with a vacuum pump, the resultant was dissolved in tetrahydrofuran (42 mL), added di-tert-butyl azodicarboxylate (DBAD) (1.46 g, 6.33 mmol) under ice-cold conditions, and the mixture was stirred at room temperature overnight. Under ice-cold conditions, the reaction solution was added water, and extracted with ethyl acetate. The organic layer was washed with brine, dried over anhydrous sodium sulfate, and concentrated in vacuo. The obtained residue was purified by silica-gel column chromatography (hexane/acetone, chloroform/methanol). The title compound (1.74 g (yield >100%)) was obtained as a white solid as a crude product.
$^1$H-NMR (CDCl$_3$) δ: 2.42 (3H, s), 4.23-4.31 (4H, m), 6.64 (1H, s), 8.04 (1H, s).

g) Preparation of 7-methyl-2,3-dihydro-[1,4]dioxino[2,3-c]pyridine 6-oxide

7-Methyl-2,3-dihydro-[1,4]dioxino[2,3-c]pyridine was used for a similar reaction and treatment as Example 6-l), and the title compound was obtained as a colorless oil.

¹H-NMR (CDCl₃) δ: 2.45 (3H, s), 4.28-4.35 (4H, m), 6.75 (1H, s), 8.09 (1H, s).

h) Preparation of (2,3-dihydro-[1,4]dioxino[2,3-c]pyridin-7-yl)methyl acetate

7-Methyl-2,3-dihydro-[1,4]dioxino[2,3-c]pyridine 6-oxide was used for a similar reaction and treatment as Example 6-l), and the title compound was obtained as a colorless oil.
¹H-NMR (CDCl₃) δ: 2.14 (3H, s), 4.29-4.35 (4H, m), 5.09 (2H, s), 6.88 (1H, s), 8.16 (1H, s).

i) Preparation of (2,3-dihydro-[1,4]dioxino[2,3-c]pyridin-7-yl)methanol (2,3-Dihydro-[1,4]dioxino[2,3-c]pyridin-7-yl)methyl acetate was used for a similar reaction and treatment as Example 6-l), and the title compound was obtained as a colorless oil.
¹H-NMR (CDCl₃) δ: 4.29-4.35 (4H, m), 4.62 (2H, s), 6.76 (1H, s), 8.12 (1H, s).

j) Preparation of 2,3-dihydro-[1,4]dioxino[2,3-c]pyridine-7-carbaldehyde (2,3-Dihydro-[1,4]dioxino[2,3-c]pyridin-7-yl)methanol was used for a similar reaction and treatment as Example 6-l), and the title compound was obtained as a colorless oil.
¹H-NMR (CDCl₃) δ: 4.39 (4H, s), 7.51 (1H, s), 8.31 (1H, s), 9.93 (1H, s).

k) Preparation of 1-(2,3-dihydro-[1,4]dioxino[2,3-c]pyridin-7-yl)ethanol 2,3-Dihydro-[1,4]dioxino[2,3-c]pyridine-7-carbaldehyde was used for a similar reaction and treatment as Example 6-l), and the title compound was obtained as a colorless oil.
¹H-NMR (CDCl₃) δ: 1.45 (3H, d, J=6.2 Hz), 4.28-4.35 (4H, m), 4.77 (1H, q, 6.2 Hz), 6.77 (1H, s), 8.09 (1H, s).

l) Preparation of 1-(2,3-dihydro-[1,4]dioxino[2,3-c]pyridin-7-yl)ethanone 1-(2,3-Dihydro-[1,4]dioxino[2,3-c]pyridin-7-yl)ethanol was used for a similar reaction and treatment as Example 6-l), and the title compound was obtained as a colorless oil.
¹H-NMR (CDCl₃) δ: 2.66 (3H, s), 4.36 (4H, s), 7.60 (1H, s), 8.20 (1H, s).

m) Preparation of 5-(2,3-dihydro-[1,4]dioxino[2,3-c]pyridin-7-yl)-5-methylimidazolidine-2,4-dione 1-(2,3-Dihydro-[1,4]dioxino[2,3-c]pyridin-7-yl)ethanone was used for a similar reaction and treatment as Example 1-l), and the title compound was obtained as a colorless oil.
¹H-NMR (CDCl₃) δ: 1.73 (3H, s), 4.29-4.37 (4H, m), 7.06 (1H, s), 8.05 (1H, s).
n) (Z)-1-(4-{4-[2-(benzyloxy)-1,1,1,3,3,3-hexafluoropropan-2-yl]-2-(prop-1-en-1-yl)phenyl}piperazin-1-yl)-2-bromoethanone and 5-(2,3-dihydro-[1,4]dioxino[2,3-c]pyridin-7-yl)-5-methyl imidazolidine-2,4-dione were used for a similar reaction and treatment as Example 14-1, and the title compound was obtained as a yellow oil.
¹H-NMR (CDCl₃) δ: 1.73 (3H, dd, J=1.9, 7.0 Hz), 1.83 (3H, s), 2.96-3.08 (4H, m), 3.57-3.75 (4H, m), 4.26-4.37 (6H, m), 4.67 (2H, s), 5.84 (1H, qd, J=7.0, 11.3 Hz), 6.41 (1H, s), 6.47 (1H, qd, J=1.9, 11.3 Hz), 6.99 (1H, d, J=8.4 Hz), 7.33-7.47 (6H, m), 7.51 (1H, s), 8.09 (1H, s).

Example 54

Preparation of 5-(2,3-dihydro-[1,4]dioxino[2,3-c]pyridin-7-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione

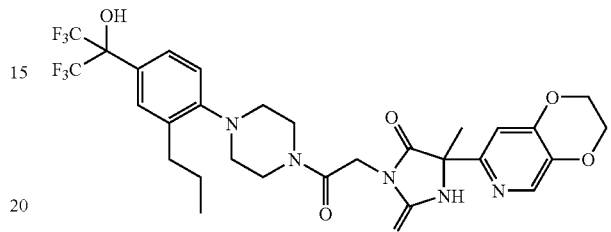

3-[2-(4-{4-[2-(Benzyloxy)-1,1,1,3,3,3-hexafluoropropan-2-yl]-2-(prop-1-en-1-yl)phenyl}piperazin-1-yl)-2-oxoethyl]-5-(2,3-dihydro-[1,4]dioxino[2,3-c]pyridin-7-yl)-5-methylimidazolidine-2,4-dione was used for a similar reaction and treatment as Example 15-1, and the title compound was obtained as a yellow oil.
¹H-NMR (CDCl₃) δ: 0.97 (3H, t, J=7.0 Hz), 1.67 (2H, qt, J=7.0, 7.3 Hz), 1.83 (3H, s), 2.66 (2H, t, J=7.3 Hz), 2.94-2.98 (4H, m), 3.59-3.77 (4H, m), 4.26-4.37 (6H, m), 6.41 (1H, s), 7.07 (1H, d, J=8.1 Hz), 7.51 (1H, d, J=8.1 Hz), 7.53 (1H, s), 8.09 (1H, s).

Example 55

Preparation of 3-[2-(4-{4-[2-(benzyloxy)-1,1,1,3,3,3-hexafluoropropan-2-yl)-2-(prop-1-en-1-yl)phenyl}piperazin-1-yl)-2-oxoethyl]-5-(2,3-dihydro-[1,4]dioxino[2,3-b]pyridin-6-yl)-5-methylimidazolidine-2,4-dione

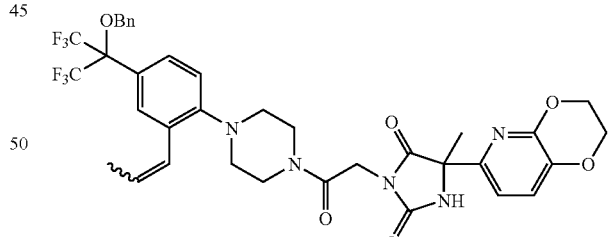

a) Preparation of 5-(2,3-dihydro-[1,4]dioxino[2,3-b]pyridin-6-yl)-5-methylimidazolidine-2,4-dione a-1) Preparation of 2,3-dihydro-[1,4]dioxino[2,3-b]pyridine 2,3-Dihydroxypyridine (2.22 g, 20.0 mmol) was dissolved in N,N'-dimethylformamide (100 mL), and added potassium carbonate (5.52 g, 40.0 mmol) at room temperature. 5 minutes after, 1,2-dibromoethane (2.6 mL, 30.0 mmol) was added at the same temperature, and stirred at 90° C. overnight.

The reaction solution was reverted to room temperature, filtered, and the obtained filtrate was concentrated in vacuo. Then, the obtained residue was added ethyl acetate. The suspension was filtered, washed ethyl acetate, and concentrated in vacuo. The title compound (157 mg (yield 5.7%)) was obtained as a colorless oil.

$^1$H-NMR (CDCl$_3$) δ: 4.26-4.28 (2H, m), 4.42-4.44 (2H, m), 6.94 (1H, dd, J=5.6, 7.6 Hz), 7.28 (1H, dd, J=1.2, 7.6 Hz), 7.69 (1H, dd, J=1.2, 5.6 Hz).

a-2) Preparation of 2,3-dihydro-[1,4]dioxino[2,3-b]pyridine 5-oxide 2,3-Dihydro-[1,4]dioxino[2,3-b]pyridine (121 mg, 790 μmol) was dissolved in dichloromethane (4.0 mL), added 3-chloroperbenzoic acid (234 mg, 950 μmol), and stirred at room temperature for 1 hour. The reaction solution was concentrated in vacuo. The obtained residue was purified by silica-gel column chromatography (chloroform/methanol), and the title compound (102 mg (yield 84%)) was obtained as a white solid.

$^1$H-NMR (CDCl$_3$) δ: 4.33-4.36 (2H, m), 4.59-4.62 (2H, m), 6.81 (1H, dd, J=6.8, 8.4 Hz), 6.95 (1H, dd, J=1.4, 8.4 Hz), 7.95 (1H, dd, J=1.4, 6.8 Hz).

a-3) Preparation of 2,3-dihydro-[1,4]dioxino[2,3-b]pyridine-6-carbonitrile

Under an argon atmosphere, 2,3-dihydro-[1,4]dioxino[2,3-b]pyridine 5-oxide (102 mg, 666 μmol) was dissolved in actonitrile (700 μL), added triethylamine (202 mg, 2.00 mmol) and trimethylsilylnitrile (529 mg, 5.33 mmol) at room temperature, and the mixture was stirred at 100° C. overnight. Under ice-cold conditions, water was added, and the reaction solution was extracted with ethyl acetate, washed with brine, dried over anhydrous sodium sulfate, and concentrated in vacuo. The obtained residue was purified by silica-gel column chromatography (chloroform/methanol), and the title compound (105 mg (yield 97%)) was obtained as a brown solid.

$^1$H-NMR (CDCl$_3$) δ: 4.33-4.36 (2H, m), 4.48-4.51 (2H, m), 7.24 (1H, d, J=8.1 Hz), 7.32 (1H, d, J=8.1 Hz).

a-4) Preparation of 1-(2,3-dihydro-[1,4]dioxino[2,3-b]pyridin-6-yl)ethanone

Under an argon atmosphere, 2,3-dihydro-[1,4]dioxino[2,3-b]pyridine-6-carbonitrile (16 mg, 99 μmol) was dissolved in tetrahydrofuran (500 μL), added methyllithium (150 μL (1.04 M in THF solution), 148 μmol) under ice-cold conditions, and the mixture was stirred at the same temperature for 5 minutes. The reaction solution was added 1M-sulfuric acid (2.0 mL), and stirred at room temperature for 3 hours. Under ice-cold conditions, the reaction solution was added a saturated aqueous solution of sodium hydrogen carbonate (pH=8 was confirmed). The reaction solution was extracted with ethyl acetate, washed with brine, dried over anhydrous sodium sulfate, and concentrated in vacuo. The obtained residue was purified by silica-gel column chromatography (hexane/ethyl acetate), and the title compound (8.3 mg (yield 47%)) was obtained as a yellow oil.

$^1$H-NMR (CDCl$_3$) δ: 2.64 (3H, s), 4.33-4.35 (2H, m), 4.49-4.51 (2H, m), 7.27 (1H, d, J=8.4 Hz), 7.21 (1H, d, J=8.4 Hz).

a-5) Preparation of 5-(2,3-dihydro-[1,4]dioxino[2,3-b]pyridin-6-yl)-5-methylimidazolidine-2,4-dione 1-(2,3-Dihydro-[1,4]dioxino[2,3-b]pyridine-6-yl)ethanone was used for a similar reaction and treatment as Example 1-1), and the title compound was obtained as a white crystal.

$^1$H-NMR (CDCl$_3$) δ: 1.75 (3H, s), 4.24-4.26 (2H, m), 4.41-4.43 (2H, m), 7.09 (1H, d, J=8.0 Hz), 7.25 (1H, d, J=8.0 Hz).

b) Preparation of 3-[2-(4-{4-[2-(benzyloxy)-1,1,1,3,3,3-hexafluoropropan-2-yl]-2-(prop-1-en-1-yl)phenyl]piperazin-1-yl]-2-oxoethyl]-5-(2,3-dihydro-[1,4]dioxino[2,3-b]pyridin-6-yl)-5-methylimidazolidine-2,4-dione (Z)-1-(4-{4-[2-(benzyloxy)-1,1,1,3,3,3-hexafluoropropan-2-yl]-2-(prop-1-en-1-yl)phenyl}piperazin-1-yl)-2-bromoethanone and 5-(2,3-dihydro-[1,4]dioxino[2,3-b]pyridin-6-yl)-5-methylimidazolidine-2,4-dione were used for a similar reaction and treatment as Example 14-1, and the title compound was obtained as a yellow oil.

$^1$H-NMR (CDCl$_3$) δ: 1.73 (3H, dd, J=1.6, 7.0 Hz), 1.84 (3H, s), 2.99-3.08 (4H, m), 3.57-3.75 (4H, m), 4.24-4.27 (2H, m), 4.36 (2H, s), 4.43-4.46 (2H, m), 4.67 (2H, s), 5.84 (1H, qd, J=7.0, 11.3 Hz), 6.20 (1H, s), 6.47 (1H, qd, J=1.6, 11.3 Hz), 7.20 (1H, d, J=7.8 Hz), 7.26-7.51 (9H, m).

Example 56

Preparation of 5-(2,3-dihydro-[1,4]dioxino[2,3-b]pyridin-6-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione

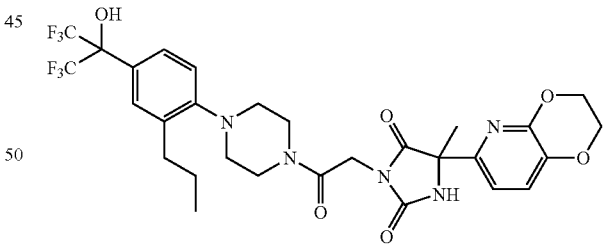

3-[2-(4-{4-[2-(Benzyloxy)-1,1,1,3,3,3-hexafluoropropan-2-yl]-2-(prop-1-en-1-yl)phenyl}piperazin-1-yl}-2-oxoethyl}-5-(2,3-dihydro-[1,4]dioxino[2,3-b]pyridin-6-yl)-5-methylimidazolidine-2,4-dione was used for a similar reaction and treatment as Example 15-1, and the title compound was obtained as a yellow oil.

$^1$H-NMR (CDCl$_3$) δ: 0.96 (3H, t, J=7.6 Hz), 1.66 (2H, qt, J=7.6, 7.6 Hz), 1.85 (3H, s), 2.66 (2H, t, J=7.6 Hz), 2.86-2.98 (4H, m), 3.59-3.76 (4H, m), 4.25-4.27 (2H, m), 4.38 (2H, s), 4.43-4.46 (2H, m), 6.25 (1H, s), 7.06 (1H, d, J=8.1 Hz), 7.20 (1H, d, J=7.8 Hz), 7.28 (1H, d, J=7.8 Hz), 7.50 (1H, d, J=8.1 Hz), 7.53 (1H, s).

Example 57

Preparation of 5-(benzofuran-6-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione

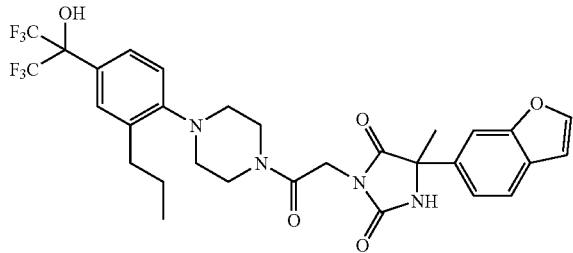 [SMILES: CCCc1cc(C(O)(C(F)(F)F)C(F)(F)F)ccc1N1CCN(C(=O)CN2C(=O)NC(C)(c3ccc4ccoc4c3)C2=O)CC1]

In Example 6, 5-(benzofuran-6-yl)-5-methylimidazolidine-2,4-dione was used in place of 5-[5-(1-methylethoxy)pyridin-2-yl] 5-methylimidazolidine-2,4-dione for a similar reaction and treatment. The title compound was obtained as a yellow oil.

$^1$H-NMR (CDCl$_3$) δ: 0.96 (3H, t, J=7.3 Hz), 1.66 (2H, qt, J=7.3, 7.6 Hz), 1.99 (3H, s), 2.66 (2H, t, J=7.6 Hz), 2.88-2.96 (4H, m), 3.60-3.75 (4H, m), 4.13 (1H, brs), 4.36 (1H, d, J=16.1 Hz), 4.38 (1H, d, J=16.1 Hz), 6.02 (1H, brs), 6.76 (1H, d, J=2.2 Hz), 7.06 (1H, d, J=8.3 Hz), 7.48 (1H, dd, J=2.2, 8.3 Hz), 7.50 (1H, d, J=8.3 Hz), 7.54 (1H, s), 7.63 (1H, d, J=8.3 Hz), 7.65 (1H, d, J=2.2 Hz), 8.00 (1H, d, J=2.2 Hz).

Example 58

Preparation of 5-(benzofuran-5-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione

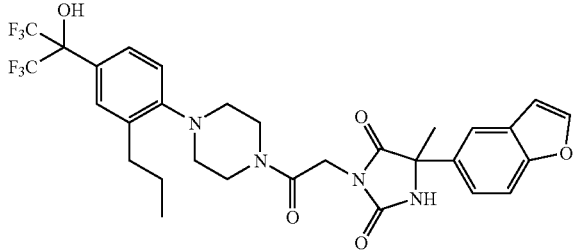 [SMILES: CCCc1cc(C(O)(C(F)(F)F)C(F)(F)F)ccc1N1CCN(C(=O)CN2C(=O)NC(C)(c3ccc4occc4c3)C2=O)CC1]

a) Preparation of 5-(benzofuran-5-yl)-5-methylimidazolidine-2,4-dione a-1) Preparation of 1-(4-(2,2-diethoxyethoxy)phenyl)ethanone

To a solution of 1-(4-hydroxyphenyl)ethanone (1.00 g, 7.34 mmol) in N,N'-dimethylformamide (24 mL), sodium hydride (purity 50%) (380 mg, 8.07 mmol), and bromoacetaldehyde diethyl acetal (1.30 mL, 8.81 mmol) were added under ice-cold conditions and stirred at 120° C. overnight. Under ice-cold conditions, the reaction solution was added water, and extracted with diethylether. The organic layer was washed with brine, dried over anhydrous sodium sulfate, and concentrated in vacuo. The obtained residue was purified by silica-gel column chromatography (hexane/ethyl acetate), and the title compound (2.47 g (yield >100%)) was obtained as a yellow oil.

$^1$H-NMR (CDCl$_3$) δ: 1.24 (6H, t, J=7.3 Hz), 2.56 (3H, s), 3.56-3.81 (4H, m), 4.06 (2H, d, J=5.1 Hz), 4.85 (1H, t, J=5.1 Hz), 6.95 (2H, d, J=7.0 Hz), 7.92 (2H, d, J=7.0 Hz).

a-2) Preparation of 1-(benzofuran-5-yl)ethanone

To a solution of 1-(4-(2,2-diethoxyethoxy)phenyl)ethanone (2.46 g, 7.34 mmol) in toluene (25 mL), was added PPA (2.50 g) and refluxed for 1 hour. Under ice-cold conditions, the reaction solution was added water, and extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (44 mg (yield 3.7%)) was obtained as a white solid.

$^1$H-NMR (CDCl$_3$) δ: 2.68 (3H, s), 6.86-6.87 (1H, m), 7.54 (1H, d, J=8.6 Hz), 7.70 (1H, d, J=2.4 Hz), 7.97 (1H, dd, J=2.4, 8.6 Hz), 8.26 (1H, d, J=1.6 Hz).

a-3) Preparation of 5-(benzofuran-5-yl)-5-methylimidazolidine-2,4-dione 1-(Benzofuran-5-yl)ethanone was used for a similar reaction and treatment as Example 1-l), and the title compound was obtained as a white crystal.

$^1$H-NMR (CDCl$_3$) δ: 1.82 (3H, s), 6.86 (1H, d, J=1.2 Hz), 7.46 (1H, dd, J=2.0, 8.4 Hz), 7.51 (1H, d, J=8.4 Hz), 7.77 (1H, d, J=2.0 Hz), 7.78 (1H, d, J=1.2 Hz).

b) Preparation of 5-(benzofuran-5-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione In Example 6, 5-(benzofuran-5-yl)-5-methylimidazolidine-2,4-dione was used in place of 5-[5-(1-methylethoxy)pyridin-2-yl]-5-methylimidazolidine-2,4-dione for a similar reaction and treatment, and the title compound was obtained as a yellow oil.

$^1$H-NMR (CDCl$_3$) δ: 0.96 (3H, t, J=7.6 Hz), 1.66 (2H, qt, J=7.6, 7.6 Hz), 1.99 (3H, s), 2.65 (2H, t, J=7.6 Hz), 2.88-2.95 (4H, m), 3.60-3.74 (4H, m), 4.36 (1H, d, J=16.1 Hz), 4.38 (1H, d, J=16.1 Hz), 6.79 (1H, d, J=2.2 Hz), 7.05 (1H, d, J=8.5 Hz), 7.46-7.54 (4H, m), 7.64 (1H, d, J=2.2 Hz), 7.82 (1H, d, J=2.2 Hz).

Example 59

Preparation of 5-(furo[2,3-c]pyridin-5-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione

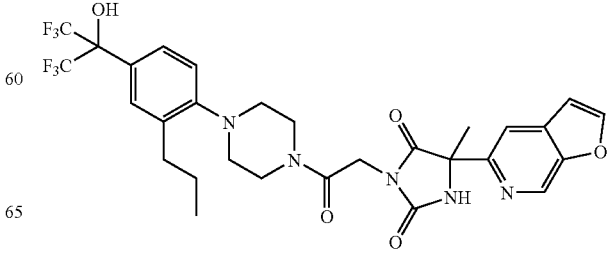

a) Preparation of 5-(furo[2,3-c]pyridin-5-yl)-5-methylimidazolidine-2,4-dione a-1) Preparation of 2-(hydroxymethyl)-5-[(4-methoxybenzyl)oxy]-4H-pyran-4-one 5-Hydroxy-2-hydroxymethyl-4H-4-pyranone (5.0 g, 35.2 mmol) was dissolved in N,N'-dimethylformamide (70 mL), and potassium tert-butoxide (4.0 g, 35.2 mmol) was added under an argon atmosphere and under ice-cold conditions. 5 minutes after, 4-methoxybenzylchloride (6.06 g, 38.7 mmol) was added at the same temperature, and stirred at 50° C. for 21 hours. Then, the reaction solution was concentrated in vacuo. After adding water and an 1N aqueous solution of sodium hydroxide, the solution was extracted with ethyl acetate. The organic layer was dried over anhydrous sodium sulfate, and concentrated in vacuo. The obtained residue was added diethylether for purification by recrystallization, and the title compound (4.80 g (yield 52%)) was obtained as a brown powder crystal.

$^1$H-NMR (CDCl$_3$) δ: 3.76 (3H, s), 4.28 (2H, s), 4.86 (2H, s), 6.31 (1H, s), 6.94 (2H, d, J=8.4 Hz), 7.34 (2H, d, J=8.4 Hz), 8.14 (1H, s).

a-2) Preparation of 2-(hydroxymethyl)-5-[(4-methoxybenzyl)oxy]pyridin-4(1H)-one 2-(Hydroxymethyl)-5-[(4-methoxybenzyl)oxy]-4H-pyran-4-one (1.2 g, 4.56 mmol) was dissolved in ethanol (3.0 mL), added an aqueous solution of ammonium (9.0 mL), sealed, and stirred at 100° C. for 6 hours. This operation was conducted for 4 lots, and the following treatments were conducted as a whole. The reaction solution was concentrated in vacuo. After adding diethylether, the reaction solution was cooled with ice. The deposited solid was filtered, washed with diethylether, and concentrated in vacuo. The title compound (4.0 g (yield 84%)) was obtained as a brown powder crystal.

$^1$H-NMR (CDCl$_3$) δ: 3.78 (3H, s), 4.56 (2H, s), 5.01 (2H, s), 6.42 (1H, s), 6.90 (2H, d J=8.4 Hz), 7.36 (2H, d, J=8.4 Hz), 7.41 (1H, s).

a-3) Preparation of {5-[(4-methoxybenzyl)oxy]-4-oxo-1,4-dihydropyridin-2-yl}methylacetate 2-(Hydroxymethyl)-5-[(4-methoxybenzyl)oxy]pyridin-4(1H)-one (3.21 g, 12.2 mmol) was dissolved in pyridine (60 mL), added acetyl chloride (1.44 g, 18.3 mmol) under ice-cold conditions, and the mixture was stirred at 60° C. overnight. Then, the reaction solution was concentrated in vacuo. Water was added under ice-cold conditions, and stirred at room temperature for 30 minutes. The deposited solid was filtered, washed with iced water and diethyl ether, concentrated in vacuo, and the title compound (3.56 g (yield 96%)) was obtained as brown powder crystal.

$^1$H-NMR (CDCl$_3$) δ: 2.11 (3H, s), 4.99 (2H, s), 3.78 (3H, s), 5.01 (2H, s), 6.52 (1H, s), 6.89 (2H, d, J=8.4 Hz), 7.35 (2H, d, J=8.4 Hz), 7.49 (1H, s).

a-4) Preparation of (5-[(4-methoxybenzyl)oxy]-4-{[(trifluoromethyl)sulfonyl]oxy}pyridin-2-yl)methyl acetate {5-[(4-Methoxybenzyl)oxy]-4-oxo-1,4-dihydropyridin-2-yl}methyl acetate (3.56 g, 11.7 mmol) was dissolved in dichloromethane (60 mL), added triethylamine (3.55 g, 35.1 mmol) and tirfluoromethanesulfonic acid anhydride (6.60 g, 23.4 mmol) under an argon atmosphere, and under ice-cold conditions, and the mixture was stirred at 0° C. for 15 minutes. The reaction solution was added water, a saturated aqueous solution of sodium hydrogen carbonate, and extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (4.84 g (yield 95%)) was obtained as a yellow oil.

$^1$H-NMR (CDCl$_3$) δ: 2.15 (3H, s), 3.82 (3H, s), 5.16 (2H, s), 5.20 (2H, s), 6.92 (2H, d, J=8.9 Hz), 7.25 (1H, s), 7.36 (2H, d, J=8.9 Hz), 8.45 (1H, s).

a-5) Preparation of {5-[(4-methoxybenzyl)oxy]-4-[(trimethylsilyl)ethynyl]pyridin-2-yl}methylacetate (5-[(4-Methoxybenzyl)oxy]-4-{[(trifluoromethyl)sulfonyl]oxy}pyridin-2-yl)methylacetate (1.2 g, 2.78 mmol) was dissolved in acetonitrile (9.3 mL), added copper iodide (53 mg, 278 μmol), ditriphenylphosphine palladium (II) dichloride (98 mg, 139 μmol), triethylamine (8.0 mL) and trimethylsilyl acetylene (819 mg, 8.34 mmol) under an argon atmosphere, and under ice-cold conditions, and the mixture was stirred at 45° C. overnight. This operation was conducted for 4 lots, and the following treatments were conducted as a whole. The reaction solution was added water, and filtered through a pad of celite. The obtained filtrate was extracted with ethyl acetate. The organic layer was washed with brine, dried over anhydrous sodium sulfate, and concentrated in vacuo. A crude product of the title compound (5.38 g) was obtained as a yellow oil.

$^1$H-NMR (CDCl$_3$) δ: 0.26 (9H, s), 2.14 (3H, s), 3.82 (3H, s), 5.11 (2H, s), 5.18 (2H, s), 6.91 (2H, d, J=8.8 Hz), 7.36-7.41 (3H, m), 8.28 (1H, s).

a-6) Preparation of {5-hydroxy-4-[(trimethylsilyl)ethynyl]pyridin-2-yl}methyl acetate (5-((4-Methoxybenzyl)oxy)-4-((trimethylsilyl)ethynyl)pyridin-2-yl)methyl acetate (5.38 g, 11.1 mmol) which is a crude product obtained in a-5) was dissolved in dichloromethane (55 mL), added trimethylsilane (1.9 mL, 35.1 mmol) and trifluoroacetate (5.5 mL) at room temperature, and the mixture was stirred overnight. The reaction solution was added a saturated aqueous solution of sodium hydrogen carbonate under ice-cold conditions (pH=8 was confirmed). The reaction solution was filtered through a pad of celite. The obtained filtrate was extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (1.54 g (yield 53%)) was obtained as a yellow oil.

$^1$H-NMR (CDCl$_3$) δ: 0.26 (9H, s), 2.14 (3H, s), 5.11 (2H, s), 7.29 (1H, s), 8.35 (1H, s).

a-7) Preparation of furo[2,3-c]pyridin-5-yl methyl acetate (5-Hydroxy-4-((trimethylsilyl)ethynyl)pyridin-2-yl)methyl acetate (1.47 g, 5.59 mmol) was dissolved in pyridine (28 mL), added copper iodide (1.28 g, 6.71 mmol) at room temperature, and refluxed for 5 hours. The reaction solution was reverted to room temperature, concentrated in vacuo. Then, the reaction solution was filtered through a pad of celite. The obtained residue was purified by silica-gel column chromatography (hexane/ethyl acetate), and the title compound (345 mg (yield 32%)) was obtained as an orange oil.

$^1$H-NMR (CDCl$_3$) δ: 2.16 (3H, s), 5.31 (2H, s), 6.81 (1H, d, J=2.4 Hz), 7.63 (1H, s), 7.78 (1H, d, J=2.4 Hz), 8.87 (1H, s).

a-8) Preparation of furo[2,3-c]pyridin-5-yl methanol

Furo[2,3-c]pyridin-5-yl methyl acetate (722 mg, 3.78 mmol) was dissolved in methanol (19 mL), added potassium carbonate (1.04 g, 7.56 mmol) at room temperature, and the mixture was stirred at room temperature overnight. The reaction solution was added 1N-aqueous solution of hydrochloric acid under ice-cold conditions, and extracted with chloroform. The organic layer was dried over anhydrous sodium sulfate, and concentrated in vacuo. The obtained residue was purified by silica-gel column chromatography (hexane/ethyl acetate), and the title compound (521 mg (yield 92%)) was obtained as a yellow oil.

$^1$H-NMR (CDCl$_3$) δ: 3.68 (1H, s), 4.85 (2H, s), 6.79 (1H, s), 7.54 (1H, s), 7.79 (1H, s), 8.83 (1H, s).

a-9) Preparation of furo[2,3-c]pyridine-5-carbaldehyde

Furo[2,3-c]pyridin-5-yl methanol (521 mg, 3.49 mmol) was dissolved in acetone (17 mL), added 2,2,6,6-tetramethylpiperidine 1-oxyl (27 mg, 170 μmol) at room temperature. Then, the reaction solution was added 1,3,5-trichloro-2,4,6-triazinetrione (892 mg, 3.84 mmol) under ice-cold conditions, and stirred at the same temperature for 5 minutes. The reaction solution was concentrated in vacuo, added water and a saturated aqueous solution of sodium hydrogen carbonate under ice-cold conditions, extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (488 mg (yield 95%)) was obtained as a yellow solid.

$^1$H-NMR (CDCl$_3$) δ: 6.98 (1H, dd, J=0.8, 2.2 Hz), 7.88 (1H, d, J=2.2 Hz), 8.32 (1H, d, J=0.8 Hz), 9.03 (1H, s), 10.18 (1H, s).

a-10) Preparation of 1-(furo[2,3-c]pyridin-5-yl)ethanol

Under an argon atmosphere, furo[2,3-c]pyridine-5-carbaldehyde (488 mg, 3.31 mmol) was dissolved in tetrahydrofuran (11 mL), and added methylmagnesium bromide (5.5 mL (1.0 M in THF solution), 4.97 mmol) under ice-cold conditions. Then, the mixture was stirred at room temperature for 1.5 hours. The reaction solution was added 1N-aqueous solution of hydrochloric acid under ice-cold conditions, and then a saturated aqueous solution of sodium hydrogen carbonate was added. The reaction solution was extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (356 mg (yield 66%)) was obtained as a yellow solid.

$^1$H-NMR (CDCl$_3$) δ: 1.56 (3H, d, J=6.2 Hz), 5.00 (1H, q, J=6.2 Hz), 6.80 (1H, d, J=2.2 Hz), 7.53 (1H, s), 7.78 (1H, d, J=2.2 Hz), 8.80 (1H, s).

a-11) Preparation of 1-(furo[2,3-c]pyridin-5-yl)ethanone 1-(Furo[2,3-c]pyridin-5-yl)ethanol (356 mg, 2.19 mmol) was dissolved in acetone (11 mL), and added 2,2,6,6-tetramethylpiperidine 1-oxyl (34 mg, 220 μmol) at room temperature. Then, the reaction solution was added 1,3,5-trichloro-2,4,6-triazinetrione (560 mg, 2.41 mmol), and stirred at the same temperature for 30 minutes. The reaction solution was concentrated in vacuo, added water and a saturated aqueous solution of sodium hydrogen carbonate under ice-cold conditions, and extracted with ethyl acetate. The organic layer was washed with brine, dried over anhydrous sodium sulfate, and concentrated in vacuo. The obtained residue was purified by silica-gel column chromatography (hexane/ethyl acetate), and the title compound (119 mg (yield 34%)) was obtained as a yellow solid.

$^1$H-NMR (CDCl$_3$) δ: 2.79 (3H, s), 6.93-6.94 (1H, m), 7.83 (1H, d, J=2.0 Hz), 8.39 (1H, d, J=0.8 Hz), 8.91 (1H, s).

a-12) Preparation of 5-(furo[2,3-c]pyridin-5-yl)-5-methylimidazolidine-2,4-dione 1-(Furo[2,3-c]pyridin-5-yl)ethanone was used for a similar reaction and treatment as Example 1-l), and the title compound was obtained as a white crystal.

$^1$H-NMR (CDCl$_3$) δ: 1.88 (3H, s), 6.99-7.00 (1H, m), 7.89 (1H, d, J=1.2 Hz), 8.02 (1H, d, J=2.0 Hz), 8.82 (1H, s).

b) Preparation of 5-(furo[2,3-c]pyridin-5-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione In Example 6, 5-(furo[2,3-c]pyridin-5-yl)-5-methylimidazolidine-2,4-dione was used in place of 5-[5-(1-methylethoxy)pyridin-2-yl]-5-methylimidazolidine-2,4-dione for a similar reaction and treatment, and the title compound was obtained as a yellow oil.

$^1$H-NMR (CDCl$_3$) δ: 0.96 (3H, t, J=7.3 Hz), 1.67 (2H, qt, J=7.3, 7.6 Hz), 1.93 (3H, s), 2.66 (2H, t, J=7.6 Hz), 2.89-2.96 (4H, m), 3.62-3.75 (4H, m), 4.19 (1H, s), 4.41 (2H, s), 6.57 (1H, s), 6.83 (1H, d, J=2.2 Hz), 7.07 (1H, d, J=8.5 Hz), 7.51 (1H, d, J=8.5 Hz), 7.54 (1H, s), 7.78 (1H, d, J=2.2 Hz), 8.01 (1H, d, J=1.0 Hz), 8.81 (1H, d, J=1.0 Hz).

Example 60

Preparation of 5-(benzofuran-6-yl)-3-(2-{(S)-4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

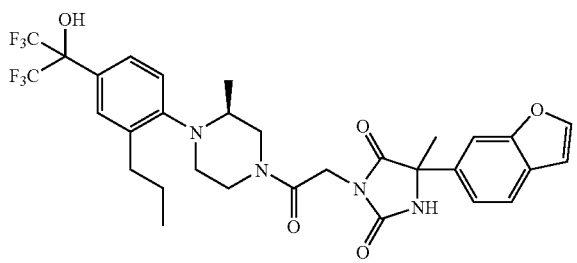 [SMILES: CCCc1cc(C(O)(C(F)(F)F)C(F)(F)F)ccc1N1CCN(C(=O)CN2C(=O)NC(C)(c3ccc4ccoc4c3)C2=O)C[C@@H]1C]

(S)-2-methyl-1-tert-butoxycarbonyl piperazine was used in place of (R)-2-methyl-1-tert-butoxycarbonyl piperazine and 5-(benzofuran-6-yl)-5-methylimidazolidine-2,4-dione was used for a similar reaction and treatment as Example 12, and the title compound was obtained as a yellow oil.

$^1$H-NMR (CDCl$_3$) δ: 0.85 (3H, d, J=6.0 Hz), 0.95 (3H, t, J=7.3 Hz), 1.62 (2H, qt, J=7.3, 7.3 Hz), 2.00 (3H, s), 2.62-3.23

(6H, m), 3.47-3.79 (3H, m), 4.35 (1H, d, J=16.3 Hz), 4.37 (1H, d, J=16.3 Hz), 5.98 (1H, s), 6.76 (1H, d, J=2.2 Hz), 7.14 (1H, d, J=8.6 Hz), 7.48 (1H, d, J=8.3 Hz), 7.51 (1H, d, J=8.6 Hz), 7.54 (1H, s), 7.63 (1H, d, J=8.3 Hz), 7.65 (1H, d, J=2.2 Hz), 7.75 (1H, s).

Example 61

Preparation of 5-(benzofuran-5-yl)-3-(2-{(S)-4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

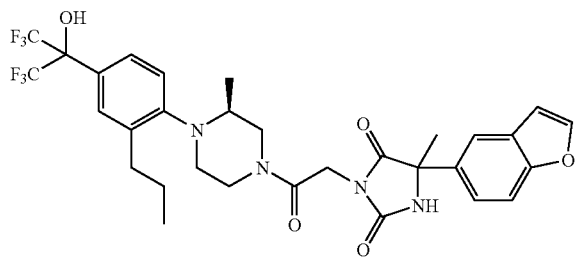 [SMILES: CCCc1cc(C(O)(C(F)(F)F)C(F)(F)F)ccc1N1CCN(C(=O)CN2C(=O)NC(C)(c3ccc4occc4c3)C2=O)C[C@@H]1C]

(S)-2-methyl-1-tert-butoxycarbonyl piperazine was used in place of (R)-2-methyl-1-tert-butoxycarbonyl piperazine, and 5-(benzofuran-5-yl)-5-methylimidazolidine-2,4-dione was used for a similar reaction and treatment as Example 12, and the title compound was obtained as a yellow oil.

¹H-NMR (CDCl₃) δ: 0.85 (3H, d, J=6.3 Hz), 0.95 (3H, t, J=7.3 Hz), 1.62 (2H, qt, J=7.3, 7.3 Hz), 2.00 (3H, s), 2.62-3.20 (6H, m), 3.44-3.81 (3H, m), 4.36 (1H, d, J=15.6 Hz), 4.40 (1H, d, J=15.6 Hz), 5.98 (1H, s), 6.80 (1H, d, J=2.2 Hz), 7.14 (1H, d, J=8.8 Hz), 7.46-7.54 (4H, m), 7.65 (1H, d, J=2.2 Hz), 7.82 (1H, s).

Example 62

Preparation of 5-(furo[2,3-c]pyridin-5-yl)-3-(2-{(S)-4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione

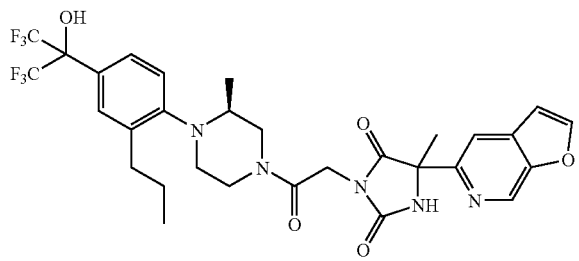 [SMILES: CCCc1cc(C(O)(C(F)(F)F)C(F)(F)F)ccc1N1CCN(C(=O)CN2C(=O)NC(C)(c3cc4ccoc4cn3)C2=O)C[C@@H]1C]

(S)-2-methyl-1-tert-butoxycarbonyl piperazine was used in place of (R)-2-methyl-1-tert-butoxycarbonyl piperazine and 5-(furo[2,3-c]pyridin-5-yl)-5-methylimidazolidine-2,4-dione was used for a similar reaction and treatment as Example 12, and the title compound was obtained as a yellow oil.

¹H-NMR (CDCl₃) δ: 0.87 (3H, d, J=6.1 Hz), 0.95 (3H, t, J=7.3 Hz), 1.62 (2H, qt, J=7.3, 7.3 Hz), 1.93 (3H, s), 2.62-3.18 (6H, m), 3.46-3.96 (3H, m), 4.37 (1H, d, J=15.8 Hz), 4.42 (1H, d, J=15.8 Hz), 6.56 (1H, s), 6.83 (1H, d, J=2.2 Hz), 7.14 (1H, d, J=8.4 Hz), 7.51 (1H, d, J=8.3 Hz), 7.55 (1H, s), 7.78 (1H, d, J=2.2 Hz), 8.02 (1H, s), 8.81 (1H, s).

Example 63

Preparation of (2S,5R,Z)-3-[2-(4-{4-[2-(benzyloxy)-1,1,1,3,3,3-hexafluoropropan-2-yl]-2-(prop-1-en-1-yl)phenyl}-2,5-dimethylpiperazin-1-yl)-2-oxoethyl]-5-(2,3-dihydrobenzo[b][1,4]dioxin-6-yl)-5-methylimidazolidine-2,4-dione

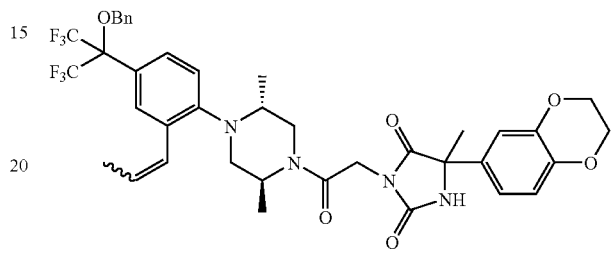

a) Preparation of (2S,5R)-4-[4-(1,1,1,3,3,3-hexafluoro-2-hydroxypropan-2-yl)-2-nitrophenyl]-2,5-dimethylpiperazine-1-carboxylic acid tert-butyl ester Similar reaction and treatment as Example 43-b) was conducted except that (2S,5R)-tert-butyl 2,5-dimethylpiperazine-1-carboxylate obtained in Example 14-1-a-2-2) was used in place of 1,1,1,3,3,3-hexafluoro-2-(4-fluoro-3-nitrophenyl)propan-2-ol obtained in Example 43-a) and tert-butyl piperazine-1-carboxylate, and the title compound was obtained as a yellow oil.

¹H-NMR (CDCl₃) δ: 1.07 (3H, d, J=6.8 Hz), 1.28 (3H, d, J=6.5 Hz), 1.48 (9H, s), 2.70-2.74 (1H, m), 3.52-3.70 (4H, m), 4.35-4.44 (1H, m), 7.07 (1H, d, J=9.2 Hz), 7.73 (1H, dd, J=1.9, 9.2 Hz), 8.15 (1H, d, J=1.9 Hz).

b) Preparation of (2S,5R)-4-{4-[2-(benzyloxy)-1,1,1,3,3,3-hexafluoropropan-2-yl]-2-nitrophenyl}-2,5-dimethyl piperazine-1-carboxylic acid tert-butyl ester (2S,5R)-4-[4-(1,1,1,3,3,3-hexafluoro-2-hydroxypropan-2-yl)-2-nitrophenyl]-2,5-dimethylpiperazine-1-carboxylic acid tert-butyl ester was used for a similar reaction and treatment as Example 43-c), and the title compound was obtained as a yellow oil.

¹H-NMR (CDCl₃) δ: 1.09 (3H, d, J=6.5 Hz), 1.29 (3H, d, J=6.8 Hz), 1.48 (9H, s), 2.70-2.75 (1H, m), 3.52-3.70 (4H, m), 4.37-4.46 (1H, m), 4.66 (2H, s), 7.08 (1H, d, J=8.9 Hz), 7.31-7.45 (5H, m), 7.65 (1H, d, J=8.9 Hz), 8.04 (1H, s).

c) Preparation of (2S,5R)-4-{2-amino-4-[2-(benzyloxy)-1,1,1,3,3,3-hexafluoropropan-2-yl]phenyl}-2,5-dimethylpiperazine-1-carboxylic acid tert-butyl ester (2S,5R)-4-{4-[2-(benzyloxy)-1,1,1,3,3,3-hexafluoropropan-2-yl]-2-nitrophenyl}-2,5-dimethylpiperazine-1-carboxylic acid tert-butyl ester was used for a similar reaction and treatment as Example 43-d), and the title compound was obtained as a yellow oil.

¹H-NMR (CDCl₃) δ: 0.95 (3H, d, J=6.2 Hz), 1.31 (3H, d, J=6.8 Hz), 1.48 (9H, s), 2.52 (1H, d, J=11.6 Hz), 3.39-3.96 (4H, m), 4.40-4.50 (1H, m), 4.66 (2H, s), 6.86 (1H, d, J=8.6 Hz), 6.94-6.98 (2H, m), 7.30-7.41 (5H, m).

d) Preparation of (2S,5R)-4-{4-[2-(benzyloxy)-1,1,1,3,3,3-hexafluoropropan-2-yl]-2-iodophenyl}-2,5-dimethyl piperazine-1-carboxylic acid tert-butyl ester (2S,5R)-4-{2-amino-4-[2-(benzyloxy)-1,1,1,3,3,3-hexafluoropropan-2-yl]phenyl}-2,5-dimethylpiperazine-1-carboxylic acid tert-butyl ester was used for a similar reaction and treatment as Example 43-e), and the title compound was obtained as a yellow oil.
¹H-NMR (CDCl₃) δ: 0.95 (3H, d, J=6.5 Hz), 1.36 (3H, d, J=6.5 Hz), 1.49 (9H, s), 2.53 (1H, d, J=10.8 Hz), 3.59-3.82 (4H, m), 4.40-4.50 (1H, m), 4.63 (2H, s), 6.91 (1H, d, J=8.4 Hz), 7.36-7.43 (5H, m), 7.54 (1H, d, J=8.4 Hz), 8.06 (1H, s).

e) Preparation of (2S,5R)-4-{4-[2-(benzyloxy)-1,1,1,3,3,3-hexafluoropropan-2-yl]-2-(prop-1-en-1-yl)phenyl}-2,5-dimethylpiperazine-1-carboxylic acid tert-butyl ester (2S,5R)-4-{4-[2-(benzyloxy)-1,1,1,3,3,3-hexafluoropropan-2-yl]-2-iodophenyl}-2,5-dimethylpiperazine-1-carboxylic acid tert-butyl ester was used for a similar reaction and treatment as Example 43-f), and the title compound was obtained as a yellow oil.
¹H-NMR (CDCl₃) δ: 0.91 (3H, d, J=6.5 Hz), 1.29 (3H, d, J=6.8 Hz), 1.48 (9H, s), 1.74 (3H, dd, J=1.9, 7.0 Hz), 2.68 (1H, d, J=11.1 Hz), 3.39-3.73 (4H, m), 4.36-4.46 (1H, m), 4.68 (2H, s), 5.80 (1H, qd, J=7.0, 11.3 Hz), 6.48 (1H, qd, J=1.9, 11.3 Hz), 6.88 (1H, d, J=8.9 Hz), 7.30-7.42 (6H, m), 7.49 (1H, s).

f) Preparation of (2S,5R)-1-{4-[2-(benzyloxy)-1,1,1,3,3,3-hexafluoropropan-2-yl]-2-(prop-1-en-1-yl)phenyl}-trans-2,5-dimethylpiperazine (2S,5R)-4-{4-[2-(benzyloxy)-1,1,1,3,3,3-hexafluoropropan-2-yl]-2-(prop-1-en-1-yl)phenyl}-2,5-dimethylpiperazine-1-carboxylic acid tert-butyl ester was used for a similar reaction and treatment as Example 43-g), and the title compound was obtained as a yellow oil.
¹H-NMR (CDCl₃) δ: 0.96 (3H, d, J=5.9 Hz), 1.45 (3H, d, J=6.8 Hz), 1.69 (3H, d, J=6.9 Hz), 3.03-2.82 (3H, m), 3.41-3.47 (2H, m), 3.58-3.69 (1H, m), 4.67 (2H, s), 5.83 (1H, qd, J=6.9, 11.4 Hz), 6.60 (1H, d, J=11.4 Hz), 7.25 (1H, d, J=9.1 Hz), 7.31-7.41 (5H, m), 7.49 (1H, dd, J=2.2, 9.1 Hz), 7.59 (1H, d, J=2.2 Hz).

g) Preparation of 1-((2S,5R)-4-(4-(2-(benzyloxy)-1,1,1,3,3,3-hexafluoropropan-2-yl)-2-(prop-1-en-1-yl)phenyl)-2,5-dimethylpiperazin-1-yl)-2-bromoethanone (2S,5R)-1-{4-[2-(benzyloxy)-1,1,1,3,3,3-hexafluoropropan-2-yl]-2-(prop-1-en-1-yl)phenyl}-2,5-dimethylpiperazine was used for a similar reaction and treatment as Example 43-h), and the title compound was obtained as a yellow oil.
¹H-NMR (CDCl₃) δ: 0.99 (3H, d, J=6.5 Hz), 1.50 (3H, d, J=6.8 Hz), 1.75 (3H, dd, J=1.9, 7.0 Hz), 2.74-2.81 (1H, m), 3.29-4.27 (6H, m), 4.68 (2H, s), 4.83-4.92 (1H, m), 5.84 (1H, qd, J=7.0, 11.3 Hz), 6.50 (1H, qd, J=1.9, 11.3 Hz), 6.91 (1H, d, J=8.6 Hz), 7.30-7.45 (6H, m), 7.51 (1H, s).

h) Preparation of (2R,5S,Z)-3-[2-(4-{4-[2-(benzyloxy)-1,1,1,3,3,3-hexafluoropropan-2-yl]-2-(prop-1-en-1-yl)phenyl}-2,5-dimethylpiperazin-1-yl)-2-oxoethyl]-5-(2,3-dihydrobenzo[b][1,4]dioxin-6-yl)-5-methylimidazolidine-2,4-dione 1-((2S,5R)-4-{4-[2-(benzyloxy)-1,1,1,3,3,3-hexafluoropropan-2-yl]-2-(prop-1-en-1-yl) phenyl}-2,5-dimethylpiperazin-1-yl)-2-bromoethanone and 5-(2,3-dihydrobenzo[b][1,4]dioxin-6-yl)-5-methylimidazolidine-2,4-dione were used for a similar reaction and treatment as Example 14-1, and the title compound was obtained as a yellow oil.
¹H-NMR (CDCl₃) δ: 0.88-1.00 (3H, m), 1.32-1.49 (3H, m), 1.74 (3H, d, J=7.1 Hz), 1.87 (3H, s), 2.70-2.80 (1H, m), 3.29-3.82 (4H, m), 4.06-4.83 (6H, m), 4.65 (1H, d, J=11.0 Hz), 4.69 (1H, d, J=11.0 Hz), 4.82-4.90 (1H, m), 5.83 (1H, qd, J=7.1, 11.7 Hz), 6.49 (1H, d, J=11.7 Hz), 6.86-6.89 (2H, m), 7.01-7.09 (2H, m), 7.33-7.44 (6H, m), 7.51 (1H, s).

Example 64

Preparation of (2S,5R)-5-(2,3-dihydrobenzo[b][1,4]dioxin-6-yl)-3-(2-(-4-(4-(1,1,1,3,3,3-hexafluoro-2-hydroxypropan-2-yl)-2-propylphenyl)-2,5-dimethylpiperazin-1-yl)-2-oxoethyl)-5-methylimidazolidine-2,4-dione

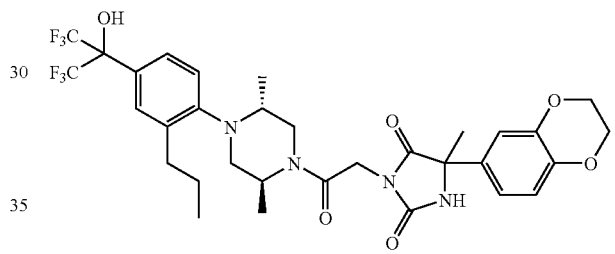

(2S,5R,Z)-3-[2-(4-{4-[2-(benzyloxy)-1,1,1,3,3,3-hexafluoropropan-2-yl]-2-(prop-1-en-1-yl)phenyl}-2,5-dimethylpiperazin-1-yl)-2-oxoethyl]-5-(2,3-dihydrobenzo[b][1,4]dioxin-6-yl)-5-methylimidazolidine-2,4-dione was used for a similar reaction and treatment as Example 15-1, and the title compound was obtained as a yellow oil.
¹H-NMR (CDCl₃) δ: 0.90-1.10 (9H, m), 1.60-1.75 (2H, m), 1.88 (3H, s), 2.54-3.41 (7H, m), 4.04-4.25 (7H, m), 6.89-7.10 (4H, m), 7.47-7.53 (1H, m), 7.53 (1H, s).

Example 65

Preparation of (2S,5R,Z)-3-(2-(4-(4-(2-(benzyloxy)-1,1,1,3,3,3-hexafluoropropan-2-yl)-2-(prop-1-en-1-yl)phenyl)-2,5-dimethylpiperazin-1-yl)-2-oxoethyl)-5-(furo[2,3-c]pyridin-5-yl)-5-methylimidazolidine-2,4-dione

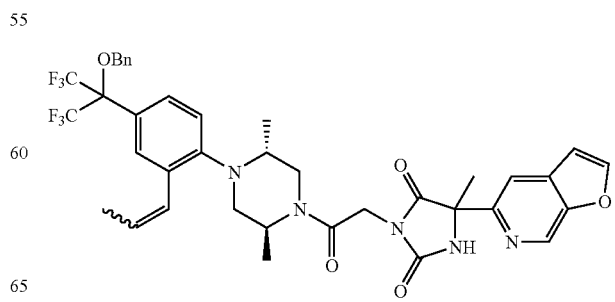

[(2S,5R,Z)-1-(4-{4-[2-(benzyloxy)-1,1,1,3,3,3-hexafluoropropan-2-yl]-2-(prop-1-en-1-yl)phenyl}-2,5-dimethylpiperazin-1-yl)]-2-bromoethanone and 5-(furo[2,3-c]pyridin-5-yl)-5-methylimidazolidine-2,4-dione were used for a similar reaction and treatment as Example 14-1, and the title compound was obtained as a yellow oil.

$^1$H-NMR (CDCl$_3$) δ: 0.90-1.02 (3H, m), 1.34-1.50 (3H, m), 1.74 (3H, d, J=7.1 Hz), 1.92 (3H, s), 2.70-2.73 (1H, m), 3.33-3.85 (4H, m), 4.29-4.34 (2H, m), 4.66 (1H, d, J=12.7 Hz), 4.69 (1H, d, J=12.7 Hz), 4.85-4.91 (1H, m), 5.84 (1H, qd, J=2.1, 12.4 Hz), 6.49 (1H, s), 6.49 (1H, d, J=12.4 Hz), 6.83 (1H, d, J=2.2 Hz), 6.89 (1H, d, J=8.5 Hz), 7.30-7.44 (6H, m), 7.51 (1H, s), 7.78 (1H, d, J=2.2 Hz), 8.00 (1H, s), 8.81 (1H, s).

Example 66

Preparation of (2S,5R)-5-(2,3-dihydrofuro[2,3-c]pyridin-5-yl)-3-(2-(4-(4-(1,1,1,3,3,3-hexafluoro-2-hydroxypropan-2-yl)-2-propylphenyl)-2,5-dimethylpiperazin-1-yl)-2-oxoethyl)-5-methylimidazolidine-2,4-dione

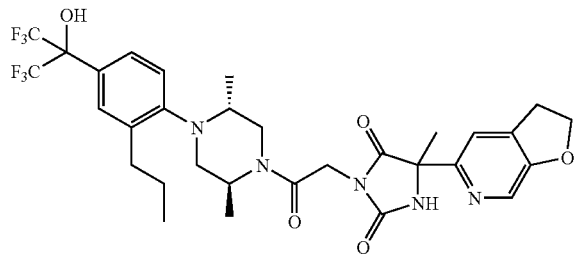 [SMILES: CCCc1cc(C(O)(C(F)(F)F)C(F)(F)F)ccc1N1C[C@H](C)N(C(=O)CN2C(=O)NC(C)(c3cc4c(cn3)OCC4)C2=O)C[C@H]1C]

(2S,5R,Z)-3-(2-(4-(4-(2-(benzyloxy)-1,1,1,3,3,3-hexafluoropropan-2-yl)-2-(prop-1-en-1-yl)phenyl)-2,5-dimethylpiperazin-1-yl)-2-oxoethyl)-5-(furo[2,3-c]pyridin-5-yl)-5-methylimidazolidine-2,4-dione was used for a similar reaction and treatment as Example 15-1, and the title compound was obtained as a yellow oil.

$^1$H-NMR (CDCl$_3$) δ: 0.88-0.99 (9H, m), 1.63-1.72 (2H, m), 1.92 (3H, s), 2.51-2.89 (3H, m), 3.20-3.89 (8H, m), 4.25-4.83 (3H, m), 6.91-6.95 (1H, m), 7.29-7.37 (2H, m), 7.72-7.76 (1H, m), 8.03-8.13 (1H, m).

Test Example 1

Transactivation Assay

<Construction of Plasmid>

The ligand-binding domain (LBD) of a human LXRα and LXRβ cDNA was inserted adjacent to an yeast GAL4-transcription factor DNA-binding domain (DBD) of a mammal expression vector pBIND (Promega) to prepare an expression construct, thereby to produce pBIND-LXRα/GAL4 and pBIND-LXRβ/GAL4, respectively. PG5luc, a GAL4-responsive reporter construct, is a known vector that is available from Promega, and contains 5 copies of GAL4-response element located adjacent to the promoter as well as a luciferase reporter gene.

<Assay>

Figure 1B:
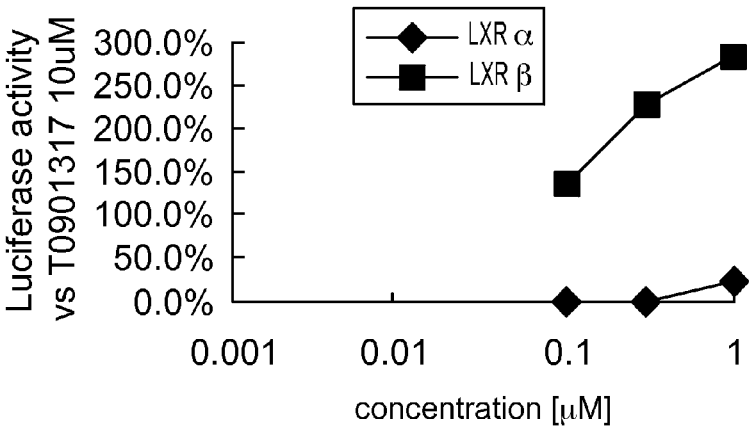
Figure 1C:
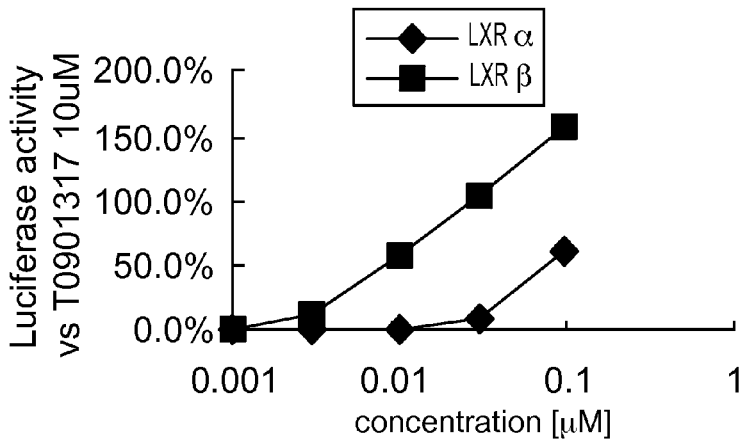
Figure 1G:
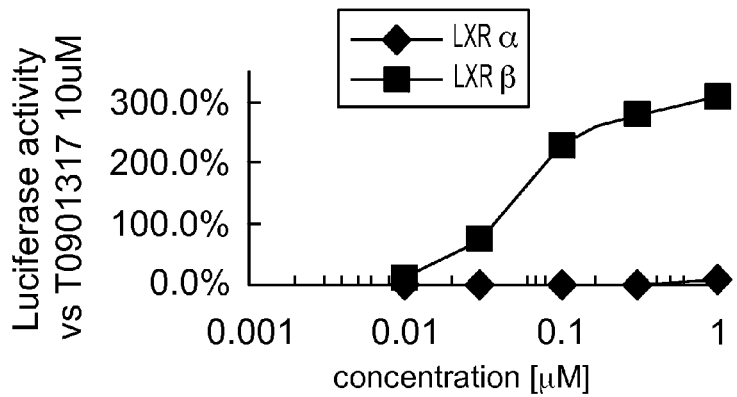
Figure 1H:
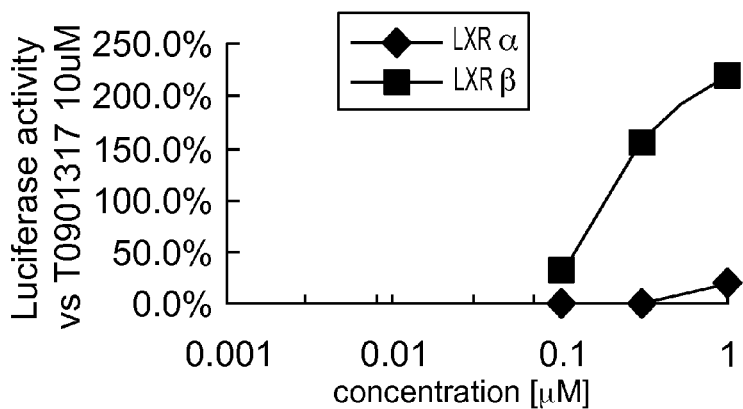
Figure 1I:
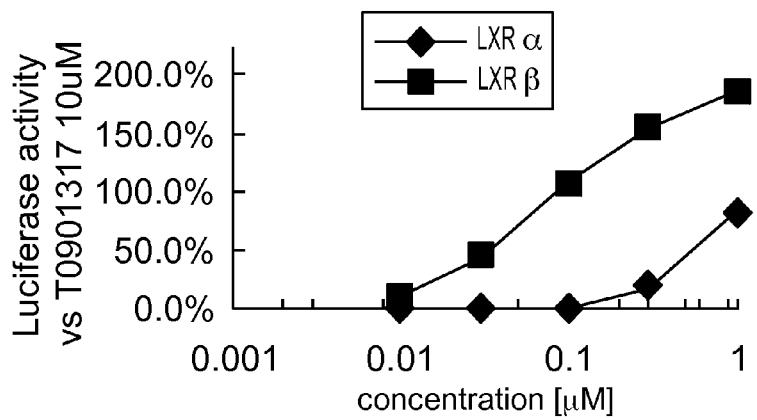
Figure 1J:
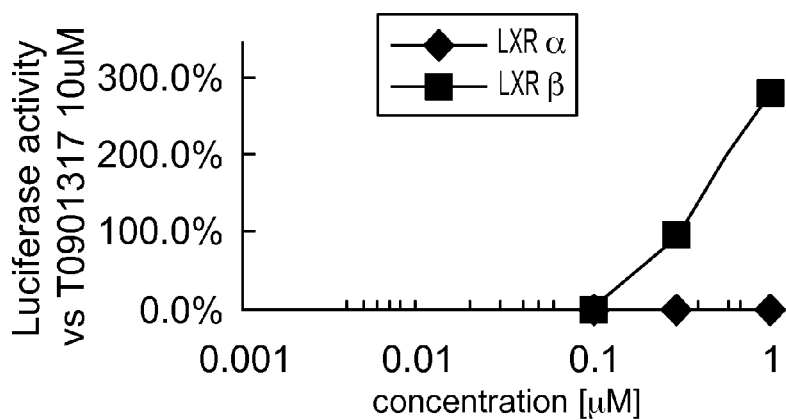
Figure 1K:
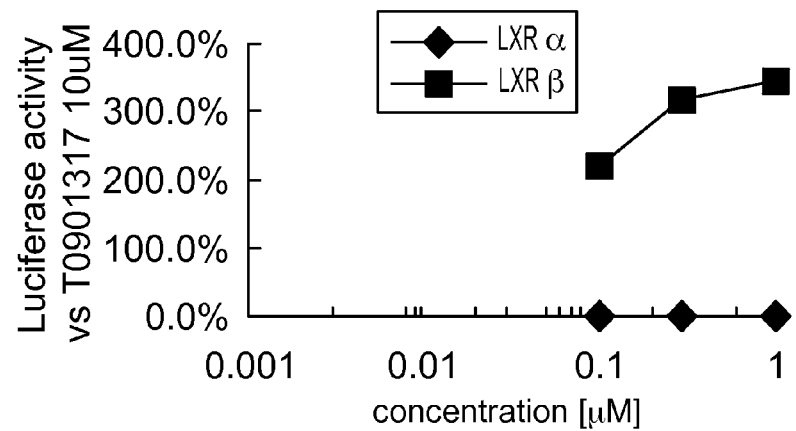
Figure 1L:
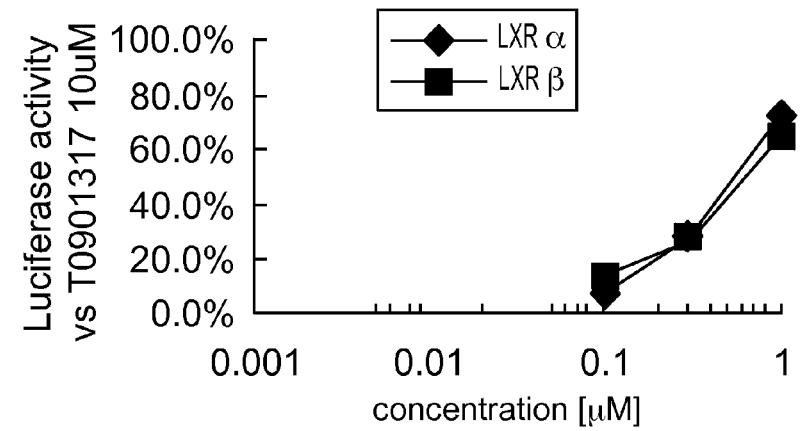
Figure 2A:
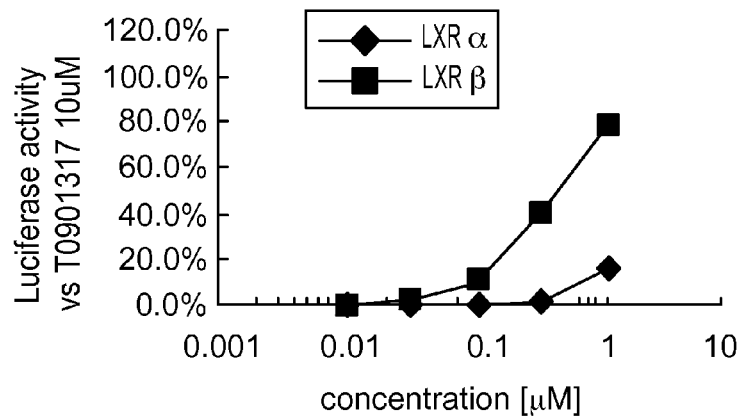
FIGS. 2a to 2g show the luciferase activity results as activity values (% eff) at the respective concentration of the test compound Examples 23, 28, 39, 50, 57, and 61, relative to the T0901317 luminescence intensity of 100 at 10 μM.
Figure 2B:
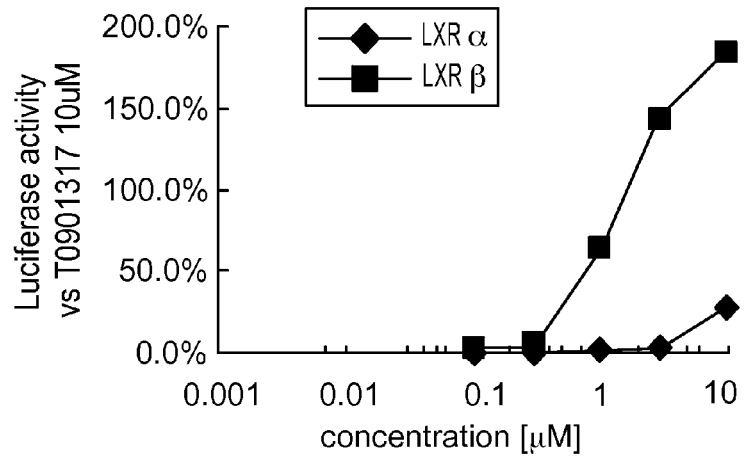
Figure 2C:
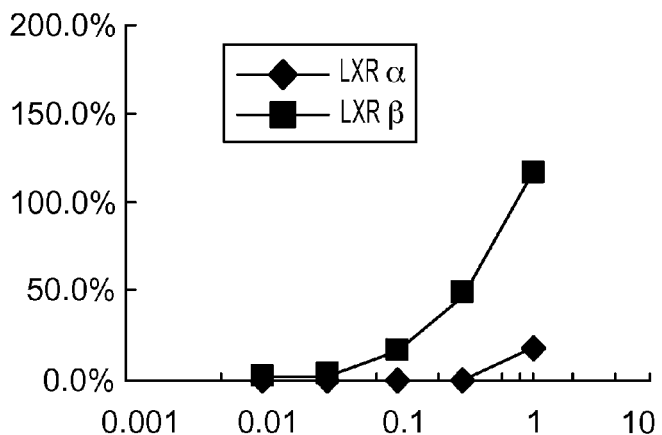
Figure 2D:
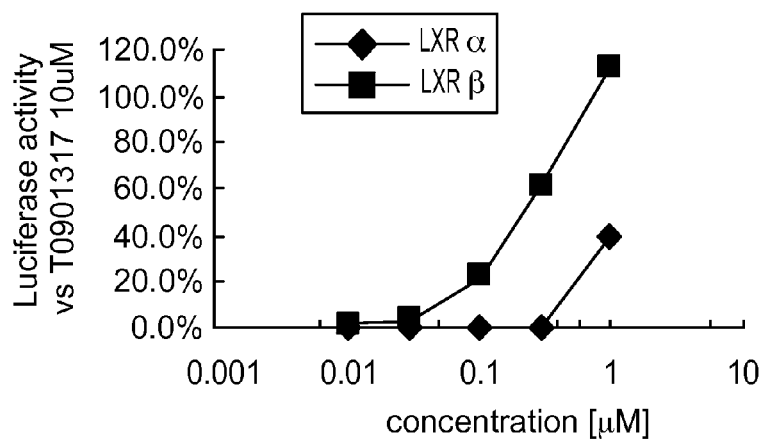
Figure 2E:
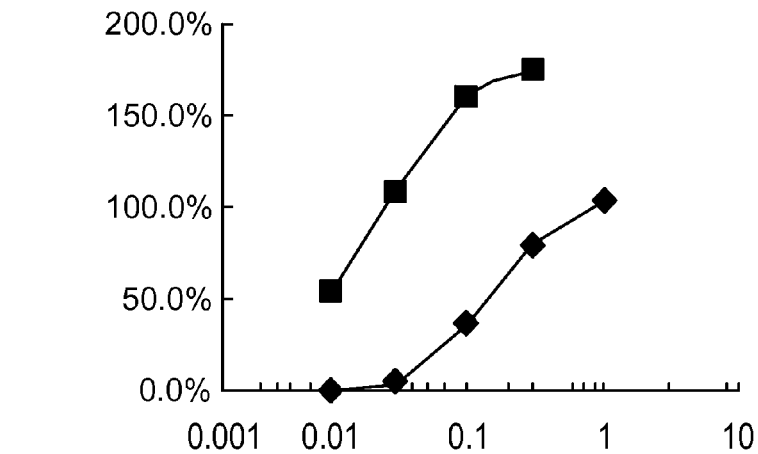
Figure 2F:
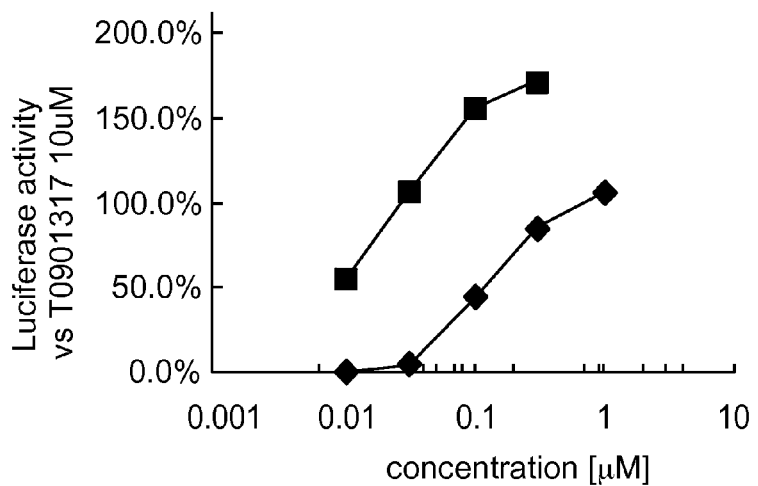
Figure 2G:
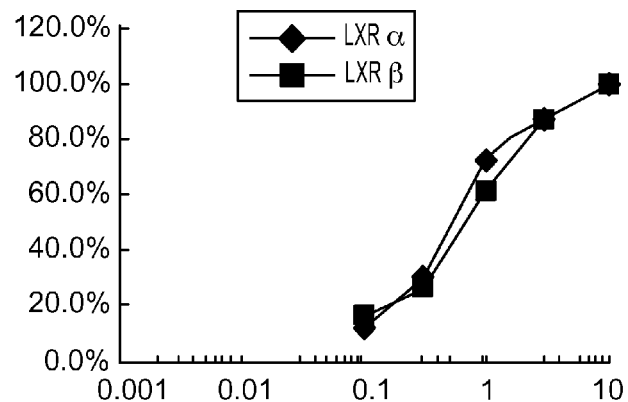

An LXRα/GAL4 or LXRβ/GAL4 hybrid and GAL4-responsive reporter vector pG5luc-stable-expression CHOK-1 cells were seeded under 5% CO$_2$ wet atmosphere at 37° C., at 20,000 cells/well on a 96-well plate containing HAM-F12 medium containing 10% immobilized bovine fetal serum, 100 units/ml of penicillin G, and 100 μg/ml of streptomycin sulfate. 24 hours later, the medium with a test compound dissolved therein over the test concentration range (0.01 μM, 0.1 μM, 1 μM, 10 μM) was added and incubated with the cells for 24 hours. By using Bright-Glo (Promega) as a luciferase assay substrate, and measuring the luminescence intensity with luminometer LB960 (Berthold Technologies), the effect of the test compound on the activation of luciferase transcription via the LXRα- or LXRβ-LBD was measured. At the same time, T0901317 (the compound of Example 12 of WO2000/54759) was assessed as a comparative compound. The luciferase activity results are shown in FIGS. 1a-1l and FIGS. 2a-2g as activity values (% eff) at the respective concentration of the test compound, relative to the T0901317 luminescence intensity of 100 at 10 μM. The activity data of the compounds having a dimethylpiperazine structure are the results of using a mixture of (2R,5S) and (2S,5R) isomers.

<Results>

As shown in FIGS. 1a-1l and FIGS. 2a-2g, it was confirmed experimentally that the carbinol compound of the present invention is an LXR agonist having a higher selectivity to LXRβ than T0901317 which is a control agent.

The invention claimed is:

1. A carbinol compound represented by the following general formula (I) or salt thereof:

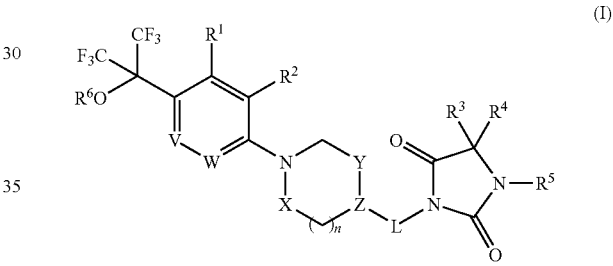

wherein (i) V is N and W is C—R$^7$, (ii) V is C—R$^7$ and W is N, or (iii) V and W independently are C—R$^7$;
wherein X and Y independently are CH$_2$ or CHCH$_3$;
wherein Z is N;
wherein each of R$^1$ and R$^2$ independently is a hydrogen atom, halogen atom, or a C$_{1-4}$ alkyl group or C$_{2-4}$ alkenyl group;
wherein R$^3$ is a C$_{1-4}$ alkyl group;
wherein R$^4$ is (i) a phenyl group optionally having substituents selected from the group consisting of a C$_{1-8}$ alkoxy group, a C$_{3-8}$ cycloalkoxy group and a C$_{3-8}$ cycloalkylthio group, or (ii) a pyridyl group, 1,3-benzodioxolyl group, 1,4-dihydrobenzodioxinyl group, 2,3-dihydrobenzofuranyl group, benzofuranyl group, furopyridinyl group, 2,3-dihydrofuropyridinyl group or 2,3-dihydro-1,4-dioxinopyridinyl group, the pyridyl group, 1,3-benzodioxonyl group, 1,4-dihydrobenzodioxinyl group, 2,3-dihydrobenzofuranyl group, benzofuranyl group, furopyridinyl group, 2,3-dihydrofuropyridinyl group or 2,3-dihydro-1,4-dioxinopyridinyl group optionally having substituents selected from the group consisting of a C$_{1-8}$ alkyl group, a C$_{1-8}$ alkoxy group and a C$_{3-8}$ cycloalkoxy group;
wherein R$^5$ is a hydrogen atom;
wherein R$^6$ is a hydrogen atom, a methoxymethyl group, ethoxyethyl group, a benzyl group or a p-methoxybenzyl group;
wherein R$^7$ is a C$_{1-4}$ alkyl group or C$_{2-4}$ alkenyl group;

wherein L is a 1,2-ethylene chain, a 1-oxo-1,2-ethylene chain, a 1,2-propylene chain or a methylene chain or ethylene chain that may be substituted with a sulfonyl group; and wherein n is integer of 1 or 2.

2. An LXR regulator containing the carbinol compound or salt thereof according to claim 1 as an active ingredient and a pharmaceutically acceptable carrier.

3. A pharmaceutical composition consisting of the carbinol compound or salt thereof according to claim 1 and a pharmaceutically acceptable carrier.

4. A method for treating atherosclerosis, arteriosclerosis, dyslipidemia, or hypercholesterolemia, comprising:
administering an effective amount of the carbinol compound or salt thereof according to claim 1 to a patient in need thereof.

5. The carbinol compound of claim 1, wherein the carbinol compound is 3-(2-{4-[4-(1,1,1,3,3,3-hexafluoro-2-hydroxypropan-2-yl)-2-propylphenyl]piperazin-1-yl}-2-oxoethyl)-5-[5-(1-methylethoxy)pyridin-2-yl]-5-methylimidazolidine-2,4-dione.

6. The carbinol compound of claim 1, wherein the carbinol compound is 3-(2-{4-[4-(1,1,1,3,3,3-hexafluoro-2-hydroxypropan-2-yl)-2-propylphenyl]piperazin-1-yl}-2-oxoethyl)-5-[4-(1-methylethoxy)phenyl]-5-methylimidazolidine-2,4-dione.

7. The carbinol compound of claim 1, wherein the carbinol compound is 5-(benzo[d][1,3]dioxol-5-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione.

8. The carbinol compound of claim 1, wherein the carbinol compound is (R)-3-(2-{4-[4-(1,1,1,3,3,3-hexafluoro-2-hydroxypropan-2-yl)-2-propylphenyl]-3-methylpiperazin-1-yl}-2-oxoethyl)-5-[4-(1-methylethoxy)phenyl]-5-methylimidazolidine-2,4-dione.

9. The carbinol compound of claim 1, wherein the carbinol compound is (S)-3-(2-{4-[4-(1,1,1,3,3,3-hexafluoro-2-hydroxypropan-2-yl)-2-propylphenyl]-3-methylpiperazin-1-yl}-2-oxoethyl)-5-[4-(1-methylethoxy)phenyl]-5-methylimidazolidine-2,4-dione.

10. The carbinol compound of claim 1, wherein the carbinol compound is either (2R,5S,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[4-(1-methylethoxy)phenyl]-5-methylimidazolidine-2,4-dione or (2S,5R,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[4-(1-methylethoxy)phenyl]-5-methylimidazolidine-2,4-dione.

11. The carbinol compound of claim 1, wherein the carbinol compound is either (2R,5S)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-[4-(1-methylethoxy)phenyl]-5-methylimidazolidine-2,4-dione or (2S,5R)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-[4-(1-methylethoxy)phenyl]-5-methylimidazolidine-2,4-dione.

12. The carbinol compound of claim 1, wherein the carbinol compound is either (2R,5S,Z)-5-(2,3-dihydrobenzofuran-5-yl)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-methylimidazolidine-2,4-dione or (2S,5R,Z)-5-(2,3-dihydrobenzofuran-5-yl)-3-(2-{4-[4-(1,1,3,3,3-hexafluoro-2-hydroxypropan-2-yl)-2-(prop-1-en-1-yl)phenyl]-2,5-dimethylpiperazin-1-yl}-2-oxoethyl)-5-methylimidazolidine-2,4-dione.

13. The carbinol compound of claim 1, wherein the carbinol compound is either (2R,5S)-5-(2,3-dihydrobenzofuran-5-yl)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-methylimidazolidine-2,4-dione or (2S,5R)-5-(2,3-dihydrobenzofuran-5-yl)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-methylimidazolidine-2,4-dione.

14. The carbinol compound of claim 1, wherein the carbinol compound is either (2R,5S,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[5-(1-methylethoxy)pyridin-2-yl]-5-methylimidazolidine-2,4-dione or (2S,5R,Z)-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-[5-(1-methylethoxy)pyridin-2-yl]-5-methylimidazolidine-2,4-dione.

15. The carbinol compound of claim 1, wherein the carbinol compound is either (2R,5S)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-[5-(1-methylethoxy)pyridin-2-yl]-5-methylimidazolidine-2,4-dione or (2S,5R)-3-(2-{4-[4-(1,1,1,3,3,3-hexafluoro-2-hydroxypropan-2-yl)-2-propylphenyl]-2,5-dimethylpiperazin-1-yl}-2-oxoethyl)-5-[5-(1-methylethoxy)pyridin-2-yl]-5-methylimidazolidine-2,4-dione.

16. The carbinol compound of claim 1, wherein the carbinol compound is (S)-5-(2,2-dimethyl-2,3-dihydrobenzofuran-5-yl)-3-(2-{4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione.

17. The carbinol compound of claim 1, wherein the carbinol compound is either (2R,5S,Z)-5-[4-(cyclopropylthio)phenyl]-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-methylimidazolidine-2,4-dione or (2S,5R,Z)-5-[4-(cyclopropylthio)phenyl]-3-(2-{4-[4-(1,1,1,3,3,3-hexafluoro-2-hydroxypropan-2-yl)-2-(prop-1-en-1-yl)phenyl]-2,5-dimethylpiperazin-1-yl}-2-oxoethyl)-5-methylimidazolidine-2,4-dione.

18. The carbinol compound of claim 1, wherein the carbinol compound is 5-(2,3-dihydrobenzofuran-5-yl)-3-(2-{4-[4-(1,1,1,3,3,3-hexafluoro-2-hydroxypropan-2-yl)-2-propylphenyl]-1,4-diazepan-1-yl}-2-oxoethyl)-5-methylimidazolidine-2,4-dione.

19. The carbinol compound of claim 1, wherein the carbinol compound is 5-(2,3-dihydro-[1,4]dioxino[2,3-b]pyridin-7-yl)-3-(2-{(S)-4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione.

20. The carbinol compound of claim 1, wherein the carbinol compound is 5-(benzofuran-6-yl)-3-(2-{4-[4-(1,1,1,3,3,3-hexafluoro-2-hydroxypropan-2-yl)-2-propylphenyl]piperazin-1-yl}-2-oxoethyl)-5-methylimidazolidine-2,4-dione.

21. The carbinol compound of claim 1, wherein the carbinol compound is 5-(benzofuran-5-yl)-3-(2-{(S)-4-[4-(1,1,1,3,3,3-hexafluoro-2-hydroxypropan-2-yl)-2-propylphenyl]-3-methylpiperazin-1-yl}-2-oxoethyl)-5-methylimidazolidine-2,4-dione.

* * * * *